US012577228B2

(12) United States Patent
Norman et al.

(10) Patent No.: US 12,577,228 B2
(45) Date of Patent: Mar. 17, 2026

(54) DIHYDROCYCLOPENTA-ISOQUINOLINE-SULFONAMIDE DERIVATIVES COMPOUNDS

(71) Applicant: UCB Biopharma SRL, Brussels (BE)

(72) Inventors: Timothy John Norman, Slough (GB); Douglas Byrne, Abingdon (GB); Julian Hugh Rowley, Slough (GB); Giancarlo Trani, Abingdon (GB); Konstantinos Rampalakos, Abingdon (GB); Nathaniel Julius Thomas Monck, Abingdon (GB); Benedicte Lallemand, Slough (GB); Gregory William Haslett, Slough (GB); Rickki Lee Connelly, Abingdon (GB); Jag Paul Heer, Slough (GB); James Madden, Abingdon (GB); Oliver Philps, Abingdon (GB); Selvaratnam Suganthan, Abingdon (GB); Zeshan Yousuf, Abingdon (GB); Richard John Mears, Abingdon (GB)

(73) Assignee: UCB Biopharma SRL, Brussels (BE)

( * ) Notice: Subject to any disclaimer, the term of this patent is extended or adjusted under 35 U.S.C. 154(b) by 737 days.

(21) Appl. No.: 17/786,394

(22) PCT Filed: Dec. 22, 2020

(86) PCT No.: PCT/EP2020/087686
§ 371 (c)(1),
(2) Date: Jun. 16, 2022

(87) PCT Pub. No.: WO2021/130259
PCT Pub. Date: Jul. 1, 2021

(65) Prior Publication Data

US 2023/0303517 A1 Sep. 28, 2023

(30) Foreign Application Priority Data

Dec. 23, 2019 (GB) ..................................... 1919213

(51) Int. Cl.

| | |
|---|---|
| ***C07D 401/14*** | (2006.01) |
| ***C07D 221/06*** | (2006.01) |
| ***C07D 401/12*** | (2006.01) |
| ***C07D 405/12*** | (2006.01) |
| ***C07D 405/14*** | (2006.01) |
| ***C07D 409/12*** | (2006.01) |
| ***C07D 413/12*** | (2006.01) |
| ***C07D 413/14*** | (2006.01) |
| ***C07D 417/12*** | (2006.01) |
| ***C07D 471/04*** | (2006.01) |
| ***C07D 487/04*** | (2006.01) |
| ***C07D 498/10*** | (2006.01) |

(52) U.S. Cl.
CPC ......... *C07D 401/14* (2013.01); *C07D 221/06* (2013.01); *C07D 401/12* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 471/04* (2013.01); *C07D 487/04* (2013.01); *C07D 498/10* (2013.01)

(58) Field of Classification Search
CPC ............................ C07D 401/14; C07D 221/06
See application file for complete search history.

(56) References Cited

U.S. PATENT DOCUMENTS 4,857,301 A 8/1989 Czarniecki et al.
5,340,811 A 8/1994 Kajihara et al.
(Continued)

FOREIGN PATENT DOCUMENTS

EP 0 418 071 3/1991
EP 0 419 676 4/1991
(Continued)

OTHER PUBLICATIONS

English Translation of Office Action for Japanese Patent Application No. 2022-538777 dated Oct. 22, 2024, 2 pages.
(Continued)

*Primary Examiner* — John S Kenyon
*Assistant Examiner* — Sara Elizabeth Bell
(74) *Attorney, Agent, or Firm* — McDonnell Boehnen Hulbert & Berghoff LLP

(57) ABSTRACT

The present invention relates to dihydrocyclopenta-isoquinoline-sulfonamide derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FcεRI receptor.

(I)

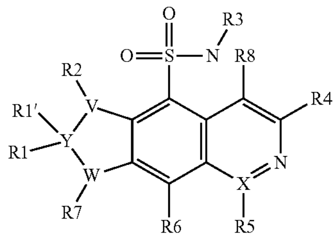

18 Claims, No Drawings

(56) References Cited

U.S. PATENT DOCUMENTS

| | | | | |
|---|---|---|---|---|
| 5,962,634 | A | 10/1999 | Jameson et al. | |
| 2007/0027184 | A1 | 2/2007 | Malecha et al. | |
| 2009/0156642 | A1 | 6/2009 | Nishida et al. | |
| 2011/0274651 | A1* | 11/2011 | Acuff .................... | A61P 31/12 514/192 |
| 2023/0050670 | A1 | 2/2023 | Norman et al. | |
| 2023/0051300 | A1 | 2/2023 | Norman et al. | |
| 2023/0192646 | A1 | 6/2023 | Norman et al. | |
| 2024/0092773 | A1 | 3/2024 | Norman et al. | |

FOREIGN PATENT DOCUMENTS

| | | |
|---|---|---|
| GB | 2270689 A | 3/1994 |
| JP | 2007 099676 | 4/2007 |
| JP | 2017-501215 | 1/2017 |
| WO | 1996/01643 | 1/1996 |
| WO | 1998/028293 | 7/1998 |
| WO | WO 2004/058709 | 7/2004 |
| WO | 2008/059368 | 11/2007 |
| WO | WO 2008/129276 | 10/2008 |
| WO | 2009041705 | 4/2009 |
| WO | 2019/243550 | 12/2019 |
| WO | 2021/130255 | 7/2021 |
| WO | 2021/130257 | 7/2021 |
| WO | 2021/130260 | 7/2021 |
| WO | 2021/130262 | 7/2021 |

OTHER PUBLICATIONS

Parisi, Gluseppe Fablo et al. "Omalizumab treatment in a 12 year-old girl with chronic spontaneous urticaria" The Journal of Dermatological Treatment (2018) vol. 29, pp. 10-11.

International Search Report dated Mar. 2, 2021 for International Application No. PCT/EP2020/087686, 3 pages.

Sarkar, Tarun et al. "A Sequential Pummerer-Diels-Alder Route for the Generation and Trapping of Furo[3,4c] pyridines: Synthesis of Heterocyclic Analogues of 1-Arylnaphthalene Lignans" Journal of Organic Chemistry (2003) vol. 68(18), pp. 6919-6927, XP055779792.

Kohno, Jun et al. "Production, Isolation and Biological Properties of TMC-120A, B and C, Novel Inhibitors of Eosinophil Survival from Aspergillus ustus TC 1118" Journal of Antibiotics (1999) vol. 52(10), pp. 913-916.

Hay, Michael et al. "Tricyclic 1-18 [1,2,4]triazine 1,4-dioxides as hypoxia selective cytotoxins" Journal of Medicinal Chemistry (2008) vol. 51(21), pp. 6853-6865.

Kitagaki, Shinji et al. "Intermolecular [4+2] Cycloaddition of o -Quinodimethanes Derived from Ene-Bis (sulfinylallenes)" Journal of Organic Chemistry (2006) vol. 71(18), pp. 6908-6914.

* cited by examiner

DIHYDROCYCLOPENTA-ISOQUINOLINE-SULFONAMIDE DERIVATIVES COMPOUNDS

CROSS-REFERENCE TO RELATED APPLICATIONS

This application is a U.S. national phase of International Application No. PCT/EP2020/087686, filed Dec. 22, 2020, which claims priority from Great Britain Application No. 1919213.7, filed Dec. 23, 2019, the disclosure of each of which is hereby incorporated by reference in its entirety.

TECHNICAL FIELD

The present invention relates to dihydrocyclopenta-isoquinoline-sulfonamide derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FcεRI receptor.

BACKGROUND OF THE INVENTION

IgE (immunoglobulin E) is a member of the immunoglobulin family and mediates allergic responses such as asthma, food allergies, type 1 hypersensitivity and the familiar sinus inflammation.

IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcεRII). Upon exposure of a mammal to an allergen, B-cells are clonally amplified which synthesize IgE that binds the allergen. This IgE in turn is released into the circulation by the B-cells where it is bound by B-cells (through FcεRII) and by mast cells and basophils through the so-called high affinity receptor (FcεRI) found on the surface of the mast cells and basophils. Such mast cells and basophils are thereby sensitized for allergen. The next exposure to the allergen cross-links the FcεRI on these cells and thus activate their release of histamine and other factors which are responsible for clinical hypersensitivity and anaphylaxis.

Currently, allergic diseases, urticaria, and asthma are usually treated with one or more of the following drugs: (1) antihistamines and antileukotrienes which antagonize the inflammatory mediators histamine and leukotrienes, (2) local or systemic (oral or injectable) corticosteroids or immunosuppressants which suppress a broad spectrum of inflammatory mechanisms, (3) short or long-acting bronchodilators which relax smooth muscle of constricted airway in asthma, or (4) mast cell stabilizers which inhibit the degranulation of mast cells that is normally triggered by IgE-binding at FcεRI, (5) biologicals which prevent the binding of IgE at FcεRI. There has been also attempts to use peptides that modulate IgE binding to FcεRI. As an example, WO96/01643 describes peptides that consist of 4-50 amino to treat immediate allergic responses.

However, there is still a need to identify compounds which have therapeutic utility in the treatment or prevention of disorders caused by IgE, particularly disorders caused by the interaction of IgE with the FcεRI receptor.

SUMMARY OF THE INVENTION

It has been found that compounds of formula (I) and their pharmaceutically acceptable salts can be used for this purpose.

DETAILED DESCRIPTION

The present invention provides compounds of formula (I) and pharmaceutically acceptable salts thereof:

(I)

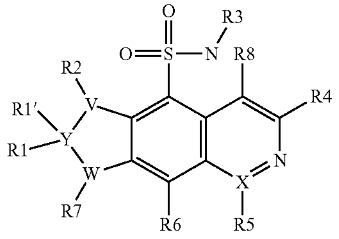

Wherein:

X, Y independently represent C or N;

V, W independently represent C or O;

If either V or W represent O then Y represents C

If Y represents N then R1' is absent

If V represents O then R2 is absent

If W represents O then R7 is absent

R1 represents a group chosen amongst:

Hydrogen; or C(O)NH—C1-6-alkyl; or C(O)NH-heteroaryl; or heteroaryl optionally substituted with one or more oxo; hydroxy; amino; C(O)$NH_2$; C(O)O—C1-6-alkyl; heteroaryl; NH—C1-6-alkyl; NH—C1-6-alkyl-C1-6-cycloalkyl; NH-heteroaryl optionally substituted with one or more $R1_a$; or C1-6-alkyl-C(O)—C1-6-alkylamino; or C1-6-alkyl-heteroaryl; or C(O)—C1-6-alkyl-heteroaryl; or NHC(O)-heteroaryl optionally substituted with one or more R12; or NH—C3-8-cycloalkyl optionally substituted with one or more $R1_a$; or NH—C3-8-heterocycloalkyl optionally substituted with one or more $R1_a$; or NHC(O)—C1-6-alkyl optionally substituted with one or more aryl; heteroaryl; or NHC(O)—NH—C1-6-alkyl; or NHC(O)O—C1-6-alkyl; or NH-aryl optionally substituted with one or more C1-6-alkyl; C(O)—C1-6-alkyl; heteroaryl optionally substituted with one or more C1-6-alkyl; or $SO_2$-C1-6-alkyl; or $SO_2$—NH—C1-6-alkyl; or NH—$SO_2$-C1-6-alkyl; or NHC(O)—C(O)-heteroaryl optionally substituted with one or more halogen; C1-6-alkyl;

$R1_a$ represents a group chosen amongst:

Hydrogen; Halogen; hydroxy; oxo; amino; C1-6-alkyl; C1-6-alkoxy; C(O)O—C1-6-alkyl; C1-6-alkylamino; cyano; C1-6-haloalkyl; C1-6-haloalkoxy; C(O)OH; C3-8-cycloalkyl;

or

—NH-Heteroaryl substituted with one or more group chosen amongst:

Hydrogen; $R1_b$; hydroxy; halogen; oxo; C1-6-alkyl; C1-6-alkoxy; C1-6-hydroxyalkyl; C1-6-haloalkyl; C1-6-alkyl-C(O)OH; C(O)$NH_2$; $SO_2NH_2$; S(O)—C1-6-alkyl; $SO_2$-C1-6-alkyl; $SO_2$NHC(O)—C1-6-alkyl; $SO_2$-C1-6-alkylamino; S(O)(NH)—C1-6-alkyl; C1-6-alkyl-C3-8-cycloalkyl; C3-8-cycloalkyl-C1-6-alkyl; C1-6-alkoxy-C3-8-cycloalkyl; C3-8-cycloalkyl-C1-6-alkoxy; C1-6-alkylamino-C3-8- cycloalkyl; C3-8-cycloalkyl-C1-6-alkylamino; C(O)OH; C(O)O—C1-6-alkyl; C(O)NH—C1-6-alkyl; NHC(O)—C1-6-alkyl; cyano;

or C3-8-heterocycloalkyl optionally substituted with one or more hydroxy; oxo; C1-6-alkyl; cyano;

or heterocycloalkyloxy optionally substituted with one or more hydroxy; oxo; C1-6-alkyl; C1-6-alkoxy; C3-8-cycloalkyl-C1-6-alkoxy; C(O)NH—C1-6-alkyl; NHSO2-C1-6-alkyl;

or heteroaryloxy optionally substituted with one or more hydroxy; oxo; C1-6-alkyl; C1-6-alkoxy;

or heteroarylamino optionally substituted with one or more hydroxy; oxo; C1-6-alkyl; C1-6-alkoxy;

or $SO_2$-heteroaryl optionally substituted with one or more C1-3-alkyl; oxo;

$R1_b$ represents a group chosen amongst:

Heteroaryl optionally substituted with one or more halogen; hydroxy; oxo; C1-6-alkyl; C1-6-alkanediyl-C(O)OH; $C(O)NH_2$; carbamoyl; C(O)O—C1-6-alkyl; S(O) NH—C1-6-alkyl; C3-8-cycloalkyl; heteroarylamino; C1-6-alkoxy, cyano; C1-6-haloalkyl; C1-6-haloalkoxy; C(O)OH;

R1' represents: hydrogen; C1-3-alkyl; C1-3-hydroxyalkyl;

R2 represents a group chosen amongst:

Hydrogen; NHC(O)NH—C1-6-alkyl; hydroxy;

R1' and R2 can form together a cyclopropyl ring incorporating V and Y

R1 and R1' can form together a heterocycloalkyl ring optionally substituted with one or more oxo; halogen; C1-6-alkyl;

R3 represents a group chosen amongst:

C1-6-alkyl optionally substituted with one or more group chosen amongst $R3^a$;

C1-3-alkanediyl-C3-6-cycloalkyl optionally substituted with one or more $R3^a$;

C1-3-alkanediyl-C3-6-heterocycloalkyl optionally substituted with one or more $R3^a$;

C3-6-heterocycloalkyl optionally substituted with one or more $R3^a$;

C3-6-cycloalkyl optionally substituted with one or more $R3^a$;

$R3^a$ represents a group chosen amongst hydrogen Halogen, C1-2-alkyl; hydroxy; C1-2-alkoxy R4 represents a group chosen amongst:

C3-6-cycloalkyl optionally substituted with one or more $R4^a$ group; or C1-6-alkanediyl-C3-6-cycloalkyl optionally substituted with one or more $R4^a$ group; or C1-6-alkanediyl-C3-6-heterocycloalkyl optionally substituted with one or more $R4^a$ group;

$R4^a$ represents a group chosen amongst hydroxy; Halogen; C1-2-alkyl.

R5 represents a group chosen amongst:

Hydrogen; hydroxy, Halogen; C1-3-alkyl optionally substituted with one or more halogen; C1-3-alkoxy;

R6 represents a group chosen amongst:

Hydrogen; halogen; amino; NHC(O) C1-6-alkyl; C1-3-alkyl optionally substituted with one or more halogen; C1-3-alkoxy;

R7 represents a group chosen amongst:

Hydrogen; NHC(O)NH—C1-6-alkyl; Halogen; hydroxy;

R1' and R7 can form together a cyclopropyl ring incorporating W and Y;

R8 represents hydrogen; halogen; hydroxy; C1-3 alkyl; cyclopropyl.

According to an embodiment, compounds of the invention are characterized by the formula wherein R4 represents cyclopropyl or spiro[2.2]pentanyl; optionally substituted with one or more group chosen independently from hydroxy;

Chloro, Fluoro, Bromo;

Methyl.

According to an embodiment, compounds of the invention are characterized by the formula wherein R1', R2, R7 are hydrogen, other substituents being defined as herein above and below.

According to an embodiment, compounds of the invention are characterized by the formula wherein wherein R4 represents cyclopropyl.

According to a further embodiment, compounds of the invention are characterized by the formula (I) wherein wherein R1 represents a group chosen amongst:

Hydrogen; or C(O)NH—C1-6-alkyl; or C(O)NH-heteroaryl; or heteroaryl optionally substituted with one or more oxo; hydroxy; amino; $C(O)NH_2$; C(O)O—C1-6-alkyl; heteroaryl; NH—C1-6-alkyl; NH—C1-6-alkyl-C1-6-cycloalkyl; NH-heteroaryl optionally substituted with one or more $R1_a$; or C1-6-alkyl-C(O)—C1-6-alkylamino; or C1-6-alkyl-heteroaryl; or C(O)—C1-6-alkyl-heteroaryl; or NHC(O)-heteroaryl optionally substituted with one or more $R1_a$; or NH—C3-8-cycloalkyl optionally substituted with one or more $R1_a$; or NH—C3-8-heterocycloalkyl optionally substituted with one or more $R1_a$; or NHC(O)—C1-6-alkyl optionally substituted with one or more aryl; heteroaryl; or NHC(O)—NH—C1-6-alkyl; or NHC(O)O—C1-6-alkyl; or NH-aryl optionally substituted with one or more C1-6-alkyl; C(O)—C1-6-alkyl; heteroaryl optionally substituted with one or more C1-6-alkyl; or $SO_2$-C1-6-alkyl; or $SO_2$—NH—C1-6-alkyl; or NH—$SO_2$-C1-6-alkyl; or NHC(O)—C(O)-heteroaryl optionally substituted with one or more halogen; C1-6-alkyl;

$R1_a$ represents a group chosen amongst:

Hydrogen; Halogen; hydroxy; oxo; amino; C1-6-alkyl; C1-6-alkoxy; C(O)O—C1-6-alkyl; C1-6-alkylamino; cyano; C1-6-haloalkyl; C1-6-haloalkoxy; C(O)OH; C3-8-cycloalkyl.

According to another embodiment, compounds of the invention are characterized by the formula (I) wherein R1 represents-NH-Heteroaryl substituted with one or more group chosen amongst:

Hydrogen; $R1_b$; hydroxy; halogen; oxo; C1-6-alkyl; C1-6-alkoxy; C1-6-hydroxyalkyl; C1-6-haloalkyl; C1-6-alkyl-C(O)OH; $C(O)NH_2$; $SO_2NH_2$; S(O)—C1-6-alkyl; $SO_2$-C1-6-alkyl; $SO_2$NHC(O)—C1-6-alkyl; $SO_2$-C1-6-alkylamino; S(O)(NH)—C1-6-alkyl; C1-6-alkyl-C3-8-cycloalkyl; C3-8-cycloalkyl-C1-6-alkyl; C1-6-alkoxy-C3-8-cycloalkyl; C3-8-cycloalkyl-C1-6-alkoxy; C1-6-alkylamino-C3-8-cycloalkyl; C3-8-cycloalkyl-C1-6-alkylamino; C(O)OH; C(O)O—C1-6-alkyl; C(O)NH—C1-6-alkyl; NHC(O)—C1-6-alkyl; cyano;

or C3-8-heterocycloalkyl optionally substituted with one or more hydroxy; oxo; C1-6-alkyl; cyano;

or heterocycloalkyloxy optionally substituted with one or more hydroxy; oxo; C1-6-alkyl; C1-6-alkoxy; C3-8-cycloalkyl-C1-6-alkoxy; C(O)NH—C1-6-alkyl; NHSO2-C1-6-alkyl;

or heteroaryloxy optionally substituted with one or more hydroxy; oxo; C1-6-alkyl; C1-6-alkoxy;

or heteroarylamino optionally substituted with one or more hydroxy; oxo; C1-6-alkyl; C1-6-alkoxy;

or $SO_2$-heteroaryl optionally substituted with one or more C1-3-alkyl; oxo;

and $R1_b$ represents a group chosen amongst:

Heteroaryl optionally substituted with one or more halogen; hydroxy; oxo; C1-6-alkyl; C1-6-alkanediyl-C(O)OH; $C(O)NH_2$; carbamoyl; C(O)O—C1-6-alkyl; S(O)NH—C1-6-alkyl; C3-8-cycloalkyl; heteroarylamino; C1-6-alkoxy, cyano; C1-6-haloalkyl; C1-6-haloalkoxy; C(O)OH.

The term "pharmaceutically acceptable salt" according to the invention embraces salts of the compounds of formula (I) with a pharmaceutically acceptable acid or base, in particular an acid addition salt. The acid addition salt form of a compound of formula (I) that occurs in its free form as a base can be obtained by treating the free base with an appropriate acid such as an inorganic acid, for example, a hydrohalic acid such as hydrochloric acid or hydrobromic acid, sulfuric acid, nitric acid, phosphoric acid and the like; or an organic acid, such as, for example, acetic acid, trifluoroacetic acid, oxalic acid, hydroxyacetic acid, propanoic acid, lactic acid, pyruvic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and the like.

The invention also relates to all stereoisomeric forms such as enantiomeric and diastereoisomeric forms of the compounds of formula (I) or mixtures thereof (including all possible mixtures of stereoisomers such as racemates). With respect to the present invention reference to a compound or compounds is intended to encompass that compound in each of its possible isomeric forms and mixtures thereof, unless the particular isomeric form is referred to specifically.

Some of the compounds of formula (I) may also exist in tautomeric forms. Such forms although not explicitly indicated in the above formula are intended to be included within the scope of the present invention.

It is to be understood that each individual atom present in formula (I), or in formulae depicted herein, may in fact be present in the form of any of its naturally occurring isotopes, with the most abundant isotope(s) being preferred. Thus, by way of example, each individual hydrogen atom present in formula (I), or in the formulae depicted herein, may be present as a 1H, 2H (deuterium) or 3H (tritium) atom, preferably 1H. Similarly, by way of example, each individual carbon atom present in formula (I), or in the formulae depicted herein, may be present as a 12C, 13C or 14C atom, preferably 12C.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Compounds according to the present invention may exist in different polymorphic forms. Although not explicitly indicated in the above formula, such forms are intended to be included within the scope of the present invention.

The present invention also includes within its scope prodrug of the compounds of formula (I) above. The term "prodrug" means a compound metabolised in vivo to a compound of the invention or its salt. A prodrug may be identified by administering the prodrug to a mammal, such as rat, mouse, monkey or man, and identifying the compound or its salt, for example in blood or urine.

In the frame of the present invention:

Ct-z represents a carbon chain which may have from t to z carbon atoms, for example a C1-7 carbon chain which may have from 1 to 7 carbon atoms;

Alkyl is a saturated, linear or branched aliphatic group; for example, a C1-6-alkyl group represents a carbon chain of 1 to 6 carbon atoms, linear or branched, for example a methyl, ethyl, propyl, isopropyl, butyl, isobutyl, tertbutyl, pentyl, hexyl. Alkyl encompass deuterated groups, where one or more hydrogen atoms are replaced with deuterium atom $^2H$.

Alkanediyl is a divalent linear or branched saturated hydrocarbon group of general formula $C_nH_{2n}$, such as $—CH_2—CH_2—$;

Alkylamino refers to one or more alkyl groups substituted on an amino radical. As examples of alkylamino one can mention methylamino; ethylamino; tertbutylamino; dimethylamino; hydroxy is a —OH group;

hydroxyalkyl is an alkyl group of which one or more hydrogen atom has been substituted with a hydroxy-group;

alkoxy, —O-alkyl group;

haloalkoxy, —O-haloalkyl group;

halogen a fluorine, chlorine, bromine or iodine atom;

haloalkyl refers to an alkyl group substituted with one or more halogen atom. As an example of haloalkyl, one can cite difluoromethyl; fluoro-isoproyl; chloro-tert-butyl;

cycloalkyl refers to a mono or bicyclic aliphatic group that may comprise a double bond without being aromatic and comprising between 3 and 14 atoms, preferably 3 to 10 atoms in the group. As an example of cycloalkyl one can mention cyclopropyl; cyclobutyl cyclobutenyl; cyclopentyl; cyclohexyl; spiro-undecanyl; spiro-[2.2]pentanyl heterocycloalkyl refers to a mono or bicyclic saturated group comprising between 3 and 14 atoms, preferably 3 to 10 atoms in the group and preferably 3 to 9 atoms in the group, that may comprise a double bond without being aromatic and wherein one or more carbon atom is replaced with an atom chosen amongst nitrogen; oxygen; sulfur. As an example of heterocycloalkyl one can mention aziridinyl; pyrrolidinyl; piperidyl; oxetane; oxa-spiro-undecanyl;

Heterocycloalkyloxy refers to a heterocycloalkyl substituted with an oxygen radical. As an example of heterocycloalkyloxy one can cite tetrahydropyranyloxy.

aryl refers to a mono- or bicyclic aromatic group comprising between 6 and 14 carbon atoms wherein at least one ring in the group is aromatic. As examples of an aryl group one can mention phenyl or naphthyl groups;

Heteroaryl refers to a mono- or bicyclic group comprising from 5 to 14 atoms, wherein at least one ring in the group is aromatic and wherein at least one atom in the group is chosen amongst nitrogen; oxygen; sulfur. As examples of a heteroaryl group one can mention triazolyl; furanyl; pyrrolyl; chromanyl; isoquinolinyl;

Heteroarylamino refers to an amino group-$NH_2$ substituted with a heteroaryl group. Example of heteroaryl group can be pyridinylamino;

Heteroaryloxy refers to a heteroaryl group substituted with an oxygen radical. As an example of heteroaryloxy one can cite pyridyloxy.

Another embodiment of the present invention concerns a pharmaceutical composition comprising a detectable amount of a compound of formula (I) or a pharmaceutically acceptable salt, solvate or co-crystal thereof in combination with a pharmaceutically acceptable diluent or carrier.

In yet another embodiment, the present invention concerns a compound of formula (I), a pharmaceutically acceptable salt, solvate or co-crystal thereof for use as a medicament, in particular for use in a method for the treatment or prevention of disorders caused by IgE, including allergy, type 1 hypersensitivity, familiar sinus inflammation, urticaria or related conditions, such as airway constriction in asthma, local inflammation in eczema, increased mucus secretion in allergic rhinitis, or increased vascular permeability.

In a further embodiment, the present invention concerns a method for the treatment or prevention of allergy, type 1 hypersensitivity, familiar sinus inflammation, urticaria or related conditions, which comprises the administration of a compound of formula (I) in a therapeutically effective amount.

In an embodiment, a compound of the invention is chosen amongst:

tert-butyl N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]carbamate;

tert-butyl N-[cis-(7RS,9SR)-3-cyclopropyl-5-(2-methylpropylsulfamoyl)-7-(pyridine-3-carbonylamino)-8,9-dihydro-7H-cyclopenta[h]isoquinolin-9-yl]carbamate;

N-[trans-(7RS,9RS)-9-amino-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylcarbamothioylamino)-8,9-dihydro-7H-cyclopenta[h]isoquinolin-7-yl]pyridine-3-carboxamide;

N-[trans-(7RS,9RS)-3-cyclopropyl-9-(ethylcarbamoylamino)-5-(2-methylpropylsulfamoyl)-8,9-dihydro-7H-cyclopenta[h]isoquinolin-7-yl]pyridine-3-carboxamide;

N-[cis-(7RS,9SR)-3-cyclopropyl-5-(2-methylpropylsulfamoyl)-9-(pyridin-3-ylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(4-pyridin-3-yl-1,2,4-triazol-3-yl)amino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[3-(pyridin-3-ylamino)-1,2,4-triazol-4-yl]-8,9-dihydro-7H-cyclopenta[h]isoquinolin-7-yl]pyridine-3-carboxamide;

N-[trans-(7RS,9RS)-3-cyclopropyl-9-[(4-ethyl-1,2,4-triazol-3-yl)amino]-5-(2-methylpropylsulfamoyl)-8,9-dihydro-7H-cyclopenta[h]isoquinolin-7-yl]pyridine-3-carboxamide;

N-[trans-(7RS,9RS)-9-(benzylamino)-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(propylamino)-8,9-dihydro-7H-cyclopenta[h]isoquinolin-7-yl]pyridine-3-carboxamide;

N-[trans-(7RS,9RS)-3-cyclopropyl-9-(2-methylpropanoylamino)-5-(2-methylpropylsulfamoyl)-8,9-dihydro-7H-cyclopenta[h]isoquinolin-7-yl]pyridine-3-carboxamide;

1-ethyl-3-[trans-(7RS,9RS)-3-cyclopropyl-9-hydroxy-5-(2-methylpropylsulfamoyl)-8,9-dihydro-7H-cyclopenta[h]isoquinolin-7-yl]urea;

1-ethyl-3-[cis-(7RS,9SR)-3-cyclopropyl-9-hydroxy-5-(2-methylpropylsulfamoyl)-8,9-dihydro-7H-cyclopenta[h]isoquinolin-7-yl]urea;

1-ethyl-3-[trans-(7RS,9RS)-3-cyclopropyl-7-hydroxy-5-(2-methylpropylsulfamoyl)-8,9-dihydro-7H-cyclopenta[h]isoquinolin-9-yl]urea;

N-[cis-(7RS,9SR)-3-cyclopropyl-9-(isoquinolin-4-ylamino)-5-(2-methylpropylsulfamoyl)-8,9-dihydro-7H-cyclopenta[h]isoquinolin-7-yl]pyridine-3-carboxamide;

1-[(4-methoxyphenyl)methyl]-3-[trans-(7RS,9RS)-3-cyclopropyl-9-[(5-methoxypyridin-3-yl)amino]-5-(2-methylpropylsulfamoyl)-8,9-dihydro-7H-cyclopenta[h]isoquinolin-7-yl]urea;

N-[trans-(7RS,9RS)-7-[(3-cyanophenyl) carbamoylamino]-3-cyclopropyl-5-(2-methylpropylsulfamoyl)-8,9-dihydro-7H-cyclopenta[h]isoquinolin-9-yl]pyridine-3-carboxamide;

N-[trans-(7RS,9RS)-7-[(4-bromophenyl)methylcarbamoylamino]-3-cyclopropyl-5-(2-methylpropylsulfamoyl)-8,9-dihydro-7H-cyclopenta[h]isoquinolin-9-yl]pyridine-3-carboxamide;

N-[trans-(7RS,9RS)-3-cyclopropyl-5-(2-methylpropylsulfamoyl)-7-(naphthalen-1-ylcarbamoylamino)-8,9-dihydro-7H-cyclopenta[h]isoquinolin-9-yl]pyridine-3-carboxamide;

1-[(5-methyl-1,2-oxazol-3-yl)methyl]-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

Ethyl N-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]carbamoyl]carbamate;

1-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]-3-[rac-(1S)-1-(3-methoxyphenyl)ethyl]urea;

1-(1-cyclopropylethyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(2-methylcyclopropyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-benzyl-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(2-phenylcyclopropyl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

1-(3,4-dihydro-2H-chromen-3-yl)-3-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]urea;

N-[trans-(7RS,9RS)-3-cyclopropyl-5-(2-methylpropylsulfamoyl)-7-[[rac-(E)-3-(2-chlorophenyl) prop-2-enoyl]amino]-8,9-dihydro-7H-cyclopenta[h]isoquinolin-9-yl]pyridine-3-carboxamide;

6-methoxy-N-[trans-(7RS,9RS)-3-cyclopropyl-5-(2-methylpropylsulfamoyl)-9-(pyridine-3-carbonylamino)-8,9-dihydro-7H-cyclopenta[h]isoquinolin-7-yl]pyridine-3-carboxamide;

methyl 3-oxo-3-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]propanoate;

N-[2-oxo-2-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]ethyl]benzamide;

5-chloro-4-methoxy-N-[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]thiophene-3-carboxamide;

ethyl 3-oxo-3-[[trans-(7RS,9RS)-9-(1H-benzimidazol-2-ylamino)-3-cyclopropyl-5-(2-methylpropylsulfamoyl)-8,9-dihydro-7H-cyclopenta[h]isoquinolin-7-yl]amino]propanoate;

N-[cis-(7RS, 9SR)-3-cyclopropyl-7-(2-methylbutanoylamino)-5-(2-methylpropylsulfamoyl)-8,9-dihydro-7H-cyclopenta[h]isoquinolin-9-yl]pyridine-3-carboxamide;

N-[cis-(7RS,9SR)-7-[[2-(4-chlorophenoxy) acetyl]amino]-3-cyclopropyl-5-(2-methylpropylsulfamoyl)-8,9-dihydro-7H-cyclopenta[h]isoquinolin-9-yl]pyridine-3-carboxamide;

3-phenyl-N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]-1,2-oxazole-5-carboxamide;

N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]quinoxaline-6-carboxamide;

N-[trans-(7RS,9RS)-3-cyclopropyl-5-(2-methylpropylsulfamoyl)-9-[[rac-(E)-3-(4-hydroxyphenyl) prop-2-enoyl]amino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]pyrido[2,3-b]pyrazine-7-carboxamide;

N-[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]-1,3-benzoxazole-2-carboxamide;

ethyl rac-(E)-4-oxo-4-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]but-2-enoate;

N-[trans-(7RS,9RS)-9-[3-(benzimidazol-1-yl) propanoylamino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[3-(2-oxopyridin-1-yl) propanoylamino]-8,9-dihydro-7H-cyclopenta[h]isoquinolin-7-yl]pyridine-3-carboxamide;

N-[trans-(7RS,9RS)-3-cyclopropyl-9-[(4-methoxy-1-benzofuran-2-carbonyl)amino]-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[3-(2-oxopyrrolidin-1-yl) propanoylamino]-8,9-dihydro-7H-cyclopenta[h]isoquinolin-7-yl]pyridine-3-carboxamide;

ethyl 5-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]pyridine-3-carboxylate;

N-[trans-(7RS,9RS)-3-cyclopropyl-9-(2-methoxyanilino)-5-(2-methylpropylsulfamoyl)-8,9-dihydro-7H-cyclopenta[h]isoquinolin-7-yl]pyridine-3-carboxamide;

N-[trans-(7RS,9RS)-9-[(4-cyanopyridin-2-yl)amino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(6-methylpyridazin-3-yl)amino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(quinolin-4-ylamino)-8,9-dihydro-7H-cyclopenta[h]isoquinolin-7-yl]pyridine-3-carboxamide;

N-[trans-(7RS,9RS)-3-cyclopropyl-9-[(5-methyl-1,2-oxazol-3-yl)methylcarbamoylamino]-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-[(2-phenylcyclopropyl) carbamoylamino]-8,9-dihydro-7H-cyclopenta[h]isoquinolin-7-yl]pyridine-3-carboxamide;

tert-butyl 2-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]carbamoylamino]propanoate;

N-[trans-(7RS,9RS)-3-cyclopropyl-9-(3,4-dihydro-2H-chromen-3-ylcarbamoylamino)-5-(2-methylpropylsulfamoyl)-8,9-dihydro-7H-cyclopenta[h]isoquinolin-7-yl]pyridine-3-carboxamide;

N-[trans-(7SR,9SR)-3-cyclopropyl-5-(2-methylpropylsulfamoyl)-9-[[rac-(1R)-1-(3-methoxyphenyl)ethyl]carbamoylamino]-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(oxan-4-ylcarbamoylamino)-8,9-dihydro-7H-cyclopenta[h]isoquinolin-7-yl]pyridine-3-carboxamide;

N-[trans-(7RS,9RS)-9-[(2-chloro-6-methylphenyl) carbamoylamino]-3-cyclopropyl-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-9-(methanesulfonamido)-5-(2-methylpropylsulfamoyl)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(2-methylpropylsulfonylamino)-8,9-dihydro-7H-cyclopenta[h]isoquinolin-7-yl]pyridine-3-carboxamide;

N-[trans-(7RS,9RS)-3-cyclopropyl-5-(2-methylpropylsulfamoyl)-9-(pyridin-3-ylsulfonylamino)-8,9-dihydro-7H-cyclopenta[h]isoquinolin-7-yl]pyridine-3-carboxamide;

5-[[trans-(7RS,9RS)-3-cyclopropyl-5-(2-methylpropylsulfamoyl)-7-(pyridine-3-carbonylamino)-8,9-dihydro-7H-cyclopenta[h]isoquinolin-9-yl]amino]pyridine-3-carboxylic acid;

1-pyridin-3-yl-3-[cis-(7RS,9SR)-3-cyclopropyl-5-(2-methylpropylsulfamoyl)-7-(pyridin-3-ylcarbamoylamino)-8,9-dihydro-7H-cyclopenta[h]isoquinolin-9-yl]urea;

cis-(7RS,9SR)-3-cyclopropyl-7,9-bis[(5-methoxypyridin-3-yl)amino]-N-(2-methylpropyl)-8,9-dihydro-7H-cyclopenta[h]isoquinoline-5-sulfonamide;

cis-(7RS,9SR)-7-amino-3-cyclopropyl-9-[(5-methoxypyridin-3-yl)amino]-N-(2-methylpropyl)-8,9-dihydro-7H-cyclopenta[h]isoquinoline-5-sulfonamide;

cis-(7RS,9SR)-7,9-bis (1H-benzimidazol-2-ylamino)-3-cyclopropyl-N-(2-methylpropyl)-8,9-dihydro-7H-cyclopenta[h]isoquinoline-5-sulfonamide;

1-ethyl-3-[cis-(7RS,9SR)-3-cyclopropyl-7-(ethylcarbamothioylamino)-5-(2-methylpropylsulfamoyl)-8,9-dihydro-7H-cyclopenta[h]isoquinolin-9-yl]thiourea;

cis-(7RS,9SR)-3-cyclopropyl-N-(2-methylpropyl)-7,9-bis[(4-pyridin-3-yl-1,2,4-triazol-3-yl)amino]-8,9-dihydro-7H-cyclopenta[h]isoquinoline-5-sulfonamide;

trans-(7RS,9RS)-3-cyclopropyl-7,9-bis[(5-methoxypyridin-3-yl)amino]-N-(2-methylpropyl)-8,9-dihydro-7H-cyclopenta[h]isoquinoline-5-sulfonamide;

trans-(7RS,9RS)-7,9-bis (1H-benzimidazol-2-ylamino)-3-cyclopropyl-N-(2-methylpropyl)-8,9-dihydro-7H-cyclopenta[h]isoquinoline-5-sulfonamide;

trans-(7RS,9RS)-3-cyclopropyl-7,9-bis[(4-ethyl-1,2,4-triazol-3-yl)amino]-N-(2-methylpropyl)-8,9-dihydro-7H-cyclopenta[h]isoquinoline-5-sulfonamide;

trans-(7RS,9RS)-3-cyclopropyl-7,9-bis[3-(ethylamino)-1,2,4-triazol-4-yl]-N-(2-methylpropyl)-8,9-dihydro-7H-cyclopenta[h]isoquinoline-5-sulfonamide;

1-ethyl-3-[trans-(7RS,9RS)-3-cyclopropyl-7-(ethylcarbamoylamino)-5-[(2-fluoro-2-methylpropyl) sulfamoyl]-8,9-dihydro-7H-cyclopenta[h]isoquinolin-9-yl]urea;

trans-(7RS,9RS)-3-cyclopropyl-7,9-bis[3-(5-methyl-1,3,4-oxadiazol-2-yl) anilino]-N-(2-methylpropyl)-8,9-dihydro-7H-cyclopenta[h]isoquinoline-5-sulfonamide;

tert-butyl N-[trans-(7RS,9RS)-3-cyclopropyl-5-(2-methylpropylsulfamoyl)-9-(2,2,2-trichloroethoxysulfonylamino)-8,9-dihydro-7H-cyclopenta[h]isoquinolin-7-yl]carbamate;

2-cyano-1-ethyl-3-[trans-(7RS,9RS)-3-cyclopropyl-5-(2-methylpropylsulfamoyl)-7-[[rac-(E)-N'-cyano-N-ethyl-carbamimidoyl]amino]-8,9-dihydro-7H-cyclopenta[h]isoquinolin-9-yl]guanidine;

1-ethyl-3-[cis-(7RS,9SR)-3-cyclopropyl-7-(ethylcarbamoylamino)-5-[(2-fluoro-2-methylpropyl) sulfamoyl]-8,9-dihydro-7H-cyclopenta[h]isoquinolin-9-yl]urea;

1-pyridin-3-yl-3-[trans-(7RS,9RS)-3-cyclopropyl-5-(2-methylpropylsulfamoyl)-7-(pyridin-3-ylcarbamoylamino)-8,9-dihydro-7H-cyclopenta[h]isoquinolin-9-yl]urea;

1-propan-2-yl-3-[trans-(7RS,9RS)-3-cyclopropyl-5-(2-methylpropylsulfamoyl)-7-(propan-2-ylcarbamoylamino)-8,9-dihydro-7H-cyclopenta[h]isoquinolin-9-yl]urea;

1-pyridin-3-yl-3-[trans-(7RS,9RS)-3-cyclopropyl-5-(2-methylpropylsulfamoyl)-7-(pyridin-3-ylcarbamothioylamino)-8,9-dihydro-7H-cyclopenta[h]isoquinolin-9-yl]thiourea;

5-methyl-N-[trans-(7RS,9RS)-3-cyclopropyl-5-(2-methylpropylsulfamoyl)-9-[(5-methylpyridine-3-carbonyl)amino]-8,9-dihydro-7H-cyclopenta[h]isoquinolin-7-yl]pyridine-3-carboxamide;

6-morpholin-4-yl-N-[trans-(7RS,9RS)-3-cyclopropyl-5-(2-methylpropylsulfamoyl)-9-[(6-morpholin-4-ylpyridine-3-carbonyl)amino]-8,9-dihydro-7H-cyclopenta[h]isoquinolin-7-yl]pyridine-3-carboxamide;

N-[trans-(7RS,9RS)-9-benzamido-3-cyclopropyl-5-(2-methylpropylsulfamoyl)-8,9-dihydro-7H-cyclopenta[h]isoquinolin-7-yl]benzamide;

4-(dimethylamino)-N-[trans-(7RS,9RS)-3-cyclopropyl-9-[[4-(dimethylamino)benzoyl]amino]-5-(2-methylpropylsulfamoyl)-8,9-dihydro-7H-cyclopenta[h]isoquinolin-7-yl]benzamide;

3,3-dimethyl-N-[trans-(7RS,9RS)-3-cyclopropyl-9-(3,3-dimethylbutanoylamino)-5-(2-methylpropylsulfamoyl)-8,9-dihydro-7H-cyclopenta[h]isoquinolin-7-yl]butanamide;

1-ethyl-3-[trans-(7RS,9RS)-3-cyclopropyl-7-(ethylcarbamoylamino)-5-[(2-fluoro-2-methylpropyl) sulfamoyl]-8,9-dihydro-7H-cyclopenta[h]isoquinolin-9-yl]urea;

N-[3-cyclopropyl-5-[(2-fluoro-2-methylpropyl) sulfamoyl]-9-(pyridine-3-carbonylamino)-8,9-dihydro-7H-cyclopenta[h]isoquinolin-7-yl]pyridine-3-carboxamide;

N-[9-amino-3-cyclopropyl-5-[(2-fluoro-2-methylpropyl) sulfamoyl]-8,9-dihydro-7H-cyclopenta[h]isoquinolin-7-yl]pyridine-3-carboxamide;

3-cyclopropyl-N-(2-fluoro-2-methylpropyl)-7-(4-oxo-1,5-dihydroimidazo[4,5-c]pyridin-2-yl)-7,8-dihydro-6H-cyclopenta[g]isoquinoline-5-sulfonamide;

7-cyclopropyl-N-(2-fluoro-2-methylpropyl)-2-(2-pyridin-3-ylacetyl)-1,3-dihydropyrrolo[3,4-g]isoquinoline-9-sulfonamide;

(7R)-3-cyclopropyl-N-(2-fluoro-2-methylpropyl)-7-[(6-fluoropyridin-3-yl)amino]-7,8-dihydro-6H-cyclopenta[g]isoquinoline-5-sulfonamide;

3-cyclopropyl-N-(3,3-difluorocyclobutyl)-7-[[6-(3-hydroxyoxetan-3-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[5-[(2-oxo-1H-pyridin-4-yl)oxy]pyridin-3-yl]amino]-7,8-dihydro-6H-cyclopenta[g]isoquinoline-5-sulfonamide;

3-cyclopropyl-N-[(3-hydroxyoxetan-3-yl)methyl]-7-[[6-(2-methyltetrazol-5-yl)pyridin-3-yl]amino]-7,8-dihydro-6H-cyclopenta[g]isoquinoline-5-sulfonamide;

5-[[(7R)-3-cyclopropyl-5-[(2-fluoro-2-methylpropyl) sulfamoyl]-7,8-dihydro-6H-cyclopenta[g]isoquinolin-7-yl]amino]-N-propan-2-ylpyridine-2-carboxamide;

3-cyclopropyl-N-(2-fluoro-2-methylpropyl)-7-[[4-(2-methylpyridin-3-yl)-1,2,4-triazol-3-yl]amino]-7,8-dihydro-6H-cyclopenta[g]isoquinoline-5-sulfonamide;

3-cyclopropyl-N-(2-fluoro-2-methylpropyl)-7-(1,2-oxazol-5-yl)-7,8-dihydro-6H-cyclopenta[g]isoquinoline-5-sulfonamide;

3-cyclopropyl-N-(2-hydroxy-2-methylpropyl)-7-[(6-methylpyridazin-3-yl)amino]-7,8-dihydro-6H-cyclopenta[g]isoquinoline-5-sulfonamide;

3-cyclopropyl-5-[(2,2-dimethylcyclopropyl) sulfamoyl]-N-pyridin-3-yl-7,8-dihydro-6H-cyclopenta[g]isoquinoline-7-carboxamide;

6-[[(7R)-3-cyclopropyl-5-[(2-fluoro-2-methylpropyl) sulfamoyl]-7,8-dihydro-6H-cyclopenta[g]isoquinolin-7-yl]amino]pyridazine-3-carboxamide;

3-cyclopropyl-N-(2-fluoro-2-methyl-propyl)-7-(1H-pyrazolo[3,4-c]pyridin-4-ylamino)-7,8-dihydro-6H-cyclopenta[g]isoquinoline-5-sulfonamide, formate salt;

3-cyclopropyl-N-(2-fluoro-2-methylpropyl)-7-[(1-methylpyrazolo[3,4-c]pyridin-4-yl)amino]-7,8-dihydro-6H-cyclopenta[g]isoquinoline-5-sulfonamide;

tert-butyl 5-[[(7R)-3-cyclopropyl-5-[(3,3-difluorocyclobutyl) sulfamoyl]-7,8-dihydro-6H-cyclopenta[g]isoquinolin-7-yl]amino]pyridine-2-carboxylate;

3-cyclopropyl-N-(2-fluoro-2-methylpropyl)-7-(pyridin-3-ylamino)-7,8-dihydro-6H-cyclopenta[g]isoquinoline-5-sulfonamide;

N-[3-cyclopropyl-5-[(2-fluoro-2-methylpropyl) sulfamoyl]-7,8-dihydro-6H-cyclopenta[g]isoquinolin-7-yl]-2-phenylacetamide;

5-[[3-cyclopropyl-5-(isobutylsulfamoyl)-7,8-dihydro-6H-cyclopenta[g]isoquinolin-7-yl]amino]pyridine-2-carboxylic acid; hydrochloride;

5-[[3-cyclopropyl-5-[(3,3-difluorocyclobutyl) sulfamoyl]-7,8-dihydro-6H-cyclopenta[g]isoquinolin-7-yl]amino]pyridine-2-carboxylic acid;

5-amino-1-[(7S)-3-cyclopropyl-5-[(2-fluoro-2-methylpropyl) sulfamoyl]-7,8-dihydro-6H-cyclopenta[g]isoquinolin-7-yl]imidazole-4-carboxamide;

7-cyclopropyl-N-(2-fluoro-2-methyl-propyl)-2-(3-pyridylmethyl)-1,3-dihydropyrrolo[3,4-g]isoquinoline-9-sulfonamide; formic acid;

(7R)-3-cyclopropyl-N-(2-fluoro-2-methylpropyl)-7-[[1-(5-methyl-1,3,4-oxadiazol-2-yl)-2-oxopyridin-4-yl]amino]-7,8-dihydro-6H-cyclopenta[g]isoquinoline-5-sulfonamide;

(7R)-3-cyclopropyl-N-(2-fluoro-2-methylpropyl)-7-[[6-(methylsulfamoyl)pyridin-3-yl]amino]-7,8-dihydro-6H-cyclopenta[g]isoquinoline-5-sulfonamide;

6-[[(7R)-3-cyclopropyl-5-[(3,3-difluorocyclobutyl) sulfamoyl]-7,8-dihydro-6H-cyclopenta[g]isoquinolin-7-yl] amino]pyridazine-3-carboxamide;

N-[5-[[(7R)-3-cyclopropyl-5-[(2-fluoro-2-methylpropyl) sulfamoyl]-7,8-dihydro-6H-cyclopenta[g]isoquinolin-7-yl]amino]pyridin-2-yl]sulfonylacetamide;

3-cyclopropyl-N-(2-fluoro-2-methyl-propyl)-7-[(1-methyl-2-oxo-4-pyridyl)amino]-7,8-dihydro-6H-cyclopenta[g] isoquinoline-5-sulfonamide; formate salt;

3-cyclopropyl-N-(2-fluoro-2-methylpropyl)-7-[(5-methyl-1,3,4-oxadiazol-2-yl)amino]-7,8-dihydro-6H-cyclopenta [g]isoquinoline-5-sulfonamide;

3-cyclopropyl-7-[(4,4-dimethyl-3-oxocyclobuten-1-yl) amino]-N-(2-fluoro-2-methylpropyl)-7,8-dihydro-6H-cyclopenta[g]isoquinoline-5-sulfonamide;

7-cyclopropyl-9-N-(2-fluoro-2-methylpropyl)-2-N-(2-methylpropyl)-1,3-dihydropyrrolo[3,4-g]isoquinoline-2,9-disulfonamide;

7-cyclopropyl-N-ethyl-9-(2-methylpropylsulfamoyl)-1,3-dihydropyrrolo[3,4-g]isoquinoline-2-carboxamide;

(7R)-3-cyclopropyl-N-(2-fluoro-2-methylpropyl)-7-[[6-(5-methyl-1,3,4-oxadiazol-2-yl)pyridazin-3-yl]amino]-7,8-dihydro-6H-cyclopenta[g]isoquinoline-5-sulfonamide;

7-cyclopropyl-N-(2-fluoro-2-methylpropyl)-2-(1H-pyrazol-5-ylmethyl)-1,3-dihydropyrrolo[3,4-g]isoquinoline-9-sulfonamide;

3-cyclopropyl-N-isobutyl-7-(pyridazin-4-ylamino)-7,8-dihydro-6H-cyclopenta[g]isoquinoline-5-sulfonamide; formic acid;

N-[3-cyclopropyl-5-[(2-fluoro-2-methylpropyl) sulfamoyl]-7,8-dihydro-6H-cyclopenta[g]isoquinolin-7-yl]-2-methylpyrazole-3-carboxamide;

(7R)-3-cyclopropyl-N-(2-fluoro-2-methylpropyl)-7-[[1-(2-hydroxyethyl) pyrazolo[3,4-c]pyridin-4-yl]amino]-7,8-dihydro-6H-cyclopenta[g]isoquinoline-5-sulfonamide;

(7R)-3-cyclopropyl-N-(2-fluoro-2-methylpropyl)-7-[[2-(2-hydroxyethyl) pyrazolo[3,4-c]pyridin-4-yl]amino]-7,8-dihydro-6H-cyclopenta[g]isoquinoline-5-sulfonamide;

13-cyclopropyl-N-(2-fluoro-2-methylpropyl)-12-azatetracyclo[8.4.0.03,8.04,6]tetradeca-1 (10),2,8,11,13-pentaene-2-sulfonamide;

(7R)-3-cyclopropyl-N-(2-fluoro-2-methylpropyl)-7-[[6-(1-methylpyrazol-3-yl)pyridin-3-yl]amino]-7,8-dihydro-6H-cyclopenta[g]isoquinoline-5-sulfonamide;

3-cyclopropyl-N-(2-fluoro-2-methylpropyl)-7-(imidazo[1,2-a]pyrazin-5-ylamino)-7,8-dihydro-6H-cyclopenta[g] isoquinoline-5-sulfonamide;

3-cyclopropyl-N-(2-fluoro-2-methylpropyl)-7-pyridin-3-yl-7,8-dihydro-6H-cyclopenta[g]isoquinoline-5-sulfonamide;

3-cyclopropyl-N-(3,3-difluorocyclobutyl)-7-(3-oxo-2-pyridin-3-yl-1H-pyrazol-5-yl)-7,8-dihydro-6H-cyclopenta[g] isoquinoline-5-sulfonamide;

3-cyclopropyl-N-(2-fluoro-2-methylpropyl)-7-[(5-hydroxy-2-methylpyrazol-3-yl)amino]-7,8-dihydro-6H-cyclopenta [g]isoquinoline-5-sulfonamide;

3-cyclopropyl-N-(2,2-dimethylpropyl)-5-[(2-fluoro-2-methylpropyl) sulfamoyl]-7,8-dihydro-6H-cyclopenta[g] cinnoline-7-carboxamide;

(7R)-7-(4-acetylanilino)-3-cyclopropyl-N-(2-fluoro-2-methylpropyl)-7,8-dihydro-6H-cyclopenta[g]isoquinoline-5-sulfonamide;

(7R)-3-cyclopropyl-N-(2-fluoro-2-methylpropyl)-7-[[6-(4-methyltriazol-1-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(4-methyltriazol-2-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(1,2,4-triazol-1-yl)pyridin-3-yl]amino]-7,8-dihydro-6H-cyclopenta[g]isoquinoline-5-sulfonamide;

(7R)-3-cyclopropyl-7-[[6-(difluoromethyl)pyridin-3-yl] amino]-N-(2-fluoro-2-methylpropyl)-7,8-dihydro-6H-cyclopenta[g]isoquinoline-5-sulfonamide;

(7R)-7-[[6-chloro-4-(cyclopropylmethoxy)pyridin-3-yl] amino]-3-cyclopropyl-N-(2-fluoro-2-methylpropyl)-7,8-dihydro-6H-cyclopenta[g]isoquinoline-5-sulfonamide;

(7R)-3-cyclopropyl-N-(2-fluoro-2-methylpropyl)-7-[[4-(oxan-4-yloxy)pyrimidin-5-yl]amino]-7,8-dihydro-6H-cyclopenta[g]isoquinoline-5-sulfonamide;

N-[5-[[3-cyclopropyl-5-[(2-fluoro-2-methylpropyl) sulfamoyl]-7,8-dihydro-6H-cyclopenta[g]isoquinolin-7-yl] amino]pyridin-3-yl]acetamide;

7-[(5-cyanopyridin-3-yl)amino]-3-cyclopropyl-N-(2-fluoro-2-methylpropyl)-7,8-dihydro-6H-cyclopenta[g]isoquinoline-5-sulfonamide;

3-cyclopropyl-N-(2-fluoro-2-methylpropyl)-7-[(5-methylsulfonylpyridin-3-yl)amino]-7,8-dihydro-6H-cyclopenta [g]isoquinoline-5-sulfonamide;

(7R)-3-cyclopropyl-N-(2-fluoro-2-methylpropyl)-7-[[2-(1H-tetrazol-5-yl)pyrimidin-5-yl]amino]-7,8-dihydro-6H-cyclopenta[g]isoquinoline-5-sulfonamide;

(7R)-3-cyclopropyl-N-(2-fluoro-2-methylpropyl)-7-[4-(2-methyltetrazol-5-yl) anilino]-7,8-dihydro-6H-cyclopenta [g]isoquinoline-5-sulfonamide;

(7R)-7-[[6-chloro-4-(1H-tetrazol-5-yl)pyridin-3-yl]amino]-3-cyclopropyl-N-(2-fluoro-2-methylpropyl)-7,8-dihydro-6H-cyclopenta[g]isoquinoline-5-sulfonamide;

(7R)-3-cyclopropyl-N-(2-fluoro-2-methylpropyl)-7-[(5-oxo-2H-pyran-3-yl)amino]-7,8-dihydro-6H-cyclopenta [g]isoquinoline-5-sulfonamide;

(7R)-3-cyclopropyl-N-(2-fluoro-2-methylpropyl)-7-[[4-(1-methylpyrazol-3-yl)oxypyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[2-(5-methyl-1,3,4-oxadiazol-2-yl)pyrimidin-5-yl]amino]-7,8-dihydro-6H-cyclopenta[g]isoquinoline-5-sulfonamide;

N-[(7R)-3-cyclopropyl-5-[(2-fluoro-2-methylpropyl) sulfamoyl]-7,8-dihydro-6H-cyclopenta[g]isoquinolin-7-yl]-1H-indole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-5-fluoro-1H-indole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-1-methylindole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-6-methoxy-1H-indole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-4-methyl-1,3-thiazole-5-carboxamide;

N-[(7R)-3-cyclopropyl-5-[(2-fluoro-2-methylpropyl) sulfamoyl]-7,8-dihydro-6H-cyclopenta[g]isoquinolin-7-yl] isoquinoline-1-carboxamide;

tert-butyl 5-[[(7R)-3-cyclopropyl-5-[(2-fluoro-2-methylpropyl) sulfamoyl]-7,8-dihydro-6H-cyclopenta[g]isoquinolin-7-yl]carbamoyl]-1,3-dihydroisoindole-2-carboxylate;

N-[(7R)-3-cyclopropyl-5-[(2-fluoro-2-methylpropyl) sulfamoyl]-7,8-dihydro-6H-cyclopenta[g]isoquinolin-7-yl]-2-(1-methylpyrazol-4-yl)-2-oxoacetamide;

lithium; 4-[[(7R)-3-cyclopropyl-5-[(2-fluoro-2-methyl-propyl) sulfamoyl]-7,8-dihydro-6H-cyclopenta[g]isoquinolin-7-yl]amino]isoquinoline-1-carboxylate;

3-cyclopropyl-N-(2-fluoro-2-methylpropyl)-7-[(6-methylsulfinylpyridin-3-yl)amino]-7,8-dihydro-6H-cyclopenta [g]isoquinoline-5-sulfonamide;

3-cyclopropyl-N-(2-fluoro-2-methylpropyl)-7-[(1-methyl-6-oxopyridazin-4-yl)amino]-7,8-dihydro-6H-cyclopenta [g]isoquinoline-5-sulfonamide;

6-bromo-N-[(7R)-3-cyclopropyl-5-[(2-fluoro-2-methylpropyl) sulfamoyl]-7,8-dihydro-6H-cyclopenta[g]isoquinolin-7-yl]-1H-indazole-3-carboxamide;

3-cyclopropyl-N-(2-fluoro-2-methylpropyl)-7-[(5-oxo-2H-furan-3-yl)amino]-7,8-dihydro-6H-cyclopenta[g]isoquinoline-5-sulfonamide.

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

The following examples illustrate how the compounds covered by formula I may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Abbreviations

DCM Dichloromethane
THF Tetrahydrofuran
EtOAc Ethyl acetate
MeCN Acetonitrile
MeOH Methanol
br s Broad singlet
obs observed
hept heptate
M Mass or Molar
Brine Saturated sodium chloride solution
HPLC High performance liquid chromatography
LCMS Liquid Chromatography Mass Spectrometry
DIPEA N,N-di-iso-propylethylamine
RT Retention time
DMF N,N'-dimethylformamide
NaOH Sodium hydroxide
TFA Trifluoroacetic acid
DMSO Dimethyl sulfoxide
EtOH Ethanol
sat. saturated
aq. aqueous
tBuXPhos Pd G3 [(2-Di-tert-butylphosphino-2',4',6'-triisopropyl-1,1'-biphenyl)-2-(2'-amino-1,1' biphenyl)] palladium (II) methanesulfonate
Xantphos Pd G3 [(4,5-Bis(diphenylphosphino)-9,9-dimethylxanthene)-2-(2'-amino-1,1'-biphenyl)]palladium (II) methanesulfonate
HATU 1-[Bis(dimethylamino)methylene]-1H-1,2,3-triazolo[4,5-b]pyridinium 3-oxid hexafluorophosphate
HBTU N,N,N',N'-Tetramethyl-O-(1H-benzotriazol-1-yl) uronium hexafluorophosphate
h or hrs hours
min minutes
IPA Isopropyl alcohol
conc. concentrated
equiv. equivalents
SCX Biotage® ISOLUTER SCX-2 Propylsulfonic acid functionalized silica
SFC Supercritical fluid chromatography
DPPA Diphenyl phosphoryl azide
TEA Triethylamine
$Pd_2(dba)_3$ Tris(dibenzylideneacetone) dipalladium (0)
XantPhos 4,5-Bis(diphenylphosphino)-9,9-dimethylxanthene
AcOH Acetic acid
AlBN 2,2'-Azobis (2-methylpropionitrile)
TBME tert-Butylmethyl ether
LiHMDS Lithium bis(trimethylsilyl)amide
SEMCl 2-(chloromethoxy)ethyl-trimethyl-silane
Bedford Catalyst Chloro($\eta^2$—P,C-tris(2,4-di-tert butylphenyl)phosphite) (tricyclohexylphosphine) palladium (II)
NBS N-bromosuccinimide
BEMP 2-tert-Butylimino-2-diethylamino-1,3-dimethylperhydro-1,3,2-diazaphosphorine
TBAB Tetrabutylammonium bromide
TBAF Tetrabutylammonium fluoride
DIPEA N,N-Diisopropylethylamine
tBuOH tert-butanol
T3P propylphosphonic anhydride
XantPhos 4,5-Bis(diphenylphosphino)-9,9-dimethylxanthene
DBU 1,8-Diazabicyclo[5.4.0]undec-7-ene
tBuXPhos 2-Di-tert-butylphosphino-2',4',6'-triisopropylbiphenyl
Pd (OAc) 2 Palladium (II) acetate
TMSCl chlorotrimethylsilane
2-Me-THF 2-methyltetrahydrofuran
DMF-DMA N,N-Dimethylformamide dimethyl acetal
DIBAL-H diisobutylaluminum hydride
EDC-HCl N-(3-Dimethylaminopropyl)-N'-ethylcarbodiimide hydrochloride LCMS Methods Method 1:

X-Bridge C18 Waters 2.1×20 mm, 2.5 μm column
Column Temperature 40° C.
Mobile Phase A: 10 mM Ammonium formate in water+0.1% formic acid
Mobile Phase B: Acetonitrile+5% water+0.1% formic acid
Gradient program: Flow rate 1 mL/minute

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 2:

Mobile Phase A: 0.1% Formic Acid in water

Mobile Phase B: 0.1% Formic Acid in Acetonitrile

Phenomenex, Kinetex-XB C18, 2.1 mm×100 mm, 1.7 μm column

Flow rate: 0.6 mL/min

Column temperature: 40° C.

Injection volume: 1μ L

Gradient:

| Time (minutes): | % A | % B |
|---|---|---|
| 0.00 | 95 | 5 |
| 5.30 | 0 | 100 |
| 5.80 | 0 | 100 |
| 5.82 | 95 | 5 |
| 7.00 | 95 | 5 |

UV 215 nM, PDA spectrum 200-400 nm, step: 1 nm

MSD Scan Positive 150-850

Method 3:

X-Bridge C18 Waters 2.1×20 mm, 2.5 μM column

Column Temperature 40° C.

Mobile Phase A: 10 mM Ammonium formate in water+0.1% formic acid

Mobile Phase B: Acetonitrile+5% water+0.1% Formic acid

Gradient program: Flow rate 1 mL/min

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 4:

Stationary phase: X-Bridge C18 Waters 2.1×20 mm, 2.5 μM column

[From 2019 onwards-Phenomenex Gemini NX—C18 2×20 mm, 3 μM]

Mobile Phase A: 10 mM Ammonium formate in water+0.1% ammonia solution

Mobile Phase B: Acetonitrile+5% water+0.1% Ammonia Solution

Flow rate: 1 ml/min

Gradient program:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 5:

Column Kinetex Core-Shell C18 Part No. 00B-4601-AN 2.1×50 mm, 5 μm

Column Temp 40° C.

Mobile Phase A: Water+0.1% Formic acid

Mobile Phase B: Acetonitrile+0.1% Formic acid

Flow rate 1.2 ml/min

Injection Vol 3 μl

Detection Signal UV 215

PDA Spectrum Range: 210-420 nm step: 1 nm

Gradient

| Time (mins) | % organic |
|---|---|
| 0.00 | 5 |
| 1.20 | 100 |
| 1.30 | 100 |
| 1.31 | 5 |

Method 6:

Stationary phase: X-Bridge C18 Waters 2.1×20 mm, 2.5 UM column

Mobile Phase A: 10 mM Ammonium formate in water+0.1% Ammonia solution

Mobile Phase B: Acetonitrile+5% water+0.1% Ammonia Solution

Flow rate: 1 ml/min

Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 7:

Stationary phase: X-Bridge C18 Waters 2.1×20 mm, 2.5 UM column

Mobile Phase A: 10 mM Ammonium formate in water+0.1% Ammonia solution

Mobile Phase B: Acetonitrile+5% water+0.1% Ammonia Solution

Flow rate: 1 ml/min

Gradient program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 8:

Column Kinetex Core-Shell C8 Part No. 00B-4608-AN 2.1×50 mm, 5 μm

Column Temp 40° C.

Mobile Phase A: Water+0.1% Formic acid

Mobile Phase B: Acetonitrile+0.1% Formic acid

Flow rate 1.2 ml/min

Injection Vol 3 μl

Detection Signal UV 215

PDA Spectrum Range: 210-420 nm step: 1 nm

Gradient

| Time (mins) | % organic |
|---|---|
| 0.00 | 5 |
| 1.83 | 100 |
| 2.25 | 100 |
| 2.26 | 5 |

Method 9:

Waters UPLC® BEH™ C18, Part No. 186002352, 2.1×100 mm, 1.7 μm

Column Temperature 40° C.

Mobile Phase A: 2 mM ammonia bicarbonate, buffered to pH 10

Mobile Phase B: Acetonitrile

Gradient program Flow rate 0.6 mL/Min

| Time | A % | B % |
|---|---|---|
| 0.00 | 95.00 | 5.00 |
| 5.30 | 0 | 100 |
| 5.80 | 0 | 100 |
| 5.82 | 95.00 | 5.00 |
| 7.00 | 95.00 | 5.00 |

Method 10:

Stationary phase: X-Bridge C18 Waters 2.1×20 mm, 2.5 UM column

Mobile Phase A: 10 mM Ammonium formate in water+0.1% Ammonia solution

Mobile Phase B: Acetonitrile+5% water+0.1% Ammonia solution

Flow rate: Pump 1:1 mL/min, Pump 2:0.5 mL/min

Gradient program: Pump 1:

| Time | A % | B % |
|---|---|---|
| 0.00 | 95.10 | 4.90 |
| 4.00 | 5.00 | 95.00 |
| 5.00 | 5.00 | 95.00 |
| 5.10 | 95.10 | 4.90 |

Pump 2:

| Time | A % | B % |
|---|---|---|
| 0.10 | 5.00 | 95.00 |
| 1.00 | 5.00 | 95.00 |
| 1.10 | 95.00 | 5.00 |

Method 11:

Stationary phase: X-Bridge C18 Waters 2.1×20 mm, 2.5 UM column

Mobile Phase A: 10 mM Ammonium formate in water+0.1% Formic acid

Mobile Phase B: Acetonitrile+5% water+0.1% Formic acid

Flow rate: 1 ml/min

Gradient program:

| Time | A % | B % |
|---|---|---|
| 0.00 | 95.00 | 5.00 |
| 1.50 | 5.00 | 95.00 |

-continued

| Time | A % | B % |
|---|---|---|
| 2.25 | 5.00 | 95.00 |
| 2.50 | 95.00 | 5.00 |

Method 12:

Stationary phase: X-Bridge C18 Waters 2.1×20 mm, 2.5 μM column

Mobile Phase A: 10 mM Ammonium formate in water+0.1% ammonia solution

Mobile Phase B: Acetonitrile+5% water+0.1% Ammonia Solution

Flow rate: 1 mL/min

Gradient program:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 13:

Column: Waters XBridge MS C18 column (3.5 μm, 100×4.6 mm)

Temperature: 45° C.

Injection volume: 5.0 μL

Flow rate: 1.9 to 2.4 mL/minute

Detection: Mass spectrometry-positive detection

PDA: 210 to 400 nm

Solvent A: water

Solvent B: Acetonitrile

Solvent D: Ammonium Formate in water 630 mg/L+500 μL/L $NH_4OH$ 30% (pH~8.5)

| Time (min) | A (%) | B (%) | D (%) | Flow (mL/min) |
|---|---|---|---|---|
| 0 | 90 | 0 | 10 | 1.9 |
| 1 | 90 | 0 | 10 | 1.9 |
| 5.5 | 2 | 88 | 10 | 2.4 |
| 8 | 2 | 88 | 10 | 2.4 |
| 8.05 | 90 | 0 | 10 | 1.9 |
| 9.90 | 90 | 0 | 10 | 1.9 |

HPLC Methods

HPLC Method 1: Column: XBridge™ Prep. C18 10 μm OBD™, 30×100 mm, Mobile Phase: 5-95% Acetonitrile (0.2% ammonium hydroxide) in Water (0.2% ammonium hydroxide) over 14 minutes, Flow Rate: 40 mL/min, UV: 215 and 254 nm HPLC Method 2: Column: Sunfire™ Prep. C18 10 μm OBD™, 30×100 mm; Mobile Phase: 5-95% Acetonitrile (0.1% formic acid) in Water (0.1% formic acid) over 14 minutes, Flow Rate: 40 mL/min UV: 215 and 254 nm HPLC Method 3: Column: XBridge™ Prep. C18 10 μm OBD™, 30×100 mm, Mobile Phase: 30-95% Acetonitrile (0.2% ammonium hydroxide) in Water (0.2% ammonium hydroxide) over 10 minutes, Flow Rate: 40 ml/min, UV: 215 and 254 nm General Procedures General Procedure 1

To a solution of amine (1 equiv.), sodium tert-butoxide (3 equiv.), aryl halide (2.5 equiv.) and tBuXPhos Pd G3 (0.15 equiv.) was added anhydrous 1,4-dioxane (20 mL/g). The mixture was degassed with 3 cycles of vacuum/$N_2$ then sealed and heated to 100° C. with stirring until the reaction was deemed complete by LCMS. The reaction was diluted with EtOAc (20 mL/g) and washed with water (10 mL/g). The aqueous layer was extracted with EtOAc (20 mL/g) and the combined organic extracts dried over $Na_2SO_4$ and concentrated in vacuo.

General Procedure 2

A mixture of amine (1 eq.), aryl halide (1.5 eq.), tBuXPhos Pd G3 (0.1 eq.) and sodium tert-butoxide (3 eq.) in anhydrous dioxane/tert-butanol (2:1, 30-50 vol) was sonicated under a flow of nitrogen for 5 minutes, then stirred at the indicated temperature until the reaction was deemed complete by LCMS. The reaction mixture was diluted with ethyl acetate or DCM (20 mL) and washed with water (10 mL)/sat. aq. $NH_4Cl$ (10 mL). The layers were separated and the aqueous was further extracted with ethyl acetate or DCM (20 mL). The combined organics were washed with sat. aq. $NH_4Cl$ (10 mL), brine (10 mL), then dried using either magnesium or sodium sulfate, filtered and concentrated under vacuum.

General Procedure 3

Thiourea (1 eq.) was dissolved in dry DMF (10-20 vol.). Formic hydrazide (3 eq.) was added followed by mercury dichloride (3 eq.) and the reaction was stirred for 5 minutes before triethylamine (3 eq.) was added. The reaction was heated to 90° C. with stirring for 1-4 hours. The reaction was allowed to cool, diluted with ethyl acetate (50 mL) and Kieselguhr added. The mixture was stirred for 5 minutes then filtered thorough kieselguhr and washed through with ethyl acetate (50 mL). The filtrate was washed with saturated aq. $NH_4Cl$, water, and brine, then dried over sodium sulfate and concentrated under vacuum. The crude material was purified by column chromatography.

General Procedure 4

The relevant carboxylic acid (1.2 equiv.) was dispensed to a vial containing a solution of DIPEA (2.5 equiv.) and HBTU (1.5 equiv.) in DMF (0.5 mL). Reaction was stirred for 10 min prior to addition of a solution of intermediate 15 (20 mg, 0.053 mmol) in DMF (0.5 mL). The reaction was stirred at ambient temperature overnight, diluted with DCM (2 mL) and washed with water (1 mL). The organic phase was partitioned and purified using column chromatography.

Intermediates

Intermediate 1

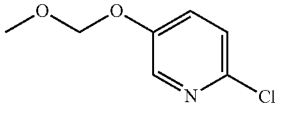

2-chloro-5-(methoxymethoxy)pyridine

A solution of 6-chloropyridin-3-ol (34 g, 262 mmol) and chloromethyl methyl ether (42.3 g, 525 mmol) in DCM (300 mL) was stirred in an ice-bath and N,N diisopropylethylamine (50 mL, 289 mmol) in DCM (50 mL) was added dropwise and stirred for 15 min. The reaction mixture was treated with water, stirred for 10 min, then $NaHCO_3$ (sat. aq. solution) was added and the mixture stirred for 30 min. The organic layer was separated, and the aqueous layer was extracted with DCM. The combined organic extracts were washed with $NaHCO_3$ (sat. aq. solution) and dried ($MgSO_4$). The crude material was purified by column chromatography eluting with a gradient of EtOAc in Hexane to give the title compound (40.5 g, 89% yield) as an oil. $^1H$ NMR (400 MHz, Chloroform-d) δ 8.19 (dd, J=3.1, 0.6 Hz, 1H), 7.37 (dd, J=8.7, 3.1 Hz, 1H), 7.31-7.20 (m, 1H), 5.19 (s, 2H), 3.50 (s, 3H).

Intermediate 2

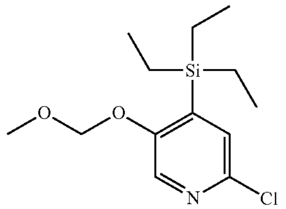 [SMILES: CC[Si](CC)(CC)c1cc(Cl)ncc1OCOC]

[2-chloro-5-(methoxymethoxy)-4-pyridyl]-triethyl-silane

A solution of Intermediate 1 (17.2 g, 96.1 mmol) in THF (300 mL) was cooled to −40° C. and treated with a solution of n-butyllithium in hexane (2.5 M, 60 mL, added over 30 mins). After stirring for a further 5 mins, triethylchlorosilane (25 mL, 149 mmol) was added and the reaction mixture was allowed to warm to room temperature. The mixture was quenched by the addition of water (200 mL) and was extracted with EtOAc (2×200 mL). The combined organic extracts were dried over $MgSO_4$ and concentrated under reduced pressure to give 40 g of the desired product as an impure oil (containing excess silane material.) $^1H$ NMR (400 MHz, Chloroform-d) δ 8.15 (s, 1H), 7.21 (d, J=0.5 Hz, 1H), 5.19 (s, 2H), 3.47 (s, 3H), 0.97-0.91 (m, 9H), 0.87-0.79 (m, 6H).

Intermediate 3

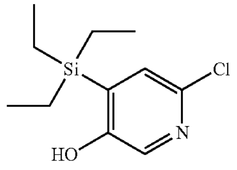

6-chloro-4-triethylsilyl-pyridin-3-ol

To a solution of intermediate 2 (31 g, 97 mmol) in dioxane (100 mL), HCl (4 M in dioxane, 100 mL) was added. The resulting mixture was stirred at room temperature for 16 hours. After this time, a white solid had precipitated. The mixture was diluted with diethyl ether (100 mL) and the resulting solid was removed by filtration (washing with ether) and dried in vacuo to give the title compound as a white solid (13.6 g, 50% yield) which was used in the next step without characterisation.

Intermediate 4

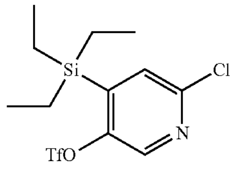 [SMILES: CC[Si](CC)(CC)c1cc(Cl)ncc1OS(=O)(=O)C(F)(F)F]

(6-chloro-4-triethylsilyl-3-pyridyl)trifluoromethanesulfonate

A solution of intermediate 3 (13.6 g, 48.5 mmol) and DIPEA (21 mL, 120.5 mmol) in DCM (250 mL) was cooled to −78° C. and treated with trifluoromethanesulfonic anhydride (1 M in DCM, 100 mL, 100 mmol, added dropwise). After the addition was completed, the mixture was allowed to warm to room temperature, and quenched with $NaHCO_3$ (sat. aq. 100 mL). The layers were separated, and the aqueous phase was extracted with DCM (100 mL). The combined organic extracts were dried over $MgSO_4$, concentrated under reduced pressure and purified by column chromatography eluting with a gradient of EtOAc in Hexane to give the title compound (17.7 g, 97% yield) as a liquid. $^1H$ NMR (250 MHz, Chloroform-d) δ 8.37 (s, 1H), 7.39 (s, 1H), 1.03-0.86 (m, 15H).

Intermediate 5

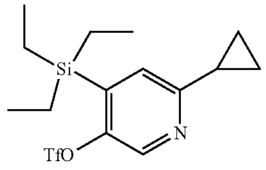 [SMILES: CC[Si](CC)(CC)c1cc(C2CC2)ncc1OS(=O)(=O)C(F)(F)F]

(6-cyclopropyl-4-triethylsilyl-3-pyridyl)trifluoromethanesulfonate

A mixture of intermediate 4 (28.4 g, 75.6 mmol), cyclopropylboronic acid (16 g, 187 mmol), Pd (OAc) 2 (850 mg, 3.8 mmol), $P(tBu)_3{\cdot}HBF_4$ (3.3 g, 11.4 mmol) and $K_3PO_4$ (40 g, 188.44 mmol) in a biphasic solution of toluene (300 mL) and water (30 mL) was stirred and heated at reflux for 30 minutes. The mixture was cooled to room temperature, the layers were separated and the aqueous was extracted with EtOAc (3×50 mL). The combined organic extracts were dried over $MgSO_4$, filtered through Celite (washing with EtOAc) and concentrated under reduced pressure. Purification by column chromatography eluting with a gradient of EtOAc in Hexane gave the title compound (26.9 g, 93% yield) as an oil. $^1H$ NMR (500 MHz, Chloroform-d) δ 8.39 (s, 1H), 7.23 (s, 1H), 2.04 (tt, J=7.8, 5.1 Hz, 1H), 1.06-1.01 (m, 4H), 1.00-0.88 (m, 15H). LCMS $[M+H]^+$383, RT 2.43 min (Method 1).

Intermediate 6

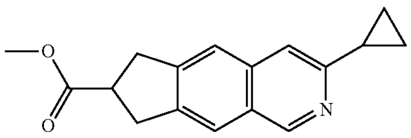 [SMILES: COC(=O)C1Cc2cc3cnc(C4CC4)cc3cc2C1]

methyl 3-cyclopropyl-7,8-dihydro-6H-cyclopenta[g]isoquinoline-7-carboxylate

A suspension of CsF (35 g, 230.41 mmol), $Ni(cod)_2$ (2 g, 7.27 mmol) and $PPh_3$ (8 g, 30.5 mmol) in MeCN (250 mL) was stirred under $N_2$ at room temperature for 5 min, turning from a yellow solution to a dark orange mixture. The mixture was treated with a solution of intermediate 5 (30 g, 78.6 mmol) and methyl 2-(prop-2-yn-1-yl) pent-4-ynoate (17.7 g, 117.8 mmol) in MeCN (250 mL, the first 25 mL was added immediately then the remaining solution added slowly over 10 min). The resulting mixture was stirred at room temperature for 3 hours under $N_2$ then passed through a plug of silica gel, eluting with EtOAc. The solvent was removed under reduced pressure and the residue by purified by column chromatography eluting with a gradient of EtOAc in Hexane to give the title compound (11 g, 51% yield) as a solid. $\delta_H$ (500 MHz, d-Chloroform) 6.90 (s, 1H), 7.68 (s, 1H), 7.51 (s, 1H), 7.38 (s, 1H), 3.74 (s, 3H), 3.44-3.31 (m, 5H), 2.19 (m, 1H), 1.04 (m, 2H), 0.96 (m, 2H).

Intermediate 7

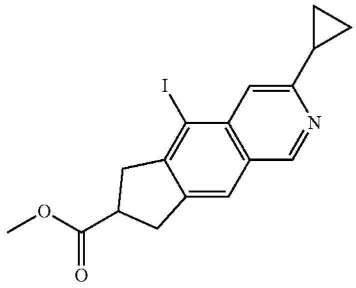 [SMILES: COC(=O)C1Cc2cc3cnc(C4CC4)cc3c(I)c2C1]

methyl 3-cyclopropyl-5-iodo-7,8-dihydro-6H-cyclopenta[g]isoquinoline-7-carboxylate Intermediate 6 (30 g, 112 mmol) was suspended in dry MeCN (1.2 L) and cooled to 4° C. in an ice bath before adding $CF_3SO_3H$ (29 mL, 333 mmol) via a glass dropping funnel. The temperature reached 8° C. during addition. The solution was allowed to warm to 9° C. and N-iodosuccinimide (37.9 g, 168 mmol) was added in one portion. The dark brown mixture was stirred at room temperature for 20 hours. Solid $Na_2CO_3$ (35.7 g, 337 mmol) was added and stirred for 30 minutes. The reaction was repeated on another 30 g of starting material. Both batches were filtered through kieselguhr and washed through with MeCN. The filtrate was concentrated under vacuum to give a brown sticky solid. 10% aq. sodium thiosulfate (1 L) was added to the solid and stirred for 5 minutes. DCM (1 L) was added and the mixture separated. The aqueous was extracted with DCM (2×500 mL) and the organics were combined, dried over magnesium sulfate and concentrated under vacuum. The material was purified by dry flash column chromatography eluting with ethyl acetate in DCM to afford the title compound (69 g, 74% Yield). 8H (250 MHz, d-Chloroform) 8.88 (s, 1H), 7.62 (s, 2H), 3.76 (s, 3H), 3.58-3.33 (m, 5H), 2.31-2.15 (m, 1H), 1.19-0.94 (m, 4H). LCMS $[M+H]^+$394.0, RT 2.00 min (Method 1).

Intermediate 8

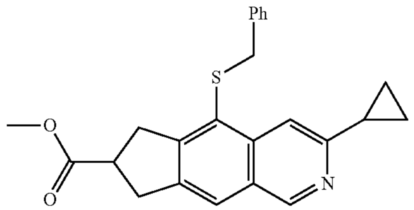 [SMILES: COC(=O)C1Cc2cc3cnc(C4CC4)cc3c(SCc3ccccc3)c2C1]

methyl 5-benzylsulfanyl-3-cyclopropyl-7,8-dihydro-6H-cyclopenta[g]isoquinoline-7-carboxylate Intermediate 7 (69 g, 168 mmol, 95% pure) was stirred in dry dioxane (500 mL). DIPEA (87 mL, 500 mmol), Xant-Phos (5.8 g, 10 mmol), $Pd_2$ (dba) 3 (4.6 g, 5 mmol) and benzyl mercaptan (25 mL, 217 mmol) were added. The reaction was heated to 100° C. with stirring for 1 hour 45 minutes. The reaction was cooled to room temperature and filtered through kieselguhr washing through with DCM. The filtrate was concentrated under vacuum and purified by dry flash using ethyl acetate in heptane to afford the title compound (75.3 g, assumed quantitative, 86% pure). $\delta_H$ (500 MHz, d-Chloroform) 9.00 (s, 1H), 8.03 (s, 1H), 7.66 (s, 1H), 7.19-7.10 (m, 3H), 6.93-6.85 (m, 2H), 3.94-3.85 (m, 2H), 3.71 (s, 3H), 3.40-3.25 (m, 2H), 3.20-3.01 (m, 3H), 2.26-2.16 (m, 1H), 1.15-1.07 (m, 2H), 1.07-1.01 (m, 2H). LCMS $[M+H]^+$ 390.2, RT 2.02 min (Method 1).

Intermediate 9

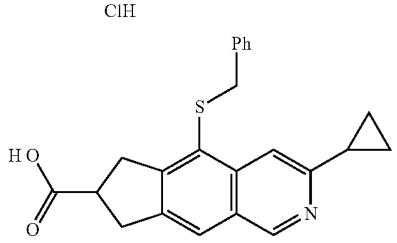

5-benzylsulfanyl-3-cyclopropyl-7,8-dihydro-6H-cyclopenta[g]isoquinoline-7-carboxylic acid hydrochloride Intermediate 8 (75.3 g, 166 mmol, 86% pure), THF (700 mL) and 2 M aq. LiOH (250 mL) were mixed for 1 hour at 50° C. Water (500 mL) was added and the THF removed under vacuum. The resulting aqueous was acidified using 3 M aq. HCl (350 mL) then cooled in an ice bath and the solid collected by vacuum filtration. The solid was washed with 1 M aq. HCl then ether (4×500 mL), transferred into a flask using MeCN and concentrated under vacuum to afford the title compound (140 g, assumed quantitative, 45% pure-wet with MeCN and water) as an HCl salt. LCMS $[M+H]^+$ 376.2, RT 1.80 min (Method 1).

Intermediate 10

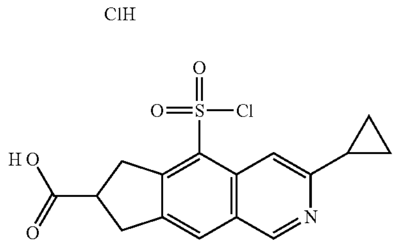

5-chlorosulfonyl-3-cyclopropyl-7,8-dihydro-6H-cyclopenta[g]isoquinoline-7-carboxylic acid hydrochloride Intermediate 9 (62.4 g, 166 mmol) was stirred in MeCN (700 mL), acetic acid (50 mL, 873 mmol) and water (15 mL, 833 mmol) until a fine suspension was obtained. The mixture was cooled in an ice bath and 1,3-dichloro-5,5-dimethylimidazolidine-2,4-dione (65.5 g, 332 mmol) was added in one portion. The suspension was stirred while warming to room temperature for 1 hour. The solid was collected by vacuum filtration, washed with MeCN followed by ether (2×250 mL) and dried in a vacuum oven at 50° C. to afford the title compound (64 g, 100% at 91% purity) as an HCl salt. LCMS was quenched with isobutylamine to give a $[M+H]^+$ 389.2, RT 1.73 min (Method 1).

Intermediate 11

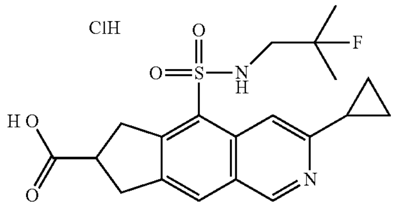

3-cyclopropyl-5-[(2-fluoro-2-methyl-propyl) sulfamoyl]-7,8-dihydro-6H-cyclopenta[g]isoquinoline-7-carboxylic acid hydrochloride 2-Fluoro-2-methylpropan-1-amine hydrochloride (25.5 g, 200 mmol) was stirred in DCM (700 mL) and DIPEA (116 mL, 666 mmol) added. Intermediate 10 (64 g, 166 mmol, 91% pure) was added slowly portion-wise over 1 hour. The reaction was stirred for 30 minutes and concentrated under vacuum. 1 M aq. HCl (1 L) was added and the mixture stirred for 30 minutes to give a brown suspension. The solid was collected by vacuum filtration, washed with 1 M aq. HCl to give a brown solid. 1 M aq. NaOH (600 mL) and 4 M aq. NaOH (200 mL) were added and washed with ethyl acetate (2×250 mL). The organic layers were combined and extracted with 2 M aq. NaOH (2×200 mL). Insoluble solid was removed by filtration. The combined aqueous layers were acidified with 6 M aq. HCl to give a thick white suspension which was collected by vacuum filtration. The solid was transferred to a flask with water and further 3 M aq. HCl was added, the lumps were broken up and the solid collected by filtration, washed with a small amount of water followed by diethyl ether (2×250 mL). The solid was dried in a vacuum oven at 50° C. to afford the title compound as an HCl salt (55.5 g, 82%). $\delta_H$ (250 MHz, $d_6$-DMSO) 9.36 (s, 1H), 8.58-8.46 (m, 2H), 8.24 (s, 1H), 3.85-3.61 (m, 2H), 3.46-3.23 (m, 3H), 3.11-2.83 (m, 2H), 2.45-2.29 (m, 1H), 1.25-0.99 (m, 10H). LCMS $[M+H]^+$ 407.0, RT 1.67 min (Method 1).

Intermediate 12

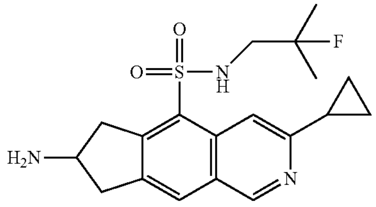 [SMILES: CC(C)(F)CNS(=O)(=O)c1c2c(cc3cnc(C4CC4)cc13)CC(N)C2]

7-amino-3-cyclopropyl-N-(2-fluoro-2-methyl-propyl)-7,8-dihydro-6H-cyclopenta[g]isoquinoline-5-sulfonamide Intermediate 11 (45.5 g, 112 mmol) was stirred in dry THF (500 mL). Triethylamine (39 mL, 280 mmol) and DPPA (29.4 mL, 137 mmol) were added. The reaction was heated to 75° C. with stirring for 1 hour 45 minutes. The reaction was cooled in an ice bath and added to 3 M aq. HCl (550 mL) at 0° C. The brown solution was stirred for 1 hour 15 minutes at room temperature. The aqueous solution was washed with ethyl acetate (450 mL, then 4×200 mL) to remove diphenyl phosphoric acid then 4 M aq. NaOH (400 mL) was added followed by 1 M aq. NaOH (200 mL). The product was extracted with ethyl acetate (3×300 mL), dried over sodium sulfate and concentrated under vacuum. The material was combined with a previous 10 g batch and purified by dry flash chromatography and column chromatography using MeOH in DCM to afford the title compound (36 g, 66% yield at 95% purity). $\delta_H$ (500 MHz, $d_6$-DMSO) 9.10 (s, 1H), 8.42 (s, 1H), 8.03 (s, 1H), 3.79-3.71 (m, 1H), 3.56 (dd, J=18.0, 6.4 Hz, 1H), 3.22 (dd, J=18.1, 4.8 Hz, 1H), 3.17 (dd, J=16.5, 6.2 Hz, 1H), 2.92 (dd, J=19.8, 3.4 Hz, 2H), 2.76 (dd, J=16.1, 4.8 Hz, 1H), 2.30-2.22 (m, 1H), 1.16 (d, J=21.4 Hz, 3H), 1.14 (d, J=21.4 Hz, 3H), 1.05-0.98 (m, 4H). LCMS $[M+H]^+$ 378.2, RT 1.36 min (Method 2).

Intermediates 13 & 14

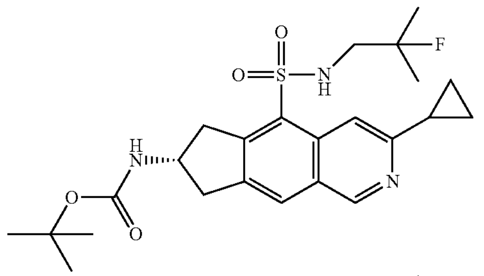

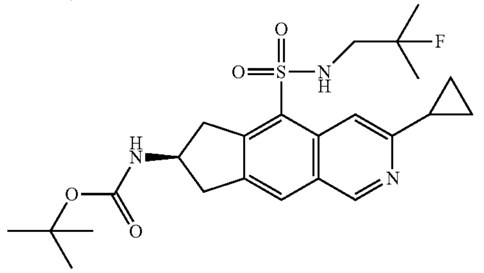

tert-butyl N-[(7S)-3-cyclopropyl-5-[(2-fluoro-2-methyl-propyl) sulfamoyl]-7,8-dihydro-6H-cyclopenta[g]isoquinolin-7-yl]carbamate (13)

tert-butyl N-[(7R)-3-cyclopropyl-5-[(2-fluoro-2-methyl-propyl) sulfamoyl]-7,8-dihydro-6H-cyclopenta[g]isoquinolin-7-yl]carbamate (14)

Intermediate 12 (29.5 g, 74.2 mmol, 95% pure), di-tert-butyl dicarbonate (17.8 g, 81.7 mmol) and triethylamine (10.4 mL, 74.2 mmol) were stirred in DCM (500 mL) at room temperature for 2.5 hours, further di-tert-butyl dicarbonate (250 mg) was added and stirred for 30 minutes. The reaction was washed with water (2×200 mL) and brine (50 mL) then dried over sodium sulfate, and concentrated under vacuum to give a brown foam. Diethyl ether was added and on standing a white precipitate formed which was collected by filtration and washed with ether. The filtrate was concentrated under vacuum and triturated with diethyl ether twice. The combined solids were dried in a vacuum oven to afford the title compounds as a racemic mixture (34.9 g, 98%). $\delta_H$ (250 MHz, d-Chloroform) 9.05 (s, 1H), 8.31 (s, 1H), 7.90 (s, 1H), 5.10-4.99 (m, 1H), 4.71 (br s, 1H), 4.49 (br s, 1H), 3.84 (dd, J=18.5, 7.0 Hz, 1H), 3.55-3.34 (m, 2H), 3.17-2.86 (m, 3H), 2.30-2.12 (m, 1H), 1.45 (s, 9H), 1.31 (d, J=21.4 Hz, 3H), 1.27 (d, J=21.5 Hz, 3H), 1.18-1.00 (m, 4H). LCMS $[M+H]^+$ 478.2, RT 3.23 min (Method 2).

The mixture of enantiomers (34.9 g) was purified by supercritical fluid LC using a CHIRALPAK IA column (50×266 mm), at 30° C., eluted with 20% IPA in $CO_2$, to give the title compounds.

Intermediate 13 (16.0 g); Chiral RT** 1.92 min (see method below).

Intermediate 14 (15.8 g); Chiral RT** 1.73 min (see method below).

**Analytical chiral HPLC was carried out using a CHIRALPAK IB column (4.6×150 mm) eluting with IPA 50% n-heptane 50% DEA 0.1% at a rate of 1.5 mL/min, at 30° C.

Intermediate 15

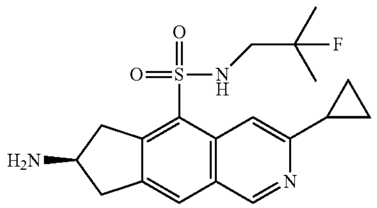

(7R)-7-amino-3-cyclopropyl-N-(2-fluoro-2-methyl-propyl)-7,8-dihydro-6H-cyclopenta[g]isoquinoline-5-sulfonamide To a stirring solution of Intermediate 14 (15.6 g, 32.7 mmol) in DCM (160 mL) cooled in an ice bath, was added trifluoroacetic acid (25.2 mL, 327 mmoL). The reaction was stirred at room temperature for 22 hours. The mixture was cooled in an ice bath, then basified to pH 12 with 4 M aq. NaOH (80 mL) followed by 1 M aq. NaOH (approx. 120 mL). The layers were separated, and the aqueous phase was extracted with a mixture of $CHCl_3$:IPA (3:1, 2×150 mL). The layers were separated, and the aqueous layer was adjusted to pH 10 with 1 M aq. HCl and then extracted with $CHCl_3$:IPA (3:1, 2×100 mL). The layers were separated, and the aqueous layer was adjusted to pH 8-9 with 1 M aq. HCl, then extracted again with $CHCl_3$/IPA (3:1, 2×100 mL). The combined organics were washed with brine (100 mL), dried over magnesium sulfate, filtered and concentrated under vacuum to afford the title compound (11.7 g, 95%). $\delta_H$ (500 MHz, $d_6$-DMSO) 9.09 (s, 1H), 8.42 (s, 1H), 8.02 (s, 1H), 3.76-3.70 (m, 1H), 3.56 (dd, J=18.0, 6.3 Hz, 1H), 3.25-3.18 (m, 1H), 3.19-3.13 (m, 1H), 2.92 (dd, J=19.8, 3.5 Hz, 2H), 2.75 (dd, J=16.1, 4.8 Hz, 1H), 2.30-2.21 (m, 1H), 1.16 (d, J=21.4 Hz, 3H), 1.14 (d, J=21.4 Hz, 3H), 1.04-0.98 (m, 4H). LCMS $[M+H]^+$ 378, RT 1.43 min (Method 1).

Intermediate 16

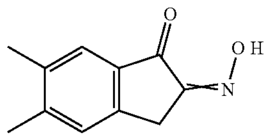

2-hydroxyimino-5,6-dimethyl-indan-1-one

To a solution of 5,6-dimethyl-2,3-dihydro-1H-inden-1-one (5.0 g, 31.21 mmol) in ether (82 mL), first saturated ethanolic HCl (1.30 mL) and then 15% ethanolic solution of ethyl nitrite (28.0 mL, 44.32 mmol) were added dropwise at 0° C. After 30 minutes at 0° C., the precipitated product was collected by filtration, washed with ether and dried. Crude title compound (5.2 g, 83%) was used in the next stage without further purification. LCMS $[M+H]^+$ 190, RT 1.70 min (Method 1).

Intermediate 17

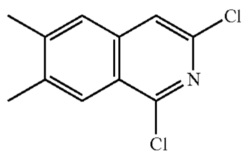

1,3-dichloro-6,7-dimethyl-isoquinoline

To a suspension of intermediate 16 (5.2 g, 26.1 mmol) in $POCl_3$ (157.7 mL), $PCl_5$ (5.98 g, 28.72 mmol) was added at 0° C. Then gaseous HCl was introduced until the solution was saturated and the reaction stirred at 60° C. for 4 hrs. A second portion of $PCl_5$ (1.9 g) was added and stirring was continued for 2 hrs at 80° C. After evaporating the solvent, water was added and the precipitate collected by filtration, washed with water and dried to give the title compound (5.9 g, 99%), which was used in the next stage without further purification. LCMS $[M+H]^+$ 226, RT 3.22 min (Method 3).

Intermediate 18

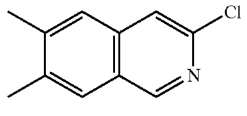

3-chloro-6,7-dimethyl-isoquinoline

A mixture of Intermediate 17 (5.9 g, 26.0 mmol), red phosphorus (1.94 g, 62.63 mmol) in AcOH (32 mL) and HI (57%) (11.7 mL, 88.7 mmol) was heated at 110° C. for 6 hrs. The hot reaction mixture was filtered and evaporated under pressure. The residue was dissolved in water and basified by addition of conc. aq. $NH_4OH$. The precipitate was collected by filtration then dissolved in DCM, washed with brine, dried over $MgSO_4$ and evaporated under pressure. Purification by column chromatography eluting with 8% to 50% EtOAc in heptane afforded the title compound (3.8 g, 76%). LCMS $[M+H]^+$ 192, RT 1.86 min (Method 1).

Intermediate 19

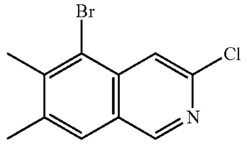

5-bromo-3-chloro-6,7-dimethyl-isoquinoline

Intermediate 18 (1.0 g, 5.22 mmol) was added in batches to sulfuric acid (5.79 mL) in DCM (50 mL) at 0° C. The reaction mixture was cooled at −10° C. and N-bromosuccinamide (1.02 g, 5.7 mmol) was added in portions and the reaction mixture was maintained at −10° C. for 1 hour, then stirred at room temperature for 16 hrs. The reaction mixture was diluted with ice water (100 mL) and the pH of the solution adjusted to 8-10 with concentrated ammonium hydroxide. The resulting solution was extracted with DCM (2×50 mL) and the combined organic layers were dried (sodium sulphate) and concentrated. The residue was purified by column chromatography eluting with 5% to 30% EtOAc in heptane to afford the title compound (1.08 g, 76%). LCMS $[M+H]^+$ 270/272, RT 3.12 min (Method 3).

Intermediate 20

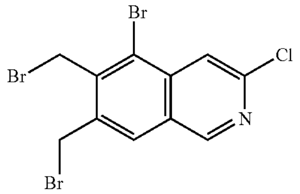 [SMILES: Clc1cc2c(Br)c(CBr)c(CBr)cc2cn1]

5-bromo-6,7-bis(bromomethyl)-3-chloro-isoquinoline

Intermediate 19 (1.1 g, 4.06 mmol) was dissolved in EtOAc (25 mL). N-bromosuccinimide (1.6 g, 0.77 mmol) followed by AIBN (66.76 mg, 0.40 mmol) were then added. The reaction mixture was refluxed, at 90° C. for 5 hours. Further N-bromosuccinimide (1.5 eq) and cat. AIBN were added and the reaction mixture heated at reflux for another 5 hours. The reaction mixture was cooled to room temperature, diluted with EtOAc and washed with aq. $Na_2S_2O_3$, water and brine. The solution was dried over $MgSO_4$ and concentrated under reduced pressure to give crude product which was purified by column chromatography eluting with 0% to 20% EtOAc in heptane to afford the title compound (647 mg, 37%). LCMS $[M+H]^+$ 428/430, RT 3.17 min (Method 3).

Intermediate 21

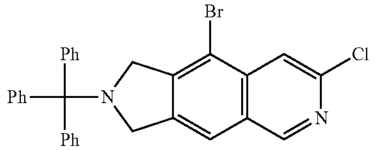 [SMILES: Clc1cc2c(Br)c3c(cc2cn1)CN(C(c1ccccc1)(c1ccccc1)c1ccccc1)C3]

9-bromo-7-chloro-2-trityl-1,3-dihydropyrrolo[3,4-g] isoquinoline

Intermediate 20 (565 mg, 1.31 mmol), tritylamine (410 mg, 1.58 mmol) and N,N-diisopropylethylamine (574 mL, 3.29 mmol) in anhydrous DMF (14 mL) was stirred for 5 hours at 70° C. After removing the solvent in vacuo, the residue was diluted to 15 mL with ethyl acetate and washed with water and brine. The organic layer was dried over anhydrous $MgSO_4$ and filtered. The filtrate was evaporated to dryness under reduced pressure and the residue was purified by column chromatography eluting with hexane/EtOAc (9:1) to give title compound (693 mg, 71%). LCMS $[M+H]^+$ 525/527, RT 2.61 min (Method 1).

Intermediate 22

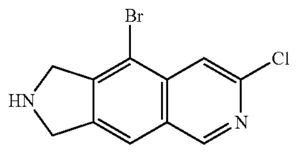 [SMILES: Clc1cc2c(Br)c3c(cc2cn1)CNC3]

9-bromo-7-chloro-2,3-dihydro-1H-pyrrolo[3,4-g] isoquinoline

Intermediate 21 (504 mg, 0.93 mmol) was dissolved in a 5% $CF_3CO_2H$ in $CH_2Cl_2$ (15 mL) solution. The mixture was stirred for 30 min at room temperature, then diluted to 10 mL with EtOH and stirred for an additional 15 min. This was evaporated to dryness under reduced pressure to give a crude product which was diluted with DCM (50 mL) and washed with sat. $NaHCO_3$. Aqueous layer was extracted with a 1:1 mixture of IPA and $CHCl_3$ (3×30 mL). Combined organic layers dried over $MgSO_4$ and concentrated under reduced pressure to afford the crude title compound (305 mg, 97%, 85% purity), which was used in the next stage without further purification. LCMS $[M+H]^+$ 283/285, RT 1.30 min (Method 1).

Intermediate 23

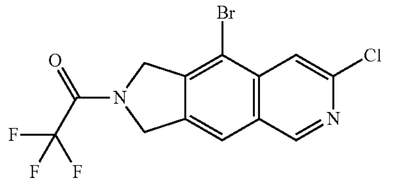 [SMILES: O=C(N1Cc2cc3cnc(Cl)cc3c(Br)c2C1)C(F)(F)F]

1-(9-bromo-7-chloro-1,3-dihydropyrrolo[3,4-g]isoquinolin-2-yl)-2,2,2-trifluoro-ethanone Intermediate 22 (220 mg, 0.77 mmol) was dissolved in THF (15 mL) then $NaHCO_3$ (97.7 mg, 1.16 mmol) followed by trifluoroacetic anhydride (130.3 μL, 0.93 mmol) were added. The solution was stirred for 1 hour at room temperature. The reaction mixture was diluted with DCM (50 mL) and washed with water (2×40 mL) before drying over $MgSO_4$ and concentrating under reduced pressure. Crude was purified by column chromatography eluting with 5% to 50% EtOAc in heptane to afford the title compound (140 mg, 48%). LCMS $[M+H]^+$ 379/381, RT 1.97 min (Method 1).

Intermediate 24

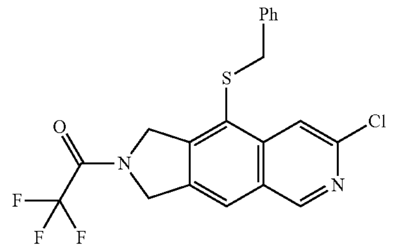 [SMILES: O=C(N1Cc2cc3cnc(Cl)cc3c(SCc3ccccc3)c2C1)C(F)(F)F]

1-(9-benzylsulfanyl-7-chloro-1,3-dihydropyrrolo[3,4-g]isoquinolin-2-yl)-2,2,2-trifluoro-ethanone To a flask were added intermediate 23 (4.32 g, 11.38 mmol), phenylmethanethiol (1.33 mL, 11.4 mmol), (9,9-dimethyl-9H-xanthene-4,5-diyl)bis(diphenylphosphane) (395.1 mg, 0.68 mmol), (1E,4E)-1,5-diphenylpenta-1,4-dien-3-one-palladium (3:2) (313 mg, 0.34 mmol) and DIPEA (4 mL, 22.7 mmol) in dioxane (200 mL). The mixture was sparged with nitrogen for 10 min, and heated at 85° C. for 16 hrs. Upon cooling to room temperature, the solvent was removed, and DCM was added followed by water. The organic layer was separated, washed with brine, dried over $MgSO_4$ and concentrated under reduced pressure to give a yellow solid which was purified by column chromatography eluting with 10% to 50% EtOAc to afford the title compound (4.48 g, 84%). LCMS $[M+H]^+$ 423, RT 2.08 min (Method 1).

Intermediate 25

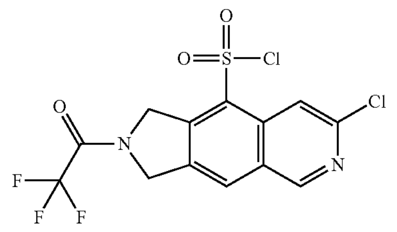 [SMILES: O=C(N1Cc2cc3cnc(Cl)cc3c(S(=O)(=O)Cl)c2C1)C(F)(F)F]

7-chloro-2-(2,2,2-trifluoroacetyl)-1,3-dihydropyrrolo[3,4-g]isoquinoline-9-sulfonyl chloride Intermediate 24 (5.1 g, 12.06 mmol) was dissolved in MeCN (120 mL) and cooled to 0° C. Water (3 mL) and AcOH (4.5 mL) were added followed by 1,3-dichloro-5,5-dimethylimidazolidine-2,4-dione (4.75 g, 24.12 mmol, portion-wise) and stirring continued at 0° C. for 1 hour. The reaction mixture was concentrated to near dryness under vacuum (bath temperature ~20° C.). The crude product was diluted with $CH_2Cl_2$ (150 mL), and the solution cooled down to ~0° C. 5% aqueous $NaHCO_3$ solution (166 mL) was added slowly at <10° C. The mixture was stirred at 0-5° C. for 15 min, and the lower organic, washed once more with water at <10° C. The lower organic was dried over $MgSO_4$, filtered and concentrated to dryness (bath temperature ~20° C.) to afford the crude title compound (5.23 g, 73%, 67% purity), which was used in the next step without further purification. LCMS $[M+H]^+$ 399, RT 1.95 min (Method 1).

Intermediate 26

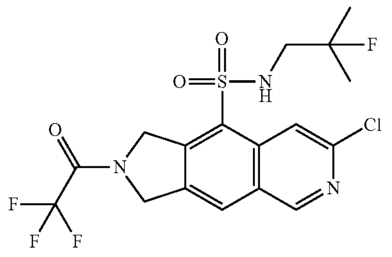 [SMILES: CC(C)(F)CNS(=O)(=O)c1c2c(cc3cnc(Cl)cc13)CN(C(=O)C(F)(F)F)C2]

7-chloro-N-(2-fluoro-2-methyl-propyl)-2-(2,2,2-trifluoroacetyl)-1,3-dihydropyrrolo[3,4-g]isoquinoline-9-sulfonamide Pre-mixed solution of 2-fluoro-2-methylpropan-1-amine hydrochloride (2.3 g, 18.09 mmol) and DIPEA (6.3 mL, 36.18 mmol) in DCM (75 mL) was added dropwise to a crude reaction mixture of Intermediate 25 (4.8 g, 12.06 mmol) in DCM (75 mL) at 0° C. The reaction mixture was stirred at room temperature for 30 min then diluted with DCM (200 mL) and water (200 mL). The aq. phase was extracted with DCM (50 mL×2) and the combined organics washed with water, dried ($Na_2SO_4$), filtered and concentrated under reduced pressure. Purification by column chromatography eluting with 30% to 80% EtOAc in heptane gave the title compound (3.15 g, 56%). LCMS $[M+H]^+$ 454, RT 1.84 min (Method 1).

Intermediate 27

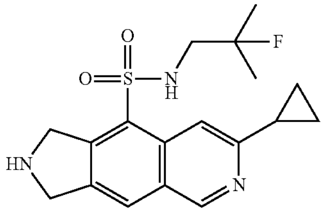 [SMILES: CC(C)(F)CNS(=O)(=O)c1c2c(cc3cnc(C4CC4)cc13)CNC2]

7-cyclopropyl-N-(2-fluoro-2-methyl-propyl)-2,3-dihydro-1H-pyrrolo[3,4-g]isoquinoline-9-sulfonamide To a mixture of Intermediate 26 (1.2 g, 1.58 mmol, 60% purity), cyclopropylboronic acid (0.409 g, 4.75 mmol) and $Cs_2CO_3$ (1.5 g, 4.75 mmol) in nitrogen sparged dioxane (20 mL), Bedford catalyst (169.4 mg, 0.159 mmol) was added. The reaction mixture was heated to 110° C. for 16 hours, then diluted with DCM (150 mL). The solution was dried over $MgSO_4$ and filtered through Celite, washing with DCM and a 1:1 mixture of DCM and MeOH. The solution was concentrated under reduced pressure and purified by column chromatography eluting with 0 to 30% MeOH in DCM to give the title compound (285 mg, 46%). LCMS $[M+H]^+$ 364, RT 1.46 min (Method 1).

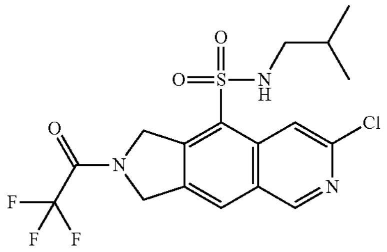 [SMILES: CC(C)CNS(=O)(=O)c1c2c(cc3cnc(Cl)cc13)CN(C(=O)C(F)(F)F)C2]

7-chloro-N-isobutyl-2-(2,2,2-trifluoroacetyl)-1,3-dihydropyrrolo[3,4-g]isoquinoline-9-sulfonamide Intermediate 24 (50 mg, 0.11 mmol) was dissolved in DCM (4 mL) and cooled to 0° C. Water (12.7 µl), AcOH (33.8 µl) and $SO_2Cl_2$ (47.7 µl, 0.59 mmol) were added and stirring continued at 0° C. for 5 min and at room temperature for 1 hour. Reaction mixture was cooled to 0° C. and an excess of isobutyl amine (94 µl, 0.94 mmol) was added and stirred at room temperature for 1 hour. The reaction was diluted with water (10 mL). The aq. phase extracted with DCM (10 mL×2) and the combined organics washed with water, dried ($Na_2SO_4$), filtered and concentrated to give the crude product. Crude was purified by column chromatography eluting with 50% to 100% EtOAc to afford the title compound (18 mg, 35%). LCMS $[M+H]^+$ 436, RT 1.91 min (Method 1).

Intermediate 29

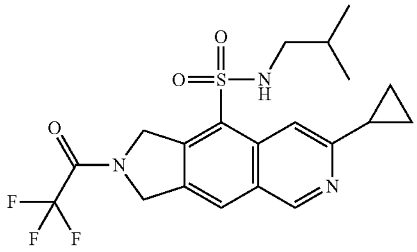 [SMILES: CC(C)CNS(=O)(=O)c1c2c(cc3cnc(C4CC4)cc13)CN(C(=O)C(F)(F)F)C2]

7-cyclopropyl-N-isobutyl-2-(2,2,2-trifluoroacetyl)-1,3-dihydropyrrolo[3,4-g]isoquinoline-9-sulfonamide A mixture of Intermediate 28 (18 mg, 0.041 mmol), cyclopropylboronic acid (8.8 mg, 0.10 mmol), Pd (OAc) 2 (0.46 mg, 2.0 µmol), $P(Cy)_3 \cdot HBF_4$ (2.2 mg, 6.19 µmol) and $K_3PO_4$ (21.9 mg, 0.10 mmol) in a mixture of toluene (1 mL) and water (0.05 mL) was heated at 120° C. for 2 hrs. The mixture was then diluted with DCM (5 mL), dried over $MgSO_4$ and filtered through Celite, washing through with DCM. The solvent was concentrated under reduced pressure and the residue purified by column chromatography eluting with 12-50% EtOAc/heptane, to give title compound (13 mg, 71%). LCMS $[M+H]^+$ 442, RT 1.94 min (Method 1).

Intermediate 30

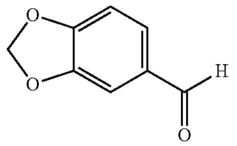 [SMILES: O=Cc1ccc2c(c1)OCO2]

1,3-benzodioxole-5-carbaldehyde

To a solution of 3,4-dihydroxybenzaldehyde (2 g, 14.48 mmol) in DMF (30 mL) was added cesium carbonate (7.08 g, 20.17 mmol) and dibromomethane (3.78 g, 20.17 mmol). The mixture was heated at 110° C. for 2 hours. Water (70 mL) was then added followed by EtOAc (40 mL). The organic layer was separated, washed with water (2×20 mL) followed by brine (10 mL) and passed through a phase separator frit. The solvent of the filtrate was removed and the resulting oil purified by flash column chromatography eluting with a gradient of 0 to 40% of EtOAc in heptane to afford the title compound as a white solid (2.17 g, 100% yield). LCMS $[2M-H]^-$ 299, RT 1.13 minutes (Method 4).

Intermediate 31

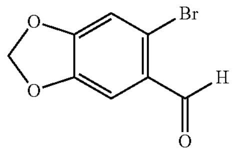 [SMILES: O=Cc1cc2c(cc1Br)OCO2]

6-bromo-1,3-benzodioxole-5-carbaldehyde

To a solution of Intermediate 30 (2170 mg, 14.5 mmol) in acetic acid (10 mL) was added bromine (2.4 g, 15.0 mmol). The solution was stirred for 5 hours before bromine (2.4 g) was added. The solution was stirred for a further 18 hours. The solvent was removed, and the oil was pre-absorbed onto silica. Purification by flash column chromatography eluting with a gradient of 0 to 20% of EtOAc in heptane afforded the title compound as a pale-yellow solid (1.1 g, 33% yield) as well as a 2:1 mixture of intermediates 31 & 30 (2.67 g). LCMS $[M+H]^+$ 228/230, RT 1.81 minutes (Method 4).

Intermediate 32

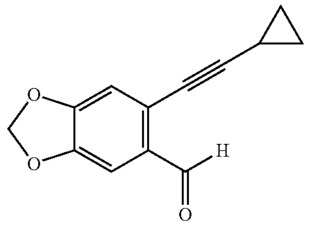 [SMILES: O=Cc1cc2c(cc1C#CC1CC1)OCO2]

6-(2-cyclopropylethynyl)-1,3-benzodioxole-5-carbaldehyde

To a solution of Intermediate 31 (200 mg, 0.87 mmol) in THF (2.5 mL) was added cyclopropylacetylene (71.4 mg, 1.05 mmol), triethylamine (177 mg, 1.75 mmol), cuprous iodide (8.35 mg, 0.044 mmol) and bis(triphenylphosphine) palladium (II) dichloride (18.4 mg, 0.026 mmol). The mixture put under a nitrogen atmosphere and heated at 50° C. for 18 hours. The reaction was cooled, and the solvent was removed to give a brown oil. The oil was purified by flash column chromatography eluting with 0 to 20% of EtOAc in heptane gradient to afford the title compound as an off-white solid (90 mg, 48% yield). LCMS $[M+H]^+$ 215, RT 2.26 minutes (Method 4).

Intermediate 33

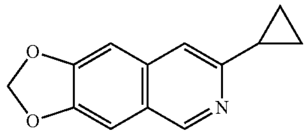 [SMILES: c1nc(C2CC2)cc2cc3c(cc12)OCO3]

7-cyclopropyl-[1,3]dioxolo[4,5-g]isoquinoline

To a suspension of Intermediate 32 (90 mg, 0.42 mmol) in tert-butanol (4 mL) was added ammonium acetate (81 mg, 1.05 mmol) and silver nitrate (7.14 mg, 0.042 mmol). The mixture was placed under a nitrogen atmosphere and heated at 35° C. for 1.5 hours. The solvent was removed, and the residue partitioned between DCM (20 mL) and saturated aqueous $NaHCO_3$ solution (10 mL). The organic layer was separated and washed with brine (10 mL), dried ($MgSO_4$) and the solvent was removed to give an oil. The oil was purified by flash column chromatography eluting with a 0 to 25% EtOAc in heptane gradient to afford the title compound as a pale brown solid (70 mg, 78% yield). LCMS $[M+H]^+$ 214, RT 1.97 minutes (Method 4).

Intermediate 34

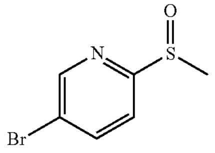

5-bromo-2-methylsulfinyl-pyridine

Sodium periodate (4.2 g, 20 mmol) was added as a slurry in water (4 mL) to a stirred solution of 5-bromo-2-methylthiopyridine (1 g, 4.8 mmol) in glacial AcOH (25 mL, 436 mmol) at 0° C. Upon completion of addition, the ice bath was removed, and the mixture was stirred at room temperature for 3.5 hours. The mixture was treated with water (50 mL) and basified by addition of solid potassium carbonate powder. The reaction mixture was extracted with EtOAc (3×50 mL). The combined organic phase was then washed with 10% aqueous sodium thiosulfate solution (50 mL), dried over $Na_2SO_4$ and concentrated in vacuo. The resulting crude oil was purified by column chromatography to afford the title compound (838 mg, 80% Yield). $^1H$ NMR (300 MHz, Chloroform-d) δ 8.68 (dd, J=2.2, 0.7 Hz, 1H), 8.08 (dd, J=8.4, 2.2 Hz, 1H), 7.93 (dd, J=8.4, 0.7 Hz, 1H), 2.85 (s, 3H).

Intermediate 35

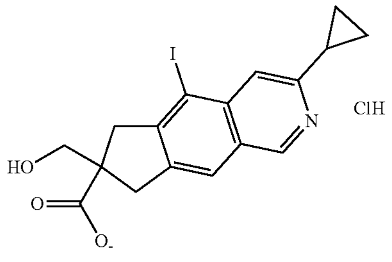

methyl 3-cyclopropyl-7-(hydroxymethyl)-5-iodo-6,8-dihydrocyclopenta[g]isoquinoline-7-carboxylate hydrochloride Intermediate 82 (72%, 9 g, 12.5 mmol) was stirred in MeOH (200 mL) and 12 M aq. HCl (27 mL) was added. The reaction was heated to 75° C. with stirring for 18 hours, further 12 M aq. HCl (10 mL) was added and the reaction stirred for an additional 24 hours at 75° C. The suspension was concentrated to 25% volume and the solid collected by vacuum filtration, washed with a little methanol followed by TBME to afford the title compound (7.28 g, 62% over 2 steps). LCMS $[M+H]^+$ 424.0, RT 1.82 min (Method 1).

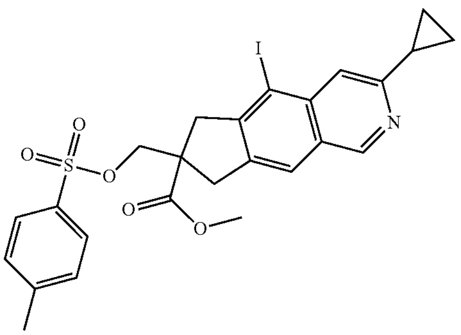 [SMILES: COC(=O)C1(COS(=O)(=O)c2ccc(C)cc2)Cc2cc3cnc(C4CC4)cc3c(I)c2C1]

methyl 3-cyclopropyl-5-iodo-7-(p-tolylsulfonyloxymethyl)-6,8-dihydrocyclopenta[g]isoquinoline-7-carboxylate To a solution of Intermediate 35 (7.28 g, 17.2 mmol) in pyridine (50 mL), 4-methylbenzenesulfonyl chloride (6.56 g, 34.4 mmol) was added portion-wise and the reaction heated to 80° C. for 2.5 hours. The reaction was allowed to cool to room temperature and quenched with saturated aq. $NH_4Cl$ (100 mL) then extracted with ethyl acetate (200 mL then 100 mL). The combined organics were washed with saturated aq. $NH_4Cl$ (100 mL), water (50 mL), saturated aq. $NaHCO_3$ (50 mL) and brine (30 mL). The organics were then dried over sodium sulfate and concentrated under vacuum. Purification by column chromatography using ethyl acetate in heptane afforded the title compound (7.94 g, 76% at 95% purity). $\delta_H$ (250 MHz, d-Chloroform) 8.88 (s, 1H), 7.73 (d, J=8.3 Hz, 2H), 7.61 (s, 1H), 7.56 (s, 1H), 7.31 (d, J=8.0 Hz, 2H), 4.20 (d, J=2.2 Hz, 2H), 3.68 (s, 4H), 3.55 (d, J=17.8 Hz, 1H), 3.30 (d, J=17.0 Hz, 1H), 3.13 (d, J=17.8 Hz, 1H), 2.43 (s, 3H), 2.35-2.16 (m, 1H), 1.20-1.00 (m, 4H). LCMS $[M+H]^+$ 577.6, RT 1.37 min (Method 5).

Intermediate 37

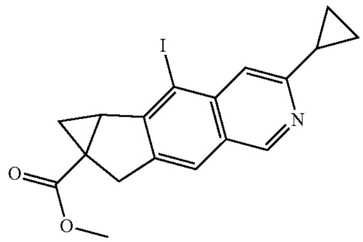 [SMILES: COC(=O)C12Cc3cc4cnc(C5CC5)cc4c(I)c3C1C2]

methyl 13-cyclopropyl-2-iodo-12-azatetracyclo[8.4.0.0^{3,8}.0^{4,6}]tetradeca-1 (10),2,8,11,13-pentaene-6-carboxylate Intermediate 36 (7.94 g, 13.8 mmol) was dissolved in dry THF (100 mL) and cooled to −78° C. 1 M LiHMDS in THF (27.5 mL) was added dropwise and the reaction stirred at −78° C. for 30 minutes. The reaction was quenched with saturated aq. $NH_4Cl$ (50 mL) and water (50 mL). The reaction was extracted with ethyl acetate (200 mL then 100 mL), the organics were washed with water (50 mL), brine (50 mL), dried over sodium sulfate and concentrated under vacuum. Purification by column chromatography using ethyl acetate in heptane afforded the title compound (5.04 g, 86% at 95% purity). $\delta_H$ (500 MHz, d-Chloroform) 8.84 (s, 1H), 7.61 (s, 1H), 7.59 (s, 1H), 3.95 (d, J=17.7 Hz, 1H), 3.77 (s, 3H), 3.40 (d, J=17.5 Hz, 1H), 3.24 (ddd, J=8.8, 4.5, 1.0 Hz, 1H), 2.27-2.20 (m, 1H), 2.15 (ddd, J=8.8, 4.5, 0.6 Hz, 1H), 1.14-1.10 (m, 2H), 1.08-1.01 (m, 2H), 0.83 (t, J=4.5 Hz, 1H). LCMS $[M+H]^+$ 405.95, RT 1.26 min (Method 5).

Intermediate 38

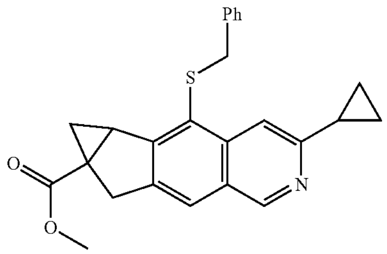 [SMILES: COC(=O)C12Cc3cc4cnc(C5CC5)cc4c(SCc4ccccc4)c3C1C2]

methyl 2-benzylsulfanyl-13-cyclopropyl-12-azatetracyclo[8.4.0.0^{3,8}.0^{4,6}]tetradeca-1 (10),2,8,11,13-pentaene-6-carboxylate Intermediate 37 (95%, 5.04 g, 11.8 mmol) was stirred in dry dioxane (70 mL). XantPhos (410 mg, 0.71 mmol), $Pd_2$ (dba) 3 (324 mg, 0.354 mmol) and DIPEA (6.17 mL, 35.5 mmol) were added followed by benzyl mercaptan (1.8 mL, 15.4 mmol). The reaction was heated to 100° C. with stirring for 1 hour 15 minutes. The reaction was cooled to room temperature and filtered through kieselguhr washing through with DCM. The filtrate was concentrated, and the residue purified by dry flash using ethyl acetate in heptane to afford the title compound (4.46 g, 94%). $\delta_H$ (500 MHz, d-Chloroform) 8.97 (s, 1H), 8.03 (s, 1H), 7.63 (s, 1H), 7.13-7.09 (m, 3H), 6.92-6.86 (m, 2H), 3.98 (d, J=12.8 Hz, 1H), 3.89 (d, J=12.8 Hz, 1H), 3.79 (d, J=17.6 Hz, 1H), 3.73 (s, 3H), 3.18 (d, J=17.4 Hz, 1H), 3.06 (dd, J=8.7, 4.3 Hz, 1H), 2.27-2.17 (m, 1H), 1.92 (dd, J=9.0, 4.4 Hz, 1H), 1.13-1.08 (m, 2H), 1.08-1.02 (m, 2H), 0.44 (t, J=4.5 Hz, 1H). LCMS $[M+H]^+$ 402.1, RT 1.19 min (Method 5).

Intermediate 39

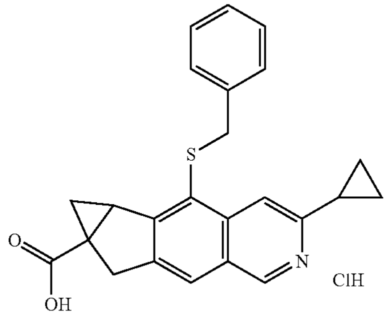 [SMILES: O=C(O)C12Cc3cc4cnc(C5CC5)cc4c(SCc4ccccc4)c3C1C2 ; Cl]

2-benzylsulfanyl-13-cyclopropyl-12-azatetracyclo [8.4.0.0^{3,8}.0^{4,6}]tetradeca-1(10),2,8,11,13-pentaene-6-carboxylic acid hydrochloride To a solution of Intermediate 38 (4.46 g, 11.1 mmol) in THF (50 mL), 2 M aq. LiOH (16.7 mL) was added. The reaction was stirred at 50° C. for 1 hour then at room temperature for 3 days. The reaction was diluted with water (15 mL) and the THF removed under vacuum. 1 M aq. HCl (30 mL) was added to the residue to form an orange gum. Further 6 M aq. HCl (1 mL) was added followed by TBME, the TBME was then removed under vacuum which resulted in a fine suspension in the aqueous layer. The solid was collected by vacuum filtration, washed with 1 M aq. HCl (30 mL), water (20 mL) then TBME (30 mL) to afford the title compound (4.86 g, quantitative). LCMS $[M+H]^+$ 388.00, RT 1.05 min (Method 5).

Intermediate 40

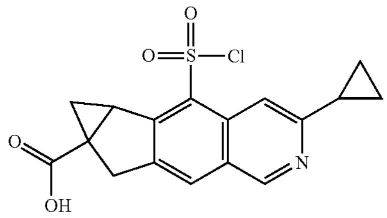 [SMILES: O=C(O)C12Cc3cc4cnc(C5CC5)cc4c(S(=O)(=O)Cl)c3C1C2]

2-chlorosulfonyl-13-cyclopropyl-12-azatetracyclo [8.4.0.0^{3,8}.0^{4,6}]tetradeca-1 (10),2,8,11,13-pentaene-6-carboxylic acid Intermediate 39 (97%, 4.86 g, 11.1 mmol) was stirred in MeCN (50 mL) and cooled in an ice bath. Water (1 mL, 55.6 mmol), acetic acid (3.18 mL, 55.6 mmol) and 1,3-dichloro-5,5-dimethylimidazolidine-2,4-dione (4.38 g, 22.2 mmol) were added. The suspension was stirred while warming to room temperature for 40 minutes. The reaction was filtered under vacuum and the solid washed with MeCN to afford the title compound (3.96 g, 97%). LCMS $[M+H]^+$ 363.95, RT 1.16 min (Method 5).

Intermediate 41

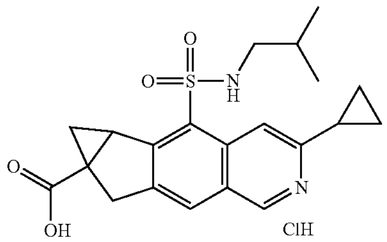 [SMILES: CC(C)CNS(=O)(=O)c1c2c(cc3cnc(C4CC4)cc13)CC1(C(=O)O)CC21 ; Cl]

13-cyclopropyl-2-(2-methylpropylsulfamoyl)-12-azatetracyclo[8.4.0.0^{3,8}.0^{4,6}]tetradeca-1 (10), 2,8,11,13-pentaene-6-carboxylic acid hydrochloride 2-methylpropan-1-amine (3.69 mL, 37.1 mmol) was dissolved in DCM (50 mL) and Intermediate 40 (2.7 g, 7.42 mmol) was added in portions. The reaction stirred for 5 minutes then concentrated under vacuum. Water (20 mL) was added to the residue followed by 1 M aq. HCl (10 mL). A white gum formed, and a further 6 M aq. HCl (3 mL) was added followed by TBME (20 mL). The mixture was partially concentrated under vacuum at 40° C. to remove the TBME which resulted in a fine solid suspension. The solid was collected by vacuum filtration, washed with 1 M aq. HCl (20 mL), water (20 mL) and TBME (20 mL). The solid was dried in a vacuum oven at 50° C. for 16 hours to afford the title compound (2.84 g, 84%). $\delta_H$ (500 MHz, $d_4$-Methanol) 9.52 (s, 1H), 8.88 (s, 1H), 8.36 (s, 1H), 4.07-4.00 (m, 1H), 3.93 (d, J=18.3 Hz, 1H), 3.41 (d, J=18.2 Hz, 1H), 2.77 (dd, J=13.0, 7.0 Hz, 1H), 2.70 (dd, J=13.0, 6.9 Hz, 1H), 2.51-2.42 (m, 1H), 2.38-2.31 (m, 1H), 1.72-1.57 (m, 1H), 1.46-1.36 (m, 2H), 1.28-1.20 (m, 2H), 0.95 (t, J=4.5 Hz, 1H), 0.80 (d, J=6.7 Hz, 3H), 0.79 (d, J=6.7 Hz, 3H). LCMS $[M+H]^+$ 401.05, RT 1.04 min (Method 5).

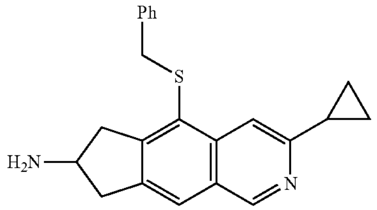 [SMILES: NC1Cc2cc3cnc(C4CC4)cc3c(SCc3ccccc3)c2C1]

5-benzylsulfanyl-3-cyclopropyl-7,8-dihydro-6H-cyclopenta[g]isoquinolin-7-amine

Intermediate 9 (10 g, 26.6 mmol) was stirred in dry THF (100 mL). Triethylamine (9.28 ml, 66.6 mmol) was added followed by DPPA (5.74 mL, 26.6 mmol) and the reaction was heated at 75° C. for 2 hours. The reaction was cooled in an ice bath and added slowly to 2 M aq. NaOH (200 mL) at 0° C. The reaction was stirred for 5 minutes then extracted with ethyl acetate (2×200 mL). Insoluble material was removed by filtration, the filtrate was dried over sodium sulfate and concentrated under vacuum. The solid was slurred in DCM and filtered, the filtrate was concentrated under vacuum to afford the title compound (9.4 g), which was used crude in the next step. LCMS $[M+H]^+$ 346.9, RT 0.91 min (Method 5).

Intermediate 43

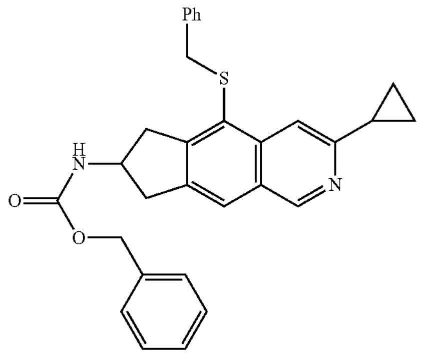 [SMILES: O=C(NC1Cc2cc3cnc(C4CC4)cc3c(SCc3ccccc3)c2C1)OCc1ccccc1]

benzyl N-(5-benzylsulfanyl-3-cyclopropyl-7,8-dihydro-6H-cyclopenta[g]isoquinolin-7-yl) carbamate Intermediate 42 (9.4 g, 27.1 mmol) was stirred in DCM (100 mL), triethylamine (9.45 mL, 67.8 mmol) was added followed by 1-{[(benzyloxy) carbonyl]oxy}pyrrolidine-2,5-dione (6.76 g, 27.1 mmol), the reaction was stirred for 40 minutes. Further 1-{[(benzyloxy) carbonyl] oxy}pyrrolidine-2,5-dione (1.2 g, 4.81 mmol) was added and the reaction stirred for 15 minutes. The reaction was washed with water (2×100 mL), brine, dried over sodium sulfate and concentrated under vacuum. The residue was purified by column chromatography using ethyl acetate in heptane and the solid obtained was triturated with diethyl ether then ethyl acetate in heptane. Further purification by column chromatography with ethyl acetate in heptane afforded the title compound (5.6 g, 43% yield over two steps). $\delta_H$ (500 MHz, $d_6$-DMSO) 9.04 (s, 1H), 7.97 (s, 1H), 7.82 (s, 1H), 7.56 (d, J=6.2 Hz, 1H), 7.43-7.26 (m, 5H), 7.19-7.07 (m, 3H), 7.03-6.89 (m, 2H), 5.14-4.98 (m, 2H), 4.19-4.10 (m, 1H), 4.03-3.91 (m, 2H), 3.31-3.24 (m, 1H), 3.15 (dd, J=17.0, 7.2 Hz, 1H), 2.99-2.87 (m, 2H), 2.24 (p, J=6.5 Hz, 1H), 1.01-0.92 (m, 4H). LCMS $[M+H]^+$ 481.2, RT 3.47 min (Method 3).

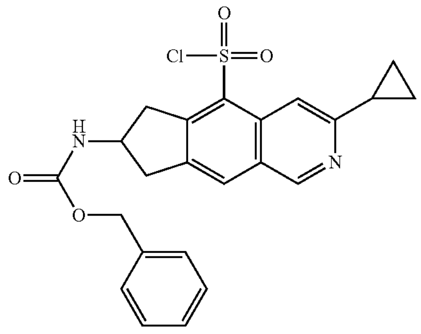 [SMILES: O=C(NC1Cc2cc3cnc(C4CC4)cc3c(S(=O)(=O)Cl)c2C1)OCc1ccccc1]

benzyl N-(5-chlorosulfonyl-3-cyclopropyl-7,8-dihydro-6H-cyclopenta[g]isoquinolin-7-yl) carbamate To a suspension of Intermediate 43 (1 g, 2.08 mmoL) in acetonitrile (25 mL) was added acetic acid (596 μL, 10.4 mmol) and water (187 μL, 10.4 mmol). The mixture was cooled to 0° C. in an ice bath. 1,3-dichloro-5,5-dimethylimidazolidine-2,4-dione (820 mg, 4.16 mmol) was added and the reaction was stirred at 0° C. for 5 minutes. The bath was removed, and the reaction was stirred at room temperature under an atmosphere of nitrogen for 40 minutes. The white precipitate was filtered off, washed through with acetonitrile and dried under high vacuum for 30 minutes to afford the title compound (960 mg, quantitative). LCMS $[M+H]^+$ 457, RT 1.37 min (Method 5).

Intermediate 45

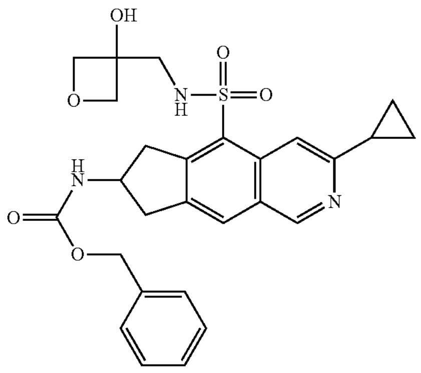 [SMILES: O=C(NC1Cc2cc3cnc(C4CC4)cc3c(S(=O)(=O)NCC3(O)COC3)c2C1)OCc1ccccc1]

benzyl N-[3-cyclopropyl-5-[(3-hydroxyoxetan-3-yl) methylsulfamoyl]-7,8-dihydro-6H-cyclopenta[g] isoquinolin-7-yl]carbamate To a stirring solution of 3-(aminomethyl) oxetan-3-ol (120 mg, 1.16 mmol) and DIPEA (549 μL, 3.15 mmoL) in anhydrous DCM (10 mL) was added Intermediate 44 (480 mg, 1.05 mmol) in one portion and the resulting solution was stirred under an atmosphere of nitrogen for 15 hours. The reaction mixture was diluted with a mixture of DCM and MeOH (3:1, respectively, 20 mL) and washed with water (10 mL) followed by sat. aq. $NH_4Cl$ (10 mL). The layers were separated, and the aqueous layer was further extracted with a mixture of DCM and MeOH (3:1, respectively, 20 mL). The combined organics were washed with brine (10 mL), then dried over magnesium sulfate, filtered and concentrated. The crude material was purified by flash chromatography eluting with a gradient of ethyl acetate in heptane, followed by a gradient of methanol in ethyl acetate to afford the title compound (403 mg, 73% yield). LCMS $[M+H]^+$ 524, RT 1.75 min (Method 1).

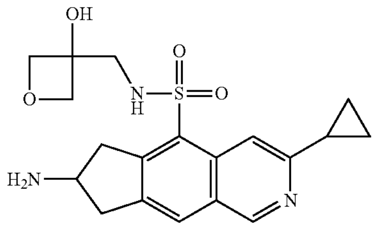 [SMILES: NC1Cc2cc3cnc(C4CC4)cc3c(S(=O)(=O)NCC3(O)COC3)c2C1]

7-amino-3-cyclopropyl-N-[(3-hydroxyoxetan-3-yl) methyl]-7,8-dihydro-6H-cyclopenta[g]isoquinoline-5-sulfonamide To a stirring suspension of Intermediate 45 (403 mg, 0.77 mmoL) in methanol (30 mL) was added 10% palladium on charcoal (50% wet, 230 mg, 0.11 mmoL) and the mixture was stirred under 1 atmosphere of hydrogen for 3 hours to give a solution. 10% palladium on charcoal (50% wet, 160 mg, 0.075 mmol) was added and the solution was stirred under 1 atmosphere of hydrogen for an additional 3 hours. The reaction was filtered through celite, washed through with methanol and the filtrate was concentrated to dryness to afford the title compound (284 mg, 95% yield). LCMS $[M+H]^+$ 390, RT 1.25 min (Method 1).

Intermediate 47

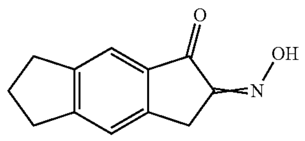 [SMILES: O=C1C(=NO)Cc2cc3c(cc21)CCC3]

2-hydroxyimino-3,5,6,7-tetrahydro-s-indacen-1-one

To a solution of 3,5,6,7-tetrahydro-2H-s-indacen-1-one (1.00 g, 5.81 mmol) in diethyl ether (18 mL) at +5° C. was introduced hydrogen chloride (0.22 mL of a saturated ethanolic solution) followed by dropwise addition of ethyl nitrite (5.12 mL of a 15% solution in ethanol, 10.24 mmol). The solution was cooled to 0° C. for 30 minutes and the resulting precipitate collected by filtration. After washing the filter-cake with diethyl ether, it was dried at the filter to furnish the title product (0.571 g, 46% yield). $\delta_H$ (500 MHz, $d_6$-DMSO) 12.51 (s, 1H), 7.53 (s, 1H), 7.41 (s, 1H), 3.67 (s, 2H), 2.92 (t, J=7.4 Hz, 2H), 2.88 (t, J=7.4 Hz, 2H), 2.05 (p, J=7.4 Hz, 2H); LCMS $[M+H]^+$ 202, RT 1.67 min (Method 1).

Intermediate 48

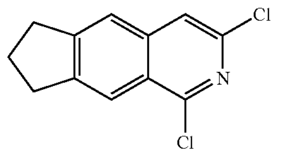 [SMILES: Clc1cc2cc3c(cc2c(Cl)n1)CCC3]

1,3-dichloro-7,8-dihydro-6H-cyclopenta[g]isoquinoline

To a solution of Intermediate 47 (0.570 g, 2.67 mmol) in phosphoryl chloride (28 g) at 0° C. under an atmosphere of nitrogen was introduced phosphorus pentachloride (0.67 g, 3.20 mmol). Gaseous hydrogen chloride was then slowly bubbled through the reaction mixture for 5 minutes. The reaction was warmed to 60° C. for 4 hours under an atmosphere of nitrogen then cooled to room temperature and re-treated with phosphorus pentachloride (0.22 g, 1.05 mmol). After warming to 80° C. for 2 hours, the reaction mixture was concentrated in-vacuo and the residue quenched with water (20 mL). The resulting mixture was subjected to sonication and stirring to furnish a suspension which was filtered. Drying the filter-cake at the filter afforded the title compound (0.994 g, quantitative, salt form not identified). $\delta_H$ (500 MHz, $d_6$-benzene) 7.82 (s, 1H), 7.10 (s, 1H), 6.79 (s, 1H), 2.50 (app. q, J=6.8 Hz, 4H), 1.64 (app. p, J=7.4 Hz, 2H); LCMS $[M+H]^+$ 238/240, RT 2.13 min (Method 1). This material was used for the next synthetic step without further purification.

Intermediate 49

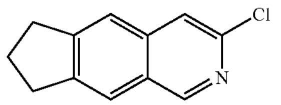 [SMILES: Clc1cc2cc3c(cc2cn1)CCC3]

3-chloro-7,8-dihydro-6H-cyclopenta[g]isoquinoline

To a solution of Intermediate 48 (0.994 g, 2.67 mmol) in glacial acetic acid (3.0 mL) were introduced red phosphorus (0.209 g, 6.75 mmol) and hydrogen iodide (2.10 g of a 57% aqueous solution, 5.50 mmol). The reaction mixture was warmed to 80° C. for 4 hours under an atmosphere of nitrogen. After cooling to room temperature, the reaction mixture was concentrated in-vacuo and the residue suspended in water (7 mL). Concentrated aqueous ammonia was introduced until the pH was basic and the precipitous mass broken down to a fine suspended solid by sonication. The solid was collected by filtration and the filter-cake washed with water (3 mL) and dried at the filter. The dried solid was dissolved in dichloromethane (60 mL) and insoluble material removed by filtration, washing the filter-cake with dichloromethane (20 mL). After the combined filtrates were washed with brine (10 mL) and dried over magnesium sulfate, decolourlising carbon (~1 g powder) was added and the solution was swirled for 30 seconds before filtering through a shallow bed of kieselguhr (vacuum filtration). The filtrate was concentrated in-vacuo to furnish the title compound (0.899 g, 83% pure, quantitative). $\delta_H$ (500 MHz, d-chloroform) 8.96 (s, 1H), 7.76 (s, 1H), 7.63 (s, 1H), 7.57 (s, 1H), 3.11-3.05 (m, 4H), 2.18 (app. p, J=7.4 Hz, 2H); LCMS $[M+H]^+$ 204/206, RT 1.94 min (Method 1). This material was used for the next synthetic step without further purification.

Intermediate 50

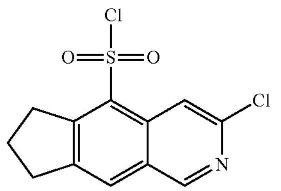 [SMILES: O=S(=O)(Cl)c1c2c(cc3cnc(Cl)cc13)CCC2]

3-chloro-7,8-dihydro-6H-cyclopenta[g]isoquinoline-5-sulfonyl chloride

A suspension of Intermediate 49 (9.290 g at 83% purity, 37.86 mmol) in chlorosulfonic acid was warmed to 80° C. for 16 hours under an atmosphere of nitrogen. After cooling to room temperature, the reaction mixture was concentrated in-vacuo and the residual oil quenched by slowly pouring onto ice (750 mL) with vigorous stirring. The resulting suspension was filtered (vacuum filtration) and the filter-cake re-suspended in water (10 mL) and the solid isolated by filtration. After air drying at the filter and in a vacuum oven at 40° C., the title compound was isolated as a grey powder (15.79 g, 60% estimated purity by $^1$H NMR, 83% yield). LCMS $[M+H]^+$ 302/304, RT 2.04 min (Method 1). This material was used for the next synthetic step without further purification.

Intermediate 51

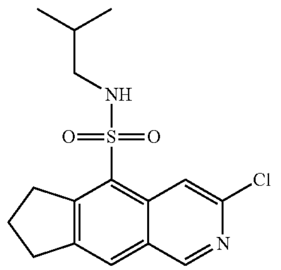 [SMILES: CC(C)CNS(=O)(=O)c1c2c(cc3cnc(Cl)cc13)CCC2]

3-chloro-N-isobutyl-7,8-dihydro-6H-cyclopenta[g]isoquinoline-5-sulfonamide

To a solution of Intermediate 50 (15.8 g at 60% purity, 31.3 mmol) in dichloromethane (500 mL) a solution of isobutylamine (16.7 g, 228 mmol) in dichloromethane (50 mL) was added dropwise under an atmosphere of nitrogen. After 2 hours the reaction mixture was diluted with dichloromethane (500 mL) and washed with water (2×200 mL) followed by brine (1×100 mL). The organic phase was dried over sodium sulfate and filtered through a shallow bed of kieselguhr (vacuum filtration). After concentrating the filtrate in-vacuo, the residue was purified by column chromatography eluting with a gradient of ethyl acetate in heptane to furnish the title compound (6.18 g, 56% yield) as a solid. $\delta_H$ (500 MHz, d-chloroform) 9.00 (s, 1H), 8.62 (s, 1H), 7.94 (s, 1H), 4.72 (t, J=6.3 Hz, 1H), 3.57 (t, J=7.5 Hz, 2H), 3.12 (t, J=8.2 Hz, 2H), 2.71 (t, J=6.6 Hz, 2H), 2.19 (p, J=7.6 Hz, 2H), 1.65 (dp, J=13.4, 6.7 Hz, 1H), 0.79 (d, J=6.7 Hz, 6H); LCMS $[M+H]^+$ 339/341, RT 1.96 min (Method 1).

Intermediate 52

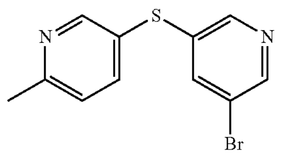

3-bromo-5-[(6-methyl-3-pyridyl) sulfanyl]pyridine

Nitrogen was bubbled through N-methylpyrrolidone (1.5 mL) for 10 minutes, then 6-methylpyridine-3-thiol** [100 mg at 70% purity, 0.56 mmol] was introduced. Separately, a pressure tube was charged with 3-bromo-5-iodo-pyridine (380 mg, 2.4 mmol) and potassium tert-butoxide (98 mg, 0.879 mmol). The 6-methylpyridine-3-thiol solution was introduced to the pressure tube, nitrogen bubbled through the mixture for a further 5 minutes then $Pd_2(dba)_3$ (73 mg, 0.080 mmol) and (oxydi-2,1-phenylene)bis(diphenylphosphine) (559 mg, 1.038 mmol) added. The pressure tube was closed and warmed to 90° C. for 70 minutes. The reaction mixture was concentrated in-vacuo to a volume of 5 mL then dichloromethane (30 mL) introduced to generate a precipitous solution. After removing the insoluble material by vacuum filtration, the filtrate was partially purified by column chromatography eluting with a gradient of 0-4% by volume of 7 M methanolic ammonia in dichloromethane to furnish the title compound (5.51 g at 50% purity LCMS-$UV_{215}$). LCMS $[M+H]^+$281/283, RT 2.36 (Method 2). $^1$H NMR disclosed the presence of 16 mol equivalents of N-methylpyrrolidone. This material was taken on to the next synthetic step without further purification.

**Prepared in two steps from 5-bromo-2-methyl-pyridine according to US2009/156642 and EP1806337 (2007).

Intermediate 53

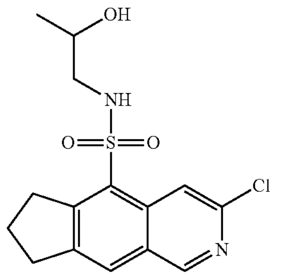 [SMILES: CC(O)CNS(=O)(=O)c1c2c(cc3cnc(Cl)cc13)CCC2]

3-chloro-N-(2-hydroxypropyl)-7,8-dihydro-6H-cyclopenta[g]isoquinoline-5-sulfonamide To a solution of 1-aminopropan-2-ol (0.058 mL, 0.75 mmol) and triethylamine (0.14 mL, 0.99 mmol) in anhydrous DCM (5 mL) was added Intermediate 50 (150 mg, 0.5 mmoL) and the resulting solution was stirred for 1 hour at room temperature under an atmosphere of nitrogen. The mixture was diluted with DCM (15 mL), washed with sat. aq. $NH_4Cl$ (10 mL), water (10 mL), brine (10 mL), then dried over magnesium sulfate, filtered and concentrated. The crude material was purified by flash column chromatography eluting with a gradient of ethyl acetate in heptane to afford the title compound (107 mg, 63% yield). $\delta_H$ (250 MHz, Chloroform-d) 9.00 (s, 1H), 8.62 (s, 1H), 7.95 (s, 1H), 5.30-5.18 (m, 1H), 3.96-3.77 (m, 1H), 3.57 (t, J=7.5 Hz, 2H), 3.12 (td, J=7.6, 1.2 Hz, 2H), 3.02 (ddd, J=12.9, 7.4, 3.3 Hz, 1H), 2.74 (ddd, J=13.0, 7.9, 5.1 Hz, 1H), 2.19 (p, J=7.6 Hz, 2H), 1.83 (br. s, 1H), 1.12 (d, J=6.3 Hz, 3H). LCMS $[M+H]^+$ 341, RT 1.71 min (Method 1).

Intermediate 54

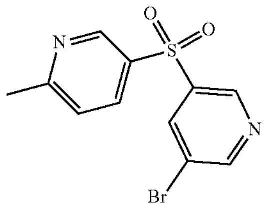 [SMILES: Cc1ccc(S(=O)(=O)c2cncc(Br)c2)cn1]

5-[(5-bromo-3-pyridyl) sulfonyl]-2-methyl-pyridine

To a solution of intermediate 52 (1.65 g at 50% purity LCMS-$UV_{215}$ containing 16 mol equivalents of N-methylpyrrolidone, estimated 125 mg, 0.445 mmol) in dichloromethane (10 mL) at room temperature was introduced 3-chloroperoxybenzoic acid (410 mg at 75% purity, 1.778 mmol) in one portion. After 24 hours, the reaction mixture was re-treated with 3-chloroperoxybenzoic acid (150 mg at 75% purity, 0.654 mmol) and allowed to continue for a further 24 hours. Dichloromethane (10 mL) and 10% w/v aqueous sodium sulphite (6 mL) were introduced and the two-phase mixture stirred vigorously for 15 minutes. The phases were separated, and the aqueous phase extracted with dichloromethane (10 mL). After washing the pooled dichloromethane extracts with saturated aqueous sodium carbonate (2×10 mL) and drying over sodium sulfate, the extracts were filtered and concentrated in-vacuo. The residue was purified by HPLC Method 3 to furnish the title compound (88.5 mg, estimated yield 63%) as a solid. $\delta_H$ (500 MHz, d-chloroform) 9.05 (d, J=2.4 Hz, 1H), 9.04 (d, J=2.0 Hz, 1H), 8.86 (d, J=2.1 Hz, 1H), 8.34 (t, J=2.1 Hz, 1H), 8.10 (dd, J=8.3, 2.5 Hz, 1H), 7.35 (d, J=8.3 Hz, 1H), 2.66 (s, 3H); LCMS $[M+H]^+$ 313/315, RT 2.44 min (Method 2).

Intermediate 55

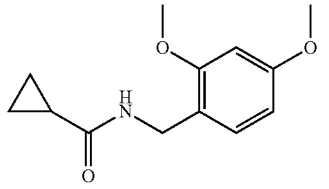 [SMILES: COc1ccc(CNC(=O)C2CC2)c(OC)c1]

N-[(2,4-dimethoxyphenyl)methyl]cyclopropanecarboxamide

Cyclopropanecarbonyl chloride (5.5 mL, 60.6 mmol) was added to a stirred solution of triethylamine (10 mL, 0.07 mol) in DCM (250 mL) at 0° C., followed by dropwise addition of 1-(2,4-dimethoxyphenyl) methanamine (10.4 g, 62.2 mmol). The solution was allowed to warm to room temperature and stirred for 15 minutes before being diluted with water (50 mL) and washed with sat. aq. $NH_4Cl$ (2×100 mL), followed by sat. aq. $NaHCO_3$ (100 mL) and then brine (50 mL). Dried over $MgSO_4$, filtered and concentrated under reduced pressure to give the title compound (14.6 g, quantitative). δη (250 MHz, d-chloroform) 7.19 (d, J=8.0 Hz, 1H), 6.49-6.37 (m, 2H), 6.02 (s, 1H), 4.38 (d, J=5.7 Hz, 2H), 3.84 (s, 3H), 3.80 (s, 3H), 1.36-1.22 (m, 1H), 1.02-0.87 (m, 2H), 0.76-0.57 (m, 2H). LCMS $[M+H]^+$ 236.2, RT 1.55 min (Method 1).

Intermediate 56

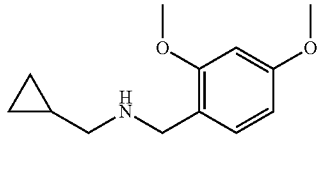 [SMILES: COc1ccc(CNCC2CC2)c(OC)c1]

N-(cyclopropylmethyl)-1-(2,4-dimethoxyphenyl) methanamine

A solution of Intermediate 55 (14.3 g, 60.6 mmol) in THF (250 mL) was cooled to 0° C. and 4 M $LiAlH_4$ in diethyl ether (18.2 mL) was added dropwise. The reaction mixture was stirred at this temperature for 15 minutes and then allowed to warm to room temperature and stirred for 30 minutes before being heated to 75° C. for 20 hours. The reaction mixture was then cooled to 0° C. and stirred rapidly whilst water (2.5 mL) was carefully added dropwise (gas evolution). This was followed by addition of 15% aq. NaOH (2.5 mL) and then water (7.5 mL). The white suspension was allowed to warm to room temperature and stirred for 30 minutes. Diethyl ether (100 mL) was added, and the suspension stirred for a further 15 minutes before filtering through Celite, washing through with diethyl ether. The filtrate was concentrated under reduced pressure and purified by column chromatography with a gradient of methanol in dichloromethane. The product containing residue was dissolved in DCM (50 mL) and washed with 2 M NaOH (2×50 mL), followed by brine. Dried over $MgSO_4$, filtered and concentrated under reduced pressure to give the title compound (6.68 g, 50%). $\delta_H$ NMR (500 MHz, Chloroform-d) 7.12 (d, J=8.1 Hz, 1H), 6.46-6.39 (m, 2H), 3.80 (s, 3H), 3.79 (s, 3H), 3.73 (s, 2H), 2.43 (d, J=6.9 Hz, 2H), 1.01-0.91 (m, 1H), 0.47-0.41 (m, 2H), 0.08-0.04 (m, 2H). 1×exchangeable proton not observed.

Intermediates 57

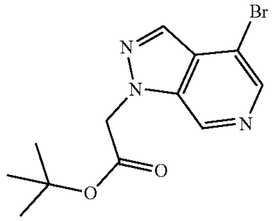 [SMILES: CC(C)(C)OC(=O)Cn1ncc2c(Br)cncc21]

tert-butyl 2-(4-bromopyrazolo[3,4-c]pyridin-1-yl) acetate (57)

4-Bromo-1H-pyrazolo[3,4-c]pyridine (200 mg, 1.01 mmol) was dissolved in THF (5 mL) and tert-butyl bromoacetate (164 μL, 1.11 mmol) was added followed by 2-tert-Butylimino-2-diethylamino-1,3-dimethylperhydro-1,3,2-diazaphosphorine (322 μL, 1.11 mmol). The reaction mixture was left to stand for 4 hours at room temperature before removing the solvent under a flow of $N_2$. The residue was purified column chromatography with a gradient of ethyl acetate in heptane to give the title compound (110 mg, 35%); OH NMR (500 MHz, Chloroform-d) 8.82 (s, 1H), 8.43 (s, 1H), 8.12 (d, J=0.6 Hz, 1H), 5.15 (s, 2H), 1.45 (s, 9H). LCMS $[M+H]^+$ 312/314, RT 1.81 min (Method 1).

Intermediate 58

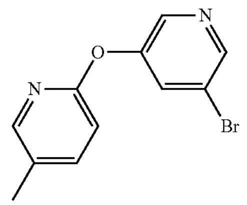

3-bromo-5-[(6-methyl-3-pyridyl)oxy]pyridine

A mixture of 3-bromo-5-fluoropyridine (200 mg, 1.14 mmoL), 6-methylpyridin-3-ol (149 mg, 1.36 mmoL) and potassium carbonate (236 mg, 1.71 mmoL) in DMF (4 mL) was heated in the microwave reactor at 200° C. for 30 minutes. The reaction mixture was diluted with 3 M aq. LiCl (10 mL) and extracted with DCM (3×10 mL). The combined organics were dried over magnesium sulfate, filtered and concentrated. The crude material was purified by flash chromatography eluting with a gradient of ethyl acetate in heptane to afford the title compound (165 mg, 53% yield). $\delta_H$ (500 MHz, DMSO-d6) 8.51 (d, J=1.9 Hz, 1H), 8.40 (d, J=2.5 Hz, 1H), 8.35 (d, J=2.9 Hz, 1H), 7.76 (t, J=2.2 Hz, 1H), 7.52 (dd, J=8.5, 2.9 Hz, 1H), 7.33 (d, J=8.5 Hz, 1H), 2.48 (s, 3H). LCMS $[M+H]^+$ 265/267, RT 1.56 min (Method 1).

Intermediate 59

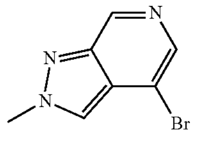

4-bromo-2-methyl-pyrazolo[3,4-c]pyridine

To NaH (60%, 242 mg, 6.06 mmol) under nitrogen was added dry DMF (8 mL) and the mixture was cooled in an ice bath. 4-bromo-1H-pyrazolo[3,4-c]pyridine (1 g, 5.05 mmol) was added and the mixture stirred while warming to room temperature over 30 minutes. Iodomethane (346 μl, 5.55 mmol) was added and the resulting orange solution was stirred for 1 hour. Water (40 mL) was added carefully and the mixture extracted with a 1:1 mixture of IPA and $CHCl_3$ (4×20 mL), dried over sodium sulfate and concentrated under vacuum. The crude material was purified by column chromatography to afford the title compound (315 mg, 29% yield). $\delta_H$ (250 MHz, Chloroform-d) 9.14 (s, 1H), 8.26 (s, 1H), 7.99 (s, 1H), 4.31 (s, 3H). LCMS $[M+H]^+$ 212/214, RT 1.04 min (Method 1).

Intermediate 60

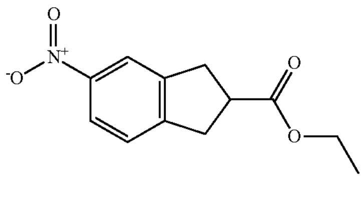

ethyl 5-nitroindane-2-carboxylate

Sulfuric acid (5 mL, 93.8 mmol) was added to 5-nitroindane-2-carboxylic acid [Synthesised according to the procedure in U.S. Pat. No. 6,262,087 B1, 2001] (20.3 g, 73.4 mmol) in EtOH (220 mL) and the reaction mixture heated at 70° C. for 3 h. The mixture was then conc. in vacuo to 20% of the original volume, diluted with DCM (150 mL) and $H_2O$ (100 mL) and the phases separated. The aqueous was extracted with DCM (2×100 mL), and the combined organics dried and conc. in vacuo to give the title compound (25.8 g) which was taken forward without purification. LCMS $[M+H]^+$ was not observed (did not ionise) RT 1.10 min (Method 6).

Intermediate 61

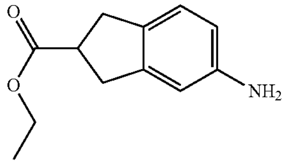

ethyl 5-aminoindane-2-carboxylate

A stirred solution of intermediate 60 (25.8 g, 82.2 mmol) in EtOH (220 mL) at room temperature was placed under an atmosphere of $N_2$. Palladium on carbon (2.5 g, 2.3 mmol) was added and the reaction mixture placed under an atmosphere of $H_2$. After 20 h, the reaction mixture was filtered through celite (200 mL EtOH washings) and conc. in vacuo. Purification by column chromatography eluting with 0-40% EtOAc in iso-hexane gave the title compound (14.2 g, 83% Yield). LCMS $[M+H]^+$ 206, RT 1.36 min (Method 7).

Intermediates 62

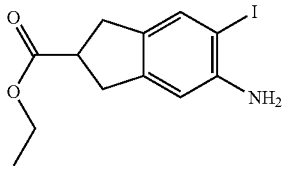 [SMILES: CCOC(=O)C1Cc2cc(N)c(I)cc2C1]

ethyl 5-amino-6-iodo-indane-2-carboxylate (62)

To a stirred solution of intermediate 61 (14.3 g, 69.3 mmol) in MeOH (300 mL) in an ice-bath was added silver sulfate (21.6 g, 69.3 mmol) followed by iodine (17.6 g, 69.3 mmol) in four portions over 5 min. After a further 5 min, the reaction warmed to room temperature and stirred for 6 h. The mixture was conc. in vacuo to 150 mL, filtered (400 mL MeOH washings) and conc. in vacuo to 50 mL. EtOAc (400 mL) and 10% aq. $Na_2SO_3$ (200 mL) were added to the solution. The aqueous was extracted with EtOAc (2×200 mL) and the combined organics dried and conc. in vacuo. Purification by column chromatography eluting with 0-15% EtOAc in iso-hexane gave the title compound (17.0 g, 50% Yield, 68% pure by LCMS). LCMS $[M+H]^+$ 332, RT 1.13 min (Method 6).

Intermediate 63

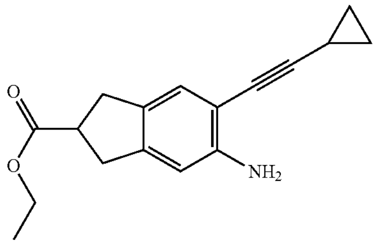 [SMILES: CCOC(=O)C1Cc2cc(N)c(C#CC3CC3)cc2C1]

ethyl 5-amino-6-(2-cyclopropylethynyl) indane-2-carboxylate

To a stirred solution of intermediates 62 (17.0 g, 34.6 mmol, 68% pure) in THF (200 mL) at room temperature were added cuprous iodide (660 mg, 3.44 mmol), bis(triphenylphosphine) palladium (II) dichloride (1.82 g, 2.59 mmol) and TEA (17 mL, 122 mmol). The reaction was purged with $N_2$ for 5 min prior to the addition of cyclopropylacetylene (6.2 mL, 70 mmol). After 17 h, the reaction mixture was filtered through celite (washing with EtOAc) and conc. in vacuo. Purification by column chromatography eluting with 0-40% EtOAc in iso-hexane gave the title compound (13.9 g, 89% Yield, 60% pure by LCMS). LCMS $[M+H]^+$ 270, RT 1.20 min (Method 6).

Intermediate 64

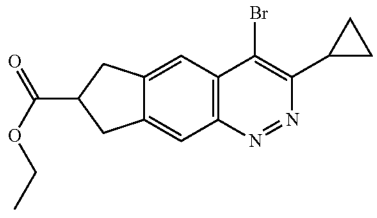 [SMILES: CCOC(=O)C1Cc2cc3nnc(C4CC4)c(Br)c3cc2C1]

ethyl 4-bromo-3-cyclopropyl-7,8-dihydro-6H-cyclopenta[g]cinnoline-7-carboxylate

To a stirred solution of intermediate 63 (13.9 g, 30.9 mmol, ~60% pure) in MeCN (250 mL) were added cupric bromide (70 mg, 0.31 mmol), (1S)-(+)-10-camphorsulfonic acid (9.73 g, 41.9 mmol) and tetrabutylammonium bromide (20.2 g, 62.2 mmol). The solution was immersed in an ice-bath and tert-butyl nitrite (5.3 mL, 40 mmol) added. After 5 min, the reaction was stirred at room temperature for 1 h then conc. in vacuo to 80 mL and filtered through silica (150 mL, 50% EtOAc in iso-hexane washings) and conc. in vacuo. Purification by column chromatography eluting with 0-30% EtOAc in iso-hexane gave the title compound (5.42 g, 49% Yield). LCMS $[M\{^{79}Br\}+H]^+$ 361, RT 1.28 min (Method 6).

Intermediate 65

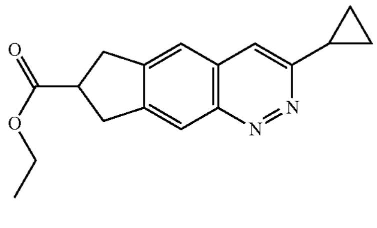 [SMILES: CCOC(=O)C1Cc2cc3cc(C4CC4)nnc3cc2C1]

ethyl 3-cyclopropyl-7,8-dihydro-6H-cyclopenta[g]cinnoline-7-carboxylate

To a stirred solution of intermediate 64 (1.43 g, 3.38 mmol) in MeCN (50 mL) were added DIPEA (14 mL) and tetrakis(triphenylphosphine) palladium (0) (230 mg, 0.197 mmol). The resultant mixture was purged with $N_2$ for 5 min then heated to 100° C. in a sealed vessel for 26 h. The reaction mixture was diluted with DCM (200 mL) and $H_2O$ (150 mL) and the phases separated. The aqueous was extracted with DCM (3×50 mL), the combined organics dried and conc. in vacuo. Purification by column chromatography eluting with 0-60% EtOAc in iso-hexane gave the title compound (905 mg, 92% Yield). LCMS $[M+H]^+$ 283, RT 1.43 min (Method 7).

Intermediate 66

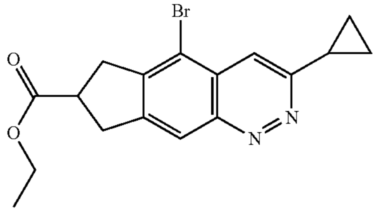 [SMILES: CCOC(=O)C1Cc2cc3nnc(C4CC4)cc3c(Br)c2C1]

ethyl 5-bromo-3-cyclopropyl-7,8-dihydro-6H-cyclopenta[g]cinnoline-7-carboxylate

To a stirred solution of intermediate 65 (3.97 g, 14.1 mmol) in DCM (250 mL) at 0° C. was slowly added methanesulfonic acid (170 mL) followed by portion-wise addition of N-bromosuccinimide (2.64 g, 14.1 mmol). After 16 h, the reaction mixture was slowly poured into sat. $Na_2CO_3$ (400 mL) at 0° C. followed by copious addition of $Na_2CO_3$. The reaction mixture was diluted with DCM (50 mL) and the phases separated. The aqueous was extracted with DCM (3×100 mL), the combined organics dried and conc. in vacuo. Purification by basic reverse phase column chromatography eluting with 0-60% MeCN in $H_2O$ gave the title compound (1.07 g, 21% Yield). LCMS $[M\{^{79}Br\}+H]^+$ 361, RT 1.23 min (Method 6).

Intermediate 67

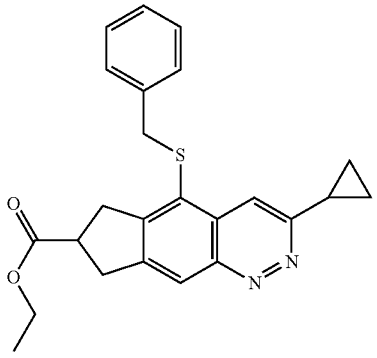 [SMILES: CCOC(=O)C1Cc2cc3nnc(C4CC4)cc3c(SCc3ccccc3)c2C1]

ethyl 5-benzylsulfanyl-3-cyclopropyl-7,8-dihydro-6H-cyclopenta[g]cinnoline-7-carboxylate To a stirred solution of intermediate 66 (4.41 g, 12.2 mmol) in 1,4-dioxane (80 mL) were added XantPhos Pd G3 (1.80 g, 1.80 mmol) and DIPEA (5.3 mL, 30 mmol). The mixture was purged with $N_2$ for 5 min before benzyl mercaptan (1.7 mL, 14 mmol) was added. The resultant reaction mixture was then heated to 120° C. in a sealed vessel for 24 h then filtered through celite (200 mL, EtOAc washings) and conc. in vacuo. Purification by column chromatography eluting with 0-40% EtOAc in iso-hexane gave the title compound (5.11 g, 96% Yield). LCMS $[M+H]^+$ 405, RT 1.38 min (Method 6).

Intermediate 68

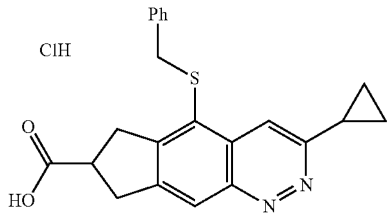 [SMILES: O=C(O)C1Cc2cc3nnc(C4CC4)cc3c(SCc3ccccc3)c2C1 ; Cl]

5-benzylsulfanyl-3-cyclopropyl-7,8-dihydro-6H-cyclopenta[g]cinnoline-7-carboxylic acid hydrochloride To a stirred solution of intermediate 67 (5.19 g, 11.9 mmol) in a mixture of THF (60 mL) and $H_2O$ (40 mL) was added lithium hydroxide monohydrate (1.50 g, 35.8 mmol). The reaction mixture was heated at 50° C. for 30 min then conc. in vacuo and acidified with 1 N HCl (100 mL). The resultant precipitate was collected by filtration then dried in vacuo to give the title compound (3.20 g) as an HCl salt. The filtrate was diluted with EtOAc (350 ml containing a few mL MeOH) and the phases separated. The aqueous was extracted with EtOAc (3×100 mL containing a few ml of MeOH) and the combined organics dried and conc. in vacuo to give a second crop of the title compound as an HCl Salt (1.24 g). In total 4.4 g of product were isolated (97% Yield). LCMS $[M+H]^+$ 377, RT 1.28 min (Method 7).

Intermediate 69

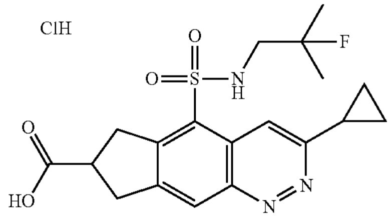 [SMILES: CC(C)(F)CNS(=O)(=O)c1c2c(cc3nnc(C4CC4)cc13)CC(C(=O)O)C2 ; Cl]

3-cyclopropyl-5-[(2-fluoro-2-methyl-propyl) sulfamoyl]-7,8-dihydro-6H-cyclopenta[g]cinnoline-7-carboxylic acid hydrochloride To a suspension of intermediate 68 (1.00 g, 2.62 mmol) in a mixture of MeCN (20 mL), DCM (20 mL), acetic acid (750 μL, 13.1 mmol) and $H_2O$ (240 μL, 13.3 mmol) at 0° C. was added 1,3-dichloro-5,5-dimethylhydantoin (875 mg, 4.44 mmol). After 1 h 15 min, further 1,3-dichloro-5,5-dimethylhydantoin (100 mg, 0.51 mmol) was added. After 25 min, the reaction mixture was cooled to −5° C. and added to a pre-stirred solution of 2-fluoro-2-methylpropan-1-amine HCl (1.34 g, 10.5 mmol) and DIPEA (1.9 mL, 11 mmol) in DCM (40 mL) at 0° C. After 15 min, the reaction mixture was diluted with 2 N HCl (50 mL) and $H_2O$ (50 mL) and the precipitate collected by filtration to give the title compound as an HCl salt (388 mg, 35% Yield). LCMS $[M+H]^+$ 408, RT 0.67 min (Method 6).

Intermediate 70

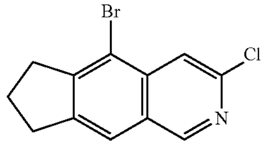 [SMILES: Clc1cc2c(Br)c3c(cc2cn1)CCC3]

5-bromo-3-chloro-7,8-dihydro-6H-cyclopenta[g]isoquinoline

Sulfuric acid (7.5 mL) was added to a flask containing Intermediate 49 (0.770 g, 3.78 mmol) and N-bromosuccinimide (478 mg, 2.66 mmol) under an atmosphere of nitrogen at 0° C. The reaction was stirred for 2.5 h during which time the ice bath was allowed to warm to room temperature. 1.5 hours into the reaction additional N-bromosuccinimide was added (278 mg, 1.55 mmol). The reaction was slowly added into ice water (~150 mL) and the pH of the solution adjusted to ~ 9 by the addition of concentrated ammonium hydroxide (~24 mL). The aq. solution was extracted with DCM (3×100 mL) and the combined organic layers passed through a phase separator, concentrated in vacuo and purified by column chromatography on silica (gradient elution with 0% to 10% EtOAc in isohexanes) to give the title compound (723 mg, 68% Yield). $^1H$ NMR (400 MHz, Chloroform-d) δ 8.93 (s, 1H), 8.01 (s, 1H), 7.71 (s, 1H), 3.25-3.14 (m, 4H), 2.23 (p, J=7.5 Hz, 2H). LCMS $[M+H]^+$ 281.6/283.6/285.6, RT 1.76 min (Method 7).

Intermediate 71

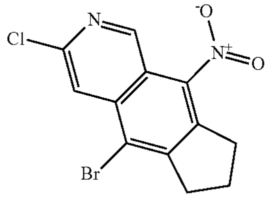

5-bromo-3-chloro-9-nitro-7,8-dihydro-6H-cyclopenta[g]isoquinoline

Potassium nitrate (282 mg, 2.79 mmol) was added to a solution of Intermediate 70 (0.723 g, 2.56 mmol) in sulfuric acid (7.5 mL) under an atmosphere of $N_2$ at 0° C. The reaction was stirred at 0° C. for 1 h 20 min. The reaction mixture was slowly added into ice water (~150 mL) and the pH of the solution adjusted to pH ~ 9 by the addition of concentrated ammonium hydroxide (~22 mL). The aq. solution was extracted with DCM (3×100 mL) and the combined organic layers passed through a phase separator and concentrated in vacuo to give the title compound (800 mg, 95% Yield), which was used without further purification. $^1H$ NMR (400 MHz, Chloroform-d) δ 9.35 (s, 1H), 8.15 (s, 1H), 3.44 (t, J=7.6 Hz, 2H), 3.28 (t, J=7.6 Hz, 2H), 2.31 (p, J=7.6 Hz, 2H). LCMS $[M+H]^+$ 326.8/328.9/330.8, RT 1.71 min (Method 7).

Intermediate 72

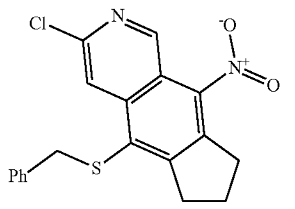

5-benzylsulfanyl-3-chloro-9-nitro-7,8-dihydro-6H-cyclopenta[g]isoquinoline

DIPEA (0.85 mL, 4.9 mmol) and benzyl mercaptan (0.30 mL, 2.5 mmol) were added to a solution of Intermediate 71 (760 mg, 2.32 mmol), 4,5-bis(diphenylphosphino)-9,9-dimethylxanthene (84.1 mg, 0.141 mmol) and tris(dibenzylideneacetone) dipalladium (0) (67.9 mg, 0.0741 mmol) in 1,4-dioxane (11.7 mL). The reaction was degassed and placed under nitrogen before stirring at 100° C. for 40 min. The reaction was cooled to room temperature and concentrated in vacuo. The residue was dissolved in DCM (50 mL) and washed with sat. aq. ammonium chloride (50 mL) followed by water (100 mL). The organic layer was passed through a phase separator, concentrated in vacuo and purified by column chromatography on silica (gradient elution with 0% to 100% EtOAc in isohexanes) to give the title compound (879 mg, quantitative). LCMS $[M+H]^+$ 370.8/372.8, RT 1.83 min (Method 7).

Intermediate 73

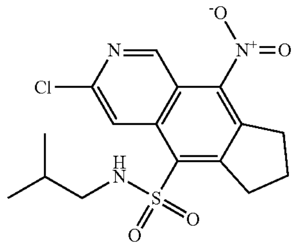

3-chloro-N-isobutyl-9-nitro-7,8-dihydro-6H-cyclopenta[g]isoquinoline-5-sulfonamide Water (0.12 mL) and acetic acid (0.07 mL) were added to a solution of Intermediate 72 (0.837 g, 2.26 mmol) in a mixture of DCM (10 mL) and MeCN (10 mL). The solution was cooled to −10° C. and 1,3-dichloro-5,5-dimethylhydantoin (0.895 g, 4.54 mmol) was added. The reaction was stirred for 0.5 h at −10° C. to −5° C. before the addition of isobutylamine (1.8 mL, 18 mmol). The reaction was stirred for a further 4 h whilst allowing the reaction to warm to 15° C. The reaction was then diluted with DCM (50 mL), washed with sat. aq. ammonium chloride (50 mL) and the aq. layer extracted with DCM (2×50 mL). The combined organic layers were passed through a phase separator, concentrated in vacuo and purified by column chromatography on silica (gradient elution with 0% to 50% EtOAc in isohexanes) to give the title compound (613 mg, 71% Yield). LCMS $[M+H]^+$ 383.8/385.8, RT 1.64 min (Method 7).

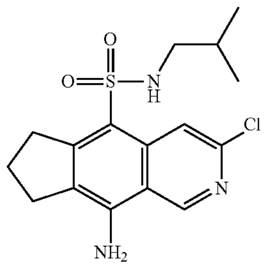 [SMILES: CC(C)CNS(=O)(=O)c1c2c(c(N)c3cnc(Cl)cc13)CCC2]

9-amino-3-chloro-N-isobutyl-7,8-dihydro-6H-cyclopenta[g]isoquinoline-5-sulfonamide Ammonium chloride (297 mg, 5.56 mmol) and zinc (377 mg, 5.65 mmol) were added to a solution of Intermediate 73 (202.0 mg, 0.5263 mmol) in a mixture of THF (4.2 mL) and MeOH (4.2 mL) under nitrogen. The reaction was stirred at room temperature for 1 h, filtered through a pad of Celite, washed through with EtOAc (100 mL) and conc. in vacuo. The resulting solid was suspended in DCM (50 mL), washed with water (25 mL) and passed through a phase separator. The solid that remained in the phase separator was washed through with MeOH and the solution was concentrated in vacuo. The solid that remained in the flask after filtering through Celite was dissolved in EtOAc (50 mL) washed with water (25 mL), passed through a phase separator, combined with the previous extractions and concentrated in vacuo to give the title compound (185 mg, 99% Yield), which was used without further purification. LCMS $[M+H]^+$ 354.0/356.0, RT 1.46 min (Method 7).

Intermediate 75

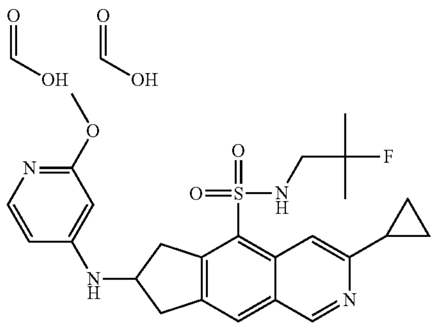

3-cyclopropyl-N-(2-fluoro-2-methyl-propyl)-7-[(2-methoxy-4-pyridyl)amino]-7,8-dihydro-6H-cyclopenta[g]isoquinoline-5-sulfonamide formic acid Intermediate 12 (50 mg, 0.13 mmol), 4-bromo-2-methoxypyridine (37.3 mg, 0.199 mmol), Sodium tert-butoxide (38.19 mg, 0.39 mmol), $Pd_2(dba)_3$ (12.1 mg, 0.013 mmol) and 2,2'-bis(diphenylphosphino)-1,1'-binaphthyl (16.5 mg, 0.026 mmol) were heated in dry toluene (1 mL) in a 20 mL pressure tube at 110° C. with stirring for 4 hours. Water (15 mL) was added and reaction extracted with DCM (3×10 mL). Organics dried over sodium sulphate and concentrated under vacuum. The brown residue was purified by acidic reverse phase HPLC to afford the title compound as a bis formate salt (35 mg, 46% yield). LCMS $[M+H]^+$ 485, RT 1.79 (Method 2).

Intermediates 76 & 77

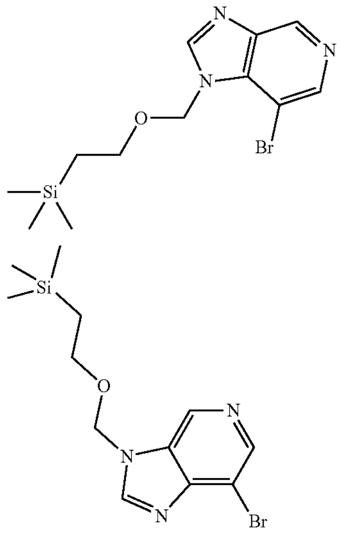

2-[(7-bromoimidazo[4,5-c]pyridin-1-yl) methoxy] ethyl-trimethyl-silane (76) 2-[(7-bromoimidazo[4,5-c]pyridin-3-yl) methoxy]ethyl-trimethyl-silane (77)

To a solution of 7-bromo-1H-imidazo[4,5-c]pyridine (100 mg, 0.5 mmol) in anhydrous THF (3 mL) was added sodium hydride (24.2 mg, 0.6 mmol) portion wise at 0° C. After stirring at 0° C. for 0.5 h, SEMCl (92.6 mg, 0.55 mmol) was added. The reaction mixture was stirred at room temperature for 5 hours, then poured into water and extracted with EtOAc (2×30 mL). The organic layers were dried ($Na_2SO_4$), filtered, and concentrated in vacuo. Crude product was purified by column chromatography using 50%-100% EtOAc in heptane to give title compounds (90 mg, 54% yield) as a ~1:1 mixture of intermediates 76 and 77. LCMS $[M+H]^+$ 328/330, RT 1.81 and 1.85 min (Method 1).

Intermediates 78 & 79

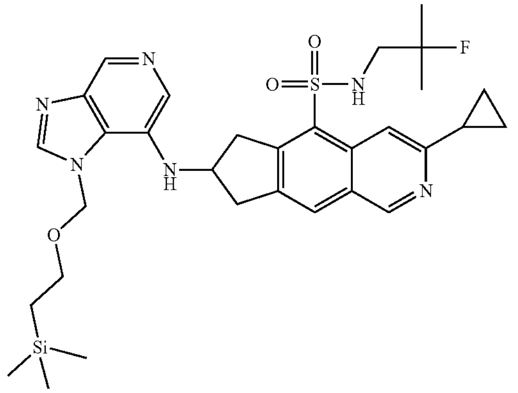

-continued

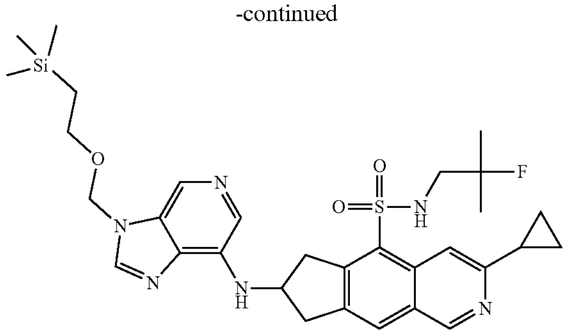

3-cyclopropyl-N-(2-fluoro-2-methyl-propyl)-7-[[1-(2-trimethylsilylethoxymethyl) imidazo[4,5-c]pyridin-7-yl]amino]-7,8-dihydro-6H-cyclopenta[g]isoquinoline-5-sulfonamide (78)

3-cyclopropyl-N-(2-fluoro-2-methyl-propyl)-7-[[3-(2-trimethylsilylethoxymethyl) imidazo[4,5-c]pyridin-7-yl]amino]-7,8-dihydro-6H-cyclopenta[g]isoquinoline-5-sulfonamide (79)

Prepared by General Procedure 1 from Intermediate 12 (50 mg, 0.13 mmol) and a 1:1 mixture of intermediates 76 and 77 (60.8 mg, 0.18 mmol). The crude was purified by column chromatography using 0% to 10% MeOH in DCM to afford a mixture of the title compounds (74 mg, 77%). LCMS $[M+H]^+$ 625, RT 1.84 and 1.88 min (Method 1).

Intermediates 80 & 81

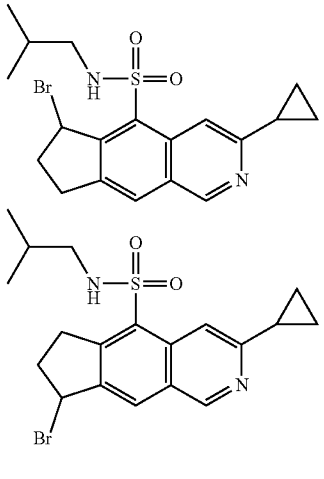

6-bromo-3-cyclopropyl-N-isobutyl-7,8-dihydro-6H-cyclopenta[g]isoquinoline-5-sulfonamide 8-bromo-3-cyclopropyl-N-isobutyl-7,8-dihydro-6H-cyclopenta[g]isoquinoline-5-sulfonamide To a solution of Intermediate Example 69 (500 mg, 1.452 mmol) in ethyl acetate (28 mL) was introduced AIBN (24 mg, 0.145 mmol) and N-bromosuccinimide (362 mg, 2.032 mmol). The reaction mixture was heated to reflux for 40 minutes under an atmosphere of nitrogen. After cooling to room temperature, the reaction mixture was adsorbed onto silica in-vacuo and the dry-loaded material purified by column chromatography using a gradient of ethyl acetate in heptane to furnish the title compounds as a 1:1 mixture of regioisomers (339 mg, 46% yield). LCMS $[M+H]^+$ 423/425, RT 2.03 min (Method 1).

Intermediate 82

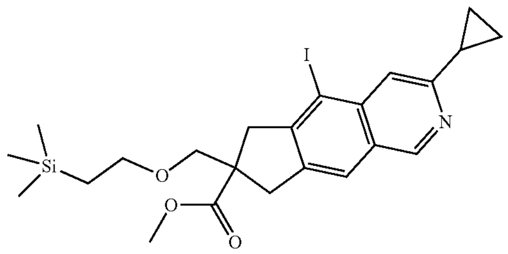 [SMILES: COC(=O)C1(COCC[Si](C)(C)C)Cc2cc3cnc(C4CC4)cc3c(I)c2C1]

methyl 3-cyclopropyl-5-iodo-7-(2-trimethylsilylethoxymethyl)-6,8-dihydrocyclopenta[g]isoquinoline-7-carboxylate To a solution of Intermediate 7 (400 mg, 1.017 mmol) in tetrahydrofuran (20 mL) at −78° C., a solution of 1 M LiHMDS in THF (2.03 mL, 2.03 mmol) was added. After 60 minutes a solution of SEMCl (509 mg, 3.05 mmol) in THF (3 mL) was introduced dropwise over 5 minutes. The reaction mixture was stirred at −78° C. for a further 60 minutes then quenched by addition of saturated aqueous ammonium chloride (2 mL) and the mixture warmed to room temperature. After concentrating in-vacuo to remove the tetrahydrofuran, the aqueous residue was diluted with ethyl acetate (40 mL). The organic layer was washed with saturated aqueous ammonium chloride (10 mL), water (2×10 mL) and brine (10 mL). The organic layer was then dried over magnesium sulfate, filtered and the filtrate purified by column chromatography eluting with a gradient of ethyl acetate in heptane to furnish the title compound (297 mg, 52% yield). $\delta_H$ (500 MHz, d-chloroform) 8.87 (s, 1H), 7.62 (s, 1H), 7.61 (s, 1H), 3.75 (s, 3H), 3.67 (dd, J=16.8, 1.4 Hz, 1H), 3.59 (d, J=8.9 Hz, 1H), 3.55 (d, J=8.9 Hz, 1H), 3.56-3.49 (m, 3H), 3.36 (dd, J=16.8, 1.0 Hz, 1H), 3.24 (d, J=17.7 Hz, 1H), 2.23 (tt, J=8.2, 4.9 Hz, 1H), 1.14-1.09 (m, 2H), 1.06-1.02 (m, 2H), 0.88 (dd, J=8.6, 7.3 Hz, 2H), −0.02 (s, 9H); LCMS $[M+H]^+$ 524, RT 2.42 (Method 1).

Intermediate 83

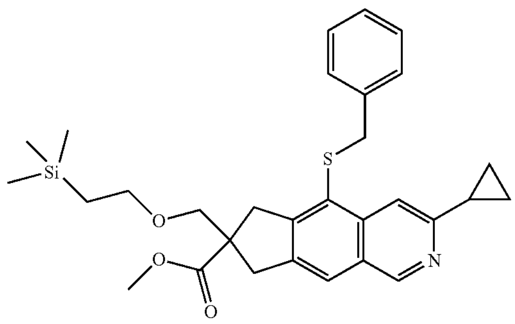 [SMILES: COC(=O)C1(COCC[Si](C)(C)C)Cc2cc3cnc(C4CC4)cc3c(SCc3ccccc3)c2C1]

methyl 5-benzylsulfanyl-3-cyclopropyl-7-(2-trimethylsilylethoxymethyl)-6,8-dihydrocyclopenta[g]isoquinoline-7-carboxylate Nitrogen was bubbled through a solution of Intermediate 82 (330 mg, 0.59 mmol) in anhydrous 1,4-dioxane (5 mL) for 5 minutes. Separately, nitrogen was bubbled through anhydrous 1,4-dioxane (1 mL) for 5 minutes, then benzyl mercaptan (117 mg, 0.946 mmol) and diisopropylethylamine (244 mg, 1.89 mmol) were introduced. Into a pressure tube were introduced $Pd_2(dba)_3$ (17 mg, 0.019 mmol), XantPhos (22 mg, 0.038 mmol), the Intermediate 82 solution and the benzyl mercaptan/diisopropylethylamine solution. The pressure tube was closed under an atmosphere of nitrogen and warmed to 100° C. for 100 minutes. After cooling to room temperature, the reaction mixture was diluted with ethyl acetate (40 mL) and washed with water (3×40 mL) followed by brine (20 mL). The organic phase was dried over magnesium sulfate, filtered and the filtrate purified by column chromatography eluting with a gradient of ethyl acetate in heptane to furnish the title compound (284 mg, 89% yield). $\delta_H$ (500 MHz, d-chloroform) 8.99 (s, 1H), 8.01 (s, 1H), 7.64 (s, 1H), 7.17-7.10 (m, 3H), 6.91 (dd, J=7.4, 2.0 Hz, 2H), 3.92 (d, J=12.8 Hz, 1H), 3.89 (d, J=12.8 Hz, 1H), 3.70 (s, 3H), 3.55-3.50 (m, 1H), 3.45 (ddd, J=9.0, 7.3, 2.2 Hz, 2H), 3.38 (d, J=9.0 Hz, 1H), 3.21 (d, J=17.7 Hz, 1H), 3.19 (dd, J=16.5, 1.1 Hz, 1H), 3.18 (d, J=9.0 Hz, 1H), 2.97 (d, J=17.7 Hz, 1H), 2.20 (tt, J=8.2, 4.9 Hz, 1H), 1.09 (tt, J=4.9, 2.2 Hz, 2H), 1.06-1.00 (m, 2H), 0.90-0.83 (m, 2H), −0.01 (s, 9H); LCMS $[M+H]^+$ 520, RT 1.78 min (Method 8).

Intermediate 84

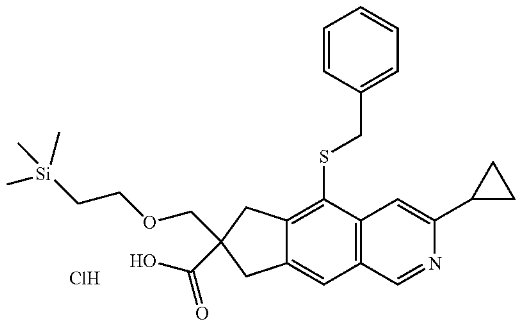 [SMILES: C[Si](C)(C)CCOCC1(C(=O)O)Cc2cc3cnc(C4CC4)cc3c(SCc3ccccc3)c2C1 ; Cl]

5-benzylsulfanyl-3-cyclopropyl-7-(2-trimethylsilylethoxymethyl)-6,8-dihydrocyclopenta[g]isoquinoline-7-carboxylic acid hydrochloride To a solution of Intermediate 83 (264 mg, 0.49 mmol) in tetrahydrofuran (5 mL) a solution of 2 M aqueous lithium hydroxide (0.38 mL, 0.76 mmol) was added. The reaction mixture was warmed to 40° C. for 11 hours then treated with additional 2 M aqueous lithium hydroxide (0.08 mL, 0.16 mmol) and the reaction continued at this temperature for a further 20 hours. After cooling to room temperature, the reaction mixture was diluted with water (10 mL) and concentrated in-vacuo to remove the tetrahydrofuran. The pH of the aqueous residue was adjusted to PH ~3 with 1 M aqueous hydrochloric acid and extracted with ethyl acetate (3×10 mL). The combined ethyl acetate extracts were washed with brine (10 mL), dried over magnesium sulfate, filtered and the filtrate concentrated in-vacuo to furnish the title compound as an HCl salt (239 mg, 92% yield). $\delta_H$ (500 MHz, d-chloroform) 9.02 (s, 1H), 8.00 (s, 1H), 7.65 (s, 1H), 7.15-7.09 (m, 3H), 6.93-6.87 (m, 2H), 3.91 (d, J=12.9 Hz, 1H), 3.89 (d, J=12.9 Hz, 1H), 3.58-3.50 (m, 3H), 3.38 (d, J=9.2 Hz, 1H), 3.34 (d, J=17.7 Hz, 1H), 3.21 (d, J=9.1 Hz, 1H), 3.19 (d, J=17.3 Hz, 1H), 2.98 (d, J=17.7 Hz, 1H), 2.21 (ddd, J=13.2, 8.1, 5.0 Hz, 1H), 1.08 (dt, J=5.2, 2.7 Hz, 2H), 1.05 (dt, J=8.3, 2.7 Hz, 2H), 0.93 (dd, J=9.1, 7.3 Hz, 2H), 0.00 (s, 9H); LCMS $[M+H]^+$ 506, RT 1.59 min (Method 8).

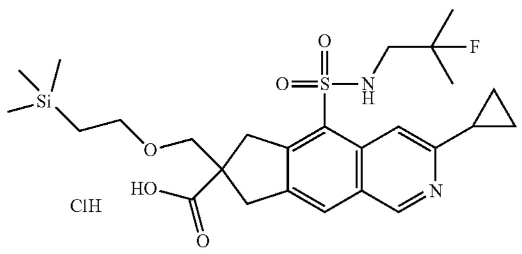 [SMILES: CC(C)(F)CNS(=O)(=O)c1c2c(cc3cnc(C4CC4)cc13)CC(COCC[Si](C)(C)C)(C(=O)O)C2 ; Cl]

3-cyclopropyl-5-[(2-fluoro-2-methyl-propyl) sulfamoyl]-7-(2-trimethylsilylethoxymethyl)-6,8-dihydrocyclopenta[g]isoquinoline-7-carboxylic acid hydrochloride To a solution of Intermediate 84 (853 mg, 1.60 mmol) in acetonitrile (14 mL) were introduced acetic acid (506 mg, 8.433 mmol), water (152 mg, 8.43 mmol) and 1,3-dichloro-5,5-dimethyl-imidazolidine-2,4-dione (665 mg, 3.37 mmol). After 30 minutes, the reaction mixture was treated with additional 1,3-dichloro-5,5-dimethyl-imidazolidine-2,4-dione (221 mg, 1.12 mmol) and stirred for 20 minutes during which time a solid precipitated. The solid was collected by vacuum filtration, washed on the filter with acetonitrile (5 mL) and air dried at the filter for 10 minutes to furnish a sulfonyl chloride intermediate which was dissolved in dichloromethane (14 mL). A solution of 2-fluoro-2-methyl-propan-1-amine hydrochloride (236 mg, 1.855 mmol) was added followed by a solution of diisopropylethylamine (763 mg, 5.903 mmol) in dichloromethane (5 mL). After 90 minutes, the reaction mixture was concentrated in-vacuo, the residue dissolved in ethyl acetate (50 mL) and washed with 1 M aqueous hydrochloric acid (2×10 mL) followed by brine (10 mL). The organic phase was dried over magnesium sulfate, filtered and the filtrate concentrated in-vacuo to furnish the title compound (790 mg, 80% yield over 2 steps) as an HCl Salt. $\delta_H$ (500 MHz, $d_6$-dmso) 9.23 (s, 1H), 8.46 (s, 1H), 8.45 (t, J=6.6 Hz, 1H), 8.13 (s, 1H), 3.90 (d, J=18.7 Hz, 1H), 3.59 (d, J=8.9 Hz, 1H), 3.54 (d, J=9.3 Hz, 1H), 3.50 (m, 3H), 3.41 (d, J=17.4 Hz, 1H), 3.15 (d, J=17.4 Hz, 1H), 3.02-2.86 (m, 2H), 2.33-2.29 (m, 1H), 1.16 (d, J=21.3 Hz, 3H), 1.09 (d, J=21.4 Hz, 3H), 1.09-1.07 (m, 4H), 0.84-0.81 (m, 2H),−0.02 (s, 9H). $\delta_F$ (235 MHz, d6-dmso, H-decoupled) −140.08; LCMS $[M+H]^+$ 537, RT 2.05 min (Method 1).

Intermediate 86

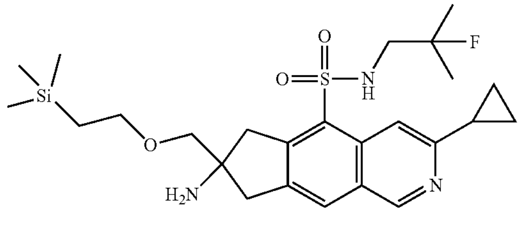 [SMILES: CC(C)(F)CNS(=O)(=O)c1c2c(cc3cnc(C4CC4)cc13)CC(N)(COCC[Si](C)(C)C)C2]

7-amino-3-cyclopropyl-N-(2-fluoro-2-methyl-propyl)-7-(2-trimethylsilylethoxymethyl)-6,8-dihydrocyclopenta[g]isoquinoline-5-sulfonamide To a solution of Intermediate 85 (737 mg, 1.19 mmol) in anhydrous tetrahydrofuran (22 mL) were introduced triethylamine (347 mg, 3.43 mmol) and diphenylphosphoryl azide (416 mg, 1.51 mmol). The reaction was warmed to 75° C. in a pressure vessel for 100 minutes under an atmosphere of nitrogen. After cooling to room temperature, the reaction mixture was poured into a rapidly stirred mixture of 1 M aqueous sodium hydroxide (40 mL) and tetrahydrofuran (40 mL) and stirring continued for 15 minutes. The pH of this mixture was adjusted to pH 7 by addition of acetic acid then to pH 8 with a 10:1 mixture of saturated aqueous sodium bicarbonate/2 M aqueous sodium carbonate. This solution was extracted with ethyl acetate (140 mL). The pH of the aqueous phase was then adjusted to pH 12 with 2 M aqueous sodium carbonate and this solution extracted with ethyl acetate (100 mL). The combined ethyl acetate extracts were washed with 2 M aqueous sodium carbonate (50 mL) and brine (50 mL), then dried over sodium sulfate and filtered through a shallow bed of kieselguhr. Concentration of the filtrate in-vacuo furnished an oil. Ethyl acetate (30 mL) was added and the solution allowed to stand until no more precipitation could be observed. The precipitate was removed by vacuum filtration and the filtrate concentrated in-vacuo to furnish the title compound (854 mg, 97% yield), which was used in the next step without additional purification. LCMS $[M+H]^+$ 508, RT 1.82 min (Method 1).

Intermediate 87

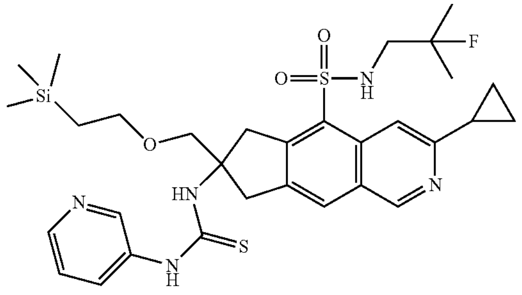 [SMILES: CC(C)(F)CNS(=O)(=O)c1c2c(cc3cnc(C4CC4)cc13)CC(COCC[Si](C)(C)C)(NC(=S)Nc1cccnc1)C2]

1-[3-cyclopropyl-5-[(2-fluoro-2-methyl-propyl) sulfamoyl]-7-(2-trimethylsilylethoxymethyl)-6,8-dihydrocyclopenta[g]isoquinolin-7-yl]-3-(3-pyridyl)thiourea To a solution of Intermediate 86 (425 mg at 69% purity LCMS-$UV_{215}$, 0.577 mmol) in anhydrous dichloromethane (20 mL), diisopropylethylamine (75 mg, 0.577 mmol) and a solution of 3-isocyanatopyridine (79 mg, 0.577 mmol) in DCM (1 mL) were added. After 17 hours at room temperature, the reaction mixture was adsorbed onto silica and the dry-loaded material purified by column chromatography eluting with a gradient of ethyl acetate in heptane to furnish the title compound (305 mg, 79% yield) as a colourless solid. $\delta_H$ (500 MHz, $d_6$-dmso) 9.62 (s, 1H), 9.12 (s, 1H), 8.51 (d, J=2.6 Hz, 1H), 8.42 (s, 1H), 8.34 (t, J=6.6 Hz, 1H), 8.26 (dd, J=4.7, 1.5 Hz, 1H), 8.08 (s, 1H), 7.93 (dd, J=2.6, 1.5 Hz, 1H), 7.91 (d, J=2.3 Hz, 1H), 7.29 (dd, J=8.4, 4.5 Hz, 1H), 4.45 (d, J=18.9 Hz, 1H), 3.94 (d, J=17.0 Hz, 1H), 3.88 (d, J=9.5 Hz, 1H), 3.80 (d, J=9.5 Hz, 1H), 3.64 (d, J=18.8 Hz, 1H), 3.60-3.53 (m, 2H), 3.30 (d, J=17.0 Hz, 1H), 2.98-2.81 (m, 2H), 2.32-2.23 (m, 1H), 1.14 (d, J=21.4 Hz, 3H), 1.09-0.99 (m, 7H), 0.91 (dd, J=8.8, 7.3 Hz, 2H), −0.01 (s, 9H); LCMS $[M+H]^+$ 644, RT 2.07 min (Method 1).

Intermediate 88

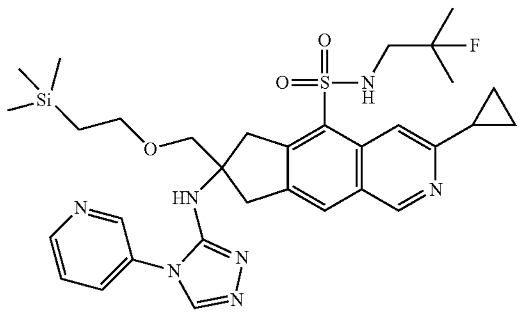 [SMILES: CC(C)(F)CNS(=O)(=O)c1c2c(cc3cnc(C4CC4)cc13)CC(COCC[Si](C)(C)C)(Nc1nncn1-c1cccnc1)C2]

3-cyclopropyl-N-(2-fluoro-2-methyl-propyl)-7-[[4-(3-pyridyl)-1,2,4-triazol-3-yl]amino]-7-(2-trimethylsilylethoxymethyl)-6,8-dihydrocyclopenta[g]isoquinoline-5-sulfonamide To a solution of Intermediate 87 (305 mg, 0.45 mmol) in anhydrous DMF (6 mL), formic hydrazide (85 mg, 1.421 mmol) and mercury (II) chloride (386 mg, 1.421 mmol) were added. After 5 minutes at room temperature, a solution of triethylamine (144 mg, 1.421 mmol) in DMF (0.5 mL) was introduced and the reaction mixture warmed to 90° C. for 60 minutes. After cooling to room temperature, the reaction mixture was poured into a suspension of kieselguhr (10 g) in dichloromethane (120 mL) and stirred for 10 minutes. This suspension was then filtered through a shallow bed of kieselguhr (vacuum filtration) and the filter-cake washed with dichloromethane (30 mL). The filtrate was concentrated in-vacuo and the residue dissolved in ethyl acetate (100 mL) then washed with water (2×30 mL) and brine (20 mL). After drying the organic phase over magnesium sulfate and filtration, the filtrate was concentrated in-vacuo to furnish the title compound (245 mg, 71% yield). $\delta_H$ (500 MHz, d-chloroform) 9.04 (s, 1H), 8.74 (d, J=4.3 Hz, 1H), 8.67 (d, J=2.1 Hz, 1H), 8.32 (s, 1H), 7.94 (s, 1H), 7.85 (s, 1H), 7.71 (d, J=8.6 Hz, 1H), 7.49 (dd, J=8.1, 4.8 Hz, 1H), 5.37 (t, J=5.7 Hz, 1H), 4.57 (s, 1H), 4.14 (d, J=18.6 Hz, 1H), 3.92 (d, J=16.9 Hz, 1H), 3.72 (d, J=18.6 Hz, 1H), 3.63 (d, J=9.2 Hz, 1H), 3.51 (d, J=9.2 Hz, 1H), 3.47 (t, J=7.6 Hz, 2H), 3.21 (d, J=17.0 Hz, 1H), 3.06-2.89 (m, 2H), 2.21 (tt, J=8.4, 4.8 Hz, 1H), 1.28 (d, J=21.5 Hz, 3H), 1.23 (d, J=21.5 Hz, 3H), 1.15-1.10 (m, 4H), 0.79 (dd, J=9.0, 7.2 Hz, 2H), −0.07 (s, 9H); LCMS $[M+H]^+$ 652, RT 3.96 min (Method 9).

Intermediate 89 & 90

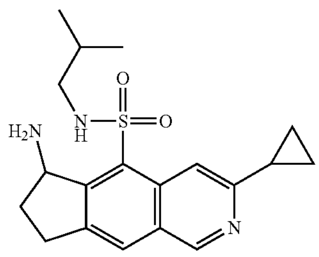

-continued

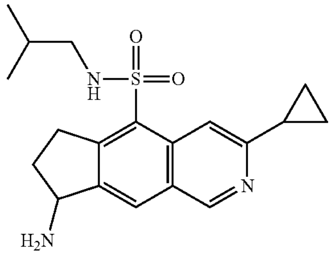

6-amino-3-cyclopropyl-N-isobutyl-7,8-dihydro-6H-cyclopenta[g]isoquinoline-5-sulfonamide 8-amino-3-cyclopropyl-N-isobutyl-7,8-dihydro-6H-cyclopenta[g]isoquinoline-5-sulfonamide To a 1:1 mixture of Intermediates 80 & 81 (160 mg at 80% estimated purity by $^1H$ NMR, 0.303 mmol) in THF (2 mL) a 0.5 M ammonia solution in THF (9 mL, 4.50 mmol) was added. The reaction mixture was warmed to 60° C. in a pressure tube for 48 hours. After cooling to room temperature, the reaction mixture was concentrated in-vacuo and the residue dissolved in tetrahydrofuran (5 mL) and concentrated in-vacuo to furnish the title compounds (201 mg at 59% purity LCMS-$UV_{215}$, quantitative). LCMS $[M+H]^+$ 360, RT 1.59 min for both regioisomers (Method 1). This material was used for the next synthetic step without further purification.

Intermediate 91

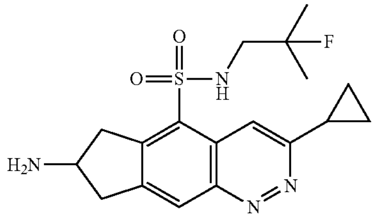 [SMILES: CC(C)(F)CNS(=O)(=O)c1c2c(cc3nnc(C4CC4)cc13)CC(N)C2]

7-amino-3-cyclopropyl-N-(2-fluoro-2-methyl-propyl)-7,8-dihydro-6H-cyclopenta[g]cinnoline-5-sulfonamide To a suspension of example 65 (75 mg, 0.14 mmol) in DCM (4 mL) at room temperature was added trifluoroacetic acid (320 μL, 4.23 mmol). After 3 h 30 min, the reaction mixture was conc. in vacuo, diluted with DCM (20 mL), $H_2O$ (10 mL) and sat. $NaHCO_3$ (5 mL). The phases were separated, and the aqueous layer extracted with DCM containing 10% IPA (4×10 mL). The combined organics were dried and conc. in vacuo to give the title compound (62 mg, quantitative). LCMS $[M+H]^+$ 379, RT 0.79 min (Method 6).

Intermediate 92

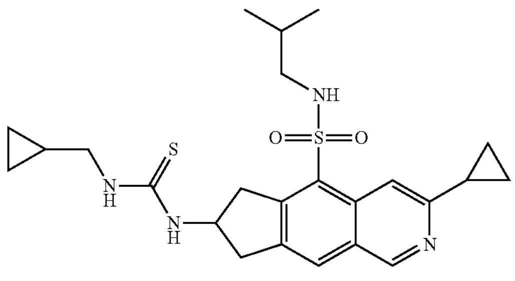 [SMILES: CC(C)CNS(=O)(=O)c1c2c(cc3cnc(C4CC4)cc13)CC(NC(=S)NCC1CC1)C2]

1-[3-cyclopropyl-5-(isobutylsulfamoyl)-7,8-dihydro-6H-cyclopenta[g]isoquinolin-7-yl]-3-(cyclopropylmethyl)thiourea Intermediate 122 (0.16 g, 0.45 mmol) was stirred in a mixture of DCM (5 mL) and DIPEA (62 μL, 0.45 mmol). (Isothiocyanatomethyl)cyclopropane (62 mg, 0.54 mmol) was added and reaction stirred for 16 hours. Further (isothiocyanatomethyl)cyclopropane (31 mg, 0.27 mmol) was added and the solution stirred for 24 hours. The reaction was concentrated under vacuum to give a white solid which was triturated with DCM in heptane to afford the title compound (162 mg, 76%). LCMS $[M+H]^+$ 473.2, RT 1.90 min (Method 1).

Intermediate 93

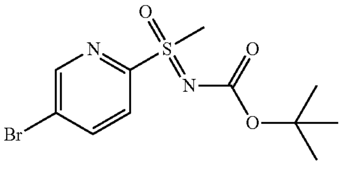 [SMILES: CC(C)(C)OC(=O)N=S(C)(=O)c1ccc(Br)cn1]

tert-butyl N-[(5-bromopyridin-2-yl)-methyl-oxo-λ6-sulfanylidene]carbamate

To a suspension of intermediate 34 (150 mg, 0.68 mmol), magnesium oxide (110 mg, 2.73 mmol), rhodium (II) acetate dimer (8 mg, 0.017 mmol) and tert-butyl carbamate (163 mg, 1.36 mmol) in DCM (3 mL) was added iodobenzene diacetate (336 mg, 1.02 mmol). The reaction mixture was stirred at room temperature for 20 hours. The reaction was filtered through celite, washing with DCM. The solvents were removed in vacuo and the resulting crude purified by column chromatography to afford the title compound (149 mg, 65% Yield). $^1H$ NMR (300 MHz, Chloroform-d) δ 8.77 (dd, J=2.0, 0.9 Hz, 1H), 8.23-8.02 (m, 2H), 3.37 (s, 3H), 1.39 (s, 9H).

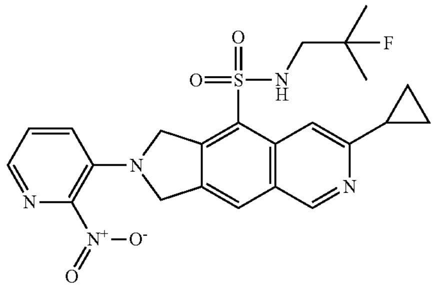 [SMILES: CC(C)(F)CNS(=O)(=O)c1c2c(cc3cnc(C4CC4)cc13)CN(c1cccnc1[N+](=O)[O-])C2]

7-cyclopropyl-N-(2-fluoro-2-methyl-propyl)-2-(2-nitro-3-pyridyl)-1,3-dihydropyrrolo[3,4-g]isoquinoline-9-sulfonamide A solution of Intermediate 27 (100 mg, 0.28 mmol), 3-fluoro-2-nitropyridine (47 mg, 0.33 mmol) and DIPEA (192 μL, 1.10 mmol) in THF (5 mL) was heated to 50° C. in a sealed tube for 5 hours. After cooling to room temperature, the solution was diluted with EtOAc (20 mL) and washed with sat. aq. $NaHCO_3$ (10 mL). The aqueous was extracted with EtOAc (10 mL) and the combined organic extracts were washed with brine (10 mL), dried over $MgSO_4$, filtered and concentrated under reduced pressure. Purification by column chromatography with a gradient of ethyl acetate in heptane gave the title compound (20 mg, 15% yield). H (500 MHz, d-chloroform) 9.18 (s, 1H), 8.29 (s, 1H), 8.03 (s, 1H), 7.98 (dd, J=4.2, 1.1 Hz, 1H), 7.58 (dd, J=8.5, 1.0 Hz, 1H), 7.51 (dd, J=8.5, 4.2 Hz, 1H), 5.27 (s, 2H), 5.19 (t, J=6.3 Hz, 1H), 4.79 (s, 2H), 3.06 (dd, J=19.8, 6.5 Hz, 2H), 2.30-2.23 (m, 1H), 1.34 (d, J=21.5 Hz, 6H), 1.23-1.19 (m, 2H), 1.15-1.09 (m, 2H). LCMS $[M+H]^+$ 486.3, RT 3.41 min (Method 2).

Intermediate 95

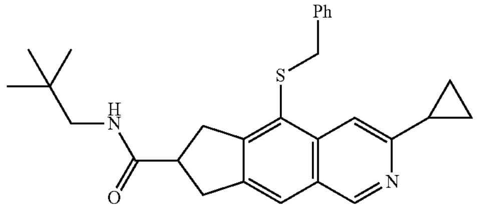 [SMILES: CC(C)(C)CNC(=O)C1Cc2cc3cnc(C4CC4)cc3c(SCc3ccccc3)c2C1]

5-benzylsulfanyl-3-cyclopropyl-N-(2,2-dimethylpropyl)-7,8-dihydro-6H-cyclopenta[g]isoquinoline-7-carboxamide Intermediate 9 (190 mg, 0.51 mmol) was dissolved in DCM (5 mL) and DIPEA (315 μL, 1.81 mmol) was added followed by HATU (210 mg, 0.55 mmol). The mixture was stirred at room temperature for 10 minutes before adding 2,2-dimethylpropan-1-amine (120 μL, 1.02 mmol). Stirring was continued at room temperature for 1 hour. The solution was then concentrated under reduced pressure and purified by column chromatography with a gradient of ethyl acetate in heptane to give the title compound (170 mg, 76% yield). $\delta_H$ (500 MHz, d-chloroform) 9.00 (s, 1H), 8.05 (s, 1H), 7.66 (s, 1H), 7.20-7.12 (m, 3H), 6.94-6.87 (m, 2H), 5.39 (t, J=5.8 Hz, 1H), 3.91 (d, J=12.8 Hz, 1H), 3.86 (d, J=12.8 Hz, 1H), 3.36 (ddd, J=15.9, 9.4, 1.6 Hz, 1H), 3.22 (ddd, J=16.0, 7.9, 0.8 Hz, 1H), 3.12 (dd, J=13.3, 6.5 Hz, 1H), 3.07 (dd, J=13.4, 6.3 Hz, 1H), 3.04-3.01 (m, 2H), 2.88 (p, J=8.7 Hz, 1H), 2.21 (tt, J=8.2, 4.9 Hz, 1H), 1.12-1.08 (m, 2H), 1.06-1.02 (m, 2H), 0.91 (s, 9H). LCMS $[M+H]^+$ 445.2, RT 2.02 min (Method 2).

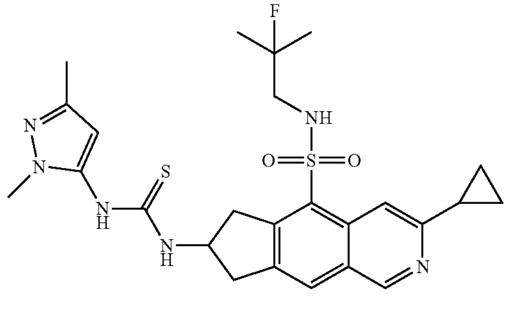 [SMILES: Cc1cc(NC(=S)NC2Cc3cc4cnc(C5CC5)cc4c(S(=O)(=O)NCC(C)(C)F)c3C2)n(C)n1]

1-[3-cyclopropyl-5-[(2-fluoro-2-methyl-propyl) sulfamoyl]-7,8-dihydro-6H-cyclopenta[g]isoquinolin-7-yl]-3-(2,5-dimethylpyrazol-3-yl)thiourea A solution of Intermediate 12 (85%, 215 mg, 0.44 mmol) and DIPEA (115 µL, 0.66 mmol) in DCM (5 mL) was treated with a solution of 5-isothiocyanato-1,3-dimethyl-1H-pyrazole (82 mg, 0.54 mmol) in DCM (1 mL) and the reaction was stirred at room temperature for 1 hour before being concentrated under reduced pressure and purified by column chromatography with a gradient of ethyl acetate in heptane to give the title compound (255 mg, 87% yield). $\delta_H$ (500 MHz, DMSO-d6) 9.13 (s, 1H), 9.11 (s, 1H), 8.43 (s, 1H), 8.35 (t, J=6.5 Hz, 1H), 8.18 (br s, 1H), 8.10 (s, 1H), 5.91 (s, 1H), 5.02 (s, 1H), 3.85 (dd, J=18.4, 7.4 Hz, 1H), 3.52 (s, 3H), 3.50-3.42 (m, 2H), 3.07 (dd, J=16.8, 5.4 Hz, 1H), 2.94 (dd, J=19.9, 6.5 Hz, 2H), 2.31-2.23 (m, 1H), 2.08 (s, 3H), 1.16 (dd, J=21.4, 4.7 Hz, 6H), 1.05-0.99 (m, 4H). LCMS $[M+H]^+$ 531.2, RT 1.77 min (Method 2).

Intermediate 97

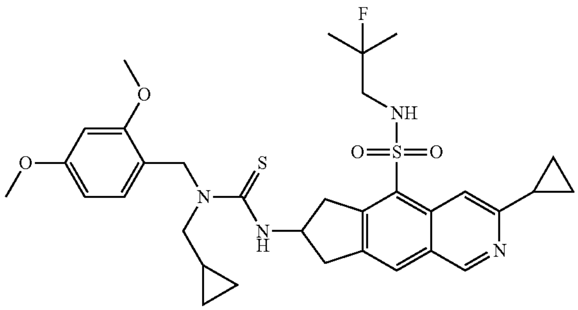 [SMILES: COc1ccc(CN(CC2CC2)C(=S)NC2Cc3cc4cnc(C5CC5)cc4c(S(=O)(=O)NCC(C)(C)F)c3C2)c(OC)c1]

3-[3-cyclopropyl-5-[(2-fluoro-2-methyl-propyl) sulfamoyl]-7,8-dihydro-6H-cyclopenta[g]isoquinolin-7-yl]-1-(cyclopropylmethyl)-1-[(2,4-dimethoxyphenyl) methyl]thiourea Phenyl chloromethanethioate (65 µL, 0.47 mmol) was dissolved in DCM (5 mL) and a solution of Intermediate 12 (160 mg, 0.42 mmol) and triethylamine (180 µL, 1.29 mmol) in DCM (2.5 mL) was added dropwise and the reaction mixture stirred for 45 minutes at room temperature. Intermediate 56 (140 mg, 0.57 mmol) was then added and the reaction stirred for 3 days at room temperature. The reaction mixture was concentrated under a flow of $N_2$ and purified by column chromatography with a gradient of ethyl acetate in heptane to give the title compound (247 mg, 91% yield). LCMS $[M+H]^+$ 641.2, RT 2.07 min (Method 2).

Intermediate 98

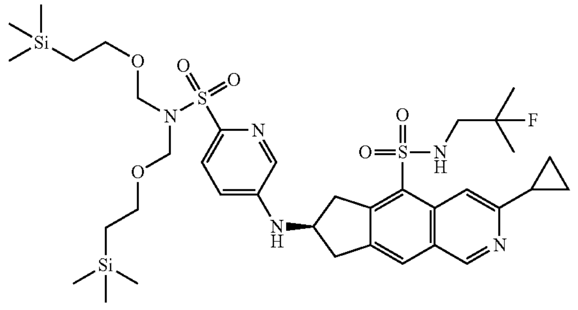 [SMILES: CC(C)(F)CNS(=O)(=O)c1c2c(cc3cnc(C4CC4)cc13)C[C@@H](Nc1ccc(S(=O)(=O)N(COCC[Si](C)(C)C)COCC[Si](C)(C)C)nc1)C2]

(7R)-7-[[6-[bis (2-trimethylsilylethoxymethyl) sulfamoyl]-3-pyridyl]amino]-3-cyclopropyl-N-(2-fluoro-2-methyl-propyl)-7,8-dihydro-6H-cyclopenta[g]isoquinoline-5-sulfonamide Prepared by General Procedure 1 from Intermediate 15 (55 mg, 0.14 mmol) and Intermediate 99 (87 mg, 0.17 mmol). The crude was purified by column chromatography using 0% to 90% EtOAc in heptane to afford the title compound (85 mg, 73% yield). LCMS $[M+H]^+$ 794, RT 2.35 min (Method 1).

Intermediate 99

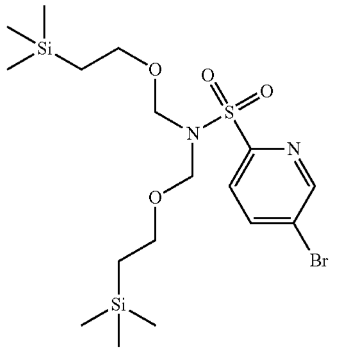 [SMILES: C[Si](C)(C)CCOCN(COCC[Si](C)(C)C)S(=O)(=O)c1ccc(Br)cn1]

5-bromo-N,N-bis (2-trimethylsilylethoxymethyl) pyridine-2-sulfonamide

A solution of 5-bromopyridine-2-sulfonamide (100 mg, 0.42 mmol) in DMF (3 mL) was stirred with sodium hydride (60% oil dispersion; 37.1 mg, 0.92 mmol) at 20° C. under an atmosphere of nitrogen. After 15 min, SEMCl (140.6 mg, 0.84 mmol) was added and the mixture was stirred for 3 hrs at 20° C. Phosphate buffer (pH 6.5, 7 mL) was added and the mixture was stirred for 10 min. The mixture was extracted with EtOAc (2×20 mL) and the combined organic layers were washed with water (2×20 mL), followed by brine (20 mL). The solution was dried ($Na_2SO_4$) and evaporated to dryness. Purification by column chromatography using 0%-20% EtOAc in heptane gave the title compound (109 mg, 52% yield). LCMS $[M+Na]^+$ 519/521, RT 2.41 min (Method 1).

Intermediate 100

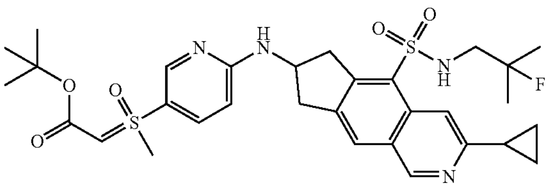 [SMILES: CC(C)(F)CNS(=O)(=O)c1c2c(cc3cnc(C4CC4)cc13)CC(Nc1ccc(S(C)(=O)=CC(=O)OC(C)(C)C)cn1)C2]

tert-butyl N-[[5-[[3-cyclopropyl-5-[(2-fluoro-2-methyl-propyl) sulfamoyl]-7,8-dihydro-6H-cyclopenta[g]isoquinolin-7-yl]amino]-2-pyridyl]-methyl-oxo-lambda6-sulfanylidene]carbamate The title compound was prepared according to General Procedure 1 using Intermediate 12 (55 mg, 0.15 mmol), Intermediate 93 (146 mg, 0.44 mmol), sodium tert-butoxide (42 mg, 0.44 mmol), tBuXPhos Pd G3 (18 mg, 0.022 mmol) and 1,4-dioxane (1 mL). Purification by column chromatography afforded the title compound (52 mg, 56% Yield). $\delta_H$ (300 MHz, d-DMSO) 9.15 (s, 1H), 8.44 (s, 1H), 8.35 (t, J=6.6 Hz, 1H), 8.13 (s, 1H), 8.10 (t, J=2.5 Hz, 1H), 7.88-7.78 (m, 1H), 7.26 (d, J=6.4 Hz, 1H), 7.21 (d, J=8.6 Hz, 1H), 4.48-4.32 (m, 1H), 4.03-3.70 (m, 1H), 3.61-3.43 (m, 2H), 3.27 (d, J=3.1 Hz, 3H), 3.07-2.82 (m, 3H), 2.30-2.21 (m, 1H), 1.26 (s, 9H), 1.19-1.00 (m, 10H).

Intermediate 101

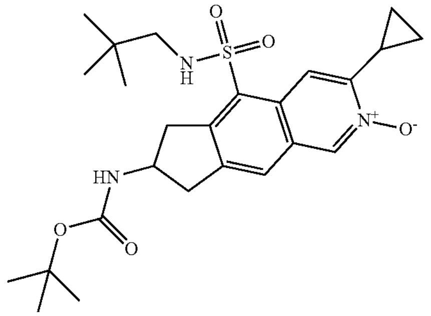 [SMILES: CC(C)(C)CNS(=O)(=O)c1c2c(cc3c[n+]([O-])c(C4CC4)cc13)CC(NC(=O)OC(C)(C)C)C2]

tert-butyl N-[3-cyclopropyl-5-[(2-fluoro-2-methyl-propyl) sulfamoyl]-2-oxido-7,8-dihydro-6H-cyclopenta[g]isoquinolin-2-ium-7-yl]carbamate To an ice-cold solution of Intermediate 12 (900 mg, 1.88 mmol) in DCM (25 mL) was added 3-chloroperbenzoic acid (790 mg, 3.20 mmol) and the reaction was stirred at 0° C. for 2 hours. The reaction was then washed with sat. aq. $NaHCO_3$ (40 mL) and the organic layer dried ($Na_2SO_4$) and concentrated in vacuo to afford the title compound (1.01 g, 92% Yield). $\delta_H$ (300 MHz, d-CDCl3) 8.95 (s, 1H), 8.37 (s, 1H), 7.72 (s, 1H), 5.36 (t, J=6.4 Hz, 1H), 4.97-4.73 (m, 1H), 4.65-4.36 (m, 1H), 3.77 (dd, J=18.6, 7.1 Hz, 1H), 3.55-3.34 (m, 2H), 3.21-2.90 (m, 3H), 2.83-2.65 (m, 1H), 1.44 (s, 9H), 1.36-1.18 (m, 8H), 1.00-0.79 (m, 2H).

Intermediate 102

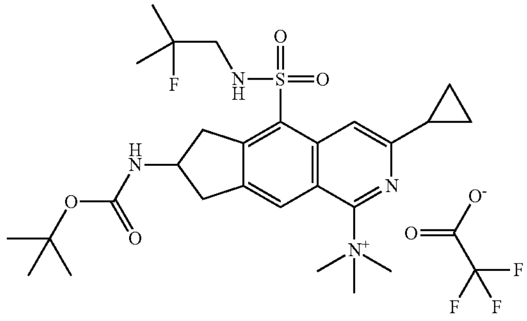 [SMILES: CC(C)(F)CNS(=O)(=O)c1c2c(cc3c([N+](C)(C)C)nc(C4CC4)cc13)CC(NC(=O)OC(C)(C)C)C2 ; O=C([O-])C(F)(F)F]

[7-(tert-butoxycarbonylamino)-3-cyclopropyl-5-[(2-fluoro-2-methyl-propyl) sulfamoyl]-7,8-dihydro-6H-cyclopenta[g]isoquinolin-1-yl]-trimethyl-ammonium 2,2,2-trifluoroacetate To a stirred solution of Intermediate 101 (1.00 g, 1.7 mmol) in DCM (85 mL) was added a 1 M solution of trimethylamine in THF (12 mmol, 12 mL). The solution was cooled in an ice bath prior to addition of trifluoroacetic anhydride (0.73 mL, 5.2 mmol). The reaction stirred for 20 min at 0° C., then washed with water, dried and concentrated in vacuo. The resulting crude was purified by column chromatography to afford the title compound (717 mg, 64% Yield). $^1H$ NMR (300 MHz, d-CDCl3) δ 8.89 (s, 1H), 8.72 (s, 1H), 6.90-6.75 (m, 1H), 5.44-5.22 (m, 1H), 4.57-4.36 (m, 1H), 3.97 (s, 9H), 3.83 (dd, J=19.4, 7.0 Hz, 1H), 3.57 (dd, J=18.8, 4.8 Hz, 1H), 3.47-3.38 (m, 1H), 3.27-2.98 (m, 3H), 2.59-2.15 (m, 1H), 1.41 (s, 9H), 1.26 (dd, J=21.5, 3.3 Hz, 6H), 1.19-0.98 (m, 4H).

Intermediate 103

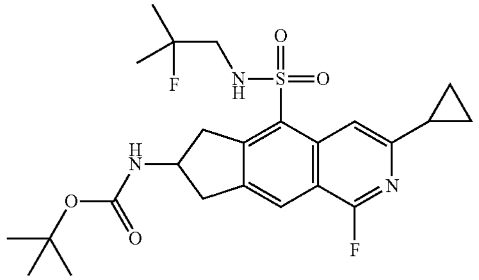 [SMILES: CC(C)(F)CNS(=O)(=O)c1c2c(cc3c(F)nc(C4CC4)cc13)CC(NC(=O)OC(C)(C)C)C2]

tert-butyl N-[3-cyclopropyl-1-fluoro-5-[(2-fluoro-2-methyl-propyl) sulfamoyl]-7,8-dihydro-6H-cyclopenta[g]isoquinolin-7-yl]carbamate To a solution of Intermediate 102 (710 mg, 1.09 mmol) in N,N-dimethylformamide (2.5 mL) was added tetrabutylammonium fluoride 1 M in THF (3.3 mL, 3.3 mmol). The reaction was sealed and heated to 75° C. with stirring for 1.5 hours. The reaction was cooled, diluted with EtOAc (10 mL) and washed with water (10 mL). The aqueous layer was extracted with EtOAc (5 ml) and the combined organic layers dried over $Na_2SO_4$ and concentrated in vacuo. The crude product was purified by column chromatography to afford the title compound (413 mg, 76% Yield). $\delta_H$ (300 MHz, d-CDCl3) 8.21 (s, 1H), 8.11 (s, 1H), 5.04 (t, J=6.5 Hz, 1H), 4.83-4.65 (m, 1H), 4.59-4.42 (m, 1H), 3.84 (dd, J=18.6, 7.2 Hz, 1H), 3.53-3.36 (m, 2H), 3.17-2.87 (m, 3H), 2.23-2.10 (m, 1H), 1.45 (s, 9H), 1.30 (dd, J=21.5, 13.2 Hz, 6H), 1.18-0.94 (m, 4H).

Intermediate 104

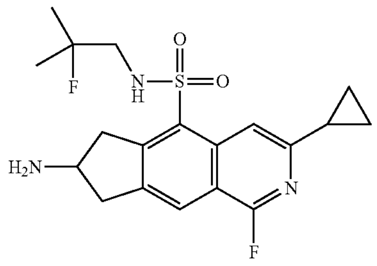 [SMILES: CC(C)(F)CNS(=O)(=O)c1c2c(cc3c(F)nc(C4CC4)cc13)CC(N)C2]

7-amino-3-cyclopropyl-1-fluoro-N-(2-fluoro-2-methyl-propyl)-7,8-dihydro-6H-cyclopenta[g]isoquinoline-5-sulfonamide To a stirred solution of Intermediate 103 (410 mg, 0.83 mmol) in DCM (8 mL) was added trifluoroacetic acid (2 mL). The reaction was stirred at ambient temperature for 2 hours then concentrated in vacuo. The residue was dissolved in a mixture of IPA (2 mL), DCM (25 mL) and sat. aq. $NaHCO_3$ (25 mL). The solution was stirred vigorously for 5 min. The organic layer partitioned and concentrated in vacuo to afford the title compound (295 mg, 84% Yield). $\delta_H$ (400 MHz, d-DMSO) 8.39 (s, 1H), 8.08 (s, 1H), 3.82-3.69 (m, 1H), 3.55 (dd, J=18.0, 6.2 Hz, 1H), 3.27-3.12 (m, 2H), 2.99-2.90 (m, 2H), 2.77 (dd, J=16.3, 4.8 Hz, 1H), 2.30-2.18 (m, 1H), 1.15 (dd, J=21.4, 10.3 Hz, 6H), 1.06-0.91 (m, 4H).

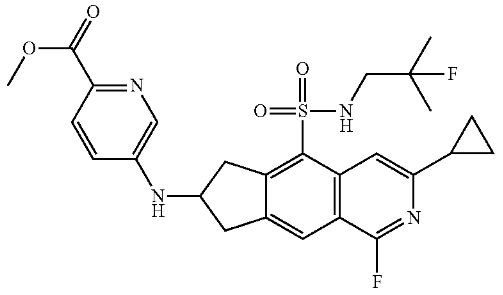 [SMILES: COC(=O)c1ccc(NC2Cc3cc4c(F)nc(C5CC5)cc4c(S(=O)(=O)NCC(C)(C)F)c3C2)cn1]

methyl 5-[[3-cyclopropyl-1-fluoro-5-[(2-fluoro-2-methyl-propyl) sulfamoyl]-7,8-dihydro-6H-cyclopenta[g]isoquinolin-7-yl]amino]pyridine-2-carboxylate The title compound was prepared according to General Procedure 1 using Intermediate 104 (50 mg, 0.13 mmol), methyl 5-bromopyridine-2-carboxylate (59 mg, 0.27 mmol), sodium tert-butoxide (38.2 mg, 0.39 mmol), tBuXPhos Pd G3 (16.3 mg, 0.019 mmol) and anhydrous 1,4-dioxane (3 mL). The reaction was heated to 45° C. for 5 hours and then purified by column chromatography to afford the title compound (36 mg, 48% Yield). δη (300 MHz, d-CDCl3) 8.25-8.17 (m, 1H), 8.11 (s, 1H), 8.03 (d, J=2.7 Hz, 1H), 7.97 (d, J=8.6 Hz, 1H), 6.91 (dd, J=8.6, 2.9 Hz, 1H), 5.30 (t, J=6.5 Hz, 1H), 4.62 (d, J=6.5 Hz, 1H), 4.49-4.36 (m, 1H), 3.93 (s, 3H), 3.86 (d, J=6.4 Hz, 1H), 3.73-3.63 (m, 1H), 3.59-3.42 (m, 1H), 3.18-2.90 (m, 3H), 2.18-2.07 (m, 1H), 1.30-1.18 (m, 6H), 0.89-0.79 (m, 4H).

Intermediate 106

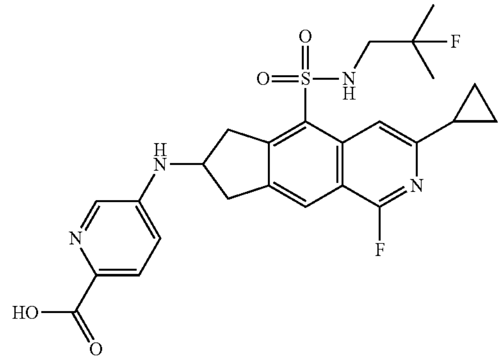 [SMILES: CC(C)(F)CNS(=O)(=O)c1c2c(cc3c(F)nc(C4CC4)cc13)CC(Nc1ccc(C(=O)O)nc1)C2]

5-[[3-cyclopropyl-1-fluoro-5-[(2-fluoro-2-methyl-propyl) sulfamoyl]-7,8-dihydro-6H-cyclopenta[g] isoquinolin-7-yl]amino]pyridine-2-carboxylic acid To a solution of Intermediate 105 (43 mg, 0.081 mmol) in a mixture of tetrahydrofuran (1 mL) and water (0.5 mL), lithium hydroxide (3 mg, 0.12 mmol) was added and the reaction heated to 50° C. for 6 hours. The reaction was acidified to pH 4 with 0.5 M HCl and extracted with EtOAc (2×2 mL). The combined organic extracts were dried over $Na_2SO_4$ and concentrated in vacuo to afford the title compound (24 mg, 49% Yield). LCMS $[M+H]^+$ 517, RT 1.89 min (Method 4).

Intermediate 107

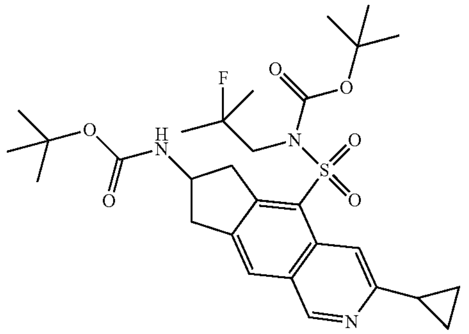 [SMILES: CC(C)(F)CN(C(=O)OC(C)(C)C)S(=O)(=O)c1c2c(cc3cnc(C4CC4)cc13)CC(NC(=O)OC(C)(C)C)C2]

tert-butyl N-[[7-(tert-butoxycarbonylamino)-3-cyclopropyl-7,8-dihydro-6H-cyclopenta[g]isoquinolin-5-yl]sulfonyl]-N-(2-fluoro-2-methyl-propyl) carbamate To a solution of Intermediate 12 (0.3 g, 0.79 mmol) and di-tert-butyl dicarbonate (0.35 g, 1.59 mmol) in anhydrous 1,4-dioxane (5 mL) was added N,N-diisopropylethylamine (0.28 mL, 1.59 mmol) followed by 4-dimethylaminopyridine (10 mg, 0.08 mmol). The reaction was stirred for 30 min then diluted with EtOAc (5 mL) and washed with 0.5 M HCl (5 mL). The organic layer was dried over $Na_2SO_4$ and concentrated in vacuo to afford the title compound (483 mg, 63% yield). $^1H$ NMR (300 MHz, Chloroform-d) $\delta_H$ 9.05 (s, 1H), 7.96 (s, 1H), 7.94 (s, 1H), 5.12 (s, 1H), 4.50 (q, J=4.8, 4.2 Hz, 1H), 4.38-4.06 (m, 2H), 3.92-3.73 (m, 1H), 3.68-3.51 (m, 1H), 3.32 (ddd, J=16.4, 5.8, 1.6 Hz, 1H), 3.13 (d, J=16.4 Hz, 1H), 2.19 (tt, J=7.4, 5.0 Hz, 1H), 1.54 (dd, J=21.3, 8.5 Hz, 6H), 1.40 (s, 9H), 1.17-1.02 (m, 13H).

Intermediate 108

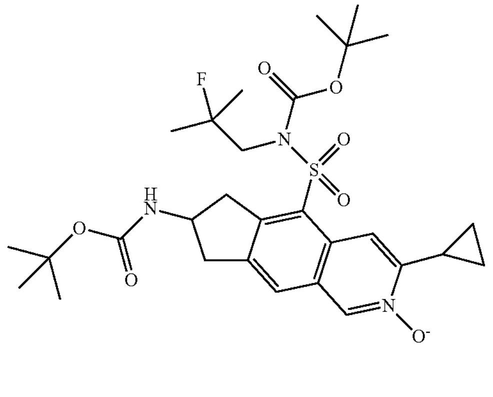

tert-butyl N-[[7-(tert-butoxycarbonylamino)-3-cyclopropyl-2-oxido-7,8-dihydro-6H-cyclopenta[g]isoquinolin-2-ium-5-yl]sulfonyl]-N-(2-fluoro-2-methyl-propyl) carbamate To an ice-cold solution of Intermediate 107 (0.30 g, 0.49 mmol) in DCM (5 mL) was added 3-chloroperoxybenzoic acid (134 mg, 0.54 mmol). The reaction was stirred at 0° C. for 2.5 hours. The reaction was washed with sat. aq. $Na_2S_2O_5$ solution (2.5 mL) followed by sat. aq. $NaHCO_3$ solution (2.5 mL). The organic layer was partitioned, dried and concentrated in vacuo. Purification by column chromatography afforded the title compound (217 mg, 63% yield). $\delta_H$ (300 MHz, d-CDCl3) 8.91 (s, 1H), 8.05 (s, 1H), 8.03-7.87 (m, 1H), 7.73 (s, 1H), 7.54-7.28 (m, 1H), 5.07 (d, J=6.5 Hz, 1H), 4.49 (s, 1H), 4.17-4.01 (m, 2H), 3.78-3.49 (m, 2H), 3.38-3.02 (m, 2H), 2.90-2.73 (m, 1H), 1.52 (dd, J=21.2, 6.2 Hz, 6H), 1.41 (s, 9H), 1.32-1.24 (m, 2H), 1.12 (s, 9H), 0.94-0.76 (m, 2H).

Intermediate 109

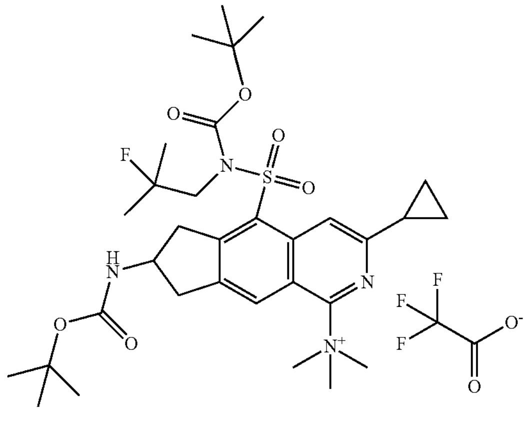

[7-(tert-butoxycarbonylamino)-5-[tert-butoxycarbonyl-(2-fluoro-2-methyl-propyl) sulfamoyl]-3-cyclopropyl-7,8-dihydro-6H-cyclopenta[g]isoquinolin-1-yl]-trimethyl-ammonium; 2,2,2-trifluoroacetate The title compound was prepared according to the same procedure as described in Intermediate 102 using Intermediate 108 (0.3 g, 0.43 mmol), DCM (15 mL), trimethylamine (2.9 mL, 2.9 mmol) and trifluoroacetic anhydride (0.18 mL, 1.29 mmol). Purification by column chromatography afforded the title compound (184 mg, 57% Yield). $\delta_H$ (300 MHz, d-CDCl3) 8.80 (s, 1H), 8.57 (s, 1H), 5.19-5.05 (m, 1H), 4.58-4.37 (m, 1H), 4.18 (d, J=19.0 Hz, 2H), 3.97 (s, 9H), 3.85-3.58 (m, 2H), 3.43 (d, J=6.1 Hz, 1H), 3.27 (d, J=17.2 Hz, 1H), 2.24 (td, J=8.3, 4.1 Hz, 1H), 1.53 (dd, J=21.3, 1.5 Hz, 6H), 1.41 (s, 9H), 1.20 (s, 9H), 1.12-1.02 (m, 4H).

Intermediate 110

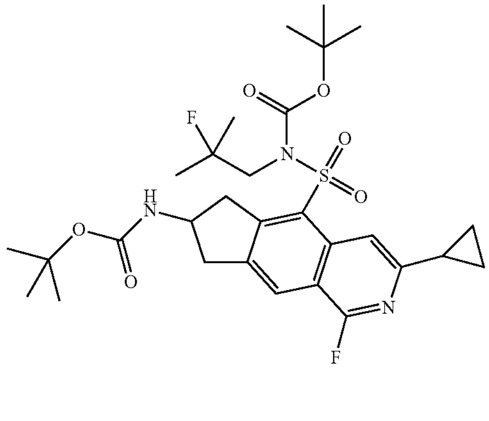 [SMILES: CC(C)(F)CN(C(=O)OC(C)(C)C)S(=O)(=O)c1c2c(cc3c(F)nc(C4CC4)cc13)CC(NC(=O)OC(C)(C)C)C2]

tert-butyl N-[[7-(tert-butoxycarbonylamino)-3-cyclopropyl-1-fluoro-7,8-dihydro-6H-cyclopenta[g]isoquinolin-5-yl]sulfonyl]-N-(2-fluoro-2-methyl-propyl) carbamate The title compound was prepared using the same procedure described for Intermediate 103 using Intermediate 109 (0.3 g, 0.40 mmol), N,N-dimethylformamide (1 mL) and tetrabutylammonium fluoride 1 M in THF (1.2 mL). Purification by column chromatography afforded the title compound (124 mg, 52% Yield). $^1$H NMR (300 MHz, d-CDCl3) $\delta_H$ 7.88 (s, 1H), 5.12 (s, 1H), 4.51 (s, 1H), 4.35-4.05 (m, 3H), 3.97-3.48 (m, 2H), 3.41-3.04 (m, 2H), 2.18-2.06 (m, 1H), 1.57-1.45 (m, 6H), 1.41 (s, 9H), 1.17 (s, 9H), 1.13-1.00 (m, 4H).

Intermediates 111 & 112

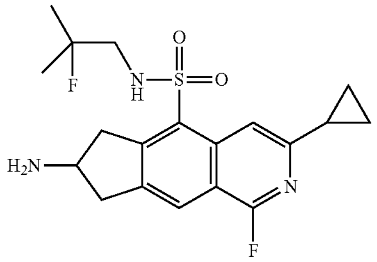

-continued

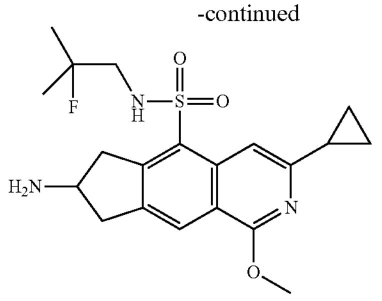

7-amino-3-cyclopropyl-1-fluoro-N-(2-fluoro-2-methyl-propyl)-7,8-dihydro-6H-cyclopenta[g]isoquinoline-5-sulfonamide (111)

7-amino-3-cyclopropyl-N-(2-fluoro-2-methyl-propyl)-1-methoxy-7,8-dihydro-6H-cyclopenta[g]isoquinoline-5-sulfonamide (112)

Intermediate 110 (74 mg, 0.12 mmol) was dissolved in DCM (5 mL) and trifluoroacetic acid (0.5 mL) was added. The reaction was stirred at ambient temperature for 1 hour. The reaction mixture was concentrated in vacuo and purified using an SCX cartridge to afford a mixture of title compounds that was carried through to the next stage without further purification. LCMS $[M+H]^+$ 396, RT 1.88 min; $[M+H]^+$ 408, RT 2.16 min (Method 10).

Intermediate 113

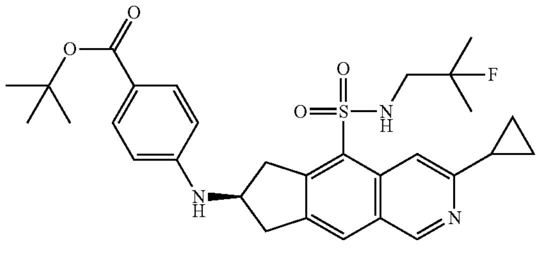 [SMILES: CC(C)(F)CNS(=O)(=O)c1c2c(cc3cnc(C4CC4)cc13)C[C@@H](Nc1ccc(C(=O)OC(C)(C)C)cc1)C2]

tert-butyl 5-[[(7R)-3-cyclopropyl-5-[(2-fluoro-2-methyl-propyl) sulfamoyl]-7,8-dihydro-6H-cyclopenta[g]isoquinolin-7-yl]amino]pyridine-2-carboxylate The title compound was prepared using General Procedure 2 with Intermediate 15 (290 mg, 0.77 mmol) and tert-butyl 5-bromopyridine-2-carboxylate (298 mg, 1.15 mmol) with stirring at room temperature for 2 hours. The crude material was purified by flash chromatography eluting with a gradient of ethyl acetate in heptane, followed by a gradient of methanol in ethyl acetate to afford the title compound (384 mg, 84% yield). LCMS $[M+H]^+$ 555, RT 1.92 min (Method 1).

Intermediate 114

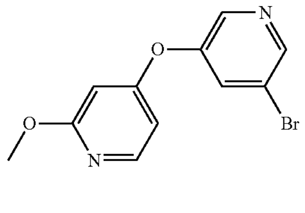 [SMILES: COc1cc(Oc2cncc(Br)c2)ccn1]

3-bromo-5-[(2-methoxy-4-pyridyl)oxy]pyridine

A mixture of 3-bromo-5-fluoropyridine (232, 1.3 mmol), 2-methoxypyridin-4-ol (150 mg, 1.2 mmol) and potassium carbonate (249 mg, 1.8 mmol) in DMF (4 mL), was heated in the microwave reactor at 200° C. for 30 minutes. The reaction mixture was diluted with sat. aq. $NH_4Cl$ (10 mL) and extracted with EtOAc (3x10 mL). The combined organics were dried over magnesium sulfate, filtered and concentrated. The crude material was purified by flash chromatography eluting with a gradient of ethyl acetate in heptane to afford the title compound (50 mg, 15% yield). LCMS $[M+H]^+$ 281/283, RT 1.76 min (Method 1).

Intermediate 115

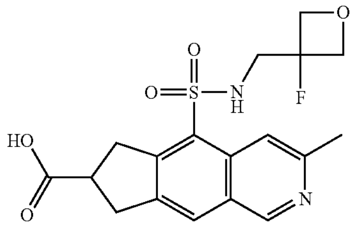 [SMILES: Cc1cc2c(S(=O)(=O)NCC3(F)COC3)c3c(cc2cn1)CC(C(=O)O)C3]

3-cyclopropyl-5-[(3-fluorooxetan-3-yl)methylsulfamoyl]-7,8-dihydro-6H-cyclopenta[g]isoquinoline-7-carboxylic acid To a stirring solution of (3-fluorooxetan-3-yl) methanamine (180 mg, 1.7 mmol) and DIPEA (0.22 mL, 1.28 mmol) in anhydrous DCM (1.5 mL) was added Intermediate 10 (500 mg, 1.42 mmol) and the mixture was stirred at room temperature for 2 hours. The reaction mixture was treated with 1 M aq. HCl (approx. 3 mL) and the white precipitate that formed was filtered off to afford the title compound (250 mg, 41% yield). The aqueous layer was then extracted with $CHCl_3$/IPA (3:1, 2x15 mL). The combined organics were washed with brine (10 mL), dried over magnesium sulfate, filtered and concentrated. The resulting residue was purified by flash chromatography eluting with a gradient of ethyl acetate in heptane, followed by a gradient of methanol in ethyl acetate to afford a second batch of the title compound (140 mg, 23% yield). $\delta_H$ (500 MHz, DMSO-d6) δ 12.47 (s, 1H), 9.14 (s, 1H), 8.54 (t, J=6.4 Hz, 1H), 8.38 (s, 1H), 8.11 (s, 1H), 4.52-4.39 (m, 4H), 3.76 (dd, J=18.3, 8.0 Hz, 1H), 3.66 (dd, J=18.3, 6.2 Hz, 1H), 3.37-3.34 (m, 2H, part. obs. by water), 3.30-3.23 (m, 3H, part. obs. by water), 2.30-2.22 (m, 1H), 1.05-0.97 (m, 4H). LCMS $[M+H]^+$ 421, RT 1.56 min (Method 1).

Intermediate 116

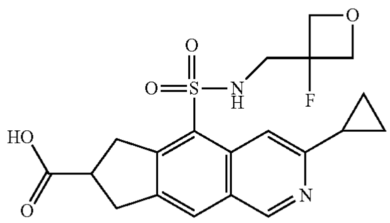 [SMILES: O=C(O)C1Cc2cc3cnc(C4CC4)cc3c(S(=O)(=O)NCC3(F)COC3)c2C1]

7-amino-3-cyclopropyl-N-[(3-fluorooxetan-3-yl) methyl]-7,8-dihydro-6H-cyclopenta[g]isoquinoline-5-sulfonamide To a stirring suspension of Intermediate 115 (250 mg, 0.6 mmol) in anhydrous THF (10 mL), was added triethylamine (210 μL, 1.49 mmol) followed by DPPA (135 μL, 0.6 mmol) and the resulting mixture was heated at reflux (75° C.) for 2 hours. The mixture was cooled and 1 M aq. HCl (10 mL) added. The mixture was stirred at room temperature for 30 minutes then washed with ethyl acetate (2×10 mL). The aqueous layer was basified with 1 M NaOH to a pH >10 and it was extracted with ethyl acetate/MeOH (5:1, 3×10 mL). The combined organics were washed with brine (10 mL), dried over magnesium sulfate, filtered and concentrated. Purification by flash chromatography with a gradient of ethyl acetate in heptane, followed by a gradient of methanol in ethyl acetate afforded the title compound (110 mg, 45% yield). LCMS $[M+H]^+$ 392, RT 1.31 min (Method 1).

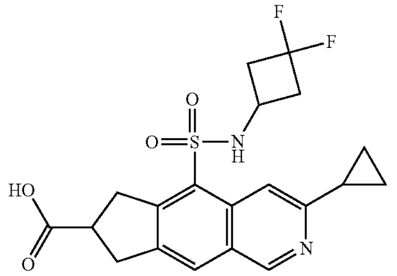 [SMILES: O=C(O)C1Cc2cc3cnc(C4CC4)cc3c(S(=O)(=O)NC3CC(F)(F)C3)c2C1]

3-cyclopropyl-5-[(3,3-difluorocyclobutyl) sulfamoyl]-7,8-dihydro-6H-cyclopenta[g]isoquinoline-7-carboxylic acid 3,3-difluorocyclobutan-1-amine hydrochloride (1.08 g, 7.50 mmol) and DIPEA (3.27 mL, 18.8 mmol) were dissolved in DCM (40 mL) before Intermediate 10 (2.20 g, 6.25 mmol) was added portion-wise. The mixture was stirred at room temperature for 15 minutes. 1 M aq. NaOH (50 mL) and DCM (50 mL) were added and the layers separated. The aqueous layer was washed with DCM (50 mL) and the basic aqueous layer was carefully acidified with 3 M aq. HCl and extracted with EtOAc (50 mL), followed by 1:1 IPA/chloroform (4×50 mL). The combined organic extracts were dried over $MgSO_4$, filtered and concentrated under reduced pressure to give the title compound (1.59 g, 54% yield). LCMS $[M+H]^+$ 423.0, RT 1.71 min (Method 1).

Intermediate 118

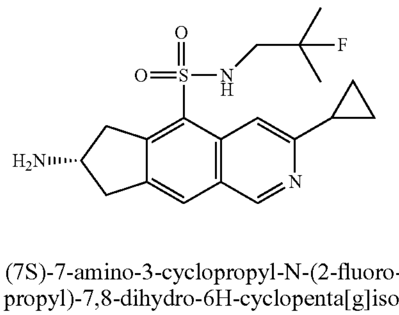

(7S)-7-amino-3-cyclopropyl-N-(2-fluoro-2-methylpropyl)-7,8-dihydro-6H-cyclopenta[g]isoquinoline-5-sulfonamide To a solution of Intermediate 13 (16 g, 35.5 mmol) in DCM (160 mL) at 0° C., trifluoroacetic acid (25.8 mL, 335 mmol) was added. The reaction was stirred for 6 hours at room temperature then cooled to 0° C. and basified to pH 8-9 with 4 M aq. NaOH (75 mL) followed by saturated aq. $NH_4Cl$. The suspension was extracted with a 1:1 mixture of $CHCl_3$ and IPA (200 mL, then 2×150 mL) and the combined organics were washed with brine (100 mL), dried over $MgSO_4$ and concentrated under vacuum. The material was suspended in EtOAc (200 mL) and 1 M aq. NaOH (100 mL) was added. The layers were separated, and the organic layer washed further with 1 M aq. NaOH. The aqueous layers were combined and extracted with EtOAc (100 mL). The combined organics were washed with brine (100 mL), dried over $MgSO_4$, concentrated under vacuum and dried in a vacuum oven to afford the title compound (10.5 g, 83%). LCMS $[M+H]^+$ 378.2, RT 1.46 min (Method 1).

Intermediate 119

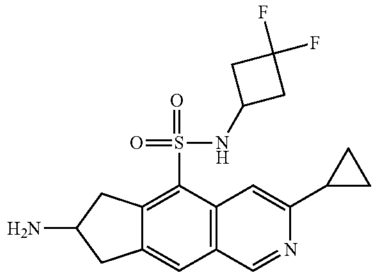 [SMILES: NC1Cc2cc3cnc(C4CC4)cc3c(S(=O)(=O)NC3CC(F)(F)C3)c2C1]

7-amino-3-cyclopropyl-N-(3,3-difluorocyclobutyl)-7,8-dihydro-6H-cyclopenta[g]isoquinoline-5-sulfonamide Intermediate 117 (1.59 g, 3.39 mmol) was stirred in dry THF (20 mL) before adding triethylamine (1.18 mL, 8.47 mmol) and DPPA (0.73 mL, 3.39 mmol). The reaction was heated at 75° C. for 45 minutes then cooled to 0° C. in an ice bath. The solution was added to a cooled solution of 3 M aq. HCl (20 mL) and the biphasic solution stirred at room temperature of 1 hour. The solution was then extracted with EtOAc (2×50 mL) and the aqueous layer basified with 1 M aq. NaOH before being extracted with EtOAc (2×50 mL). The combined organic extracts were washed with 1 M aq. NaOH resulting in precipitation. The layers were separated and the aqueous layer extracted with a 1:1 mixture of IPA and $CHCl_3$ (2×50 mL). The combined organic extracts were dried ($MgSO_4$), filtered and concentrated under reduced pressure. Purification by column chromatography with a gradient of methanol in dichloromethane gave the title compound (516 mg, 39% yield). $\delta_H$ (500 MHz, $d_6$-DMSO) 9.14 (s, 1H), 8.36 (s, 1H), 8.10 (s, 1H), 3.88-3.80 (m, 1H), 3.60-3.53 (m, 2H), 3.31 (dd, J=18.2, 4.2 Hz, 1H), 3.23 (dd, J=17.0, 6.4 Hz, 1H), 2.84 (dd, J=16.3, 4.2 Hz, 1H), 2.71-2.59 (m, 2H), 2.43-2.30 (m, 1H), 2.29-2.16 (m, 2H), 1.06-0.98 (m, 4H). 3× exchangeable protons not observed. LCMS $[M+H]^+$ 394.2, RT 1.49 min (Method 1).

Intermediate 120

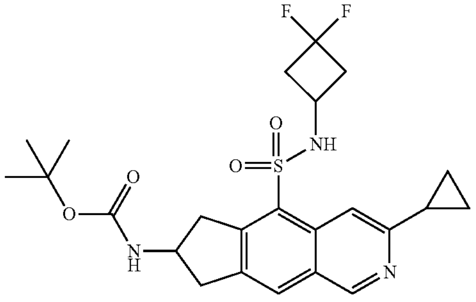 [SMILES: CC(C)(C)OC(=O)NC1Cc2cc3cnc(C4CC4)cc3c(S(=O)(=O)NC3CC(F)(F)C3)c2C1]

tert-butyl N-[3-cyclopropyl-5-[(3,3-difluorocyclobutyl) sulfamoyl]-7,8-dihydro-6H-cyclopenta[g] isoquinolin-7-yl]carbamate Intermediate 119 (0.41 g, 1.02 mmol) was stirred in DCM (10 mL). Triethylamine (0.14 mL, 1.02 mmol) was then added followed by di-tert-butyl dicarbonate (0.25 g, 1.13 mmol) and the reaction mixture was stirred at room temperature for 3 hours. The reaction mixture was then diluted with DCM (20 mL) and washed with water (2×20 mL), dried over sodium sulfate and concentrated under vacuum. Diethyl ether was added and sonicated to give a precipitate which was collected by vacuum filtration and dried to afford the title compound (400 mg, 78% yield). $\delta_H$ (500 MHz, $d_6$-DMSO) 9.15 (s, 1H), 8.48 (d, J=7.3 Hz, 1H), 8.34 (s, 1H), 8.09 (s, 1H), 7.23 (d, J=5.5 Hz, 1H), 4.33-4.16 (m, 1H), 3.69 (dd, J=18.3, 7.2 Hz, 1H), 3.63-3.48 (m, 1H), 3.42-3.31 (m, 1H), 3.32 (s, 1H), 2.95 (dd, J=16.6, 5.9 Hz, 1H), 2.69-2.54 (m, 2H), 2.42-2.17 (m, 3H), 1.39 (s, 9H), 1.07-0.98 (m, 4H). LCMS $[M+H]^+$ 494.2, RT 3.38 min (Method 2).

Intermediate 121

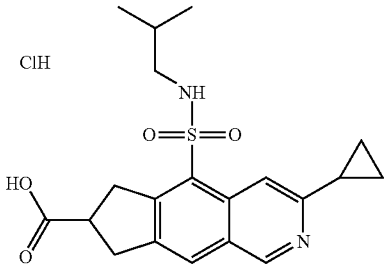 [SMILES: CC(C)CNS(=O)(=O)c1c2c(cc3cnc(C4CC4)cc13)CC(C(=O)O)C2 ; Cl]

3-cyclopropyl-5-(isobutylsulfamoyl)-7,8-dihydro-6H-cyclopenta[g]isoquinoline-7-carboxylic acid; hydrochloride Intermediate 10 (0.6 g, 1.6 mmol) was stirred in MeCN (30 mL), acetic acid (0.46 mL, 7.99 mmol) and water (0.14 mL, 7.99 mmol) were added followed by 1,3-dichloro-5,5-dimethylimidazolidine-2,4-dione (0.63 g, 3.2 mmol). The reaction was stirred at room temperature for 45 minutes. The solid sulfonyl chloride was collected by vacuum filtration, suspended in DCM (150 mL) and cooled to 0° C. 2-methylpropan-1-amine (2 ml, 20.1 mmol) was then added, and the solution stirred for 16 hours at room temperature. The reaction was concentrated under vacuum, 1 M aq. HCl (50 mL) was added and sonicated to afford a white solid which was collected by vacuum filtration followed by concentrating under vacuum with MeCN to afford the title compound as an HCl Salt (511 mg, 82% yield). $\delta_H$ (500 MHz, $d_6$-DMSO) δ 9.22 (s, 1H), 8.44 (s, 1H), 8.14 (s, 1H), 8.07 (t, J=5.9 Hz, 1H), 3.80-3.25 (m, 5H, obs. water), 2.61-2.52 (m, 2H), 2.34-2.25 (m, 1H), 1.54 (hept, J=6.7 Hz, 1H), 1.11-1.00 (m, 4H), 0.70 (d, J=6.8 Hz, 3H), 0.69 (d, J=6.7 Hz, 3H). LCMS $[M+H]^+$ 389.2, RT 1.73 min (Method 1).

Intermediate 122

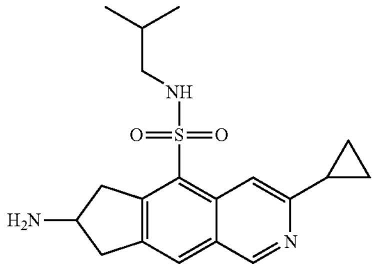 [SMILES: CC(C)CNS(=O)(=O)c1c2c(cc3cnc(C4CC4)cc13)CC(N)C2]

7-amino-3-cyclopropyl-N-isobutyl-7,8-dihydro-6H-cyclopenta[g]isoquinoline-5-sulfonamide To a solution of Intermediate 121 (0.51 g, 1.32 mmol) in dry THF (15 mL), triethylamine (0.46 mL, 3.29 mmol) and DPPA (0.31 mL, 1.45 mmol) were added. The reaction was heated to 75° C. for 2.5 hours, allowed to cool then added dropwise into 1 M aq. HCl (15 mL) and heated at 30° C. for 30 minutes then at 40° C. for 30 minutes. Saturated aq. $Na_2CO_3$ (25 mL) was added to the solution which was then extracted with DCM (50 mL, then 20 mL). The combined organics were washed with saturated aq. $Na_2CO_3$ (2×25 mL), dried over sodium sulfate and concentrated under vacuum. Purification using an SCX column followed by column chromatography using MeOH in DCM afforded the tile compound (326 mg, 63% yield). $\delta_H$ (500 MHz, $d_6$-DMSO) δ 9.09 (s, 1H), 8.39 (s, 1H), 8.03 (s, 1H), 7.93 (s, 1H), 3.78-3.69 (m, 1H), 3.55 (dd, J=18.0, 6.3 Hz, 1H), 3.24-3.13 (m, 2H), 2.75 (dd, J=16.1, 4.8 Hz, 1H), 2.54 (d, J=6.9 Hz, 2H), 2.28-2.19 (m, 1H), 1.54 (hept, J=6.7 Hz, 1H), 1.03-0.97 (m, 4H), 0.69 (d, J=6.7 Hz, 6H). LCMS $[M+H]^+$ 360.2, RT 1.49 min (Method 1).

Intermediate 123

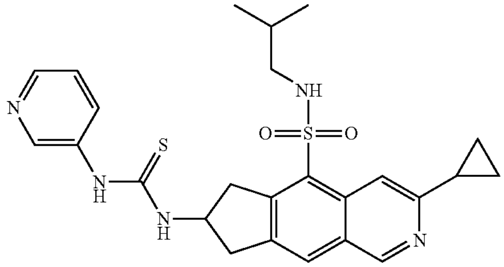 [SMILES: CC(C)CNS(=O)(=O)c1c2c(cc3cnc(C4CC4)cc13)CC(NC(=S)Nc1cccnc1)C2]

1-[3-cyclopropyl-5-(isobutylsulfamoyl)-7,8-dihydro-6H-cyclopenta[g]isoquinolin-7-yl]-3-(3-pyridyl) thiourea To a solution of Intermediate 122 (0.16 g, 0.45 mmol) in DCM (5 mL), DIPEA (62 μL, 0.45 mmol) was added followed by 3-isothiocyanatopyridine (60 μL, 0.54 mmol). The suspension was stirred for 16 hours before a second portion of 3-isothiocyanatopyridine (30 μL, 0.27 mmol) was added. The reaction mixture was stirred for 2 hours. The white suspension was diluted with heptane (5 ml), filtered and the solid washed with DCM to afford the title compound (210 mg, 93% yield). $\delta_H$ (500 MHz, $d_6$-DMSO) δ 9.50 (s, 1H), 9.15 (s, 1H), 8.54 (d, J=2.4 Hz, 1H), 8.42 (s, 1H), 8.34-8.24 (m, 2H), 8.14 (s, 1H), 8.05 (t, J=5.8 Hz, 1H), 7.97 (d, J=8.0 Hz, 1H), 7.33 (dd, J=8.2, 4.7 Hz, 1H), 5.01 (s, 1H), 3.82 (dd, J=18.2, 6.7 Hz, 1H), 3.56 (dd, J=18.4, 5.2 Hz, 1H), 3.48 (dd, J=17.1, 6.9 Hz, 1H), 3.11 (dd, J=16.6, 4.9 Hz, 1H), 2.54 (t, J=6.2 Hz, 2H), 2.29-2.22 (m, 1H), 1.60-1.49 (m, 1H), 1.07-0.98 (m, 4H), 0.75-0.63 (m, 6H). LCMS $[M+H]^+$ 496.2, RT 1.77 min (Method 1).

Intermediate 124

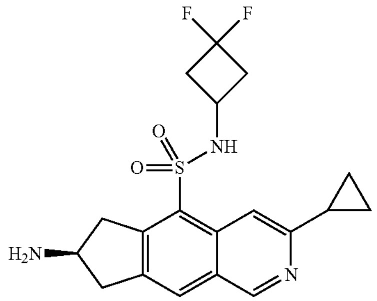 [SMILES: N[C@@H]1Cc2cc3cnc(C4CC4)cc3c(S(=O)(=O)NC3CC(F)(F)C3)c2C1]

(7R)-7-amino-3-cyclopropyl-N-(3,3-difluorocyclobutyl)-7,8-dihydro-6H-cyclopenta[g]isoquinoline-5-sulfonamide Intermediate 131 (9.1 g, 18.4 mmol) was dissolved in DCM (70 mL) and TFA (14 mL, 182 mmol) added. The reaction mixture was stirred at room temperature for 16 hours before being concentrated under vacuum. The resultant oil was dissolved in ethyl acetate (200 mL) and 1 M aq. NaOH (200 mL) was added. The layers were separated, and the aqueous layer extracted with ethyl acetate (200 mL). The combined organic extracts were washed with 1 M aq. NaOH (50 mL) and the aqueous layer extracted with ethyl acetate (2×50 mL). The organic extracts were combined, washed with brine, dried over sodium sulfate and concentrated under vacuum. The light brown solid was then triturated with TBME and collected by vacuum filtration to afford the title compound (6 g, 79% yield). $\delta_H$ (500 MHz, $d_6$-DMSO) 9.12 (s, 1H), 8.36 (s, 1H), 8.07 (s, 1H), 3.81-3.72 (m, 1H), 3.62-3.53 (m, 1H), 3.49 (dd, J=18.1, 6.1 Hz, 1H), 3.23 (dd, J=18.0, 4.2 Hz, 1H), 3.15 (dd, J=16.4, 5.7 Hz, 1H), 2.75 (dd, J=16.0, 4.2 Hz, 1H), 2.68-2.57 (m, 2H), 2.44-2.29 (m, 1H), 2.27-2.09 (m, 2H), 1.07-0.98 (m, 4H). 3x exchangeable protons not observed. LCMS $[M+H]^+$ 394.0, RT 1.47 min (Method 1).

Intermediate 125

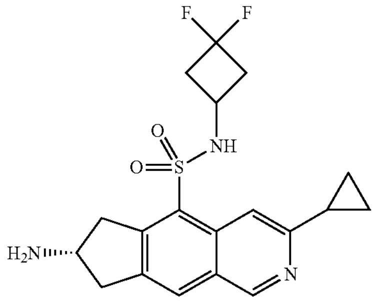 [SMILES: N[C@H]1Cc2cc3cnc(C4CC4)cc3c(S(=O)(=O)NC3CC(F)(F)C3)c2C1]

(7S)-7-amino-3-cyclopropyl-N-(3,3-difluorocyclobutyl)-7,8-dihydro-6H-cyclopenta[g]isoquinoline-5-sulfonamide Intermediate 130 (8.64 g, 17.5 mmol) was dissolved in DCM (70 mL) and TFA (13.6 mL, 178 mmol) added. The reaction mixture was stirred at room temperature for 16 hours before being concentrated under vacuum. The resultant oil was dissolved in ethyl acetate (200 mL) and 1 M aq. NaOH (200 mL) was added. The layers were separated, and the aqueous layer was extracted with ethyl acetate (200 mL). The combined organic extracts were washed with 1 M aq NaOH (50 mL) and the aqueous layer was extracted with ethyl acetate (2×50 mL). The organic extracts were combined, washed with brine, dried over sodium sulfate and concentrated under vacuum to afford a light brown solid which was triturated with TBME and collected by vacuum filtration to afford the title compound (6 g, 84% yield). $\delta_H$ (500 MHz, $d_6$-DMSO) 9.12 (s, 1H), 8.35 (s, 1H), 8.07 (s, 1H), 3.80-3.72 (m, 1H), 3.61-3.53 (m, 1H), 3.49 (dd, J=18.1, 6.1 Hz, 1H), 3.23 (dd, J=18.0, 4.2 Hz, 1H), 3.15 (dd, J=16.9, 6.1 Hz, 1H), 2.75 (dd, J=16.0, 4.2 Hz, 1H), 2.71-2.57 (m, 2H), 2.44-2.30 (m, 1H), 2.28-2.09 (m, 2H), 1.08-0.96 (m, 4H). 3× exchangeable protons not observed. LCMS $[M+H]^+$ 394.0, RT 1.48 min (Method 1).

Intermediates 126 & 127

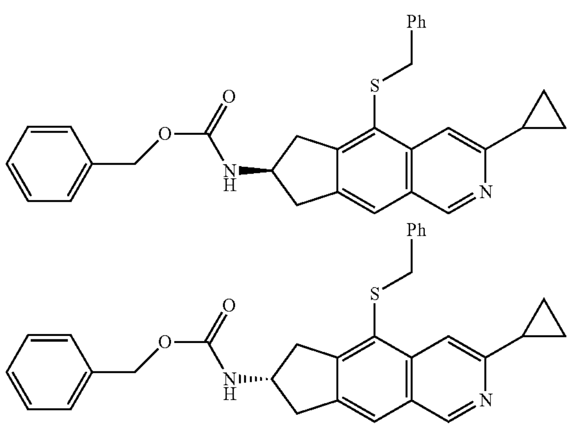

benzyl N-[(7R)-5-benzylsulfanyl-3-cyclopropyl-7,8-dihydro-6H-cyclopenta[g]isoquinolin-7-yl]carbamate (126)

benzyl N-[(7S)-5-benzylsulfanyl-3-cyclopropyl-7,8-dihydro-6H-cyclopenta[g]isoquinolin-7-yl]carbamate (127)

To a solution of Intermediate 9 (10 g, 26.6 mmol) in THF (100 mL), triethylamine (9.28 mL, 66.6 mmol) was added followed by DPPA (5.74 mL, 26.6 mmol). The reaction was heated to 75° C. for 2 hours. Benzyl alcohol (8.28 mL, 79.9 mmol) was then added and the mixture heated at 75° C. for 6.5 hours. Once at room temperature 1 M aq. NaOH (100 mL) was added and the reaction mixture was extracted with ethyl acetate (2×200 mL). The combined organics were dried over sodium sulfate and concentrated under vacuum to give an orange solid which was triturated with diethyl ether twice to give a white solid. The solid was purified by column chromatography using ethyl acetate in heptane to afford the title compound as a racemate (1.6 g). The filtrate from the diethyl ether trituration was purified by column chromatography using ethyl acetate in heptane to afford a second batch of the racemic product (3.2 g). Two batches combined (5 g, 38% yield). $\delta_H$ (500 MHz, $d_6$-DMSO) δ 9.04 (s, 1H), 7.97 (s, 1H), 7.82 (s, 1H), 7.56 (d, J=6.3 Hz, 1H), 7.42-7.27 (m, 5H), 7.15 (s, 3H), 7.04-6.94 (m, 2H), 5.03 (s, 2H), 4.21-4.10 (m, 1H), 4.05-3.90 (m, 2H), 3.29 (dd, J=16.2, 7.2 Hz, 1H), 3.15 (dd, J=17.0, 7.1 Hz, 1H), 3.02-2.85 (m, 2H), 2.24 (p, J=6.5 Hz, 1H), 1.02-0.92 (m, 4H). LCMS $[M+H]^+$ 481.2, RT 2.10 min (Method 1).

The racemate (8.4 g) [Note: the additional 3.4 grams was obtained from another experiment] was purified by supercritical fluid LC using a CHIRALCEL ODI column (50×290 mm), at 30° C. eluted with 20% EtOH in $CO_2$, to give the title compounds as single isomers:

Intermediate 126 Chiral RT**=2.20 min (4.1 g)

Intermediate 127 Chiral RT**=2.68 min (4.1 g)

**Analytical chiral HPLC was carried out using a CHIRALPAK IB column (4.6×150 mm) eluting with IPA 50% n-heptane 50% DEA 0.1% at a rate of 1.5 ml/min, at 30° C.

Intermediate 128

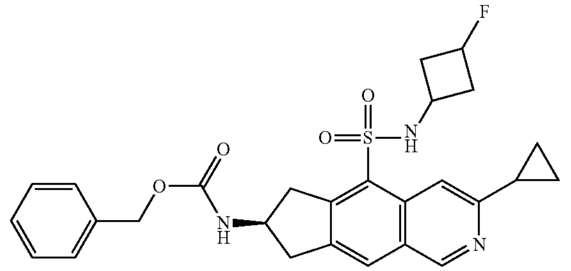 [SMILES: O=C(N[C@@H]1Cc2cc3cnc(C4CC4)cc3c(S(=O)(=O)NC3CC(F)C3)c2C1)OCc1ccccc1]

benzyl N-[(7R)-3-cyclopropyl-5-[(3-fluorocyclobutyl) sulfamoyl]-7,8-dihydro-6H-cyclopenta[g]isoquinolin-7-yl]carbamate Intermediate 126 (0.5 g, 1.04 mmol) was stirred in a mixture of MeCN (10 mL), acetic acid (300 μL, 5.2 mmol) and water (94 μL, 5.2 mmol). The suspension was cooled in an ice bath and 1,3-dichloro-5,5-dimethylimidazolidine-2,4-dione (410 mg, 2.08 mmol) was added. The reaction was allowed to warm to room temperature and after 1.5 hours the suspension was filtered under vacuum and the solid washed with MeCN to afford a sulfonyl chloride as a white solid. This was added to a stirring solution of 3-fluorocyclobutan-1-amine hydrochloride (144 mg, 1.14 mmol) and DIPEA (0.72 mL, 4.16 mmol) in DCM (10 mL). After 1 hour the reaction was concentrated under vacuum and purified by column chromatography using ethyl acetate in heptane to afford the title compound (410 mg, 77%). LCMS $[M+H]^+$ 510.0, RT 1.92 min (Method 2).

Intermediate 129

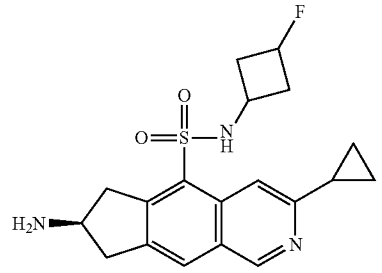 [SMILES: N[C@@H]1Cc2cc3cnc(C4CC4)cc3c(S(=O)(=O)NC3CC(F)C3)c2C1]

(7R)-7-amino-3-cyclopropyl-N-(3-fluorocyclobutyl)-7,8-dihydro-6H-cyclopenta[g]isoquinoline-5-sulfonamide To Intermediate 128 (350 mg, 0.69 mmol) and 5% Pd on $CaCO_3$ poisoned with lead (Lindlar catalyst, 5%, 439 mg, 0.08 mmol) was added water (4 mL) and THF (12 mL). The reaction was stirred under 1 atm of $H_2$ for 3 hours. Additional 5% Pd on $CaCO_3$ poisoned with lead (5%, 200 mg, 0.04 mmol) was added and reaction stirred under 1 atm of $H_2$ for 2 hours. The reaction was filtered through kieselguhr and the filtrate concentrated under vacuum. The yellow oil was purified by column chromatography using MeOH in DCM. The oil obtained was dissolved in DCM and heptane added, the solution was concentrated under vacuum to give a solid which was triturated with heptane and collected by vacuum filtration to afford the title compound (207 mg, 72%) as a mixture of cis and trans isomers. LCMS $[M+H]^+$ 376.2, RT 1.39 & 1.42 min (Method 2).

Intermediates 130 & 131

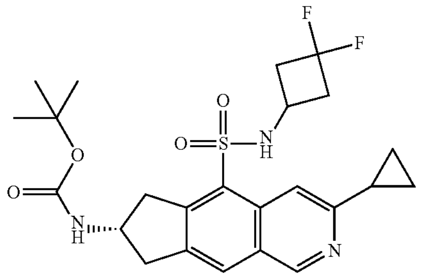

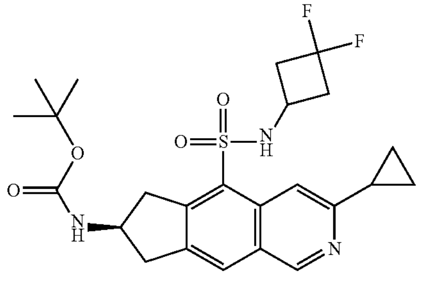

tert-butyl N-[(7S)-3-cyclopropyl-5-[(3,3-difluorocyclobutyl) sulfamoyl]-7,8-dihydro-6H-cyclopenta[g] isoquinolin-7-yl]carbamate (130)

tert-butyl N-[(7R)-3-cyclopropyl-5-[(3,3-difluorocyclobutyl) sulfamoyl]-7,8-dihydro-6H-cyclopenta[g] isoquinolin-7-yl]carbamate (131)

Intermediate 120 (0.3 g) was separated by chiral SFC using Column IF 50*250 at 30° C., with a flow rate 360 mL/min, collecting at 220 nm and eluting with 20% MeOH+ $CO_2$. To afford the title compounds.

Intermediate 130 (S isomer, 135 mg) Chiral RT**=2.51 min

Intermediate 131 (R isomer, 138 mg) Chiral RT**=3.89 min

**Chiral analysis was carried out by Normal Phase using a Chiralpak IF-3 150×4.6 mm, 3 μM, flow rate 1.5 mL/min eluting with 49% dichloromethane: 49% n-heptane: 2% ethanol (+0.1% diethylamine), using an 8 min run time on an Agilent 1290 Infinity UV directed system.

Intermediate 132

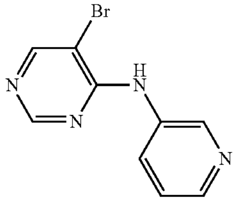 [SMILES: Brc1cncnc1Nc1cccnc1]

5-bromo-N-(3-pyridyl)pyrimidin-4-amine

A solution of 1 M potassium bis(trimethylsilyl)amide in THF (1.24 mL, 1.24 mmol) was added to a solution of 3-aminopyridine (127 mg, 1.33 mmol) in THF (4.5 mL) at −78° C. The reaction was stirred for 5 min before the addition of a solution of 5-bromo-4-chloropyrimidine (220 mg, 1.08 mmol) in THF (0.5 mL). The reaction was stirred for a further 1.5 h at −78° C., then quenched by the slow addition of sat. aq. $NH_4Cl$ (20 mL) and DCM (10 mL) at 0° C. The layers were separated, and the aq. layer extracted with DCM (2×15 mL). The organic layers were passed through a phase separator, concentrated in vacuo and purified by column chromatography on silica (gradient elution with 0% to 100% EtOAc in isohexanes; 0-20% MeOH in EtOAc) to give the title compound (94.2 mg, 35% Yield). $^1H$ NMR (300 MHz, Chloroform-d) δ 8.75 (d, J=2.7 Hz, 1H), 8.62 (s, 1H), 8.52 (s, 1H), 8.41 (dd, J=4.7, 1.6 Hz, 1H), 8.25-8.18 (m, 1H), 7.37-7.26 (m, 2H).

Intermediate 133

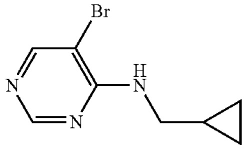 [SMILES: Brc1cncnc1NCC1CC1]

5-bromo-N-(cyclopropylmethyl)pyrimidin-4-amine

Cyclopropylmethylamine (0.12 mL, 1.4 mmol) and DIPEA (0.22 mL, 1.3 mmol) were added to a solution of 5-bromo-4-chloropyrimidine (104 mg, 0.509 mmol) in MeCN (2.5 mL). The reaction was stirred at 120° C. in the microwave for 1 h, concentrated in vacuo and purified by column chromatography on silica (gradient elution with 0% to 100% EtOAc in isohexanes) to give the title compound (116 mg, quantitative). LCMS $[M+H]^+$ 228.2/230.2, RT 0.93 min (Method 6).

Intermediate 134

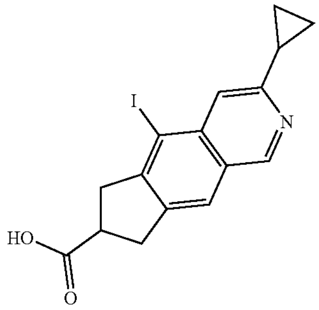 [SMILES: O=C(O)C1Cc2cc3cnc(C4CC4)cc3c(I)c2C1]

3-cyclopropyl-5-iodo-7,8-dihydro-6H-cyclopenta[g] isoquinoline-7-carboxylic acid To a stirred solution of Intermediate 7 (4 g, 8.84 mmol) in THF (40 mL) was added aqueous 2M lithium hydroxide monohydrate (8.84 mL, 17.7 mmol) and the mixture stirred at 50° C. for 1.5 hours. Reaction diluted with water and the solvent was reduced in vacuo. The remaining aqueous solution was acidified to pH=1 with 1M HCl. The thick paste that formed was diluted with water, filtered under suction, then dried in vacuo at 40° C. overnight to afford the title compound (3.66 g) as a pale yellow solid. LCMS $[M+H]^+$ 380, RT 1.76 min (Method 1).

Intermediate 135

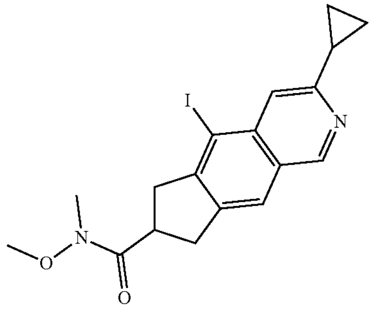 [SMILES: CON(C)C(=O)C1Cc2cc3cnc(C4CC4)cc3c(I)c2C1]

3-cyclopropyl-5-iodo-N-methoxy-N-methyl-7,8-dihydro-6H-cyclopenta[g]isoquinoline-7-carboxamide To a stirring suspension of Intermediate 134 (1.8 g, 4.75 mmol) in anhydrous DMF (30 mL) was added N,O-dimethylhydroxylamine hydrochloride (695 mg, 7.12 mmol) followed by triethylamine (2.3 mL, 16.6 mmol) and the mixture stirred at room temperature under an atmosphere of nitrogen for 10 minutes. HATU (2.17 g, 5.7 mmol) was added and stirring was continued at room temperature for 72 hours. The mixture was diluted with ethyl acetate (70 mL), washed with 1M HCl (30 mL), water (30 mL), 1M NaOH (30 mL), water (30 mL), brine (30 mL), then dried over magnesium sulfate, filtered and concentrated. The residue was purified by silica column chromatography, eluting with 0 to 100% ethyl acetate in heptane to afford the title compound (1.72 g, 81% yield) as a yellow gum. $^1$H NMR (250 MHz, Chloroform-d) $\delta_H$ 8.88 (s, 1H), 7.67-7.55 (m, 2H), 3.87-3.68 (m, 4H), 3.51 (t, J=8.4 Hz, 2H), 3.40 (dd, J=8.7, 3.7 Hz, 2H), 3.27 (s, 3H), 2.32-2.15 (m, 1H), 1.18-0.96 (m, 4H). LCMS $[M+H]^+$ 423, RT 1.89 min (Method 1).

Intermediate 136

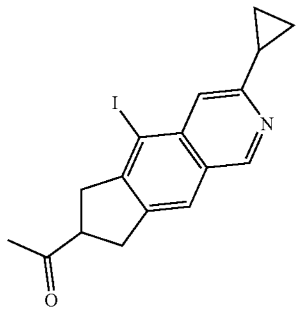 [SMILES: CC(=O)C1Cc2cc3cnc(C4CC4)cc3c(I)c2C1]

1-(3-cyclopropyl-5-iodo-7,8-dihydro-6H-cyclopenta[g]isoquinolin-7-yl) ethenone

To a stirred solution of Intermediate 135 (1.72 g, 4.1 mmol) in anhydrous THF (20 mL) cooled to −78° C. under nitrogen, was added methylmagnesium bromide (3.2M in 2-Me-THF) (2.54 mL, 8.13 mmol) dropwise and the mixture was allowed to reach 0° C. and was left stirring for 1 hour. Sat. aq. $NH_4Cl$ (10 mL) was added dropwise, the mixture allowed to warm to room temperature, diluted with water (20 mL) and extracted with ethyl acetate (2×30 mL). The combined organics were washed with brine (20 mL), dried over magnesium sulfate, filtered and concentrated in vacuo to afford the title compound (1.42 g, 89% yield) as a yellow gum which solidified upon standing.

$^1$H NMR (250 MHz, Chloroform-d) $\delta_H$ 8.89 (s, 1H), 7.63 (s, 2H), 3.57-3.43 (m, 3H), 3.37 (d, J=7.3 Hz, 2H), 2.30 (s, 3H), 2.29-2.13 (m, 1H), 1.19-0.95 (m, 4H). LCMS $[M+H]^+$ 378, RT 1.91 min (Method 1).

Intermediate 137

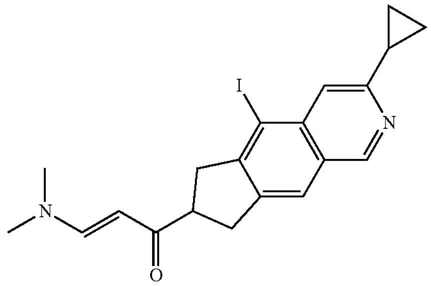 [SMILES: CN(C)/C=C/C(=O)C1Cc2cc3cnc(C4CC4)cc3c(I)c2C1]

(E)-1-(3-cyclopropyl-5-iodo-7,8-dihydro-6H-cyclopenta[g]isoquinolin-7-yl)-3-(dimethylamino) prop-2-en-1-one A stirring suspension of Intermediate 136 (200 mg, 0.53 mmol) in DMF-DMA (0.7 mL, 5.3 mmol) was heated in a sealed tube to 105° C. for 7 hours. The reaction was cooled to room temperature, the brown solid dissolved in ethyl acetate (20 mL), washed with sat. aq. $NH_4Cl$/water (1:1, 15 mL), water (10 mL), brine (10 mL), dried over magnesium sulfate, filtered and concentrated under reduced pressure. Residue purified by silica column chromatography, eluting with 0 to 100% ethyl acetate in heptane, followed by 0 to 30% methanol in ethyl acetate to afford the title compound (152 mg, 66% yield) as a red solid. $^1$H NMR (250 MHz, Chloroform-d) $\delta_H$ 8.86 (s, 1H), 7.70-7.57 (m, 3H), 5.12 (d, J=12.5 Hz, 1H), 3.58-3.25 (m, 5H), 3.08 (br. s, 3H), 2.86 (br. s, 3H), 2.31-2.14 (m, 1H), 1.17-0.94 (m, 4H). LCMS $[M+H]^+$ 433, RT 1.85 min (Method 1).

Intermediate 138

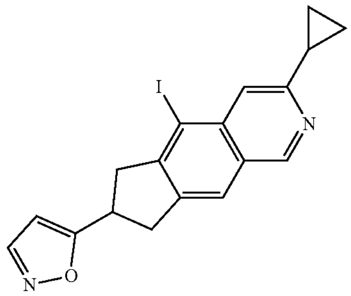 [SMILES: Ic1c2c(cc3cnc(C4CC4)cc13)CC(c1ccno1)C2]

5-(3-cyclopropyl-5-iodo-7,8-dihydro-6H-cyclopenta[g]isoquinolin-7-yl) isoxazole

A mixture of Intermediate 137 (865 mg, 2 mmol) and hydroxylamine hydrochloride (186 mg, 2.1 mmol) in ethanol (15 mL) was stirred at 85° C. for 84 hours under an atmosphere of nitrogen. The solvent was reduced in vacuo and the residue purified by silica column chromatography, eluting with 0 to 100% ethyl acetate in heptane to afford the title compound (650 mg, 81% yield) as a red solid. $^1$H NMR (250 MHz, Chloroform-d) $\delta_H$ 8.90 (s, 1H), 8.17 (d, J=1.5 Hz, 1H), 7.67 (s, 1H), 7.65 (s, 1H), 6.06 (d, J=1.0 Hz, 1H), 4.04-3.82 (m, 1H), 3.80-3.52 (m, 2H), 3.54-3.27 (m, 2H), 2.33-2.16 (m, 1H), 1.18-0.93 (m, 4H). LCMS $[M+H]^+$ 403, RT 2.01 min (Method 1).

Intermediate 139

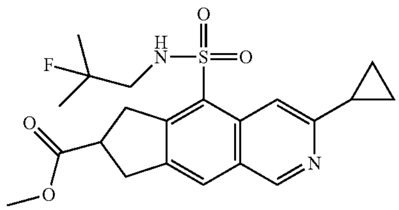 [SMILES: COC(=O)C1Cc2cc3cnc(C4CC4)cc3c(S(=O)(=O)NCC(C)(C)F)c2C1]

methyl 3-cyclopropyl-5-[(2-fluoro-2-methyl-propyl) sulfamoyl]-7,8-dihydro-6H-cyclopenta[g]isoquinoline-7-carboxylate Acetyl chloride (130 μL, 1.83 mmol) was added to methanol (80 mL) and stirred for 10 minutes before adding Intermediate 11 (91%, 4 g, 8.96 mmol). The suspension was stirred and heated at 40° C. for 2.5 hours. Solvent removed, residues dissolved in EtOAc (200 mL), washed with saturated aqueous $NaHCO_3$ (2×100 mL), dried over $MgSO_4$, filtered and concentrated to afford the title compound (3.63 g, 91% yield) as a pale brown solid.

$^1$H NMR (500 MHz, DMSO-$d_6$) $\delta_H$ 9.12 (s, 1H), 8.43 (s, 1H), 8.34 (s, 1H), 8.08 (s, 1H), 3.78 (dd, J=18.4, 8.6 Hz, 1H), 3.67-3.58 (m, 4H), 3.47-3.39 (m, 1H), 3.40-3.33 (m, 1H), 3.26 (dd, J=17.0, 7.0 Hz, 1H), 2.93 (dt, J=21.5, 10.7 Hz, 2H), 2.31-2.23 (m, 1H), 1.16 (d, J=21.4 Hz, 3H), 1.14 (d, J=21.4 Hz, 3H), 1.05-0.99 (m, 4H). LCMS [M+H]$^+$ 421.2, RT 1.83 min (Method 1)

Intermediate 140

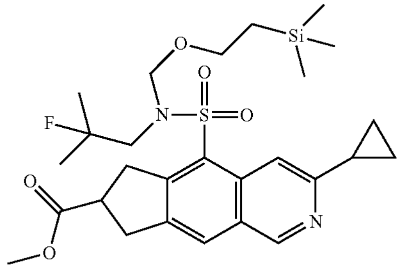 [SMILES: COC(=O)C1Cc2cc3cnc(C4CC4)cc3c(S(=O)(=O)N(COCC[Si](C)(C)C)CC(C)(C)F)c2C1]

methyl 3-cyclopropyl-5-[(2-fluoro-2-methyl-propyl)-(2-trimethylsilylethoxymethyl) sulfamoyl]-7,8-dihydro-6H-cyclopenta[g]isoquinoline-7-carboxylate Intermediate 139 (94%, 3.63 g, 8.11 mmol) was dissolved in DMF (60 mL) and cooled to 0° C. before adding NaH (60%, 380 mg, 9.5 mmol) portionwise. Reaction stirred at 0° C. for 10 minutes then 2-(chloromethoxy)ethyl](trimethyl) silane (1.7 mL, 9.61 mmol) was added. Reaction allowed to warm to room temperature, stirred for 15 minutes, quenched with water (100 mL), then extracted with EtOAc (2×100 mL). The combined organic extracts were washed with water (100 mL) then brine (50 mL), dried over $MgSO_4$, filtered and concentrated under reduced pressure. Residue purified by silica column chromatography eluting with 15-30% EtOAc/heptane to afford the title compound (3.42 g, 76% yield) as a pale yellow solid.

$^1$H NMR (500 MHz, Chloroform-d) $\delta_H$ 9.02 (s, 1H), 8.24 (s, 1H), 7.88 (s, 1H), 4.96 (s, 2H), 3.92-3.84 (m, 1H), 3.84-3.78 (m, 1H), 3.72 (s, 3H), 3.60 (dd, J=20.7, 15.5 Hz, 1H), 3.50 (dd, J=23.8, 15.5 Hz, 1H), 3.43-3.33 (m, 3H), 3.32-3.21 (m, 2H), 2.23-2.14 (m, 1H), 1.28 (d, J=21.5 Hz, 3H), 1.14-1.02 (m, 7H), 0.67-0.56 (m, 2H),−0.13 (s, 9H). LCMS [M+H]$^+$ 551.2, RT 2.24 min (Method 1)

Intermediate 141

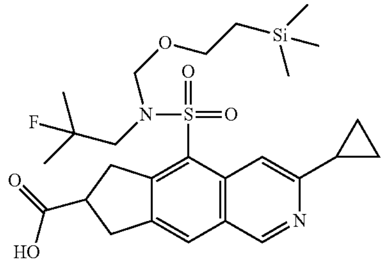 [SMILES: CC(C)(F)CN(COCC[Si](C)(C)C)S(=O)(=O)c1c2c(cc3cnc(C4CC4)cc13)CC(C(=O)O)C2]

3-cyclopropyl-5-[(2-fluoro-2-methyl-propyl)-(2-trimethylsilylethoxymethyl) sulfamoyl]-7,8-dihydro-6H-cyclopenta[g]isoquinoline-7-carboxylic acid Intermediate 140 (105 mg, 0.191 mmol), 2M aq. lithium hydroxide (0.28 mL, 0.84 mmol) and THF (3 mL) were heated for 3 hours at 40° C. in a stirred pressure tube under nitrogen. Reaction neutralised with 1M aq. HCl then pH 6.5 buffer (3 mL) was added. Mixture extracted with ethyl acetate (2×40 mL), the combine ethyl acetate extracts washed with brine (10 mL), dried over $MgSO_4$, filtered and concentrated in-vacuo to afford the title compound (98.7 mg, 92% yield) as a colourless oil.

$^1$H NMR (500 MHz, d-chloroform) $\delta_H$ 9.07 (s, 1H), 8.24 (s, 1H), 7.89 (s, 1H), 4.96 (d, J=10.8 Hz 1H), 4.95 (d, J=10.8 Hz, 1H), 3.93-3.83 (m, 2H), 3.58 (dd, J=21.0, 15.5 Hz, 1H), 3.48 (dd, J=23.4, 15.5 Hz, 1H), 3.40 (m, 3H), 3.32-3.21 (m, 2H), 2.25-2.18 (m, 1H), 1.25 (d, J=21.4 Hz, 3H), 1.09 (d, J=21.4 Hz, 3H), 1.09-1.05 (m, 4H), 0.66-0.55 (m, 2H),−0.14 (s, 9H). LCMS [M+H]$^+$ 537, RT 4.14 min (Method 2)

Intermediate 142

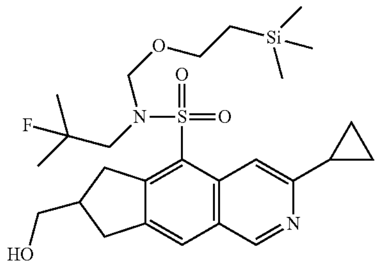 [SMILES: CC(C)(F)CN(COCC[Si](C)(C)C)S(=O)(=O)c1c2c(cc3cnc(C4CC4)cc13)CC(CO)C2]

3-cyclopropyl-N-(2-fluoro-2-methyl-propyl)-7-(hydroxymethyl)-N-(2-trimethylsilylethoxymethyl)-7,8-dihydro-6H-cyclopenta[g]isoquinoline-5-sulfonamide Intermediate 141 (110 mg, 0.20 mmol) was dissolved in THF (2.5 mL) and cooled to 0° C. before addition of 1.2 M DIBAL-H in toluene (198 µL). Reaction stirred at 0° C. for 30 mins and a further 200 µl of 1.2 M DIBAL-H in toluene added. After 15 minutes reaction quenched with water (20 µL) followed by 15% aqueous NaOH (20 µL) and more water (50 µL). After stirring for 15 mins reaction diluted with EtOAc (20 mL), washed with aqueous Rochelle's salt (2×20 mL) then brine (20 mL) and dried over $MgSO_4$. Solvent removed to afford the title compound (110 mg, 94% purity) as a colourless solid. LCMS [M+H]$^+$ 523.2, RT 2.11 min (Method 1)

Intermediate 143

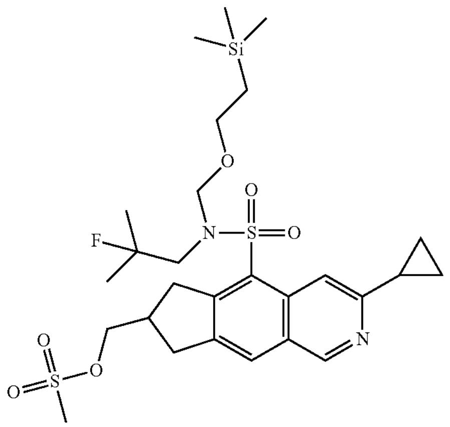 [SMILES: CC(C)(F)CN(COCC[Si](C)(C)C)S(=O)(=O)c1c2c(cc3cnc(C4CC4)cc13)CC(COS(C)(=O)=O)C2]

[3-cyclopropyl-5-[(2-fluoro-2-methyl-propyl)-(2-trimethylsilylethoxymethyl) sulfamoyl]-7,8-dihydro-6H-cyclopenta[g]isoquinolin-7-yl]methyl methane-sulfonate Intermediate 142 (94%, 110 mg, 0.2 mmol) was dissolved in DCM (2 mL) and DIPEA (86 μL, 0.49 mmol) followed by methanesulfonyl chloride (23 μL, 0.3 mmol) added. The solution was stirred at room temperature for 15 minutes, concentrated and purified by silica column chromatography, eluting with 30-60% EtOAc/heptane, to afford the title compound (100 mg, 84% yield) as a colourless oil. LCMS $[M+H]^+$ 601.2, RT 2.18 min (Method 1)

Intermediate 144

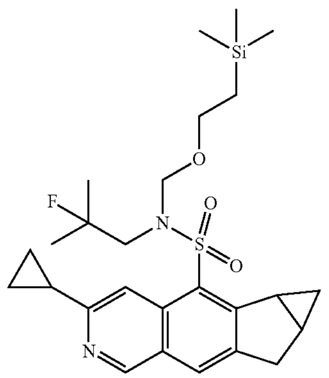 [SMILES: CC(C)(F)CN(COCC[Si](C)(C)C)S(=O)(=O)c1c2c(cc3cnc(C4CC4)cc13)CC1CC21]

13-cyclopropyl-N-(2-fluoro-2-methyl-propyl)-N-(2-trimethylsilylethoxymethyl)-12-azatetracyclo [8.4.0.03,8.04,6]tetradeca-1 (10),2,8,11,13-pentaene-2-sulfonamide Potassium cyanide (12 mg, 0.18 mmol), was added to a mixture of Intermediate 143 (100 mg, 0.17 mmol) and TBAB (11 mg, 0.03 mmol) in DMF/water (2 mL/0.2 mL). The mixture was stirred and heated at 100° C. for 3 hours, diluted with EtOAc (25 mL), washed with water (3×25 mL) then brine (25 mL), dried over $MgSO_4$, and concentrated. Residues purified by silica column chromatography eluting with 5-25% EtOAc/heptane to afford the title compound (75% yield) as a white solid.

$^1$H NMR (500 MHz, Chloroform-d) $\delta_H$ 8.93 (s, 1H), 8.31 (s, 1H), 7.77 (s, 1H), 4.98-4.91 (m, 2H), 3.67 (dd, J=22.9, 15.4 Hz, 1H), 3.57-3.45 (m, 2H), 3.39-3.31 (m, 1H), 3.29-3.18 (m, 2H), 3.11 (d, J=17.2 Hz, 1H), 2.23-2.16 (m, 1H), 2.11-2.05 (m, 1H), 1.45-1.37 (m, 1H), 1.30 (d, J=21.5 Hz, 3H), 1.14 (d, J=21.3 Hz, 3H), 1.11-1.07 (m, 2H), 1.07-1.02 (m, 2H), 0.57-0.52 (m, 2H), 0.21-0.15 (m, 1H),−0.16 (s, 9H). LCMS $[M+H]^+$ 505.4, RT 5.19 min (Method 2)

Intermediate 145

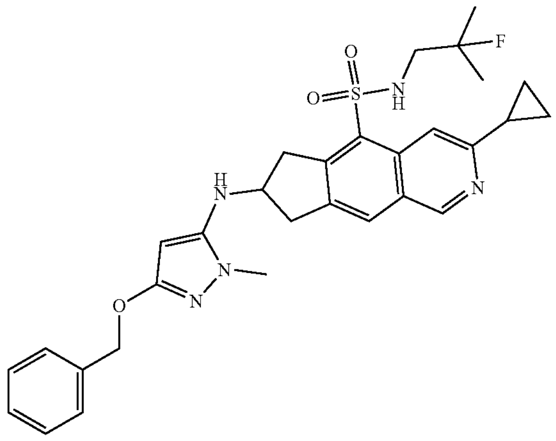 [SMILES: Cn1nc(OCc2ccccc2)cc1NC1Cc2cc3cnc(C4CC4)cc3c(S(=O)(=O)NCC(C)(C)F)c2C1]

7-[(5-benzyloxy-2-methyl-pyrazol-3-yl)amino]-3-cyclopropyl-N-(2-fluoro-2-methyl-propyl)-7,8-dihydro-6H-cyclopenta[g]isoquinoline-5-sulfonamide To a solution of Intermediate 12 (45 mg, 0.119 mmol) in anhydrous 1,4-dioxane (1 mL) were added Intermediate 188 (38 mg, 0.121 mmol), sodium tert-butoxide (35 mg, 0.364 mmol) and tBuXPhos Pd G3 (15 mg, 0.0183 mmol). The reaction was heated to 100° C. for 2 hours under a nitrogen atmosphere. Reaction cooled to room temperature, filtered through Celite, solvent removed, and residue purified by silica column chromatography eluting with 0-100% ethyl acetate in iso-hexane to afford the title compound (78% yield) as a brown oil. LCMS $[M+H]^+$ 564.4, RT 1.26 min (Method 1)

Intermediate 146

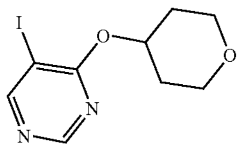 [SMILES: Ic1cncnc1OC1CCOCC1]

5-iodo-4-tetrahydropyran-4-yloxy-pyrimidine

To tetrahydro-4-pyranol (34 mg, 0.321 mmol) in 1,4-dioxane (1.1 mL) were added 4-chloro-5-iodopyrimidine (53 mg, 0.210 mmol) followed by sodium tert-butoxide (78 mg, 0.813 mmol) and the reaction stirred at room temperature under nitrogen for 2 hours, followed by 45 minutes at 80° C. The crude solution was used in the next step. LCMS $[M+H]^+$ 307.0, RT 1.33 min (Method 6).

Intermediate 147

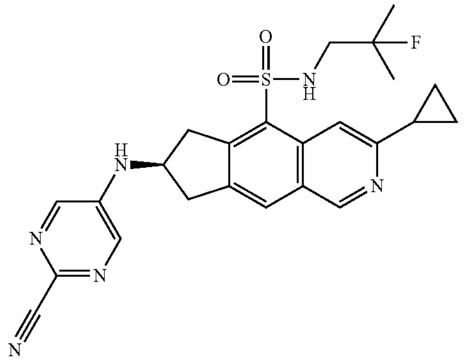 [SMILES: CC(C)(F)CNS(=O)(=O)c1c2c(cc3cnc(C4CC4)cc13)C[C@@H](Nc1cnc(C#N)nc1)C2]

(7R)-7-[(2-cyanopyrimidin-5-yl)amino]-3-cyclopropyl-N-(2-fluoro-2-methyl-propyl)-7,8-dihydro-6H-cyclopenta[g]isoquinoline-5-sulfonamide Intermediate 15 (50 mg, 0.133 mmol) was dissolved in 1,4-dioxane (2 mL) and tBuXPhos Pd G3 (16 mg, 0.0195 mmol), sodium tert-butoxide (38 mg, 0.395 mmol) and 5-bromopyrimidine-2-carbonitrile (49 mg, 0.266 mmol) were added and the reaction stirred at room temperature for 18 hours. Reaction diluted with EtOAc, filtered through celite, and purified by silica column chromatography eluting with 0 to 100% EtOAc in hexane to afford the title compound (26 mg, 41% yield) as a yellow oil. LCMS $[M+H]^+$ 481.2, RT 1.08 min (Method 6).

Intermediate 148

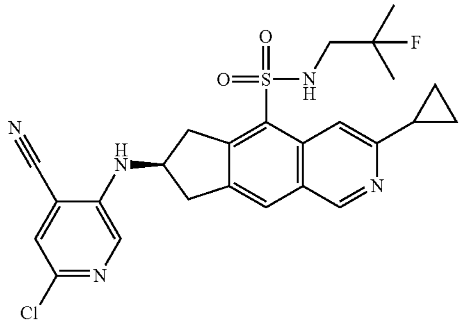 [SMILES: CC(C)(F)CNS(=O)(=O)c1c2c(cc3cnc(C4CC4)cc13)C[C@@H](Nc1cnc(Cl)cc1C#N)C2]

(7R)-7-[(6-chloro-4-cyano-3-pyridyl)amino]-3-cyclopropyl-N-(2-fluoro-2-methyl-propyl)-7,8-dihydro-6H-cyclopenta[g]isoquinoline-5-sulfonamide Intermediate 15 (60 mg, 0.159 mmol) was dissolved in 1,4-dioxane (2 mL) and tBuXPhos Pd G3 (13 mg, 0.0159 mmol) and sodium tert-butoxide (45 mg, 0.468 mmol) and 5-bromo-2-chloro-pyridine-4-carbonitrile (58 mg, 0.2667 mmol) were added. Heated at 70° C. for 3 hours. Reaction diluted with EtOAc, filtered through celite and purified by silica column chromatography, eluting with 0 to 100% EtOAc in hexane to afford the title compound (30 mg, 37% yield). LCMS $[M+H]^+$ 514.1, RT 1.22 min (Method 6).

Intermediate 149

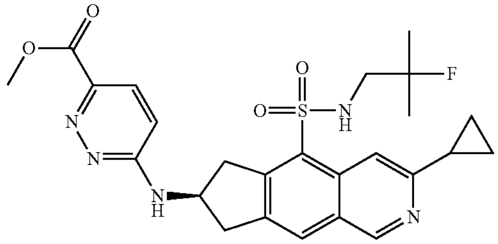 [SMILES: COC(=O)c1ccc(N[C@@H]2Cc3cc4cnc(C5CC5)cc4c(S(=O)(=O)NCC(C)(C)F)c3C2)nn1]

methyl 6-[[(7R)-3-cyclopropyl-5-[(2-fluoro-2-methyl-propyl) sulfamoyl]-7,8-dihydro-6H-cyclopenta[g]isoquinolin-7-yl]amino]pyridazine-3-carboxylate In a pressure tube, to a suspension of Intermediate 15 (200 mg, 0.53 mmol) and methyl 6-bromopyridazine-3-carboxylate (138 mg, 0.64 mmol) in tert-butanol (8 mL) was added DIPEA (0.28 mL, 1.59 mmol). The mixture was sealed and heated at 110° C. for 18 hours. The solvent was removed to give a brown oil which was purified by silica column chromatography, eluting with 0-100% EtOAc/heptane to afford the title compound (144 mg, 52% yield).

$^1$H NMR (250 MHz, Chloroform-d) $\delta_H$ 9.06 (s, 1H), 8.30 (s, 1H), 7.92 (s, 1H), 7.88 (s, 1H), 6.68 (d, J=9.3 Hz, 1H), 5.42-5.27 (m, 1H), 5.15-5.02 (m, 1H), 4.99-4.86 (m, 1H), 4.01 (s, 3H), 3.77-3.50 (m, 2H), 3.27-2.86 (m, 3H), 2.30-2.10 (m, 1H), 1.39-1.01 (m, 10H). LCMS $[M+H]^+$ 514.0, RT 1.71 min (Method 1)

Intermediate 150

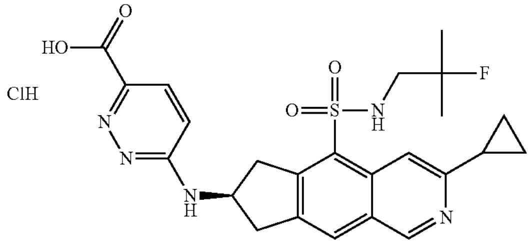 [SMILES: Cl ; CC(C)(F)CNS(=O)(=O)c1c2c(cc3cnc(C4CC4)cc13)C[C@@H](Nc1ccc(C(=O)O)nn1)C2]

6-[[(7R)-3-cyclopropyl-5-[(2-fluoro-2-methyl-propyl) sulfamoyl]-7,8-dihydro-6H-cyclopenta[g]isoquinolin-7-yl]amino]pyridazine-3-carboxylic acid hydrochloride To a solution of Intermediate 149 (53 mg, 0.1 mmol) in THF (3 mL)/water (0.75 mL) was added lithium hydroxide hydrate (1:1) (13 mg, 0.31 mmol). The solution was stirred at room temperature for 18 hours. The solvent was removed and 1N HCl (2 mL) was added and the solvent removed to quantitatively afford the title compound as a brown gum. LCMS $[M+H]^+$ 500.0, RT 1.56 min (Method 1).

Intermediate 151

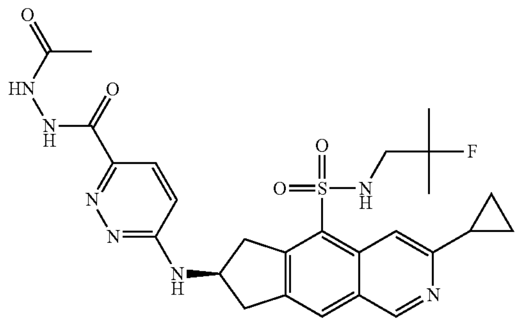 [SMILES: CC(=O)NNC(=O)c1ccc(N[C@@H]2Cc3cc4cnc(C5CC5)cc4c(S(=O)(=O)NCC(C)(C)F)c3C2)nn1]

(7R)-7-[[6-(acetamidocarbamoyl)pyridazin-3-yl] amino]-3-cyclopropyl-N-(2-fluoro-2-methyl-propyl)-7,8-dihydro-6H-cyclopenta[g]isoquinoline-5-sulfonamide To a solution of Intermediate 150 (51 mg, 0.1 mmol) in DMF (3 mL) was added triethylamine (0.04 mL, 0.31 mmol), acetohydrazide (9.1 mg, 0.12 mmol), 3H-[1,2,3] triazolo[4,5-b]pyridin-3-ol (20.8 mg, 0.15 mmol) and N-[3-(dimethylamino) propyl]-N'-ethylcarbodiimide hydrochloride (1:1) (29.4 mg, 0.15 mmol). The solution was stirred for 18 hours followed by addition of N-[(dimethylamino) (3H-[1,2,3]triazolo[4,5-b]pyridin-3-yloxy)methylidene]-N-methylmethanaminium hexafluorophosphate (38.8 mg, 0.1 mmol) and stirring for 2 hours. Water (10 mL) and EtOAc (15 mL) were added, the organic layer separated and washed with water (2×5 mL), dried ($Na_2SO_4$) and the solvent removed. Residue purified by silica column chromatography, eluting with 0-10% 7M $NH_3$ in methanol/DCM) to afford the title compound (42 mg, 74% yield). LCMS $[M+H]^+$ 556, RT 1.60 min (Method 1).

Intermediate 152

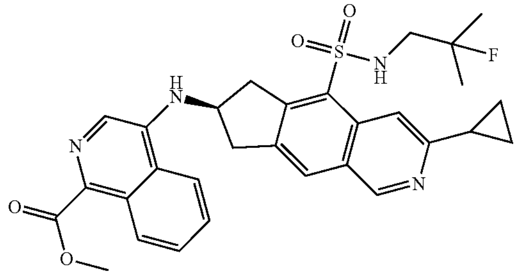 [SMILES: COC(=O)c1ncc(N[C@@H]2Cc3cc4cnc(C5CC5)cc4c(S(=O)(=O)NCC(C)(C)F)c3C2)c2ccccc12]

methyl 4-[[(7R)-3-cyclopropyl-5-[(2-fluoro-2-methyl-propyl) sulfamoyl]-7,8-dihydro-6H-cyclopenta[g]isoquinolin-7-yl]amino]isoquinoline-1-carboxylate Intermediate 15 (50 mg, 0.133 mmol), methyl 4-bromoisoquinoline-1-carboxylate (109 mg, 0.397 mmol), sodium tert-butoxide (38 mg, 0.397 mmol) and tBuXPhos Pd G3 (16 mg, 0.0199 mmol) were degassed with 3 cycles of vacuum/nitrogen prior to addition of dry 1,4-dioxane (2 mL). A further cycle of vac/nitrogen then the reaction was sealed and stirred at room temperature for 45 minutes, followed by 2.5 hours at 70° C. Reaction diluted with water (3 mL) and extracted with EtOAc (3 mL). The organic extracts were dried over $Na_2SO_4$ concentrated in vacuo and purified by silica column chromatography eluting with 0-100% EtOAc in isohexane followed by 0-5% MeOH in EtOAc to afford the title compound (64 mg, 86% yield).

$^1H$ NMR (400 MHz, DMSO-d6) $\delta_H$ 9.16 (s, 1H), 8.86-8.77 (m, 1H), 8.49-8.43 (m, 1H), 8.42-8.28 (m, 2H), 8.15 (s, 1H), 8.07 (s, 1H), 7.73-7.62 (m, 2H), 7.12 (d, J=6.2 Hz, 1H), 4.77-4.62 (m, 1H), 4.03 (dd, J=18.5, 7.1 Hz, 1H), 3.89 (s, 3H), 3.78-3.57 (m, 2H), 3.29-3.23 (m, 1H), 2.90 (dd, J=20.3, 6.2 Hz, 2H), 2.31-2.23 (m, 1H), 1.12-0.98 (m, 10H). LCMS $[M+H]^+$ 563.2, RT 2.31 min (Method 10)

Intermediate 153

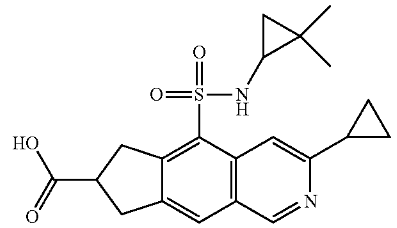 [SMILES: CC1(C)CC1NS(=O)(=O)c1c2c(cc3cnc(C4CC4)cc13)CC(C(=O)O)C2]

3-cyclopropyl-5-[(2,2-dimethylcyclopropyl) sulfamoyl]-7,8-dihydro-6H-cyclopenta[g]isoquinoline-7-carboxylic acid To a stirring solution of 2,2-dimethylcyclopropanamine hydrochloride (1:1) (42 mg, 0.34 mmol) and DIPEA (0.15 mL, 0.85 mmol) in anhydrous DCM (1 mL) was added Intermediate 10 (100 mg, 0.28 mmol) and the mixture stirred at room temperature for 4 hours. The mixture was diluted with DCM (2 mL) and treated with 1M aq. HCl (1 mL). The layers were separated and the aqueous extracted with DCM/MeOH (10:1, 2×10 mL). The combined organics were washed with brine (10 mL), dried over magnesium sulfate, filtered and concentrated to afford the title compound (61 mg, 50% yield) as a white solid. LCMS $[M+H]^+$ 401, RT 1.75 min (Method 1).

Intermediate 154

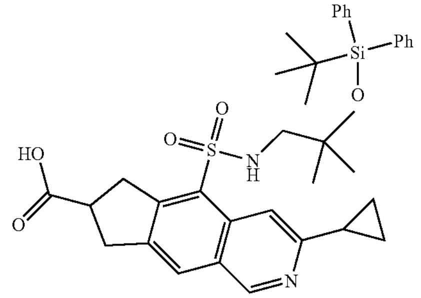

5-[[2-[tert-butyl(diphenyl) silyl]oxy-2-methyl-propyl]sulfamoyl]-3-cyclopropyl-7,8-dihydro-6H-cyclopenta[g]isoquinoline-7-carboxylic acid To a stirring solution of Intermediate 193 (490 mg, 1.5 mmol) and DIPEA (0.74 mL, 4.3 mmol) in anhydrous DCM (10 mL) was added Intermediate 10 (500 mg, 1.4 mmol) and the mixture stirred at room temperature for 2 hours. The mixture was diluted with DCM (20 mL), water (10 mL) and 1M aq. HCl (10 mL). The layers were separated and the aqueous was extracted with DCM (2×20 mL). The combined organics were washed with 1M HCl (10 mL), brine (10 mL), dried over magnesium sulfate, filtered and concentrated. The crude material was purified by silica column chromatography eluting with 0 to 100% ethyl acetate in heptane, followed by 0 to 20% methanol in ethyl acetate to afford the title compound (660 mg, 70% yield). LCMS $[M+H]^+$ 643, RT 2.28 min (Method 1).

Intermediate 155

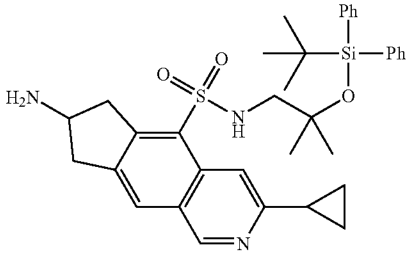 [SMILES: CC(C)(CNS(=O)(=O)c1c2c(cc3cnc(C4CC4)cc13)CC(N)C2)O[Si](c1ccccc1)(c1ccccc1)C(C)(C)C]

7-amino-N-[2-[tert-butyl(diphenyl) silyl]oxy-2-methyl-propyl]-3-cyclopropyl-7,8-dihydro-6H-cyclopenta[g]isoquinoline-5-sulfonamide To Intermediate 154 (430 mg, 0.67 mmol) in anhydrous THF (12 mL), was added triethylamine (233 μL, 1.67 mmol) followed by DPPA (144 μL, 0.67 mmol) and the resulting mixture heated at reflux for 2.5 hours. The reaction was allowed to cool to room temperature, 1M aq. HCl (12 mL) was added and the mixture was stirred at room temperature for 1.5 hours. 1M NaOH was added until pH 10, the mixture extracted with ethyl acetate (3×20 mL) and the combined organics washed with brine (10 mL), dried over magnesium sulfate, filtered and concentrated. The residue was purified using a 5 g SCX cartridge, washing with DCM (×2), MeOH (×3) and eluted with ammonia (7N in methanol) to afford the title compound (340 mg, 64% yield, 77% UV purity) as a pale yellow solid. LCMS $[M+H]^+$ 614, RT 2.06 min (Method 1).

Intermediate 156

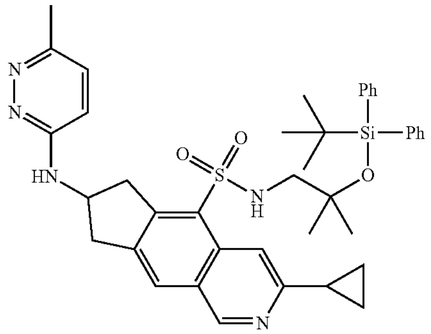 [SMILES: Cc1ccc(NC2Cc3cc4cnc(C5CC5)cc4c(S(=O)(=O)NCC(C)(C)O[Si](c4ccccc4)(c4ccccc4)C(C)(C)C)c3C2)nn1]

N-[2-[tert-butyl(diphenyl) silyl]oxy-2-methyl-propyl]-3-cyclopropyl-7-[(6-methylpyridazin-3-yl) amino]-7,8-dihydro-6H-cyclopenta[g]isoquinoline-5-sulfonamide A mixture Intermediate 155 (100 mg, 0.16 mmol), 3-bromo-6-methylpyridazine (43 mg, 0.24 mmol), tBuXPhos Pd G3 (20 mg, 0.024 mmol) and sodium tert-butoxide (47 mg, 0.29 mmol) in anhydrous dioxane/tBuOH (2:1, 4.5 mL) was stirred at room temperature for 1 hour. The reaction mixture was diluted with ethyl acetate (10 mL), washed with water (10 mL), the layers separated and the aqueous extracted with ethyl acetate (15 mL). The combined organics were washed with sat. aq. $NH_4Cl$ (10 mL), brine (10 mL), dried over magnesium sulfate, filtered and concentrated. The residue was purified by silica column chromatography eluting with 0 to 100% ethyl acetate in heptane, followed by 0 to 20% methanol in ethyl acetate to afford the title compound (23% yield) as a yellow film. LCMS $[M+H]^+$ 706, RT 2.19 min (Method 1).

Intermediate 157

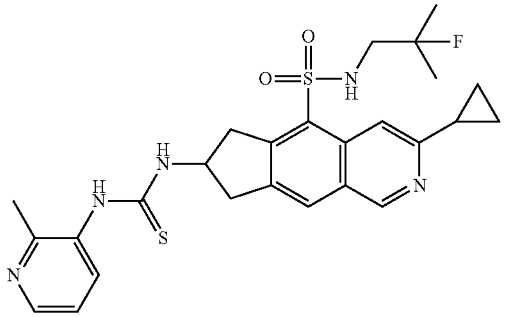 [SMILES: Cc1ncccc1NC(=S)NC1Cc2cc3cnc(C4CC4)cc3c(S(=O)(=O)NCC(C)(C)F)c2C1]

1-[3-cyclopropyl-5-[(2-fluoro-2-methyl-propyl) sulfamoyl]-7,8-dihydro-6H-cyclopenta[g]isoquinolin-7-yl]-3-(2-methyl-3-pyridyl)thiourea To a solution of Intermediate 12 (300 mg, 0.8 mmol) in anhydrous DCM (10 mL) was added a solution of 3-isothiocyanato-2-methylpyridine (120 mg, 0.8 mmol) in DCM (1 mL) and the resulting solution stirred at room temperature overnight under an atmosphere of nitrogen. The white precipitate formed was filtered off and washed with DCM to afford the title compound (326 mg, 75% yield) as a white solid. LCMS $[M+H]^+$ 528, RT 1.68 min (Method 1).

Intermediates 158 & 159

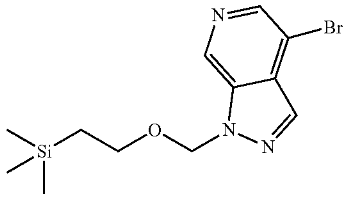

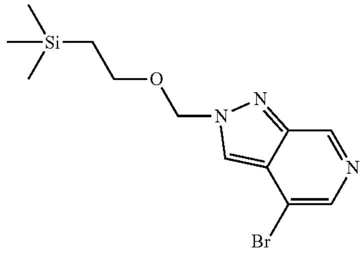

2-[(4-bromopyrazolo[3,4-c]pyridin-1-yl) methoxy] ethyl-trimethyl-silane

2-[(4-bromopyrazolo[3,4-c]pyridin-2-yl) methoxy] ethyl-trimethyl-silane

NaH (60%, 24 mg, 0.61 mmol) was stirred in dry DMF (3 mL) and cooled in an ice batch. 4-bromo-1H-pyrazolo[3,4-c]pyridine (100 mg, 0.5 mmol) was added and the mixture allowed to warm to room temperature with stirring for 20 minutes. [2-(chloromethoxy)ethyl](trimethyl) silane (98 μL, 0.56 mmol) was added and the reaction stirred for 2 hours. Reaction was quenched with water (20 mL) and extracted with ethyl acetate (30 mL). The organics were washed with sat. aq. $NH_4Cl$ (10 mL), water (10 mL), dried over sodium sulfate and concentrated. Residue purified by silica column chromatography eluting with 0-60% ethyl acetate in heptane to afford a 65:35 mixture of the two title compounds (120 mg, 72% yield) as a yellow oil. LCMS $[M+H]^+$ 328.0/330.0, RT 1.99/2.06 min (Method 1)

Intermediates 160 & 161

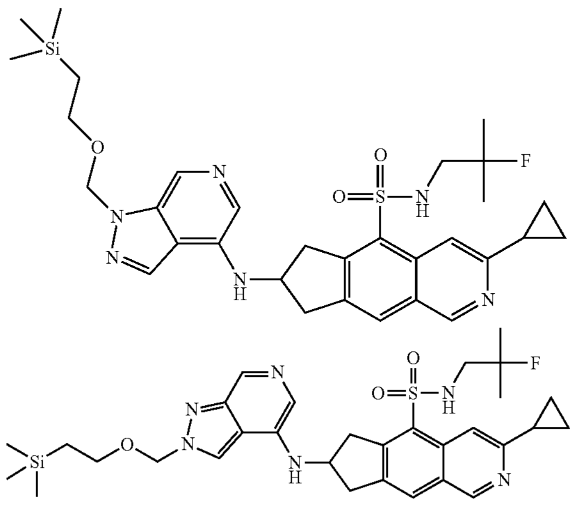

3-cyclopropyl-N-(2-fluoro-2-methyl-propyl)-7-[[1-(2-trimethylsilylethoxymethyl) pyrazolo[3,4-c]pyridin-4-yl]amino]-7,8-dihydro-6H-cyclopenta[g]isoquinoline-5-sulfonamide 3-cyclopropyl-N-(2-fluoro-2-methyl-propyl)-7-[[2-(2-trimethylsilylethoxymethyl) pyrazolo[3,4-c]pyridin-4-yl]amino]-7,8-dihydro-6H-cyclopenta[g]isoquinoline-5-sulfonamide Intermediate 12 (50 mg, 0.132 mmol), 65:35 isomer mixture of Intermediates 158 and 159 (43 mg, 0.132 mmol), sodium tert-butoxide (38 mg, 0.397 mmol) and tBuXPhos Pd G3 (11 mg, 0.013 mmol) in dioxane (3 mL) and tBuOH (1.5 mL) in a 20 mL pressure tube was flushed with nitrogen, sealed and heated to 110° C. with stirring for 3 hours. Water (10 mL) was added and reaction extracted with DCM (3×10 mL), organics dried over sodium sulfate and concentrated under vacuum. The residue was purified by silica column chromatography eluting with 0-10% MeOH in DCM to afford the title compound as two batches. Batch 1:49 mg, 44% yield as single isomer and Batch 2:27 mg, 22% yield as a mixture of both title compound isomers (21% & 57%).

Batch 1: LCMS $[M+H]^+$ 625.2, RT 1.94 min (93%) (Method 1)

Batch 2: LCMS $[M+H]^+$ 625.2, RT 1.94 min (21%), 625.2, RT 1.90 min (57%), (Method 1)

Intermediate 162

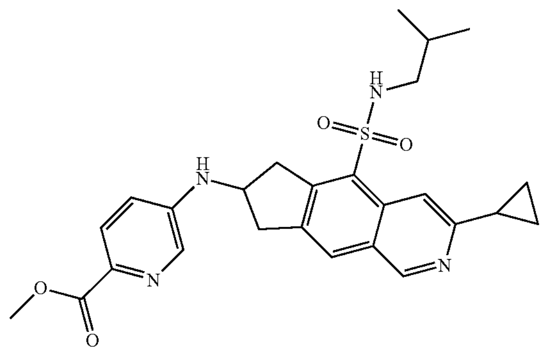 [SMILES: COC(=O)c1ccc(NC2Cc3cc4cnc(C5CC5)cc4c(S(=O)(=O)NCC(C)C)c3C2)cn1]

methyl 5-[[3-cyclopropyl-5-(isobutylsulfamoyl)-7,8-dihydro-6H-cyclopenta[g]isoquinolin-7-yl]amino] pyridine-2-carboxylate Intermediate 122 (50 mg, 0.14 mmol), methyl 5-bromopyridine-2-carboxylate (45 mg, 0.21 mmol), sodium tert-butoxide (27 mg, 0.28 mmol) and tBuXPhos Pd G3 (11 mg, 0.01 mmol) were heated in dioxane (3 mL) and tBuOH (1.5 mL) in a sealed tube with stirring at 110° C. for 1 hour 45 minutes. Reaction was allowed to cool, concentrated under vacuum and purified by silica column chromatography eluting with 0-20% MeOH in DCM followed by preparative, basic reverse phase HPLC to afford the title compound (28 mg, 41% yield) as a white solid. LCMS $[M+H]^+$ 495.2, RT 1.82 min (Method 1).

Intermediate 163

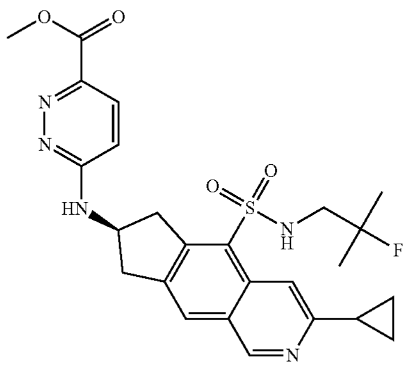 [SMILES: COC(=O)c1ccc(N[C@@H]2Cc3cc4cnc(C5CC5)cc4c(S(=O)(=O)NCC(C)(C)F)c3C2)nn1]

methyl 6-[[(7R)-3-cyclopropyl-5-[(2-fluoro-2-methyl-propyl) sulfamoyl]-7,8-dihydro-6H-cyclopenta[g]isoquinolin-7-yl]amino]pyridazine-3-carboxylate Intermediate 15 (300 mg, 0.79 mmol) and methyl 6-bromopyridazine-3-carboxylate (207 mg, 0.95 mmol) and DIPEA (415 μL, 2.38 mmol) were heated in tBuOH (10 mL) with stirring in a sealed tube at 110° C. for 16 hours. Reaction was concentrated under vacuum and the residue purified by silica column chromatography eluting with 0-100% ethyl acetate in heptane to afford a brown solid which was dissolved in DCM and precipitated with heptane. The solid was collected by filtration to afford the title compound (152 mg, 37% yield) as a grey solid.

$^1$H NMR (500 MHz, DMSO-d6) $\delta_H$ 9.15 (s, 1H), 8.44 (s, 1H), 8.33 (br s, 1H), 8.13 (s, 1H), 7.92 (d, J=4.6 Hz, 1H), 7.76 (d, J=9.3 Hz, 1H), 6.86 (d, J=9.3 Hz, 1H), 4.83 (br s, 1H), 3.90 (dd, J=18.5, 7.1 Hz, 1H), 3.86 (s, 3H), 3.61-3.50 (m, 2H), 3.09 (dd, J=16.6, 4.9 Hz, 1H), 2.95-2.85 (m, 2H), 2.32-2.24 (m, 1H), 1.12 (d, J=21.4 Hz, 3H), 1.10 (d, J=21.4 Hz, 3H), 1.07-0.99 (m, 4H). LCMS $[M+H]^+$ 514.2, RT 2.45 min (Method 1).

Intermediate 164

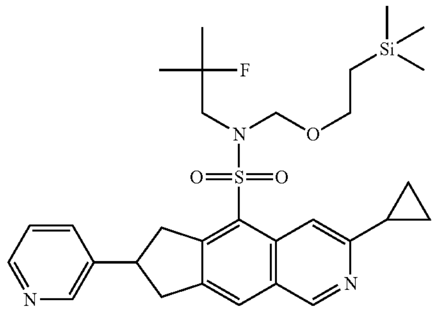 [SMILES: CC(C)(F)CN(COCC[Si](C)(C)C)S(=O)(=O)c1c2c(cc3cnc(C4CC4)cc13)CC(c1cccnc1)C2]

3-cyclopropyl-N-(2-fluoro-2-methyl-propyl)-7-(3-pyridyl)-N-(2-trimethylsilylethoxymethyl)-7,8-dihydro-6H-cyclopenta[g]isoquinoline-5-sulfonamide Solution A: To Intermediate 141 (25 mg, 0.047 mmol) was introduced a solution of HATU (18 mg in 0.2 mL anhydrous DMF, 0.047 mmol) at room temperature under an atmosphere of nitrogen. A solution of trimethylamine (5 mg in 0.1 mL anhydrous DMF, 0.047 mmol) was then added and the reaction mixture stirred for 1 hour.

Solution B: Isopropylmagnesium chloride lithium chloride complex (1.18 mL of a 1.3 M solution in tetrahydrofuran, 1.53 mmol) was diluted with anhydrous tetrahydrofuran (1.2 mL) and cooled to 0° C. under an atmosphere of nitrogen. 3-Bromopyridine (220 mg, 1.39 mmol) was then introduced dropwise and stirring continued at 0° C. for 30 minutes. Zinc (II) chloride (1.67 mL of a 1.0 M solution in anhydrous tetrahydrofuran, 1.67 mmol) was then added.

Separately, a flask was charged with nickel (II) chloride glyme complex (2 mg, 0.009 mmol) and 4-tert-butyl-2-(4-tert-butyl-2-pyridyl)pyridine (5 mg, 0.019 mmol). Anhydrous DMF (0.2 mL) was introduced under an atmosphere of nitrogen at room temperature followed by Solution A. After 5 minutes, Solution B (0.52 mL, 0.093 mmol) was introduced and the reaction mixture diluted with anhydrous THF (0.2 mL). After 20 hours, the reaction mixture was concentrated in-vacuo and the residue diluted with ethyl acetate (20 mL). This solution was washed with water (3×15 mL), the organic phase dried over magnesium sulfate and filtered. The filtrate was concentrated in-vacuo to furnish a crude residue containing the title compound (27% purity LCMS-$UV_{215}$, $[M+H]^+$ 570, RT 4.87 min (Method 9) which was used for the next synthetic step without purification.

Intermediate 165

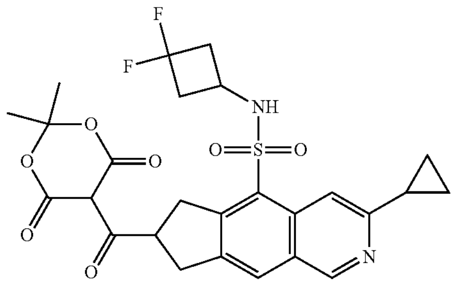 [SMILES: CC1(C)OC(=O)C(C(=O)C2Cc3cc4cnc(C5CC5)cc4c(S(=O)(=O)NC4CC(F)(F)C4)c3C2)C(=O)O1]

3-cyclopropyl-N-(3,3-difluorocyclobutyl)-7-(2,2-dimethyl-4,6-dioxo-1,3-dioxane-5-carbonyl)-7,8-dihydro-6H-cyclopenta[g]isoquinoline-5-sulfonamide To a solution of Intermediate 117 (500 mg, 1.184 mmol) and Meldrum's acid (188 mg, 1.302 mmol) in anhydrous dichloromethane (10 mL) was introduced 4-dimethylaminopyridine (217 mg, 1.775 mmol). After cooling to 0° C. under an atmosphere of nitrogen, EDC·HCl (318 mg, 1.657 mmol) was added portionwise over 20 minutes then the reaction mixture warmed to room temperature. The reaction mixture was concentrated in-vacuo after 24 hours to furnish the crude title compound (649 mg at 67% purity LCMS-$UV_{215}$) which was used for the next synthetic step without additional purification. LCMS $[M+H]^+$ 549, RT 1.81 min (Method 1).

Intermediate 166

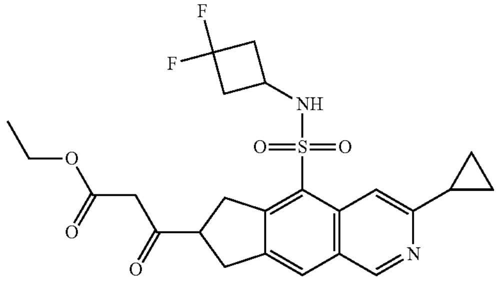 [SMILES: CCOC(=O)CC(=O)C1Cc2cc3cnc(C4CC4)cc3c(S(=O)(=O)NC3CC(F)(F)C3)c2C1]

ethyl 3-[3-cyclopropyl-5-[(3,3-difluorocyclobutyl)sulfamoyl]-7,8-dihydro-6H-cyclopenta[g]isoquinolin-7-yl]-3-oxo-propanoate A solution of Intermediate 165 (649 mg, 67% purity) in ethanol was heated to reflux for 48 hours under an atmosphere of nitrogen. The pH of the reaction mixture was adjusted to pH 1 with 10% trifluoroacetic acid in ethanol and refluxing continued for a further 4 hours. The reaction mixture was concentrated in-vacuo, ethyl acetate (40 mL) introduced to the residue and this solution washed with 0.1M aqueous hydrochloric acid (5 mL), water (2×5 mL) and brine (5 mL). The organic phase was dried over sodium sulfate, filtered and concentrated in-vacuo to afford the title compound (716 mg at 83% purity LCMS-$UV_{215}$) which was used for the next synthetic step without additional purification. LCMS $[M+H]^+$ 493, RT 3.16 min (Method 2).

Intermediate 167

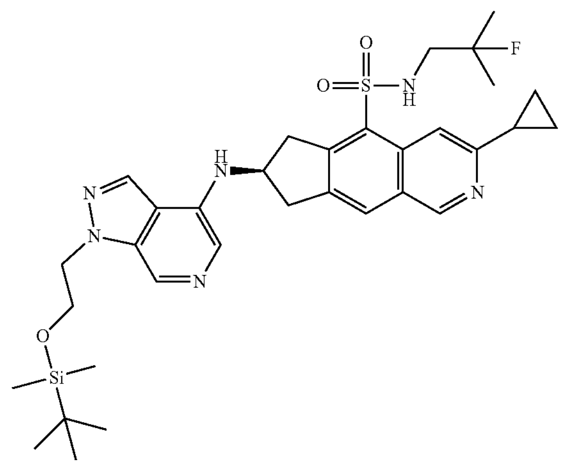 [SMILES: CC(C)(F)CNS(=O)(=O)c1c2c(cc3cnc(C4CC4)cc13)C[C@@H](Nc1cncc3c1cnn3CCO[Si](C)(C)C(C)(C)C)C2]

(7R)-7-[[1-[2-[tert-butyl(dimethyl) silyl]oxyethyl] pyrazolo[3,4-c]pyridin-4-yl]amino]-3-cyclopropyl-N-(2-fluoro-2-methyl-propyl)-7,8-dihydro-6H-cyclopenta[g]isoquinoline-5-sulfonamide Intermediate 15 (50 mg, 0.13 mmol), Intermediate 191 (65 mg, 0.18 mmol), sodium tert-butoxide (38 mg, 0.4 mmol) and tBuXPhos Pd G3 (11 mg, 13.25 μmol) were dissolved in dioxane (3 mL) and tBuOH (1.5 mL) and stirred at room temperature for 16 hours. The reaction mixture was filtered through Celite, concentrated and purified by silica column chromatography eluting with 0-10% MeOH/DCM to afford the title compound (20 mg, 23% yield) as a yellow oil. LCMS $[M+2H]^{2+}$ 327.2, RT 1.96 min (Method 1)

Intermediate 168

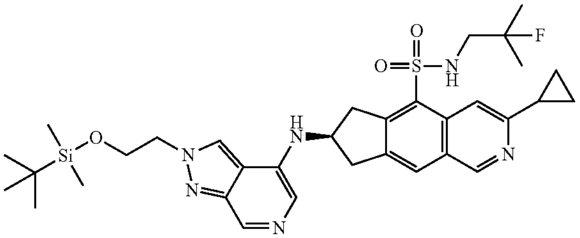 [SMILES: CC(C)(F)CNS(=O)(=O)c1c2c(cc3cnc(C4CC4)cc13)C[C@@H](Nc1cncc3nn(CCO[Si](C)(C)C(C)(C)C)cc13)C2]

(7R)-7-[[2-[2-[tert-butyl(dimethyl) silyl]oxyethyl] pyrazolo[3,4-c]pyridin-4-yl]amino]-3-cyclopropyl-N-(2-fluoro-2-methyl-propyl)-7,8-dihydro-6H-cyclopenta[g]isoquinoline-5-sulfonamide Intermediate 15 (50 mg, 0.13 mmol), Intermediate 192 (65 mg, 0.18 mmol), sodium tert-butoxide (38 mg, 0.4 mmol) and tBuXPhos Pd G3 (11 mg, 13.25 μmol) were dissolved in dioxane (3 mL) and tBuOH (1.5 mL) and stirred at room temperature for 16 hours. Reaction filtered through Celite, concentrated and purified by silica column chromatography eluting with 0-100 EtOAc/heptane, then 0-5% MeOH/DCM, to afford the title compound (30 mg, 35% yield) as a yellow oil. LCMS $[M+2H]^{2+}$ 327.2, RT 1.94 min (Method 1)

Intermediate 169

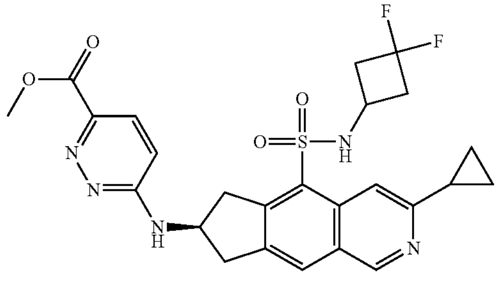 [SMILES: COC(=O)c1ccc(N[C@@H]2Cc3cc4cnc(C5CC5)cc4c(S(=O)(=O)NC4CC(F)(F)C4)c3C2)nn1]

methyl 6-[[(7R)-3-cyclopropyl-5-[(3,3-difluorocyclobutyl) sulfamoyl]-7,8-dihydro-6H-cyclopenta[g] isoquinolin-7-yl]amino]pyridazine-3-carboxylate Intermediate 124 (100 mg, 0.25 mmol) and methyl 6-bromopyridazine-3-carboxylate (66 mg, 0.30 mmol) were heated in tert-butanol (6 mL) with DIPEA (133 μL, 0.76 mmol) at 110° C. in a sealed tube for 16 hours. Reaction was concentrated and purified by silica column chromatography eluting with 0-100% ethyl acetate in heptane to afford the title compound (64 mg, 39% yield, 82% purity) as a brown oil. LCMS $[M+H]^+$ 530.1, RT 1.74 min (Method 1)

Intermediate 170

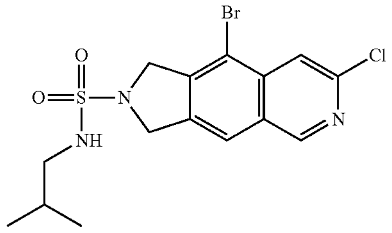 [SMILES: CC(C)CNS(=O)(=O)N1Cc2cc3cnc(Cl)cc3c(Br)c2C1]

9-bromo-7-chloro-N-isobutyl-1,3-dihydropyrrolo[3,4-g]isoquinoline-2-sulfonamide

To Intermediate 22 (33 mg, 0.11 mmol) in DCM (3 mL) was added DIPEA (41 μL, 0.23 mmol) and 2-methylpropyl) sulfamyl chloride (23.9 mg, 0.14 mmol) in DCM (1 mL). Reaction was stirred at room temperature for 1 hour then diluted with DCM (30 mL) and saturated $NaHCO_3$ (10 mL), the organic layer separated and the aqueous extracted with DCM (20 mL). Combined organics dried over sodium sulfate and concentrated under vacuum. Residue purified by silica column chromatography eluting with 20% to 70% EtOAc in heptane to afford the title compound (40 mg, 82% yield) as a white solid. LCMS $[M+H]^+$ 418/420, RT 2.01 min (Method 1).

Intermediate 171

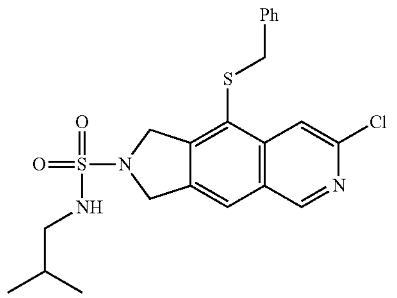 [SMILES: CC(C)CNS(=O)(=O)N1Cc2cc3cnc(Cl)cc3c(SCc3ccccc3)c2C1]

9-benzylsulfanyl-7-chloro-N-isobutyl-1,3-dihydro-pyrrolo[3,4-g]isoquinoline-2-sulfonamide To Intermediate 170 (40 mg, 0.096 mmol) were added phenylmethanethiol (12.3 µL, 0.10 mmol), (9,9-dimethyl-9H-xanthene-4,5-diyl)bis(diphenylphosphane) (2.6 mg, 0.006 mmol), (1E,4E)-1,5-diphenylpenta-1,4-dien-3-one-palladium (3:2) (1.71 mg, 0.003 mmol) and DIPEA (33.2 µL, 0.19 mmol) in dioxane (2 mL). The mixture was de-gassed with nitrogen for 20 minutes and heated at 90° C. for 6 hours. The solvent was removed and DCM and water were added, the organic layer separated, washed with brine, dried over $MgSO_4$ and concentrated under reduced pressure. The residue was purified by silica column chromatography eluting with 20% to 60% EtOAc in heptane to afford the title compound as an off white solid (47 mg, 91% yield, 86% purity). LCMS $[M+H]^+$ 462, RT 2.10 min (Method 1).

Intermediate 172

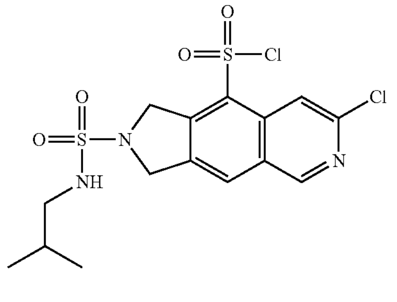 [SMILES: CC(C)CNS(=O)(=O)N1Cc2cc3cnc(Cl)cc3c(S(=O)(=O)Cl)c2C1]

7-chloro-2-(isobutylsulfamoyl)-1,3-dihydropyrrolo[3,4-g]isoquinoline-9-sulfonyl chloride Intermediate 171 (47 mg, 0.10 mmol) was dissolved in acetonitrile (2 mL) and cooled to 0° C. Water (10 µL) and acetic acid (29 µL) followed by 1,3-dichloro-5,5-dimethyl-imidazolidine-2,4-dione (40 mg, 0.20 mmol) were added and stirring continued at 0° C. for 5 minutes and at room temperature for 1 hour. White solids were filtered off and washed with cold acetonitrile to afford the title compound (22 mg, 45% yield, 91% purity) as a white solid. LCMS in MeOH $[M+H]^+$ 438, RT 2.01 min (+methyl ester) (Method 1).

Intermediate 173

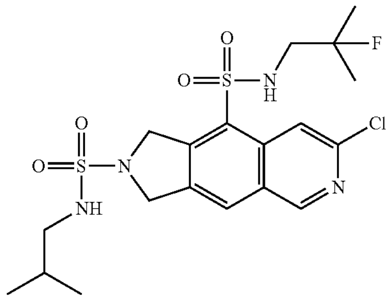 [SMILES: CC(C)CNS(=O)(=O)N1Cc2cc3cnc(Cl)cc3c(S(=O)(=O)NCC(C)(C)F)c2C1]

7-chloro-$N_9$-(2-fluoro-2-methyl-propyl)-$N_2$-isobutyl-1,3-dihydropyrrolo[3,4-g]isoquinoline-2,9-disulfonamide To a solution of Intermediate 172 (20 mg, 0.046 mmol, 91% purity) in DCM (2 mL), a pre mixed solution of 2-fluoro-2-methylpropan-1-amine hydrochloride (7.0 mg, 0.05 mmol) and DIPEA (19.8 µL, 0.11 mmol) in DCM (1 mL) was added dropwise at 0° C. and reaction mixture stirred at room temperature for 30 minutes. Reaction was diluted with DCM (20 mL), washed with water, the combined organic layers dried over $MgSO_4$ and concentrated under reduced pressure to give a crude product which was purified by silica column chromatography eluting with 25% to 60% EtOAc in heptane to afford the title compound (20 mg, 89% yield) as a white solid.

$^1H$ NMR (500 MHz, Chloroform-d) $\delta_H$ 9.11 (s, 1H), 8.55 (s, 1H), 8.03 (s, 1H), 5.25 (t, J=6.3 Hz, 1H), 5.16 (s, 2H), 4.84 (s, 2H), 4.46 (t, J=6.3 Hz, 1H), 3.08 (dd, J=20.0, 6.4 Hz, 2H), 2.97 (t, J=6.6 Hz, 2H), 1.87-1.77 (m, 1H), 1.28 (d, J=21.4 Hz, 6H), 0.96 (d, J=6.7 Hz, 6H). LCMS $[M+H]^+$ 493.2, RT 1.88 min (Method 1).

Intermediate 174

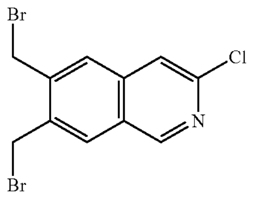 [SMILES: Clc1cc2cc(CBr)c(CBr)cc2cn1]

6,7-bis(bromomethyl)-3-chloro-isoquinoline

Intermediate 18 (750 mg, 3.91 mmol) was dissolved in EtOAc (40 mL) and NBS (1.46 g, 8.21 mmol) followed by AIBN (64.2 mg, 0.39 mmol) were added. The reaction mixture was split into two large microwave vials and heated at 100° C. for 30 minutes. The reactions were combined, diluted with EtOAc, washed with aqueous $Na_2S_2O_3$, water and brine, dried over $MgSO_4$ and concentrated to give crude product which was purified by silica column chromatography eluting with 0% to 40% EtOAc in heptane to afford the title compound (320 mg, 21% yield) as an off white solid.

$^1H$ NMR (500 MHz, Chloroform-d) OH 9.05 (s, 1H), 8.00 (s, 1H), 7.79 (s, 1H), 7.70 (s, 1H), 4.84 (s, 2H), 4.82 (s, 2H). LCMS $[M+H]^+$ 349.8/351.8, RT 3.05 min (Method 1).

Intermediate 175

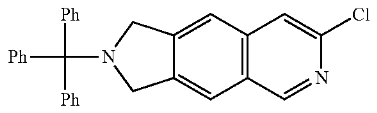 [SMILES: Clc1cc2cc3c(cc2cn1)CN(C(c1ccccc1)(c1ccccc1)c1ccccc1)C3]

7-chloro-2-trityl-1,3-dihydropyrrolo[3,4-g]isoquinoline

Intermediate 174 (100 mg, 0.28 mmol), tritylamine (74 mg, 0.28 mmol) and N,N diisopropylethylamine (0.12 mL, 0.71 mmol) in anhydrous DMF (2 mL) were stirred for 2 hours at 60° C. under nitrogen followed by addition of a further 0.5 equivalents tritylamine and stirring for a further 3 hours at 60° C. Solvent was removed, the residue diluted to 15 mL with ethyl acetate and washed with water and brine, dried over anhydrous $MgSO_4$ and the solvent removed. The residue was purified by silica column chromatography eluting with hexane/EtOAc, 9:1 to afford the title compound (127 mg, 99% yield) as pale yellow solid.

$^1H$ NMR (500 MHz, Chloroform-d) $\delta_H$ 8.92 (s, 1H), 7.63-7.57 (m, 8H), 7.43 (s, 1H), 7.34-7.28 (m, 6H), 7.21-7.16 (m, 3H), 4.00 (s, 4H). LCMS $[M+H]^+$ 447, RT 2.21 min (Method 1).

Intermediate 176

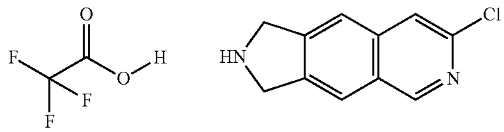 [SMILES: O=C(O)C(F)(F)F ; Clc1cc2cc3c(cc2cn1)CNC3]

7-chloro-2,3-dihydro-1H-pyrrolo[3,4-g]isoquinoline; 2,2,2-trifluoroacetic acid

Intermediate 175 (127 mg, 0.28 mmol) in 10% trifluoroacetic acid in dichloromethane (10 mL) was stirred for 30 minutes at room temperature under nitrogen, then diluted to 5 mL with ethanol and stirred for an additional 15 minutes. Solvent was removed and the residue (95 mg, 87% yield) used without further purification. LCMS $[M+H]^+$ 205.2, RT 0.47 min (Method 1).

Intermediate 177

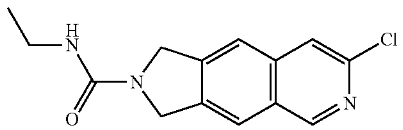 [SMILES: CCNC(=O)N1Cc2cc3cnc(Cl)cc3cc2C1]

7-chloro-N-ethyl-1,3-dihydropyrrolo[3,4-g]isoquinoline-2-carboxamide

To a solution of Intermediate 176 (90 mg, 0.28 mmol) in DCM (6 mL) was added isocyanatoethane (24.5 μL, 0.031 mmol) followed by DIPEA (123 μL, 0.70 mmol). The reaction was stirred at room temperature for 1 hour and the resulting solid filtered off and washed with DCM to afford the title compound (41 mg, 53% yield) as an off white solid. LCMS $[M+H]^+$ 276.2, RT 1.67 min (Method 1).

Intermediate 178

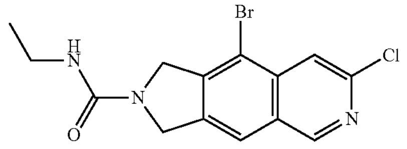 [SMILES: CCNC(=O)N1Cc2cc3cnc(Cl)cc3c(Br)c2C1]

9-bromo-7-chloro-N-ethyl-1,3-dihydropyrrolo[3,4-g]isoquinoline-2-carboxamide

Intermediate 177 (25 mg, 0.091 mmol) was added in batches to sulfuric acid (141 μL) in DCM (3 mL) at 0° C. The reaction mixture was cooled to −10° C. and N-bromosuccinamide (17.7 mg, 0.1 mmol) added in portions. The reaction was maintained at −10° C. for 2 hours then at room temperature for 16 hours. An additional equivalent of N-bromosuccinamide was added and stirred at room temperature for 6 hours. The reaction mixture was diluted with 20 ml of ice water and the pH of the solution adjusted to 8-10 with concentrated ammonium hydroxide. The resulting solution was extracted with DCM (2×15 mL), dried (sodium sulfate) and concentrated. The residue was purified by silica column chromatography eluting with 50% to 100% EtOAc in heptane then 1% to 10% MeOH in DCM to afford the title compound (22 mg, 55% yield, 80% purity) as a white solid.

$^1H$ NMR (500 MHz, Methanol-$d_4$) $\delta_H$ 9.11 (s, 1H), 8.07 (s, 1H), 8.06 (s, 1H), 4.95 (s, 2H), 4.86 (s, 2H), 3.29 (q, J=7.3 Hz, 2H), 1.19 (t, J=7.2 Hz, 3H). LCMS $[M+H]^+$ 354/356, RT 1.74 min (Method 1).

Intermediate 179

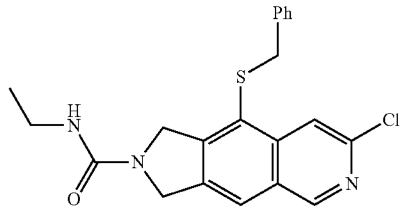 [SMILES: CCNC(=O)N1Cc2cc3cnc(Cl)cc3c(SCc3ccccc3)c2C1]

9-benzylsulfanyl-7-chloro-N-ethyl-1,3-dihydropyrrolo[3,4-g]isoquinoline-2-carboxamide To a sealed tube were added Intermediate 178 (22 mg, 0.05 mmol, 80% purity), phenylmethanethiol (6.39 μL, 0.055 mmol), (9,9-dimethyl-9H-xanthene-4,5-diyl)bis(diphenylphosphane) (1.72 mg, 0.003 mmol), (1E,4E)-1,5-diphenylpenta-1,4-dien-3-one-palladium (3:2) (1.36 mg, 0.001 mmol) and DIPEA (17.2 μL, 0.099 mmol) in dioxane (1 mL). The mixture was de-gassed with nitrogen for 20 minutes, sealed and heated at 85° C. for 18 hours. The solvent was removed and DCM and water were added, the organic layer separated, washed with brine, dried over $MgSO_4$ and concentrated under reduced pressure. The residue was purified by silica column chromatography eluting with 50% to 100% EtOAc followed by 0 to 10% MeOH in DCM to afford the title compound (25 mg, 72% yield, 57% purity) as a white solid. LCMS $[M+H]^+$ 398.2, RT 1.82 min (Method 1).

Intermediate 180

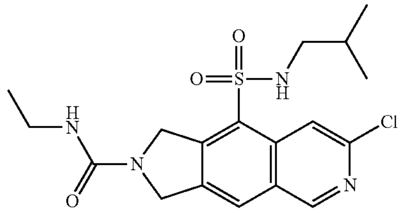 [SMILES: CCNC(=O)N1Cc2cc3cnc(Cl)cc3c(S(=O)(=O)NCC(C)C)c2C1]

7-chloro-N-ethyl-9-(isobutylsulfamoyl)-1,3-dihydro-pyrrolo[3,4-g]isoquinoline-2-carboxamide Intermediate 179 (25 mg, 0.044 mmol) was dissolved in DCM (2 mL) and cooled to 0° C. Water (4.5 μL), acetic acid (12.1 μL) and thionyl chloride (17.8 μL, 0.22 mmol) were added and stirring continued at 0° C. for 5 minutes and at room temperature for 1 hour. Reaction mixture was cooled to 0° C., isobutyl amine (34.9 μL, 0.35 mmol) added and the reaction stirred at room temperature for 1 hour. The reaction was diluted with water (10 mL), the aqueous phase extracted with DCM (2×10 mL) and the combined organics washed with water, dried ($Na_2SO_4$), filtered and concentrated to give the crude product which was purified by silica column chromatography eluting with 50% to 100% EtOAc in heptane, followed by 0 to 10% MeOH in DCM to afford the title compound (20 mg, 62% yield, 56% purity) as a white solid. LCMS $[M+H]^+$ 411.2, RT 1.73 min (Method 1).

Intermediate 181

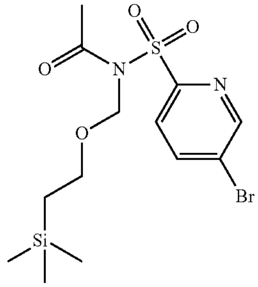 [SMILES: CC(=O)N(COCC[Si](C)(C)C)S(=O)(=O)c1ccc(Br)cn1]

N-[(5-bromo-2-pyridyl) sulfonyl]-N-(2-trimethylsilylethoxymethyl) acetamide

A solution of N-[(5-bromopyridin-2-yl) sulfonyl]acetamide (85 mg, 0.30 mmol) in DMF (3 mL) was stirred with sodium hydride (60% oil dispersion, 13.4 mg, 0.33 mmol) at 0° C. then warmed to 20° C. under nitrogen. After 15 minutes the reaction was cooled to 0° C. and 2-(chloromethoxy)ethyl-trimethyl-silane (50.7 mg, 0.30 mmol) was added and the mixture stirred for 3 hours at 20° C. Phosphate buffer (pH 6.5, 6 mL) was added and the mixture stirred for 10 min. The mixture was extracted with EtOAc (2×20 mL) and the combined organic layers were washed with water (2×20 mL), followed by brine (20 mL). The solution was dried ($Na_2SO_4$) and evaporated to dryness. Residue purified by silica column chromatography eluting with 0%-20% EtOAc in heptane to afford the title compound (71 mg, 57% yield) as a colourless oil.

$^1H$ NMR (500 MHz, DMSO-d6) $\delta_H$ 8.87 (d, J=2.2 Hz, 1H), 8.43 (dd, J=8.4, 2.3 Hz, 1H), 8.06 (d, J=8.4 Hz, 1H), 5.29 (s, 2H), 3.69-3.63 (m, 2H), 2.31 (s, 3H), 0.87-0.82 (m, 2H), 0.00 (s, 9H). LCMS $[M+Na]^+$ 431/433, RT 2.07 min (Method 1)

Intermediates 182 & 183

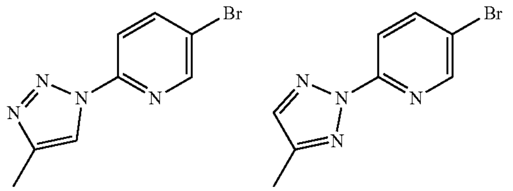

5-bromo-2-(4-methyltriazol-1-yl)pyridine & 5-bromo-2-(4-methyltriazol-2-yl)pyridine 5-bromo-2-chloropyridine (500 mg, 2.47 mmol), and caesium carbonate (1770 mg, 5.43 mmol) were suspended in N,N-dimethylacetamide (5 mL) under an atmosphere of nitrogen in a ChemGlass 30 mL vessel. To this mixture was added 4-methyl-1H-1,2,3-triazole (325 mg, 3.72 mmol) and the resulting suspension heated at 130° C. for 3 hours. Reaction poured into water (25 mL), solids filtered off, washed with water (×3) and dried under suction overnight to yield 421 mg of a 57:39 mixture of Intermediates 182 & 183 as a white solid. LCMS $[M+H]^+$ 239/241, RT 0.88 min (Intermediate 182) & 0.91 min (Intermediate 183) (Method 6)

Intermediates 184

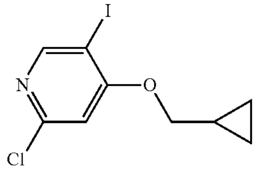 [SMILES: Clc1cc(OCC2CC2)c(I)cn1]

2-chloro-4-(cyclopropylmethoxy)-5-iodo-pyridine

To cyclopropanemethanol (45 μL, 0.569 mmol) in DMF (1.5 mL) under an atmosphere of nitrogen and in an 8 mL vial with pressure tested cap, was added potassium tert-butoxide (72 mg, 0.629 mmol). After 10 minutes 2,4-dichloro-5-iodopyridine (150 mg, 0.520 mmol) was added and stirred at room temperature for 18 hours. Reaction quenched with 10% aqueous ammonium chloride (2 mL) and extracted with DCM (2×3 mL). DCM layers filtered through phase separator, solvent removed and residue purified by silica column chromatography, eluting with 0-15% EtOAc/DCM then 40% EtOAc/DCM to afford the title compound (68 mg, 41% yield) as a white solid.

$^1$H NMR (300 MHz, Chloroform-d) $\delta_H$ 8.51 (s, 1H), 6.71 (s, 1H), 3.97 (d, J=6.8 Hz, 2H), 1.39-1.27 (m, 1H), 0.75-0.64 (m, 2H), 0.49-0.39 (m, 2H). LCMS $[M+H]^+$ 310.0, RT 1.20 min (Method 6).

Intermediate 185

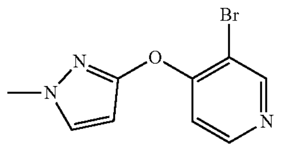

3-bromo-4-(1-methylpyrazol-3-yl)oxy-pyridine 1-methyl-1H-pyrazol-3-ol (114 mg, 1.120 mmol), 3-bromo-4-chloropyridine (200 mg, 1.019 mmol) and caesium carbonate (498 mg, 1.527 mmol) were suspended in DMF (7 mL) and the mixture sealed and heated to 80° C. for 2.5 hours. The reaction was diluted with water (10 mL), extracted with EtOAc (2×10 mL), the organics dried ($Na_2SO_4$), concentrated and purified by silica column chromatography, eluting with a 0-100% gradient of EtOAc in isohexane to afford the title compound (117 mg, 45% yield) as a colourless liquid.

$^1$H NMR (300 MHz, Chloroform-d) $\delta_H$ 8.67 (s, 1H), 8.34 (d, J=5.6 Hz, 1H), 7.33 (d, J=2.3 Hz, 1H), 6.97 (d, J=5.6 Hz, 1H), 5.95 (d, J=2.3 Hz, 1H), 3.86 (s, 3H). LCMS $[M+H]^+$ 254.0/256.0, RT 1.14 min (Method 6).

Intermediate 186

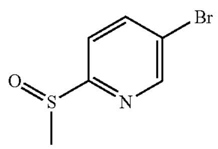

5-bromo-2-methylsulfinyl-pyridine

Sodium periodate (4.2 g, 20 mmol) was added as a slurry in water (4 mL) to a stirred solution of 5-bromo-2-methylthiopyridine (1 g, 4.8 mmol) in acetic acid (25 mL) at 0° C. Upon completion of addition, the ice bath was removed and the mixture was stirred at room temperature for 3.5 hours. The reaction was treated with water (50 mL), basified through addition of solid potassium carbonate powder and extracted with EtOAc (3×50 mL). The combined organic phase was washed with 10% aqueous sodium thiosulfate solution (50 mL), then dried over $Na_2SO_4$ and the solvent removed. The resulting crude oil was purified by silica column chromatography, eluting with 0-100% EtOAc in heptanes to afford the title compound (838 mg, 80% yield) as a colourless oil that crystallised on standing.

$^1$H NMR (300 MHz, Chloroform-d) $\delta_H$ 8.68 (dd, J=2.2, 0.7 Hz, 1H), 8.08 (dd, J=8.4, 2.2 Hz, 1H), 7.93 (dd, J=8.4, 0.7 Hz, 1H), 2.85 (s, 3H).

Intermediate 187

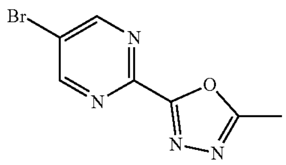

2-(5-bromopyrimidin-2-yl)-5-methyl-1,3,4-oxadiazole

To a suspension of 5-bromopyrimidine-2-carbohydrazide (1 g, 4.6 mmol), triethylamine (700 mg, 6.9 mmol) and DCM (15 mL) was added acetic anhydride (520 mg, 5.1 mmol). Acetonitrile (10 mL) was added and the reaction stirred at room temperature for 45 minutes. The mixture was concentrated, suspended in DCM (5 ml), sonicated for 3 minutes and the precipitate collected and dried. Crude precipitate was suspended in acetonitrile (10 mL) and triethylamine (2.80 g, 28 mmol) added. p-toluenesulphonyl chloride (1300 mg, 6.9 mmol) was added and the reaction stirred for 1 hour at room temperature. The reaction mixture was concentrated, dissolved in water (10 mL) and extracted with EtOAc (2×10 mL). The combined organic extracts were dried over $Na_2SO_4$ and concentrated in vacuo. The crude product was purified by silica column chromatography eluting with a 0-10% gradient of MeOH in DCM to afford the title compound as a light brown solid $^1$H NMR (300 MHz, DMSO-d6) $\delta_H$ 9.24 (s, 2H), 2.63 (s, 3H).

Intermediate 188

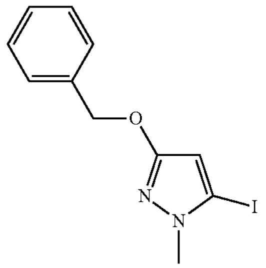

3-benzyloxy-5-iodo-1-methyl-pyrazole

To a colourless solution of 3-benzyloxy-1-methyl-pyrazole (246 mg, 1.31 mmol) in anhydrous THF (5 mL) at −78° C. was added N-butyllithium. After 30 min, a 5 mL solution of iodine in anhydrous THF was added and allowed to warm to room temperature overnight. Reaction quenched with 2 mL sat. $NH_4Cl$ (aq.) and 2 mL 1M $Na_2S_2O_5$ (aq.), diluted with 20 mL 1.5 M $Na_2CO_3$ (aq.), extracted into 3×30 mL DCM, dried and concentrated. Residue purified by silica column chromatography eluting with 0-100% ethyl acetate followed by reverse phase basic C18 column chromatography, eluting with 0-100% MeCN in water to afford the title compound (54.5 mg, 11.5% yield). LCMS $[M+H]^+$ 315.0, RT 1.19 min (Method 1).

Intermediate 189

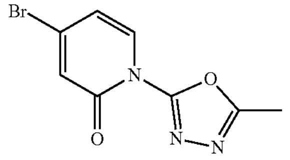

4-bromo-1-(5-methyl-1,3,4-oxadiazol-2-yl)pyridin-2-one 4-bromopyridin-2-ol (59 mg, 0.33 mmol) and 2-bromo-5-methyl-1,3,4-oxadiazole (50 mg, 0.30 mmol) in DMF (2.0 mL) was flushed with nitrogen, then potassium carbonate (84 mg, 0.61 mmol) was added and stirring continued in a microwave oven at 90° C. for 1.5 hours. The mixture was partitioned between water and EtOAc, the organic layer dried ($MgSO_4$), evaporated and the residue purified by silica column chromatography eluting with 40% to 100% EtOAc in n-heptane to afford the title compound (36 mg, 40% yield at 88% purity) as a white solid.

$^1H$ NMR (500 MHz, Chloroform-d) $\delta_H$ 7.46-7.42 (m, 1H), 6.95-6.91 (m, 1H), 6.47 (dd, J=7.6, 2.0 Hz, 1H), 2.63 (s, 3H). LCMS $[M+H]^+$ 256/258, RT 1.20 min (Method 1)

Intermediate 190

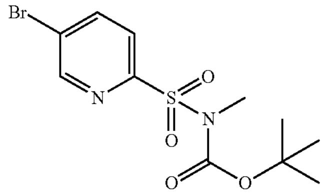 [SMILES: CN(C(=O)OC(C)(C)C)S(=O)(=O)c1ccc(Br)cn1]

tert-butyl N-[(5-bromo-2-pyridyl) sulfonyl]-N-methyl-carbamate

To a solution of tert-butyl N-[(5-bromo-2-pyridyl) sulfonyl]carbamate (30 mg, 0.089 mmol) in anhydrous DMF (3 mL) was added sodium hydride (4.6 mg, 0.11 mmol) at 0° C. After stirring at 0° C. for 0.5 h, iodomethane (6.6 μL, 0.10 mmol) was added. The reaction mixture was stirred at room temperature for 3 hours. Reaction mixture poured into water (10 mL), EtOAc (25 mL) was added, EtOAc layer was washed with water (2×10 mL). The organic layer was dried ($Na_2SO_4$), filtered, and concentrated in vacuo. The residue was purified by silica column chromatography eluting with 0%-30% EtOAc in heptane to afford the title compound (26 mg, 83% yield) as a white solid. $^1H$ NMR (500 MHz, Chloroform-d) $\delta_H$ 8.72-8.70 (m, 1H), 8.06 (dd, J=8.3, 2.2 Hz, 1H), 7.97 (dd, J=8.3, 0.6 Hz, 1H), 3.44 (s, 3H), 1.32 (s, 9H). LCMS $[M+Na]^+$ 373/375, RT 1.88 min (Method 1)

Intermediates 191 and 192

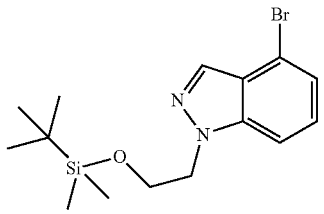

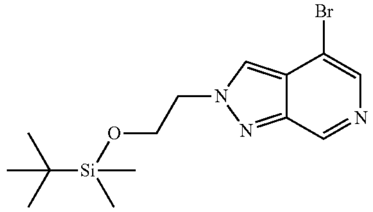

2-(4-bromopyrazolo[3,4-c]pyridin-1-yl) ethoxy-tert-butyl-dimethyl-silane and 2-(4-bromopyrazolo[3,4-c]pyridin-2-yl) ethoxy-tert-butyl-dimethyl-silane 4-bromo-1H-pyrazolo[3,4-c]pyridine (220 mg, 1.11 mmol) was dissolved in THF (5 mL) and (2-bromoethoxy)(tert-butyl)dimethylsilane (262 μL, 1.22 mmol) followed by BEMP (354 μL, 1.22 mmol) was added. The reaction mixture was heated to 40° C. with stirring for 8 hours then left to stand at room temperature for 16 hours. Reaction concentrated and residue purified by silica column chromatography eluting with 15-40% EtOAc/heptane to afford Intermediate 191 200 mg and Intermediate 192 139 mg as white solids.

Intermediate 191: 1H NMR (500 MHz, Chloroform-d) $\delta_H$ 8.96 (s, 1H), 8.36 (s, 1H), 8.07 (s, 1H), 4.59 (t, J=5.1 Hz, 2H), 4.04 (t, J=5.1 Hz, 2H), 0.70 (s, 9H),−0.21 (s, 6H).

LCMS $[M+H]^+$ 356/358, RT 2.12 min (Method 1)

Intermediate 192: 1H NMR (500 MHz, Chloroform-d) $\delta_H$ 9.14 (s, 1H), 8.26-8.23 (m, 1H), 8.10-8.08 (m, 1H), 4.60-4.55 (m, 2H), 4.11-4.06 (m, 2H), 0.82 (s, 9H),−0.11 (s, 6H).

LCMS $[M+H]^+$ 356/358, RT 2.06 min (Method 1)

Intermediate 193

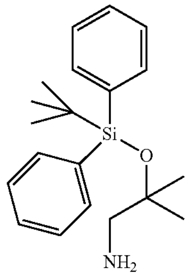 [SMILES: CC(C)(CN)O[Si](c1ccccc1)(c1ccccc1)C(C)(C)C]

2-[tert-butyl(diphenyl) silyl]oxy-2-methyl-propan-1-amine

To a stirring solution of 1-amino-2-methylpropan-2-ol (300 mg, 3.37 mmol) in dichloromethane (5 mL) was added 1H-imidazole (687 mg, 10 mmol) followed by tert-butyl (chloro) diphenylsilane (1.2 g, 4.38 mmol) and the resulting solution was stirred at room temperature for 22 hours. The mixture was partitioned between DCM (20 mL) and water (15 mL). The layers were separated and the aqueous phase extracted with DCM (15 mL). Then combined organics were washed with brine (15 mL), dried over magnesium sulfate, filtered and concentrated. The residue was purified by silica column chromatography eluting with 0 to 100% ethyl acetate in heptane, followed by 0 to 20% methanol in ethyl acetate to afford the title compound (875 mg, 79% yield) as a colourless oil. $^1$H NMR (500 MHz, DMSO-d6) $\delta_H$ 7.70-7.63 (m, 4H), 7.50-7.35 (m, 6H), 2.44 (s, 2H), 1.38 (br. s, 2H), 1.01 (s, 6H), 0.96 (s, 9H).

EXAMPLES

Example 1

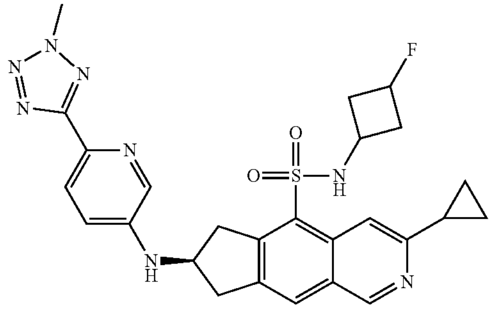 [SMILES: Cn1nnc(-c2ccc(N[C@@H]3Cc4cc5cnc(C6CC6)cc5c(S(=O)(=O)NC5CC(F)C5)c4C3)cn2)n1]

(7R)-3-cyclopropyl-N-(3-fluorocyclobutyl)-7-[[6-(2-methyltetrazol-5-yl)pyridin-3-yl]amino]-7,8-dihydro-6H-cyclopenta[g]isoquinoline-5-sulfonamide The title compound was obtained using General Procedure 2 with Intermediate 129 (110 mg, 0.26 mmol) and 5-bromo-2-(2-methyl-2H-tetrazol-5-yl)pyridine (95 mg, 0.4 mmol) at room temperature. Purification by column chromatography followed by reverse phase HPLC (acidic conditions) afforded the title compound (33 mg, 23%) as a mixture of cis/trans isomers. $\delta_H$ (500 MHz, $d_6$-DMSO) 9.16 (s, 1H), 8.42-8.32 (m, 2H), 8.16 (s, 1H), 8.14 (d, J=2.8 Hz, 1H), 7.92-7.86 (m, 1H), 7.20-7.13 (m, 1H), 6.74 (dd, J=6.4, 2.7 Hz, 1H), 5.16-4.82 (m, 1H, Isomer B), 4.60-4.41 (m, 1H, Isomer A), 4.41-4.36 (m, 4H), 3.88-3.80 (m, 1H), 3.83-3.74 (m, 1H, Isomer B), 3.60-3.46 (m, 2H), 3.19-3.10 (m, 1H, Isomer A), 3.04 (dd, J=16.4, 4.5 Hz, 1H), 2.35-2.18 (m, 2H Isomer A+1H), 2.18-1.96 (m, 4H, Isomer B), 1.88-1.71 (m, 2H, Isomer A), 1.11-1.00 (m, 4H). LCMS [M+H]$^+$ 535.2, RT 2.64 min (Method 2).

Example 2

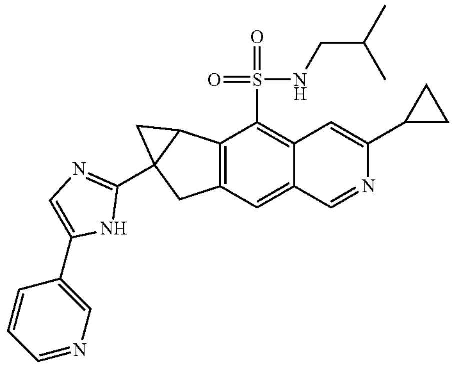 [SMILES: CC(C)CNS(=O)(=O)c1c2c(cc3cnc(C4CC4)cc13)CC1(c3ncc(-c4cccnc4)[nH]3)CC21]

13-cyclopropyl-~{N}-(2-methylpropyl)-6-(5-pyridin-3-yl-1~{H}-imidazol-2-yl)-12-azatetracyclo [8.4.0.0^{3,8}.0^{4,6}]tetradeca-1,3 (8),9,11,13-pentaene-2-sulfonamide To a solution of Intermediate 41 (100 mg, 0.25 mmol) in dry MeCN (3 mL), DIPEA (174 µL, 1.0 mmol) was added followed by 2-bromo-1-(pyridin-3-yl) ethanone hydrobromide (70 mg, 0.25 mmol). The reaction was stirred at room temperature for 2 hours. 2-bromo-1-(pyridin-3-yl) ethanone hydrobromide (20 mg, 0.07 mmol) and DIPEA (100 µL, 0.57 mmol) were added and the reaction stirred for a further 1 hour. 2-bromo-1-(pyridin-3-yl) ethanone hydrobromide (35 mg, 0.12 mmol) was added and reaction stirred for 1 hour. The orange solution was diluted with ethyl acetate (40 mL) and washed with saturated aq. $NaHCO_3$ (2×20 mL), brine (10 mL), dried over sodium sulfate and concentrated under vacuum. The residue was suspended in dry toluene (3 mL) and ammonium acetate (95 mg, 1.25 mmol) added. The mixture was then heated at 110° C. for 16 hours in a pressure tube. The reaction was diluted with ethyl acetate (50 mL) and MeOH (5 mL) and washed with saturated aq. $NaHCO_3$ (30 mL). The aqueous was extracted further with 10% MeOH in EtOAc (20 mL). The combined organics were washed with brine, dried over sodium sulfate and concentrated under vacuum. The orange residue was purified by column chromatography then triturated with ethyl acetate and washed with a 1:1 mixture of ethyl acetate and heptane followed by heptane to afford the title compound (20 mg, 16% yield). $\delta_H$ (500 MHz, $d_6$-DMSO) 12.20 (s, 1H), 9.12 (s, 1H), 8.99 (d, J=1.7 Hz, 1H), 8.42 (s, 1H), 8.37 (dd, J=4.7, 1.4 Hz, 1H), 8.13 (s, 1H), 8.10 (dt, J=7.9, 1.7 Hz, 1H), 8.07-7.99 (m, 1H), 7.73 (s, 1H), 7.35 (dd, J=7.8, 4.8 Hz, 1H), 4.02 (d, J=17.6 Hz, 1H), 3.74 (dd, J=9.0, 3.6 Hz, 1H), 3.50 (d, J=17.4 Hz, 1H), 2.68-2.54 (m, 2H), 2.29-2.19 (m, 2H), 1.65-1.52 (m, 1H), 1.07-0.98 (m, 4H), 0.88 (t, J=4.3 Hz, 1H), 0.72 (d, J=6.7 Hz, 3H), 0.72 (d, J=6.7 Hz, 3H). LCMS [M+H]$^+$ 500.3, RT 2.01 min (Method 2).

Example 3

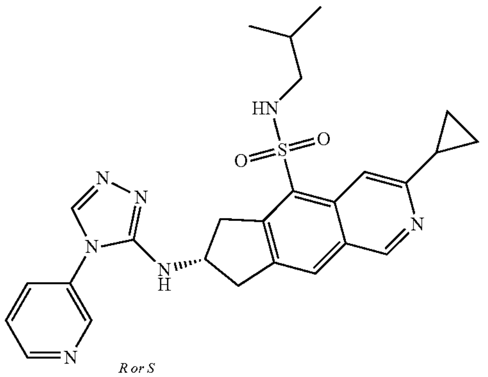 [SMILES: CC(C)CNS(=O)(=O)c1c2c(cc3cnc(C4CC4)cc13)C[C@H](Nc1nncn1-c1cccnc1)C2]

R or S (7R*)-3-cyclopropyl-N-(2-methylpropyl)-7-[(4-pyridin-3-yl-1,2,4-triazol-3-yl)amino]-7,8-dihydro-6H-cyclopenta[g]isoquinoline-5-sulfonamide [* or S]

The title compound was obtained using General Procedure 3 with Intermediate 123 (210 mg, 0.42 mmol). Purification by column chromatography using MeOH in DCM followed by chiral HPLC separation afforded the title compound as a single isomer (18.7 mg, 9% yield). Chiral RT**=4.68. $\delta_H$ (500 MHz, $d_6$-DMSO) 9.11 (s, 1H), 8.66 (d, J=2.4 Hz, 1H), 8.62 (dd, J=4.8, 1.4 Hz, 1H), 8.39 (s, 1H), 8.35 (s, 1H), 8.07 (s, 1H), 7.97 (s, 1H), 7.90 (ddd, J=8.2, 2.6, 1.5 Hz, 1H), 7.59-7.52 (m, 1H), 6.37 (d, J=5.8 Hz, 1H), 4.47 (h, J=6.2 Hz, 1H), 3.85 (dd, J=18.6, 7.2 Hz, 1H), 3.53 (dd, J=18.6, 5.9 Hz, 1H), 3.46 (dd, J=17.3, 7.2 Hz, 1H), 3.12 (dd, J=17.1, 6.1 Hz, 1H), 2.53-2.51 (m, 2H, obs. DMSO), 2.29-2.20 (m, 1H), 1.57-1.47 (m, 1H), 1.03-0.99 (m, 4H), 0.66 (d, J=6.7 Hz, 6H). LCMS $[M+H]^+$ 504.2, RT 2.12 (Method 2).

**Chiral analysis was carried out using a Chiralcel OD-H 25 cm column eluting with 50:50 Ethanol: Methanol and a 10 min run time.

Example 4

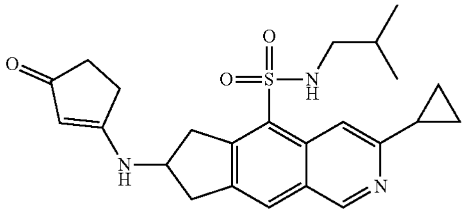 [SMILES: CC(C)CNS(=O)(=O)c1c2c(cc3cnc(C4CC4)cc13)CC(NC1=CC(=O)CC1)C2]

3-cyclopropyl-N-(2-methylpropyl)-7-[(3-oxocyclopenten-1-yl)amino]-7,8-dihydro-6H-cyclopenta[g]isoquinoline-5-sulfonamide A mixture of Intermediate 122 (40 mg, 0.11 mmol), cyclopentane-1,3-dione (11 mg, 0.11 mmol) and acetic acid (6.36 µL, 0.11 mmol) in 1,2-dichloroethane (4 mL) with 4 Å molecular sieves was heated at 90° C. for 3.5 hours in a pressure tube. The reaction mixture was washed with saturated aq. $NaHCO_3$ (2 mL) and extracted with DCM (2×3 mL). The organics were dried over sodium sulfate and concentrated under vacuum. The residue was purified by column chromatography using MeOH in DCM to afford the title compound (28 mg, 57% yield). $\delta_H$ (500 MHz, $d_6$-DMSO) 9.15 (s, 1H), 8.41 (s, 1H), 8.12 (s, 1H), 8.03 (t, J=4.9 Hz, 1H), 7.83 (d, J=6.1 Hz, 1H), 4.97 (s, 1H), 4.24-4.14 (m, 1H), 3.74 (dd, J=18.4, 6.9 Hz, 1H), 3.52 (dd, J=18.5, 4.2 Hz, 1H), 3.44 (dd, J=17.2, 7.1 Hz, 1H), 3.05 (dd, J=16.7, 4.0 Hz, 1H), 2.52-2.49 (m, 2H, obs. DMSO), 2.47-2.40 (m, 2H), 2.29-2.22 (m, 1H), 2.18-2.09 (m, 2H), 1.59-1.46 (m, 1H), 1.06-0.98 (m, 4H), 0.69 (d, J=6.6 Hz, 3H), 0.69 (d, J=6.6 Hz, 3H). LCMS $[M+H]^+$ 440.2, RT 2.42 min (Method 2).

Example 5

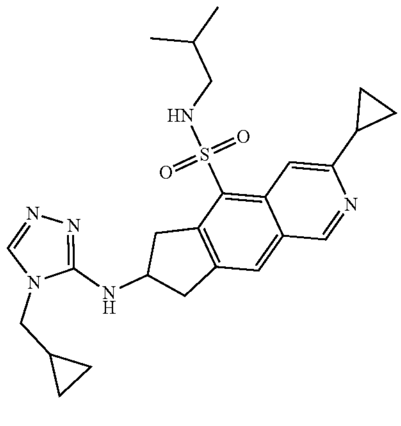 [SMILES: CC(C)CNS(=O)(=O)c1c2c(cc3cnc(C4CC4)cc13)CC(Nc1nncn1CC1CC1)C2]

3-cyclopropyl-7-[[4-(cyclopropylmethyl)-1,2,4-triazol-3-yl]amino]-N-(2-methylpropyl)-7,8-dihydro-6H-cyclopenta[g]isoquinoline-5-sulfonamide The title compound was obtained using General Procedure 3 with Intermediate 92 (184 mg, 0.39 mmol). Purification by column chromatography using MeOH in DCM followed by reverse phase HPLC (basic conditions) afforded the title compound (68 mg, 36% yield). $\delta_H$ (500 MHz, $d_6$-DMSO) 9.12 (s, 1H), 8.41 (s, 1H), 8.09 (s, 1H), 8.04 (s, 1H), 7.97 (s, 1H), 6.16 (d, J=5.6 Hz, 1H), 4.43 (h, J=5.7 Hz, 1H), 3.81 (dd, J=18.5, 7.0 Hz, 1H), 3.61-3.53 (m, 3H), 3.46 (dd, J=17.3, 7.0 Hz, 1H), 3.12 (dd, J=16.7, 5.2 Hz, 1H), 2.54-2.51 (m, 2H), 2.29-2.20 (m, 1H), 1.52 (hept, J=6.7 Hz, 1H), 1.14-1.05 (m, 1H), 1.05-0.97 (m, 4H), 0.67 (d, J=6.7 Hz, 6H), 0.48-0.42 (m, 2H), 0.30-0.25 (m, 2H). LCMS $[M+H]^+$ 481.2, RT 2.14 min (Method 2).

Example 6

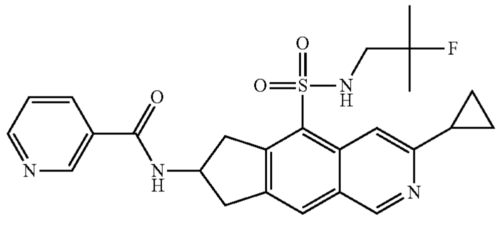 [SMILES: CC(C)(F)CNS(=O)(=O)c1c2c(cc3cnc(C4CC4)cc13)CC(NC(=O)c1cccnc1)C2]

N-[3-cyclopropyl-5-[(2-fluoro-2-methylpropyl) sulfamoyl]-7,8-dihydro-6H-cyclopenta[g]isoquinolin-7-yl]pyridine-3-carboxamide Intermediate 12 (30 mg, 0.08 mmol) was dissolved in DCM (3 mL) and DIPEA (42 μL, 0.24 mmol) was added followed by pyridine-3-carbonyl chloride hydrochloride (17 mg, 0.10 mmol). The reaction was stirred at room temperature for 30 minutes. Further pyridine-3-carbonyl chloride hydrochloride (10 mg, 0.06 mmol) was added and the suspension stirred for 30 minutes. A drop of DIPEA was added and the suspension stirred for 1 hour. The solid was collected by filtration, washed with DCM and dried in a vacuum oven to afford the title compound (20 mg, 52% yield). $\delta_H$ (500 MHz, $d_6$-DMSO) 9.15 (s, 1H), 9.02-8.96 (m, 1H), 8.88 (d, J=6.8 Hz, 1H), 8.69 (dd, J=4.8, 1.6 Hz, 1H), 8.44 (s, 1H), 8.37-8.28 (m, 1H), 8.18 (dt, J=8.0, 2.0 Hz, 1H), 8.11 (s, 1H), 7.52-7.43 (m, 1H), 4.74 (h, J=6.6 Hz, 1H), 3.88 (dd, J=18.5, 7.6 Hz, 1H), 3.54 (dd, J=18.5, 6.1 Hz, 1H), 3.46 (dd, J=17.1, 7.5 Hz, 1H), 3.13 (dd, J=17.3, 5.9 Hz, 1H), 2.94 (dd, J=20.1, 3.7 Hz, 2H), 2.31-2.23 (m, 1H), 1.13 (d, J=21.4 Hz, 3H), 1.12 (d, J=21.4 Hz, 3H), 1.06-0.99 (m, 4H). LCMS $[M+H]^+$ 483.2, RT 2.21 min (Method 2).

Example 7

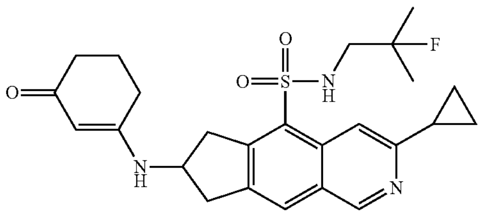 [SMILES: CC(C)(F)CNS(=O)(=O)c1c2c(cc3cnc(C4CC4)cc13)CC(NC1=CC(=O)CCC1)C2]

3-cyclopropyl-N-(2-fluoro-2-methylpropyl)-7-[(3-oxocyclohexen-1-yl)amino]-7,8-dihydro-6H-cyclopenta[g]isoquinoline-5-sulfonamide A mixture of Intermediate 12 (45 mg, 0.12 mmol) and cyclohexane-1,3-dione (18 mg, 0.16 mmol) in 1,2-dichloroethane (4 mL) with acetic acid (6.8 μL, 0.12 mmol) and 4 Å molecular sieves was heated to 90° C. for 3 hours. The reaction was purified by SCX followed by trituration with ethanol to afford the title compound (40 mg, 70% yield). $\delta_H$ (500 MHz, $d_6$-DMSO) 9.14 (s, 1H), 8.43 (s, 1H), 8.11 (s, 1H), 7.21 (d, J=5.7 Hz, 1H), 4.96 (s, 1H), 4.25-4.14 (m, 1H), 3.76 (dd, J=18.4, 7.0 Hz, 1H), 3.51 (dd, J=18.4, 3.9 Hz, 1H), 3.42 (dd, J=17.5, 7.0 Hz, 1H), 3.03 (dd, J=16.6, 4.2 Hz, 1H), 2.98-2.84 (m, 2H), 2.32-2.20 (m, 3H), 2.09 (t, J=6.3 Hz, 2H), 1.83-1.74 (m, 2H), 1.15 (d, J=21.4 Hz, 3H), 1.14 (d, J=21.4 Hz, 3H), 1.08-0.96 (m, 4H). LCMS $[M+H]^+$ 472, RT 2.34 min (Method 2).

Example 8

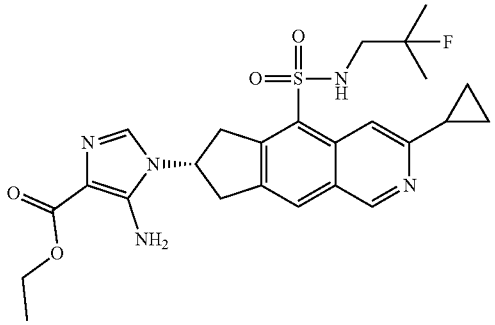 [SMILES: CCOC(=O)c1ncn([C@H]2Cc3cc4cnc(C5CC5)cc4c(S(=O)(=O)NCC(C)(C)F)c3C2)c1N]

ethyl 5-amino-1-[(7S)-3-cyclopropyl-5-[(2-fluoro-2-methylpropyl) sulfamoyl]-7,8-dihydro-6H-cyclopenta[g]isoquinolin-7-yl]imidazole-4-carboxylate A mixture of ethyl 2-amino-2-cyano-acetate* (197 mg, 1.06 mmol, 69% pure) and triethylorthoformate (176 μL, 1.06 mmol) in MeCN (10 mL) was heated at 90° C. for 1 hour in a pressure tube to give a green solution. Once at room temperature, Intermediate 118 (400 mg, 1.06 mmol) was added and the reaction was stirred at room temperature for 1 hour. The solid precipitate that formed was collected by vacuum filtration (washing with diethyl ether and MeCN) and dried in a vacuum oven to afford the title compound (442 mg, 81% yield). $\delta_H$ (500 MHz, $d_6$-DMSO) 9.17 (s, 1H), 8.45 (s, 1H), 8.41 (t, J=6.3 Hz, 1H), 8.18 (s, 1H), 7.03 (s, 1H), 6.17 (s, 2H), 5.01-4.92 (m, 1H), 4.15 (q, J=7.0 Hz, 2H), 3.97 (dd, J=18.2, 7.1 Hz, 1H), 3.71 (dd, J=18.2, 5.3 Hz, 1H), 3.59 (dd, J=16.7, 7.2 Hz, 1H), 3.41 (dd, J=16.6, 5.5 Hz, 1H), 2.96-2.80 (m, 2H), 2.32-2.24 (m, 1H), 1.22 (t, J=7.1 Hz, 3H), 1.15 (d, J=21.5 Hz, 3H), 1.10 (d, J=21.4 Hz, 3H), 1.06-1.00 (m, 4H). LCMS $[M+H]^+$ 516.2, RT 2.03 min (Method 2).

*Prepared according to the procedure in the following patent: WO2008/59368, 2008, A2.

Example 9

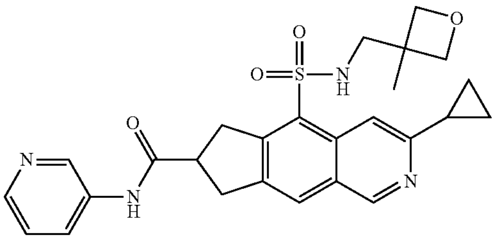 [SMILES: CC1(CNS(=O)(=O)c2c3c(cc4cnc(C5CC5)cc24)CC(C(=O)Nc2cccnc2)C3)COC1]

3-cyclopropyl-5-[(3-methyloxetan-3-yl)methylsulfamoyl]-N-pyridin-3-yl-7,8-dihydro-6H-cyclopenta[g]isoquinoline-7-carboxamide Intermediate 10 (97%, 70 mg, 0.19 mmol) was added in portions to a mixture of (3-methyloxetan-3-yl) methanamine (20 mg, 0.19 mmol) and DIPEA (100 μL, 0.58 mmol) in DMF (1 mL). The reaction stirred for 1 hour. DIPEA (67 μL, 0.39 mmol), pyridin-3-amine (27 mg, 0.29 mmol) and HATU (88 mg, 0.23 mmol) were then added and the mixture stirred for 1 hour. The reaction was diluted with DCM (3 mL) and washed with water (2 mL), saturated aq. $NH_4Cl$ (2 mL) and water (2 mL). The organic layer was dried over sodium sulfate and concentrated under vacuum. Purification by column chromatography afforded the title compound (9 mg, 9% yield). $\delta_H$ (500 MHz, $d_6$-DMSO) 10.35 (s, 1H), 9.15 (s, 1H), 8.77 (d, J=2.4 Hz, 1H), 8.42 (s, 1H), 8.26 (dd, J=4.7, 1.4 Hz, 1H), 8.18 (t, J=6.4 Hz, 1H), 8.12 (s, 1H), 8.08-8.02 (m, 1H), 7.34 (dd, J=8.3, 4.7 Hz, 1H), 4.23 (t, J=6.0 Hz, 2H), 4.04 (dd, J=5.9, 1.9 Hz, 2H), 3.87 (dd, J=18.4, 8.4 Hz, 1H), 3.68 (dd, J=18.4, 7.0 Hz, 1H), 3.50 (p, J=7.8 Hz, 1H), 3.44-3.33 (m, 2H), 2.99-2.85 (m, 2H), 2.30-2.20 (m, 1H), 1.08 (s, 3H), 1.06-0.99 (m, 4H).

LCMS $[M+H]^+$ 493.1, RT 1.64 min (Method 2).

Example 10

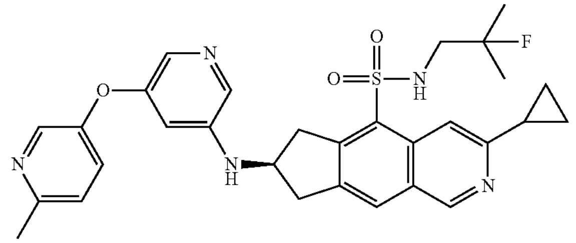 [SMILES: Cc1ccc(Oc2cncc(N[C@@H]3Cc4cc5cnc(C6CC6)cc5c(S(=O)(=O)NCC(C)(C)F)c4C3)c2)cn1]

(7R)-3-cyclopropyl-N-(2-fluoro-2-methylpropyl)-7-[[5-(6-methylpyridin-3-yl)oxypyridin-3-yl]amino]-7,8-dihydro-6H-cyclopenta[g]isoquinoline-5-sulfonamide The title compound was obtained using General Procedure 2 with Intermediate 15 (50 mg, 0.13 mmol) and Intermediate 58 (53 mg, 0.2 mmol) at 80° C. for 2 hours. The reaction mixture was concentrated to dryness and the crude purified by HPLC Method 2 to afford the title compound (41 mg, 55% yield). $\delta_H$ (500 MHz, DMSO-d6) 9.13 (s, 1H), 8.43 (s, 1H), 8.33 (t, J=6.4 Hz, 1H), 8.27 (d, J=2.8 Hz, 1H), 8.10 (s, 1H), 7.82 (s, 1H), 7.57 (s, 1H), 7.41 (dd, J=8.5, 2.9 Hz, 1H), 7.28 (d, J=8.5 Hz, 1H), 6.60 (t, J=2.2 Hz, 1H), 6.41 (d, J=6.5 Hz, 1H), 4.31-4.21 (m, 1H), 3.78 (dd, J=18.3, 6.7 Hz, 1H), 3.49-3.41 (m, 2H), 2.96 (dd, J=16.5, 4.2 Hz, 1H), 2.88 (dd, J=20.2, 6.3 Hz, 2H), 2.45 (s, 3H), 2.31-2.23 (m, 1H), 1.12 (d, J=21.4 Hz, 3H), 1.10 (d, J=21.4 Hz, 3H), 1.06-0.97 (m, 4H). LCMS $[M+H]^+$ 562, RT 2.23 min (Method 2).

Example 11

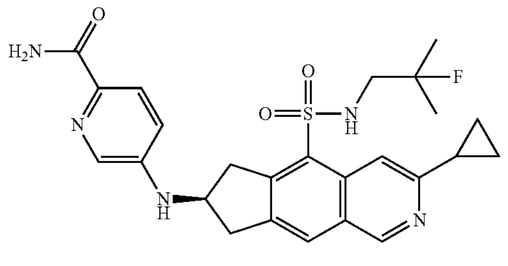 [SMILES: CC(C)(F)CNS(=O)(=O)c1c2c(cc3cnc(C4CC4)cc13)C[C@@H](Nc1ccc(C(N)=O)nc1)C2]

5-[[(7R)-3-cyclopropyl-5-[(2-fluoro-2-methylpropyl)sulfamoyl]-7,8-dihydro-6H-cyclopenta[g]isoquinolin-7-yl]amino]pyridine-2-carboxamide To a solution of Example 15 (30 mg, 0.06 mmol) in anhydrous DMF (0.5 mL), HATU (28 mg, 0.072 mmol), DIPEA (31 µL, 0.18 mmol) and ammonium chloride (32 mg, 0.6 mmol) were added. The mixture was stirred for 1.5 hours at room temperature. The reaction mixture was concentrated in vacuo and the residue purified by HPLC Method 2 to afford the title compound (14 mg, 48% yield). $\delta_H$ (500 MHz, DMSO-d6) 9.14 (s, 1H), 8.44 (s, 1H), 8.38-8.31 (m, 1H), 8.12 (s, 1H), 7.97 (d, J=2.7 Hz, 1H), 7.80 (d, J=8.6 Hz, 1H), 7.68 (d, J=2.5 Hz, 1H), 7.17-7.16 (m, 1H), 7.08 (dd, J=8.6, 2.7 Hz, 1H), 6.81 (d, J=6.4 Hz, 1H), 4.40-4.32 (m, 1H), 3.84 (dd, J=18.4, 6.7 Hz, 1H), 3.54-3.46 (m, 2H), 3.01 (dd, J=16.5, 4.3 Hz, 1H), 2.89 (dd, J=20.2, 5.6 Hz, 2H), 2.28 (p, J=7.0, 6.5 Hz, 1H), 1.11 (d, J=21.4 Hz, 3H), 1.09 (d, J=21.4 Hz, 3H), 1.04-1.00 (m, 4H). LCMS $[M+H]^+$ 498, RT 2.40 min (Method 2).

Example 12

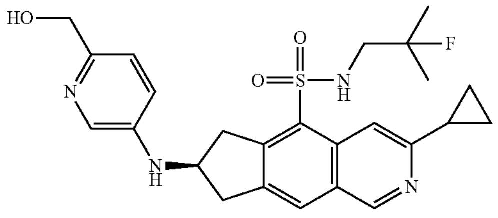 [SMILES: CC(C)(F)CNS(=O)(=O)c1c2c(cc3cnc(C4CC4)cc13)C[C@@H](Nc1ccc(CO)nc1)C2]

(7R)-3-cyclopropyl-N-(2-fluoro-2-methylpropyl)-7-[[6-(hydroxymethyl)pyridin-3-yl]amino]-7,8-dihydro-6H-cyclopenta[g]isoquinoline-5-sulfonamide The title compound was obtained using General Procedure 2 with Intermediate 15 (50 mg, 0.13 mmoL) and (5-bromopyridin-2-yl) methanol (37 mg, 0.2 mmol) at 110° C. for 3 hours. Purification by column chromatography followed by HPLC Method 2 afforded the title compound (57 mg, 44% yield). $\delta_H$ (500 MHz, DMSO-d6) 9.13 (s, 1H), 8.43 (s, 1H), 8.32 (t, J=6.5 Hz, 1H), 8.10 (s, 1H), 7.91 (d, J=2.5 Hz, 1H), 7.18 (d, J=8.4 Hz, 1H), 7.02 (dd, J=8.4, 2.8 Hz, 1H), 6.04 (d, J=6.5 Hz, 1H), 5.06 (br. s, 1H), 4.40 (s, 2H), 4.32-4.23 (m, 1H), 3.82 (dd, J=18.3, 6.7 Hz, 1H), 3.51-3.42 (m, 2H), 2.97 (dd, J=16.6, 4.5 Hz, 1H), 2.89 (dd, J=20.2, 6.5 Hz, 2H), 2.31-2.23 (m, 1H), 1.13 (d, J=21.4 Hz, 3H), 1.10 (d, J=21.4 Hz, 3H), 1.05-0.97 (m, 4H). LCMS $[M+H]^+$ 485, RT 1.61 min (Method 2).

Example 13

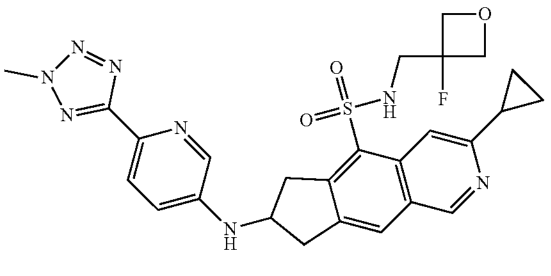 [SMILES: Cn1nnc(-c2ccc(NC3Cc4cc5cnc(C6CC6)cc5c(S(=O)(=O)NCC5(F)COC5)c4C3)cn2)n1]

3-cyclopropyl-N-[(3-fluorooxetan-3-yl)methyl]-7-[[6-(2-methyltetrazol-5-yl)pyridin-3-yl]amino]-7,8-dihydro-6H-cyclopenta[g]isoquinoline-5-sulfonamide The title compound was obtained using General Procedure 2 with Intermediate 116 (65 mg, 0.17 mmoL) and 5-bromo-2-(2-methyltetrazol-5-yl)pyridine (60 mg, 0.25 mmol), at room temperature for 18 hours. The reaction mixture was concentrated to dryness and the crude was purified by HPLC Method 1 to afford the title compound (34.5 mg, 38% yield). $\delta_H$ (500 MHz, DMSO-d6) 9.16 (s, 1H), 8.53 (s, 1H), 8.40 (s, 1H), 8.17-8.12 (m, 2H), 7.88 (d, J=8.6 Hz, 1H), 7.16 (dd, J=8.7, 2.8 Hz, 1H), 6.76 (d, J=6.4 Hz, 1H), 4.49-4.35 (m, 8H), 3.91 (dd, J=18.3, 6.8 Hz, 1H), 3.58-3.49 (m, 2H), 3.30-3.19 (m, 2H, part. obs. by water peak), 3.04 (dd, J=16.5, 4.6 Hz, 1H), 2.31-2.23 (m, 1H), 1.07-0.97 (m, 4H). LCMS $[M+H]^+$ 551, RT 2.89 min (Method 9).

Example 14

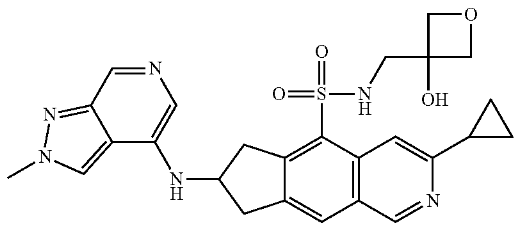 [SMILES: Cn1cc2c(NC3Cc4cc5cnc(C6CC6)cc5c(S(=O)(=O)NCC5(O)COC5)c4C3)cncc2n1]

3-cyclopropyl-N-[(3-hydroxyoxetan-3-yl)methyl]-7-[(2-methylpyrazolo[3,4-c]pyridin-4-yl)amino]-7,8-dihydro-6H-cyclopenta[g]isoquinoline-5-sulfonamide The title compound was obtained using General Procedure 2 with Intermediate 46 (135 mg, 0.35 mmol) and Intermediate 59 (110 mg, 0.52 mmol) at 80° C. for 2 hours. Purification by column chromatography afford the title compound (32 mg, 18% yield). $\delta_H$ (500 MHz, DMSO-d6) 9.15 (s, 1H), 8.47 (s, 1H), 8.41-8.35 (m, 2H), 8.18 (t, J=6.0 Hz, 1H), 8.14 (s, 1H), 7.38 (s, 1H), 6.42 (d, J=6.4 Hz, 1H), 5.78 (s, 1H), 4.54-4.46 (m, 1H), 4.26 (d, J=9.1 Hz, 4H), 4.15 (s, 3H), 3.95 (dd, J=18.4, 7.0 Hz, 1H), 3.67-3.55 (m, 2H), 3.11 (dd, J=16.8, 4.6 Hz, 1H), 3.00-2.87 (m, 2H), 2.32-2.24 (m, 1H), 1.05-0.98 (m, 4H). LCMS $[M+H]^+$ 521, RT 1.40 min (Method 2).

Example 15

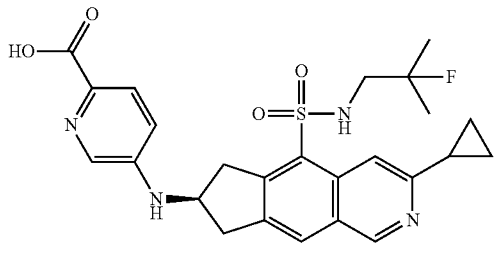 [SMILES: CC(C)(F)CNS(=O)(=O)c1c2c(cc3cnc(C4CC4)cc13)C[C@@H](Nc1ccc(C(=O)O)nc1)C2]

5-[[(7R)-3-cyclopropyl-5-[(2-fluoro-2-methylpropyl)sulfamoyl]-7,8-dihydro-6H-cyclopenta[g]isoquinolin-7-yl]amino]pyridine-2-carboxylic acid To a stirring solution of Intermediate 113 (384 mg, 0.69 mmol) in DCM (10 mL), trifluoroacetic acid (1 mL, 13.9 mmol) was added and the resulting solution allowed to stir at room temperature under an atmosphere of nitrogen for 60 hours. Trifluoroacetic acid (0.5 mL, 16.5 mmol) was added and stirring was continued for a total of 84 hours. The solution was concentrated in vacuo and the residue purified using an SCX cartridge (eluting with methanol and 7N ammonia in methanol) followed by HPLC Method 2 to afford the title compound (21.6 mg). $\delta_H$ 500 MHz, DMSO-d6) 9.14 (s, 1H), 8.44 (s, 1H), 8.34 (br. s, 1H), 8.12 (s, 1H), 8.04 (s, 1H), 7.83 (d, J=8.6 Hz, 1H), 7.05 (dd, J=8.7, 2.7 Hz, 1H), 7.00 (br. s, 1H), 4.44-4.31 (m, 1H), 3.85 (dd, J=18.3, 6.7 Hz, 1H), 3.55-3.46 (m, 2H, part. obs. by water peak), 3.01 (dd, J=16.7, 4.2 Hz, 1H), 2.89 (d, J=20.2 Hz, 2H), 2.28 (p, J=7.1, 6.4 Hz, 1H), 1.12 (d, J=21.4 Hz, 3H), 1.09 (d, J=21.4 Hz, 3H), 1.04-0.99 (m, 4H), COOH not observed. LCMS $[M+H]^+$ 499, RT 1.99 min (Method 2).

Example 16

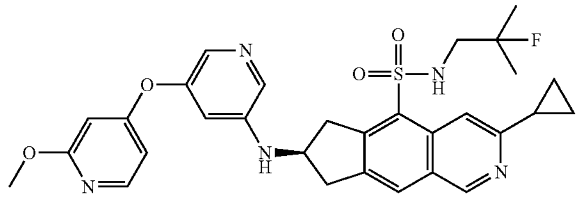 [SMILES: COc1cc(Oc2cncc(N[C@@H]3Cc4cc5cnc(C6CC6)cc5c(S(=O)(=O)NCC(C)(C)F)c4C3)c2)ccn1]

(7R)-3-cyclopropyl-N-(2-fluoro-2-methylpropyl)-7-[[5-(2-methoxypyridin-4-yl)oxypyridin-3-yl]amino]-7,8-dihydro-6H-cyclopenta[g]isoquinoline-5-sulfonamide The title compound was obtained using General Procedure 2 with Intermediate 15 (50 mg, 0.13 mmol) and Intermediate 114 (50 mg, 0.18 mmol) at 80° C. for 2 hours. The reaction mixture was concentrated to dryness and the crude purified by HPLC Method 2 to afford the title compound (11 mg, 14% yield). $\delta_H$ (500 MHz, DMSO-d6) 9.13 (s, 1H), 8.43 (s, 1H), 8.33 (t, J=6.5 Hz, 1H), 8.11 (s, 1H), 8.09 (d, J=5.8 Hz, 1H), 7.96-7.90 (m, 1H), 7.65 (d, J=1.7 Hz, 1H), 6.80 (t, J=2.3 Hz, 1H), 6.64 (dd, J=5.8, 2.2 Hz, 1H), 6.54 (d, J=6.5 Hz, 1H), 6.27 (d, J=2.1 Hz, 1H), 4.33-4.24 (m, 1H), 3.83 (s, 3H), 3.80 (dd, J=18.4, 6.8 Hz, 1H), 3.51-3.43 (m, 2H), 2.98 (dd, J=16.5, 4.5 Hz, 1H), 2.88 (dd, J=20.2, 6.5 Hz, 2H), 2.31-2.23 (m, 1H), 1.11 (d, J=21.4 Hz, 3H), 1.10 (d, J=21.4 Hz, 3H), 1.05-0.98 (m, 4H). LCMS $[M+H]^+$ 578, RT 2.79 min (Method 2).

Example 17

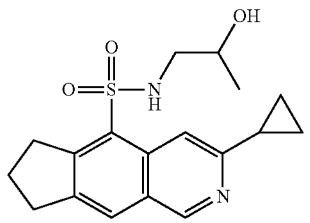 [SMILES: CC(O)CNS(=O)(=O)c1c2c(cc3cnc(C4CC4)cc13)CCC2]

3-cyclopropyl-N-(2-hydroxypropyl)-7,8-dihydro-6H-cyclopenta[g]isoquinoline-5-sulfonamide A mixture of Intermediate 53 (105 mg, 0.3 mmol), cyclopropyl boronic acid (79 mg, 0.92 mmol) and 2 M potassium carbonate (0.62 mL, 1.24 mmol) in 1,4-dioxane (3 mL) was degassed by sonicating under a flow of nitrogen for 5 minutes. Bedford catalyst (33 mg, 0.031 mmol) was added and the mixture heated to 120° C. in a microwave reactor for 2 hours. Cyclopropyl boronic acid (79 mg, 0.92 mmol) was added and the mixture was degassed by sonicating under a flow of nitrogen for 5 minutes. Bedford catalyst (33 mg, 0.031 mmol) was added and the mixture was heated in the microwave for an extra hour at 120° C. The mixture was partitioned between ethyl acetate (15 mL) and water (10 mL), the layers were separated and the aqueous was further extracted with ethyl acetate (10 mL). The combined organics were washed with brine (10 mL), dried over magnesium sulfate, filtered and concentrated. Purification by flash chromatography eluting with a gradient of ethyl acetate in heptane afforded the title compound (32 mg, 30% yield). $\delta_H$ (250 MHz, Chloroform-d) 9.04 (s, 1H), 8.33 (s, 1H), 7.89 (s, 1H), 5.22-5.09 (m, 1H), 3.94-3.76 (m, 1H), 3.55 (t, J=7.5 Hz, 2H), 3.09 (t, J=7.5 Hz, 2H), 2.99 (ddd, J=13.0, 7.3, 3.3 Hz, 1H), 2.70 (ddd, J=13.1, 7.9, 5.4 Hz, 1H), 2.29-2.05 (m, 3H), 1.80 (br. s, 1H), 1.18-0.96 (m, 7H). LCMS $[M+H]^+$ 347, RT 2.06 min (Method 2).

Example 18

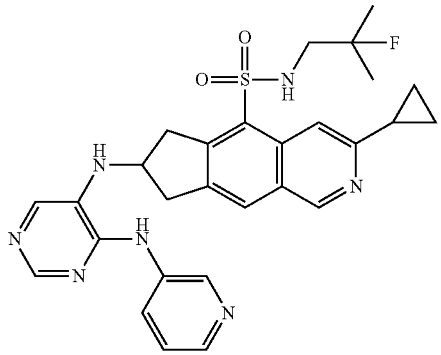 [SMILES: CC(C)(F)CNS(=O)(=O)c1c2c(cc3cnc(C4CC4)cc13)CC(Nc1cncnc1Nc1cccnc1)C2]

3-cyclopropyl-N-(2-fluoro-2-methylpropyl)-7-[[4-(pyridin-3-ylamino)pyrimidin-5-yl]amino]-7,8-dihydro-6H-cyclopenta[g]isoquinoline-5-sulfonamide Intermediate 12 (49.2 mg, 0.13 mmol), intermediate 132 (48.6 mg, 0.19 mmol), tBuXPhos Pd G3 (16.1 mg, 0.019 mmol) and sodium tert-butoxide (39.2 mg, 0.408 mmol) were placed under an atmosphere of $N_2$ and suspended in 1,4-dioxane (1.30 mL). The vial was sparged with nitrogen and the reaction was stirred at 100° C. for 10 min, tert-butyl alcohol (0.40 mL) was added and the reaction stirred for a further 40 min at 100° C. Additional tBuXPhos Pd G3 (65.1 mg, 0.079 mmol) was added and the reaction stirred at room temperature for 1 hour before being stirred at 70° C. for further 1.5 hours. The reaction was diluted with DCM (20 mL) and washed with sat. aq. $NaHCO_3$ (20 mL). The layers were separated, and the aq. layer extracted with DCM (2×15 mL). The combined organic layers where passed through a phase separator, concentrated in vacuo and purified by column chromatography on silica (gradient elution with 0% to 100% EtOAc in isohexanes; 0-20% MeOH in EtOAc) followed by basic preparative HPLC to give the title compound (1 mg, 1% Yield). 1H NMR (300 MHz, Methanol-d4) 9.08 (s, 1H), 8.77 (dd, J=2.6, 0.7 Hz, 1H), 8.50 (s, 1H), 8.23 (ddd, J=8.4, 2.6, 1.4 Hz, 1H), 8.19 (dd, J=4.8, 1.4 Hz, 1H), 8.17 (s, 1H), 8.12 (s, 1H), 7.93 (s, 1H), 7.38 (ddd, J=8.4, 4.8, 0.7 Hz, 1H), 4.54-4.44 (m, 1H), 3.93 (dd, J=18.5, 6.2 Hz, 1H), 3.81 (dd, J=18.5, 3.7 Hz, 1H), 3.64 (dd, J=16.7, 6.4 Hz, 1H), 3.22 (dd, J=16.7, 3.5 Hz, 1H), 2.99 (dd, J=19.9, 2.0 Hz, 2H), 2.36-2.24 (m, 1H), 1.14-1.01 (m, 10H). LCMS $[M+H]^+$ 548.2, RT 1.74 min (Method 10).

Example 19

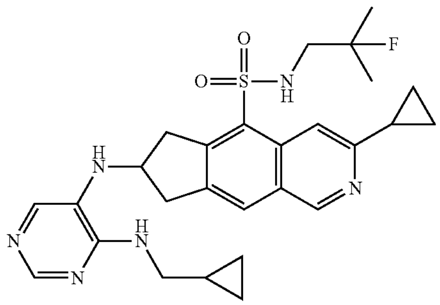 [SMILES: CC(C)(F)CNS(=O)(=O)c1c2c(cc3cnc(C4CC4)cc13)CC(Nc1cncnc1NCC1CC1)C2]

3-cyclopropyl-7-[[4-(cyclopropylmethylamino)pyrimidin-5-yl]amino]-N-(2-fluoro-2-methylpropyl)-7,8-dihydro-6H-cyclopenta[g]isoquinoline-5-sulfonamide Intermediate 12 (48.7 mg, 0.13 mmol), intermediate 133 (39.7 mg, 0.174 mmol, tBuXPhos Pd G3 (14.5 mg, 0.0177 mmol) and sodium tert-butoxide (36.9 mg, 0.384 mmol) were placed under an atmosphere of $N_2$ and suspended in 1,4-dioxane (1.30 mL). The reaction was stirred at room temperature for 3 h before being diluted with DCM (20 mL) and washed with sat. aq. $NaHCO_3$ (20 mL). The layers were separated, and the aq. layer extracted with DCM (2×15 mL). The combined organic layers where passed through a phase separator, concentrated in vacuo and purified by column chromatography on silica (gradient elution with 0% to 100% EtOAc in isohexanes; 0-20% MeOH in EtOAc) to give the title compound (42 mg, 62% Yield). $^1H$ NMR (400 MHz, DMSO-d6) δ 9.15 (s, 1H), 8.45 (s, 1H), 8.36 (t, J=6.4 Hz, 1H), 8.13 (s, 1H), 7.96 (s, 1H), 7.59 (s, 1H), 6.60 (t, J=5.3 Hz, 1H), 5.15 (d, J=5.4 Hz, 1H), 4.35-4.25 (m, 1H), 3.86 (dd, J=18.6, 6.8 Hz, 1H), 3.61-3.50 (m, 2H), 3.23-3.17 (m, 2H), 3.03 (dd, J=16.9, 4.4 Hz, 1H), 2.90 (dd, J=20.3, 6.3 Hz, 2H), 2.33-2.24 (m, 1H), 1.14 (d, J=11.0 Hz, 3H), 1.08 (d, J=11.1 Hz, 3H), 1.06-0.99 (m, 5H), 0.47-0.40 (m, 2H), 0.22-0.16 (m, 2H). LCMS $[M+H]^+$ 525.2, RT 1.94 min (Method 10).

Example 20

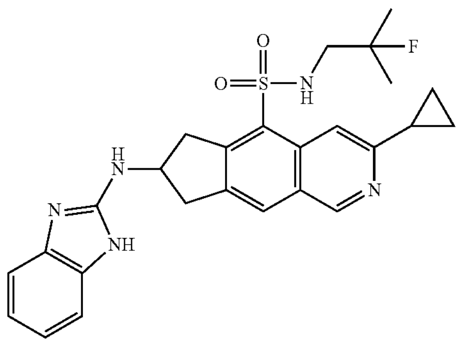 [SMILES: CC(C)(F)CNS(=O)(=O)c1c2c(cc3cnc(C4CC4)cc13)CC(Nc1nc3ccccc3[nH]1)C2]

7-(1H-benzimidazol-2-ylamino)-3-cyclopropyl-N-(2-fluoro-2-methylpropyl)-7,8-dihydro-6H-cyclopenta[g]isoquinoline-5-sulfonamide Hydrochloric acid (4 mol/L) in 1,4-dioxane (0.040 mL, 0.16 mmol) was added to a microwave vial under nitrogen containing Intermediate 12 (57 mg, 0.15 mmol), 2-chlorobenzimidazole (37.4 mg, 0.245 mmol) and 1-butanol (2.3 mL). The reaction was stirred at 150° C. in the microwave for 0.5 h, concentrated in vacuo, dissolved in DCM (20 mL) and washed with sat. aq. $NaHCO_3$ (20 mL). The layers were separated, and the aq. layer extracted with DCM (2×10 mL). The combined organic layers where passed through a phase separator, concentrated in vacuo and purified by basic preparative HPLC to give the title compound (3 mg, 4% Yield). $^1H$ NMR (400 MHz, DMSO-d6) δ 10.72 (s, 1H), 9.14 (s, 1H), 8.46 (s, 1H), 8.33 (s, 1H), 8.11 (s, 1H), 7.24-7.08 (m, 2H), 6.97-6.80 (m, 3H), 4.62-4.51 (m, 1H), 3.85 (dd, J=18.4, 6.9 Hz, 1H), 3.60 (dd, J=18.4, 5.2 Hz, 1H), 3.47 (ddd, J=16.3, 6.9, 1.4 Hz, 1H), 3.14 (dd, J=16.6, 5.3 Hz, 1H), 2.92 (d, J=19.9 Hz, 2H), 2.28 (tt, J=7.6, 5.5 Hz, 1H), 1.15 (d, J=13.5 Hz, 3H), 1.10 (d, J=13.6 Hz, 3H), 1.06-0.99 (m, 4H). LCMS $[M+H]^+$ 494.0, RT 1.63 min (Method 10).

Example 21

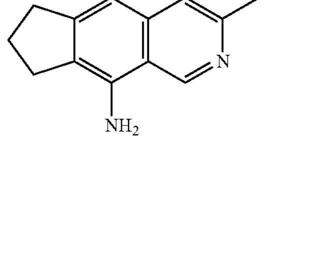

9-amino-3-cyclopropyl-N-(2-methylpropyl)-7,8-dihydro-6H-cyclopenta[g]isoquinoline-5-sulfonamide 1,4-Dioxane (1.5 mL) was added to a flask containing Intermediate 74 (61 mg, 0.17 mmol), cyclopropylboronic acid (48.3 mg, 0.53 mmol), cesium carbonate (139 mg, 0.42 mmol) and chloro($\eta^2$—P,C-tris(2,4-di-tert-butylphenyl) phosphite) (tricyclohexylphosphine) palladium (II) (9.1 mg, 0.008 mmol) under nitrogen. The reaction was degassed and placed under nitrogen before stirring in the microwave for 3 h at 120° C. Additional cyclopropylboronic acid (48.6 mg, 0.54 mmol), chloro($\eta^2$—P,C-tris(2,4-di-tert-butylphenyl) phosphite) (tricyclohexylphosphine) palladium (II) (19.1 mg, 0.018 mmol), cesium carbonate (340 mg, 1.03 mmol) and 1,4-dioxane (1 mL) were added and the reaction degassed and placed under nitrogen again before stirring in the microwave for a further 3 h at 120° C. The reaction was diluted with DCM (30 mL) and washed with water (25 mL). The aq. layer was extracted with DCM (2×25 mL), the combined organic layers were passed through a phase separator, concentrated in vacuo and purified by column chromatography on silica (gradient elution with 0% to 100% EtOAc in iso-hexanes) to give the title compound (30.2 mg, 49% Yield). $^1H$ NMR (400 MHz, Chloroform-d) δ 9.12 (s, 1H), 8.36 (s, 1H), 4.73 (s, 2H), 4.59 (t, J=6.6 Hz, 1H), 3.55 (t, J=7.6 Hz, 2H), 2.85 (t, J=7.5 Hz, 2H), 2.64 (t, J=6.7 Hz, 2H), 2.25-2.13 (m, 3H), 1.73-1.60 (m, 1H), 1.16-1.09 (m, 2H), 1.09-1.00 (m, 2H), 0.81 (d, J=6.7 Hz, 6H). LCMS $[M+H]^+$ 360.0, RT 1.31 min (Method 11).

Example 22

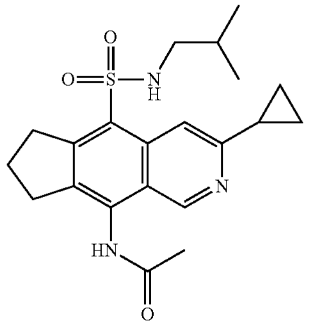 [SMILES: CC(=O)Nc1c2c(c(S(=O)(=O)NCC(C)C)c3cc(C4CC4)ncc13)CCC2]

N-[3-cyclopropyl-5-(2-methylpropylsulfamoyl)-7,8-dihydro-6H-cyclopenta[g]isoquinolin-9-yl]acetamide Pyridine (11.0 μL, 0.136 mmol) then acetic anhydride were added to a suspension of Intermediate 74 (45 mg, 0.127 mmol) in DCM (2 mL) under nitrogen. The reaction was stirred at room temperature for 24.5 h, then at 40° C. for 1.5 h, then at room temperature for a further 1.5 hours. 4-Dimethylaminopyridine (1.7 mg, 0.014 mmol) was added after the reaction had been stirring for 6.5 hours. Additional DCM (2 mL), pyridine (36.0 μL, 0.445 mmol) and acetic anhydride (36.8 μL, 0.38 mmol) were added after the reaction had been stirring for 8.5 hours. A further addition of acetic anhydride (0.19 mL, 2.0 mmol) as well as triethylamine (0.32 mL, 2.3 mmol) took place after the reaction had been stirring for 26 h. After 27.5 hours in total, the reaction was diluted with DCM (10 mL) and water (10 mL) and the layers separated. The aq. layer was extracted with DCM (2×10 mL), and the combined organic layers were passed through a phase separator and concentrated in vacuo. The resultant liquid was diluted with DCM (15 mL), washed with 1 M aq. HCl (10 mL), passed through a phase separator and concentrated in vacuo to give a solid containing a mixture of acetylated products (47.7 mg).

The solid was dissolved in DCM (2.0 mL) under an atmosphere of nitrogen and triethylamine (0.24 mL, 1.7 mmol) followed by acetic anhydride (0.13 mL, 1.3 mmol) were added. The reaction was stirred at room temperature for 20 hours. 4-Dimethylaminopyridine (6.0 mg, 0.049 mmol) was added after the reaction had been stirring for 3 h. After the reaction had been stirred for 20 h it was diluted with DCM (10 mL) and water (10 mL) and the layers were separated. The aq. layer was extracted with DCM (2×10 mL) and the combined organic layers washed with 1M aq. HCl (10 mL), passed through a phase separator and concentrated in vacuo to give the crude acetylated material (70.0 mg).

Cyclopropylboronic acid (52.1 mg, 0.576 mmol) palladium (II) acetate (8.5 mg, 0.038 mmol), tricyclohexylphosphonium tetrafluoroborate (18.3 mg, 0.0482 mmol) and potassium phosphate tribasic (97.0 mg, 0.457 mmol) were added to the crude acetylation material in a mixture of toluene (1.5 mL) and water (0.15 mL, 8.3 mmol). The reaction was degassed, placed under nitrogen and stirred in the microwave for 3 h at 120° C. The reaction was diluted with DCM (40 mL), washed with water (15 mL) and the aq. layer extracted with DCM (2×20 mL). The combined organic layers were passed through a phase separator, concentrated in vacuo and purified by column chromatography on silica (gradient elution with 0% to 100% EtOAc in isohexanes then 0% to 10% MeOH in EtOAc) to give a mixture of products (28.3 mg).

This mixture of products was dissolved in MeOH (6 mL). Aq. sodium hydroxide (2 mL, 1 mol/L) was added and the reaction stirred for 3 days. The reaction was neutralised by the addition of aq. 1 M HCl (2 mL, 2 mmol) then concentrated in vacuo. The residue was dissolved in DCM (30 mL) and washed with water (15 mL). The aq. layer was extracted with DCM (2×20 mL) and the combined organic layers passed through a phase separator, concentrated in vacuo and purified by column chromatography followed by basic preparative HPLC to give the title compound (3 mg, 6% Yield). 1H NMR (400 MHz, DMSO-d6) δ 10.18 (s, 1H), 9.18 (s, 1H), 8.44 (s, 1H), 7.96 (s, 1H), 3.47 (t, J=7.5 Hz, 2H), 2.86 (t, J=7.6 Hz, 2H), 2.60-2.54 (obs m, 2H), 2.27 (p, J=6.6 Hz, 1H), 2.19 (s, 3H), 2.02 (p, J=7.5 Hz, 2H), 1.58 (hept, J=6.7 Hz, 1H), 1.05-0.99 (m, 4H), 0.74 (d, J=6.7 Hz, 6H). LCMS $[M+H]^+$ 402.2, RT 1.90 min (Method 10).

Examples 23 & 24

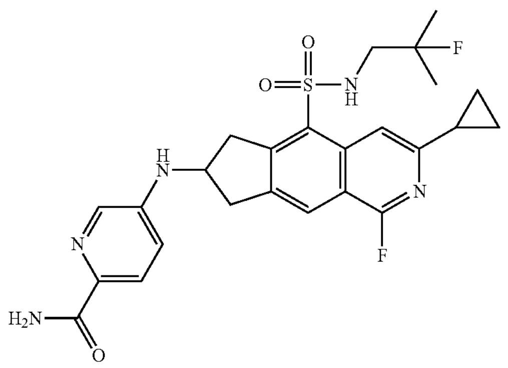

-continued

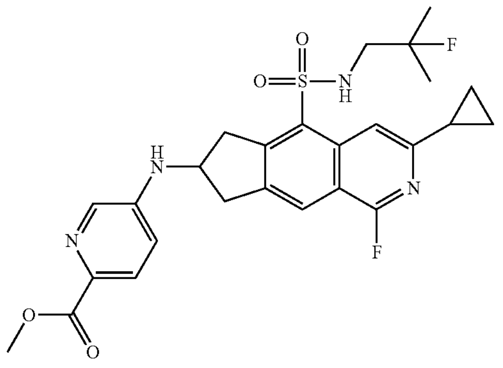

5-[[3-cyclopropyl-1-fluoro-5-[(2-fluoro-2-methyl-propyl) sulfamoyl]-7,8-dihydro-6H-cyclopenta[g] isoquinolin-7-yl]amino]pyridine-2-carboxamide (23)

methyl 5-[[3-cyclopropyl-1-fluoro-5-[(2-fluoro-2-methyl-propyl) sulfamoyl]-7,8-dihydro-6H-cyclopenta[g]isoquinolin-7-yl]amino]pyridine-2-carboxylate (24)

To a solution of intermediate 106 (24 mg, 0.04 mmol) in tetrahydrofuran (1 mL) was added HATU (19 mg, 0.05 mmol), ammonium chloride (10 mg, 0.20 mmol) and then N,N-diisopropylethylamine (17 μL, 0.10 mmol) and the reaction was stirred at ambient temperature for 1.5 hours. The reaction was diluted with water (1 mL) and extracted with EtOAc (2×1 mL). The organic layer was dried over $Na_2SO_4$ and concentrated in vacuo. The products were purified using column chromatography to afford the title compounds:

Example 23 (1.9 mg, 9.3% Yield) $\delta_H$ (400 MHz, d-MeOH) 8.44-8.36 (m, 1H), 8.18 (s, 1H), 8.03-7.97 (m, 1H), 7.89 (dd, J=8.7, 0.6 Hz, 1H), 7.10 (dd, J=8.7, 2.8 Hz, 1H), 4.48-4.40 (m, 1H), 3.90 (dd, J=18.4, 6.4 Hz, 1H), 3.67 (dd, J=18.5, 4.0 Hz, 1H), 3.61-3.52 (m, 1H), 3.17-3.07 (m, 1H), 2.99 (d, J=20.1 Hz, 2H), 2.29-2.19 (m, 1H), 1.11 (dd, J=21.1, 16.8 Hz, 6H), 1.06-1.00 (m, 3H). LCMS $[M-H]^-$ 514.2, RT 2.19 min (Method 10).

Example 24 (0.5 mg, 2% Yield) $\delta_H$ (400 MHz, d-MeOH) 8.43-8.38 (m, 1H), 8.19 (s, 1H), 8.03-7.99 (m, 1H), 7.96 (dd, J=8.7, 0.6 Hz, 1H), 7.12 (dd, J=8.8, 2.8 Hz, 1H), 4.49-4.39 (m, 1H), 3.95-3.86 (m, 4H), 3.67 (dd, J=18.5, 4.0 Hz, 1H), 3.57 (ddd, J=16.6, 6.8, 1.5 Hz, 1H), 3.16-3.10 (m, 1H), 2.99 (dd, J=20.0, 1.6 Hz, 2H), 2.30-2.19 (m, 1H), 1.11 (dd, J=21.1, 15.1 Hz, 6H), 1.06-1.01 (m, 4H). LCMS $[M+H]^+$ 531.0, RT 2.35 min (Method 10).

Examples 25 & 26

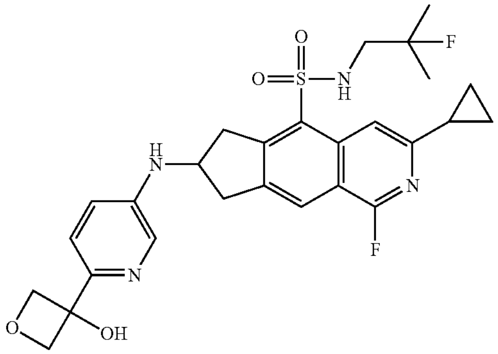

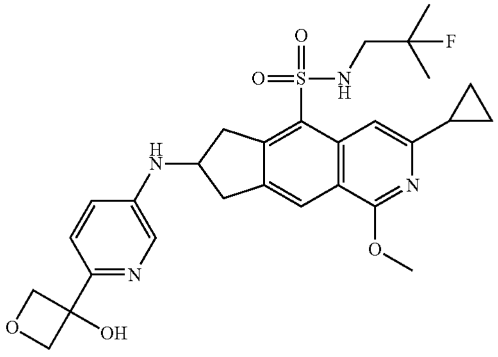

3-cyclopropyl-1-fluoro-N-(2-fluoro-2-methylpropyl)-7-[[6-(3-hydroxyoxetan-3-yl)pyridin-3-yl]amino]-7,8-dihydro-6H-cyclopenta[g]isoquinoline-5-sulfonamide (25)

3-cyclopropyl-N-(2-fluoro-2-methylpropyl)-7-[[6-(3-hydroxyoxetan-3-yl)pyridin-3-yl]amino]-1-methoxy-7,8-dihydro-6H-cyclopenta[g]isoquinoline-5-sulfonamide (26)

The title compounds were prepared according to General Procedure 1 using a mixture of Intermediates 111 & 112 (40 mg, ~80 μmol), sodium tert-butoxide (12 mg, 0.12 mmol), tBuXPhos Pd G3 (5 mg, 0.006 mmol), 3-(5-bromo-2-pyridyl) oxetan-3-ol (28 mg, 0.12 mmol) and 1,4-dioxane (0.5 mL). The products were purified by reverse phase HPLC (basic conditions) to afford:

Example 25 (1 mg, 5% Yield) $\delta_H$ (400 MHz, d-MeOH) 8.43-8.37 (m, 1H), 8.19-8.14 (m, 1H), 8.01 (dd, J=2.9, 0.7 Hz, 1H), 7.47 (dd, J=8.6, 0.7 Hz, 1H), 7.14 (dd, J=8.6, 2.8 Hz, 1H), 5.01-4.95 (m, 2H), 4.79 (d, J=6.3 Hz, 2H), 4.45-4.33 (m, 1H), 4.10-3.80 (m, 1H), 3.71-3.50 (m, 2H), 3.16-3.06 (m, 1H), 2.98 (d, J=19.9 Hz, 2H), 2.29-2.16 (m, 1H), 1.18-0.99 (m, 10H). LCMS $[M+H]^+$ 545.2, RT 2.18 min (Method 10).

Example 26 (4 mg, 18% Yield) $\delta_H$ (400 MHz, d-MeOH) 8.29-8.25 (m, 1H), 8.04 (d, J=0.9 Hz, 1H), 8.01 (dd, J=2.8, 0.7 Hz, 1H), 7.46 (dd, J=8.7, 0.7 Hz, 1H), 7.13 (dd, J=8.6, 2.9 Hz, 1H), 5.02-4.96 (m, 2H), 4.82-4.76 (m, 2H), 4.41-4.33 (m, 1H), 4.10-3.78 (m, 4H), 3.63-3.46 (m, 2H), 3.05 (dd, J=16.2, 4.3 Hz, 1H), 2.94 (d, J=19.5 Hz, 2H), 2.21-2.12 (m, 1H), 1.20-0.93 (m, 10H). LCMS $[M-H]^-$ 555.2, RT 2.46 min (Method 10).

Example 27

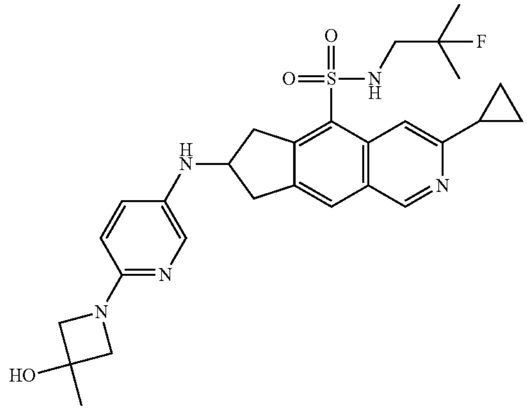 [SMILES: CC(C)(F)CNS(=O)(=O)c1c2c(cc3cnc(C4CC4)cc13)CC(Nc1ccc(N3CC(C)(O)C3)nc1)C2]

3-cyclopropyl-N-(2-fluoro-2-methylpropyl)-7-[[6-(3-hydroxy-3-methylazetidin-1-yl)pyridin-3-yl]amino]-7,8-dihydro-6H-cyclopenta[g]isoquinoline-5-sulfonamide The title compound was prepared according to General Procedure 1, using Intermediate 12 (50 mg, 0.13 mmol), 1-(5-bromo-2-pyridyl)-3-methyl-azetidin-3-ol (121 mg, 0.40 mmol), sodium tert-butoxide (28 mg, 0.40 mmol), tBuXPhos Pd G3 (16 mg, 0.02 mmol) and 1,4-dioxane (5 mL). Purification by column chromatography afforded the title compound (24 mg, 34% Yield). $\delta_H$ (300 MHz, d-MeOH) 9.12 (s, 1H), 8.43 (s, 1H), 8.36-8.23 (m, 1H), 8.08 (s, 1H), 7.60 (d, J=2.7 Hz, 1H), 6.99 (dd, J=8.8, 2.8 Hz, 1H), 6.31 (d, J=8.7 Hz, 1H), 5.39 (s, 1H), 5.30 (d, J=6.6 Hz, 1H), 4.30-4.07 (m, 1H), 3.85-3.56 (m, 5H), 3.42 (dd, J=17.6, 5.5 Hz, 2H), 3.01-2.83 (m, 3H), 2.33-2.18 (m, 1H), 1.42 (s, 3H), 1.13 (dd, J=21.4, 6.9 Hz, 6H), 1.06-0.95 (m, 4H). LCMS $[M-H]^-$ 538.2, RT 1.63 min (Method 12).

Example 28

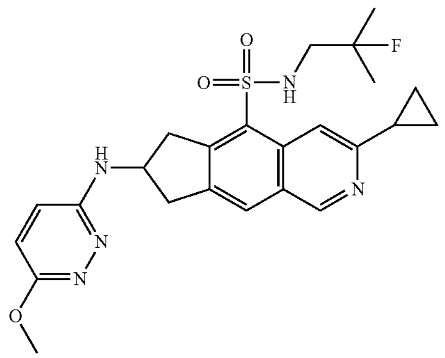 [SMILES: COc1ccc(NC2Cc3cc4cnc(C5CC5)cc4c(S(=O)(=O)NCC(C)(C)F)c3C2)nn1]

3-cyclopropyl-N-(2-fluoro-2-methylpropyl)-7-[(6-methoxypyridazin-3-yl)amino]-7,8-dihydro-6H-cyclopenta[g]isoquinoline-5-sulfonamide The title compound was prepared according to General Procedure 1 using Intermediate 12 (120 mg, 0.32 mmol), 3-bromo-6-methoxypyridazine (158 mg, 0.80 mmol), sodium tert-butoxide (92 mg, 0.95 mmol), tBuXPhos Pd G3 (39 mg, 0.048 mmol) and 1,4-dioxane (5 mL). Purification by column chromatography afforded the title compound (98 mg, 63% Yield). $\delta_H$ (300 MHz, d-DMSO) 9.13 (s, 1H), 8.43 (s, 1H), 8.32 (t, J=6.2 Hz, 1H), 8.11 (s, 1H), 6.94-6.80 (m, 2H), 6.78 (d, J=5.7 Hz, 1H), 4.67-4.52 (m, 1H), 3.87 (s, 3H), 3.85-3.77 (m, 1H), 3.60-3.40 (m, 2H), 3.10-2.80 (m, 3H), 2.39-2.17 (m, 1H), 1.12 (dd, J=21.4, 7.0 Hz, 6H), 1.05-0.99 (m, 4H). LCMS [M−H]$^-$ 484.2, RT 1.77 min (Method 12).

Example 29

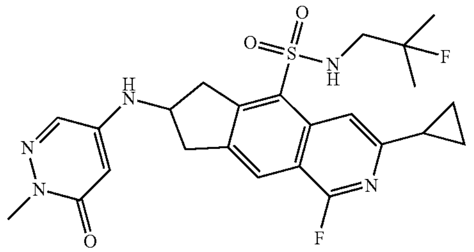 [SMILES: Cn1ncc(NC2Cc3cc4c(F)nc(C5CC5)cc4c(S(=O)(=O)NCC(C)(C)F)c3C2)cc1=O]

3-cyclopropyl-1-fluoro-N-(2-fluoro-2-methyl-propyl)-7-[(1-methyl-6-oxo-pyridazin-4-yl)amino]-7,8-dihydro-6H-cyclopenta[g]isoquinoline-5-sulfonamide The title compound was prepared according to General Procedure 1 using Intermediate 104 (50 mg, 0.13 mmol), 5-iodo-2-methyl-pyridazin-3-one (78 mg, 0.33 mmol), sodium tert-butoxide (38 mg, 0.40 mmol), tBuXPhos Pd G3 (16 mg, 0.02 mmol) and 1,4-dioxane (0.5 mL). Purification by column chromatography afforded the title compound (5.9 mg, 9% Yield). $\delta_H$ (400 MHz, d-DMSO) 8.51-8.44 (m, 1H), 8.44-8.36 (m, 1H), 8.19 (s, 1H), 7.37 (d, J=2.6 Hz, 1H), 7.20 (d, J=6.2 Hz, 1H), 5.66 (d, J=2.7 Hz, 1H), 4.29-4.16 (m, 1H), 3.84-3.73 (m, 1H), 3.57-3.43 (m, 5H), 3.04 (dd, J=17.0, 3.9 Hz, 1H), 2.98-2.86 (m, 2H), 2.31-2.21 (m, 1H), 1.13 (dd, J=21.3, 6.5 Hz, 6H), 1.08-0.91 (m, 4H). LCMS [M+H]$^+$ 504.0, RT 2.02 min (Method 10).

Example 30

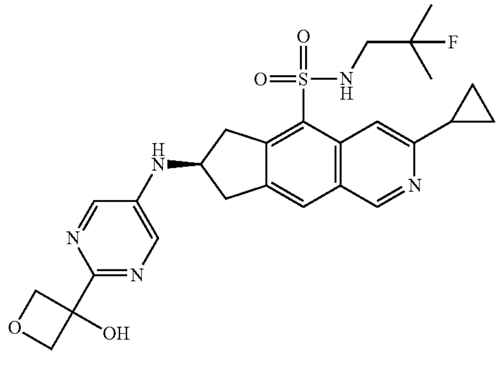 [SMILES: CC(C)(F)CNS(=O)(=O)c1c2c(cc3cnc(C4CC4)cc13)C[C@@H](Nc1cnc(C3(O)COC3)nc1)C2]

(7R)-3-cyclopropyl-N-(2-fluoro-2-methylpropyl)-7-[[2-(3-hydroxyoxetan-3-yl)pyrimidin-5-yl]amino]-7,8-dihydro-6H-cyclopenta[g]isoquinoline-5-sulfonamide The title compound was prepared according to General Procedure 1 using Intermediate 15 (68 mg, 0.18), sodium tert-butoxide (52 mg, 0.54 mmol), tBuXPhos Pd G3 (22 mg, 0.027 mmol), 3-(5-bromopyrimidin-2-yl) oxetan-3-ol (104 mg, 0.45 mmol) and 1,4-dioxane (5 mL). Purification by column chromatography afforded the title compound (42 mg, 45% Yield). $\delta_H$ (400 MHz, d-DMSO) 9.16-9.11 (m, 1H), 8.46-8.42 (m, 1H), 8.34 (t, J=6.5 Hz, 1H), 8.25 (s, 2H), 8.17-8.08 (m, 1H), 6.51 (d, J=6.5 Hz, 1H), 5.99 (s, 1H), 4.96-4.89 (m, 2H), 4.66-4.60 (m, 2H), 4.46-4.30 (m, 1H), 3.86 (dd, J=18.3, 6.7 Hz, 1H), 3.59-3.39 (m, 2H), 3.00 (dd, J=16.7, 4.7 Hz, 1H), 2.90 (ddd, J=20.0, 6.5, 1.8 Hz, 2H), 2.32-2.24 (m, 1H), 1.12 (dd, J=21.4, 8.0 Hz, 6H), 1.06-0.96 (m, 4H). LCMS [M+H]$^+$ 528.2, RT 1.64 min (Method 12).

Example 31

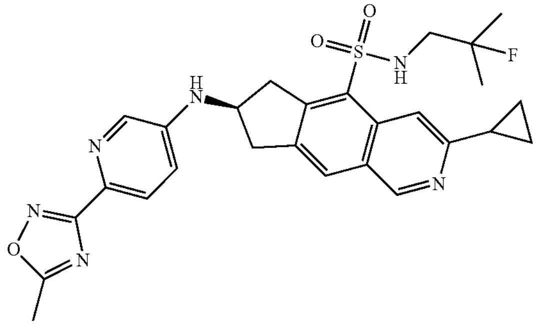 [SMILES: Cc1nc(-c2ccc(N[C@@H]3Cc4cc5cnc(C6CC6)cc5c(S(=O)(=O)NCC(C)(C)F)c4C3)cn2)no1]

(7R)-3-cyclopropyl-N-(2-fluoro-2-methylpropyl)-7-[[6-(5-methyl-1,2,4-oxadiazol-3-yl)pyridin-3-yl]amino]-7,8-dihydro-6H-cyclopenta[g]isoquinoline-5-sulfonamide The title compound was prepared according to General Procedure 1 using Intermediate 15 (50 mg, 0.13 mmol), 3-(5-bromo-2-pyridyl)-5-methyl-1,2,4-oxadiazole (95 mg, 0.40 mmol), sodium tert-butoxide (38 mg, 0.40 mmol), tBuXPhos Pd G3 (1 6 mg, 0.020 mmol) and 1,4-dioxane (2 mL). Purification by column chromatography afford the title compound (28 mg, 39% Yield). $\delta_H$ (400 MHz, d-DMSO) 9.15 (s, 1H), 8.47-8.41 (m, 1H), 8.35 (t, J=6.5 Hz, 1H), 8.16-8.08 (m, 2H), 7.81 (d, J=8.6 Hz, 1H), 7.12 (dd, J=8.7, 2.8 Hz, 1H), 6.88 (d, J=6.4 Hz, 1H), 4.43-4.29 (m, 1H), 3.85 (dd, J=18.3, 6.7 Hz, 1H), 3.59-3.46 (m, 2H), 3.03 (dd, J=16.7, 4.5 Hz, 1H), 2.89 (dd, J=20.2, 6.2 Hz, 2H), 2.62 (s, 3H), 2.32-2.25 (m, 1H), 1.11 (dd, J=21.4, 10.1 Hz, 6H), 1.05-0.99 (m, 4H). LCMS [M−H]$^-$ 535.2, RT 2.02 min (Method 10).

Example 32

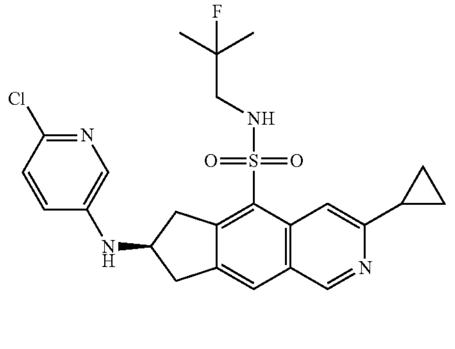 [SMILES: CC(C)(F)CNS(=O)(=O)c1c2c(cc3cnc(C4CC4)cc13)C[C@@H](Nc1ccc(Cl)nc1)C2]

(7R)-7-[(6-chloropyridin-3-yl)amino]-3-cyclopropyl-N-(2-fluoro-2-methylpropyl)-7,8-dihydro-6H-cyclopenta[g]isoquinoline-5-sulfonamide The title compound was prepared according to General Procedure 1 using Intermediate 15 (50 mg, 0.13 mmol), 5-bromo-2-chloropyridine (40 mg, 0.2 mmol), sodium tert-butoxide (38 mg, 0.40 mmol), tBuXPhos Pd G3 (16 mg, 0.02 mmol) and 1,4-dioxane (2.5 mL). Purification using column chromatography afforded the title compound (60 mg, 83% Yield). $\delta_H$ (400 MHz, d-DMSO) 9.14 (s, 1H), 8.45-8.40 (m, 1H), 8.37-8.29 (m, 1H), 8.11 (s, 1H), 7.78 (d, J=2.9 Hz, 1H), 7.19 (d, J=8.6 Hz, 1H), 7.08 (dd, J=8.7, 3.0 Hz, 1H), 6.39 (d, J=6.5 Hz, 1H), 4.32-4.22 (m, 1H), 3.81 (dd, J=18.3, 6.7 Hz, 1H), 3.53-3.42 (m, 2H), 2.97 (dd, J=16.4, 4.4 Hz, 1H), 2.88 (dd, J=20.2, 4.5 Hz, 2H), 2.31-2.22 (m, 1H), 1.11 (dd, J=21.4, 10.0 Hz, 6H), 1.06-0.96 (m, 4H). LCMS $[M+H]^+$ 489.0, RT 2.33 min (Method 10)

Example 33

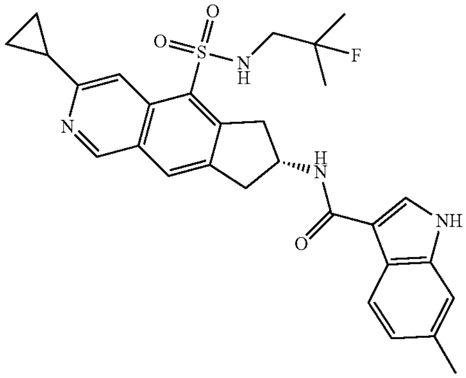 [SMILES: Cc1ccc2c(C(=O)N[C@@H]3Cc4cc5cnc(C6CC6)cc5c(S(=O)(=O)NCC(C)(C)F)c4C3)c[nH]c2c1]

N-[(7R)-3-cyclopropyl-5-[(2-fluoro-2-methylpropyl)sulfamoyl]-7,8-dihydro-6H-cyclopenta[g]isoquinolin-7-yl]-6-methyl-1H-indole-3-carboxamide The title compound was obtained using General Procedure 4 with intermediate 15 (20 mg, 0.053 mmol) and 6-methyl-1H-indole-3-carboxylic acid. Purification by column chromatography afforded the title compound (7 mg, 25% yield). $^1H$ NMR (400 MHz, DMSO-d6) δ 11.39-11.35 (m, 1H), 8.45 (s, 1H), 8.42-8.26 (m, 1H), 8.10 (s, 1H), 8.05 (d, J=6.8 Hz, 1H), 8.01 (d, J=8.1 Hz, 1H), 7.93 (d, J=2.7 Hz, 1H), 7.23-7.13 (m, 1H), 6.93 (dd, J=8.5, 1.4 Hz, 1H), 4.80-4.62 (m, 1H), 3.87 (dd, J=18.5, 7.6 Hz, 1H), 3.57-3.39 (m, 2H), 3.15-3.02 (m, 1H), 2.94 (d, J=20.1 Hz, 2H), 2.39 (s, 3H), 2.31-2.24 (m, 1H), 1.12 (dd, J=21.4, 6.8 Hz, 6H), 1.06-0.94 (m, 4H). One proton not observed, possibly masked by solvent signals. LCMS $[M-H]^-$ 533, RT 2.17 min (Method 10).

Example 34

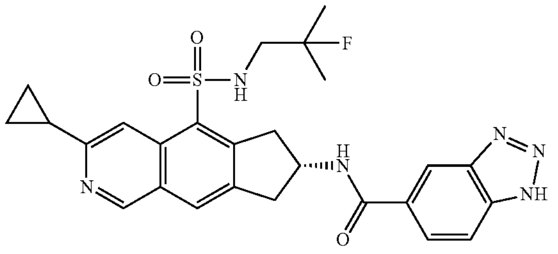 [SMILES: CC(C)(F)CNS(=O)(=O)c1c2c(cc3cnc(C4CC4)cc13)C[C@@H](NC(=O)c1ccc3[nH]nnc3c1)C2]

N-[(7R)-3-cyclopropyl-5-[(2-fluoro-2-methylpropyl)sulfamoyl]-7,8-dihydro-6H-cyclopenta[g]isoquinolin-7-yl]-1H-benzotriazole-5-carboxamide The title compound was prepared according to General Procedure 4 using Intermediate 15 (20 mg, 0.053 mmol), benzotriazole-5-carboxylic acid, HATU (1.5 equiv.) instead of HBTU, DIPEA (3 equiv.) and DMF (1 mL). Purification by column chromatography afforded the title compound (10 mg, 37% yield). $^1H$ NMR (400 MHz, Methanol-d4) δ 9.08 (s, 1H), 8.51 (s, 1H), 8.46-8.35 (m, 1H), 8.12-8.03 (m, 1H), 8.01-7.91 (m, 1H), 7.91-7.82 (m, 1H), 4.95-4.85 (m, 1H), 4.03 (dd, J=18.6, 7.4 Hz, 1H), 3.68 (dd, J=18.6, 6.2 Hz, 1H), 3.63-3.53 (m, 1H), 3.29-3.21 (m, 1H), 3.06 (dd, J=20.3, 6.7 Hz, 2H), 2.36-2.25 (m, 1H), 1.14 (d, J=21.2 Hz, 6H), 1.11-1.08 (m, 4H). Exchangeable protons not observed. LCMS $[M+H]^+$ 523, RT 1.50 (Method 10).

Example 35

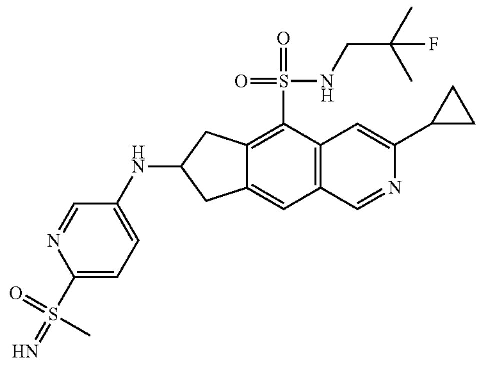 [SMILES: CC(C)(F)CNS(=O)(=O)c1c2c(cc3cnc(C4CC4)cc13)CC(Nc1ccc(S(C)(=N)=O)nc1)C2]

3-cyclopropyl-N-(2-fluoro-2-methylpropyl)-7-[[6-(methylsulfonimidoyl)pyridin-3-yl]amino]-7,8-dihydro-6H-cyclopenta[g]isoquinoline-5-sulfonamide To a solution of Intermediate 100 (45 mg, 0.071 mmol) in DCM (0.5 mL) was added trifluoroacetic acid (0.5 mL). The reaction was stirred at ambient temperature overnight, concentrated in vacuo and purified by basic reverse phase column chromatography to afford the title compound (21 mg, 59% Yield). 0H (300 MHz, d-DMSO) 9.15 (s, 1H), 8.44 (s, 1H), 8.35 (t, J=6.5 Hz, 1H), 8.13 (s, 1H), 8.05 (d, J=2.6 Hz, 1H), 7.81 (d, J=8.7 Hz, 1H), 7.14 (dd, J=8.7, 2.8 Hz, 1H), 7.02 (d, J=6.4 Hz, 1H), 4.45-4.31 (m, 1H), 3.92 (s, 1H), 3.86 (dd, J=18.4, 6.8 Hz, 1H), 3.59-3.42 (m, 2H), 3.07-2.96 (m, 4H), 2.89 (dd, J=20.2, 6.5 Hz, 2H), 2.32-2.24 (m, 1H), 1.11 (dd, J=21.4, 6.5 Hz, 6H), 1.02 (d, J=7.8 Hz, 4H). LCMS $[M-H]^-$ 530.2, RT 1.59 min (Method 12).

Example 36

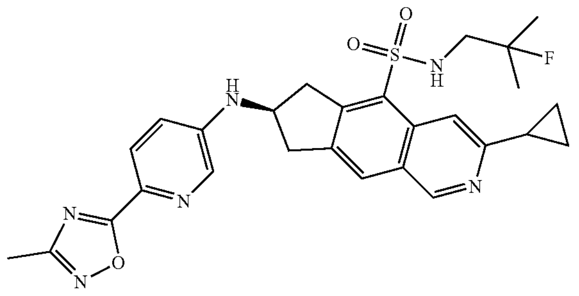 [SMILES: Cc1noc(-c2ccc(N[C@@H]3Cc4cc5cnc(C6CC6)cc5c(S(=O)(=O)NCC(C)(C)F)c4C3)cn2)n1]

(7R)-3-cyclopropyl-N-(2-fluoro-2-methylpropyl)-7-[[6-(3-methyl-1,2,4-oxadiazol-5-yl)pyridin-3-yl]amino]-7,8-dihydro-6H-cyclopenta[g]isoquinoline-5-sulfonamide To a mixture of Intermediate 15 (50 mg, 0.13 mmol), sodium tert-butoxide (38 mg, 0.40 mmol), tBuXPhos Pd G3 (17 mg, 0.021 mmol) and 5-(5-bromo-2-pyridyl)-3-methyl-1,2,4-oxadiazole (42 mg, 0.17 mmol) was added 1,4-dioxane (1 mL). After 64 hours the mixture was diluted with dichloromethane (10 mL) and water (5 mL). The organics were purified by flash chromatography. Lyophilisation furnished the title compound as an off-white solid (8 mg, 11% Yield). $^1$H NMR (400 MHz, DMSO-d6) $\delta_H$ 9.16 (d, J=0.8 Hz, 1H), 8.45 (d, J=1.0 Hz, 1H), 8.37 (t, J=6.3 Hz, 1H), 8.17 (d, J=2.7 Hz, 1H), 8.15 (s, 1H), 7.98 (d, J=8.7 Hz, 1H), 7.24 (d, J=6.4 Hz, 1H), 7.16 (dd, J=8.8, 2.8 Hz, 1H), 4.50-4.35 (m, 1H), 3.87 (dd, J=18.4, 6.7 Hz, 1H), 3.59-3.48 (m, 2H), 3.05 (dd, J=16.7, 4.5 Hz, 1H), 2.90 (dd, J=20.2, 5.5 Hz, 2H), 2.38 (s, 3H), 2.31-2.24 (m, 1H), 1.18-1.07 (m, 6H), 1.06-1.01 (m, 4H); LCMS $[M+H]^+$ 537, RT 2.14 min (Method 10).

Example 37

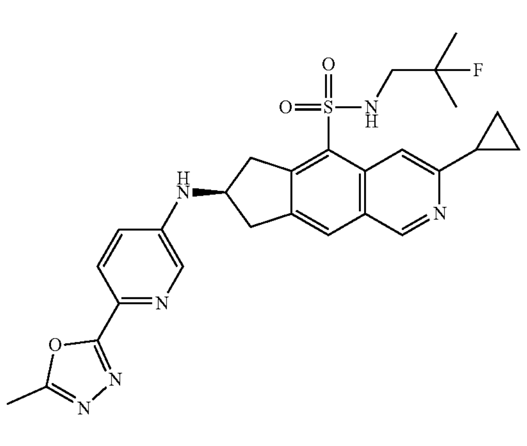 [SMILES: Cc1nnc(-c2ccc(N[C@@H]3Cc4cc5cnc(C6CC6)cc5c(S(=O)(=O)NCC(C)(C)F)c4C3)cn2)o1]

(7R)-3-cyclopropyl-N-(2-fluoro-2-methylpropyl)-7-[[6-(5-methyl-1,3,4-oxadiazol-2-yl)pyridin-3-yl]amino]-7,8-dihydro-6H-cyclopenta[g]isoquinoline-5-sulfonamide To a mixture of Intermediate 15 (710 mg, 1.88 mmol), sodium tert-butoxide (535 mg, 5.56 mmol), tBuXPhos Pd G3 (228 mg, 0.278 mmol) and 2-(5-bromo-2-pyridyl)-5-methyl-1,3,4-oxadiazole (670 mg, 2.79 mmol) was added 1,4-dioxane (12 mL). After 30 minutes the mixture was diluted with dichloromethane (30 mL) and water (20 mL). The organics were purified by flash chromatography. Lyophilisation furnished the title compound as an off-white solid (730 mg, 72% yield). $\delta_H$ (300 MHz, DMSO-d6) 9.15 (s, 1H), 8.44 (d, J=0.9 Hz, 1H), 8.39-8.30 (m, 1H), 8.13 (s, 1H), 8.12 (d, J=2.8 Hz, 1H), 7.88 (d, J=8.6 Hz, 1H), 7.15 (dd, J=8.7, 2.8 Hz, 1H), 7.00 (d, J=6.3 Hz, 1H), 4.47-4.33 (m, 1H), 3.86 (dd, J=18.4, 6.7 Hz, 1H), 3.59-3.45 (m, 2H), 3.03 (dd, J=16.6, 4.5 Hz, 1H), 2.97-2.84 (m, 2H), 2.55 (s, 3H), 2.34-2.23 (m, 1H), 1.11 (dd, J=21.4, 6.9 Hz, 6H), 1.05-0.99 (m, 4H); LCMS $[M+H]^+$ 537, RT 1.95 min (Method 10).

Example 38

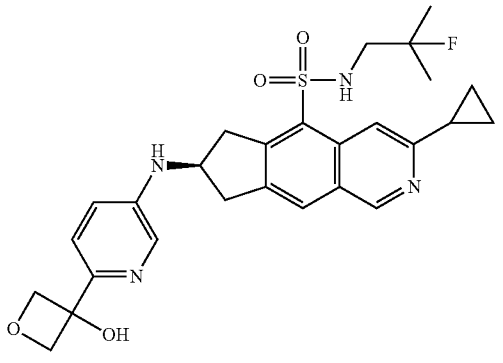 [SMILES: CC(C)(F)CNS(=O)(=O)c1c2c(cc3cnc(C4CC4)cc13)C[C@@H](Nc1ccc(C3(O)COC3)nc1)C2]

(7R)-3-cyclopropyl-N-(2-fluoro-2-methylpropyl)-7-[[6-(3-hydroxyoxetan-3-yl)pyridin-3-yl]amino]-7,8-dihydro-6H-cyclopenta[g]isoquinoline-5-sulfonamide To a mixture of Intermediate 15 (520 mg, 1.38 mmol), sodium tert-butoxide (400 mg, 4.16 mmol), tBuXPhos Pd G3 (170 mg, 0.21 mmol) and 3-(5-bromo-2-pyridyl) oxetan-3-ol (480 mg, 2.1 mmol) was added 1,4-dioxane (10 mL). The mixture was heated to 100° C. for 90 minutes before being cooled and partitioned between dichloromethane (20 mL) and water (20 mL). The aqueous layer was extracted with dichloromethane (2×10 mL) and ethyl acetate (2×10 mL). The organics were concentrated under reduced pressure and purified by reverse phase flash chromatography. Lyophilisation furnished the title compound as an off-white solid (402 mg, 55% yield). $\delta_H$ (400 MHz, DMSO-d6) 9.14 (d, J=0.7 Hz, 1H), 8.45 (d, J=0.9 Hz, 1H), 8.32 (d, J=5.7 Hz, 1H), 8.12 (d, J=1.2 Hz, 1H), 8.04 (dd, J=2.8, 0.7 Hz, 1H), 7.34 (d, J=8.5 Hz, 1H), 7.05 (dd, J=8.6, 2.8 Hz, 1H), 6.23-6.17 (m, 2H), 4.87 (dd, J=6.1, 2.6 Hz, 2H), 4.62-4.58 (m, 2H), 4.35-4.27 (m, 1H), 3.83 (dd, J=18.4, 6.7 Hz, 1H), 3.54-3.44 (m, 2H), 3.00 (dd, J=16.7, 4.6 Hz, 1H), 2.95-2.84 (m, 2H), 2.32-2.24 (m, 1H), 1.12 (dd, J=21.4, 11.0 Hz, 6H), 1.06-0.98 (m, 4H); LCMS $[M+H]^+$ 527, RT 1.69 min (Method 10).

Example 39

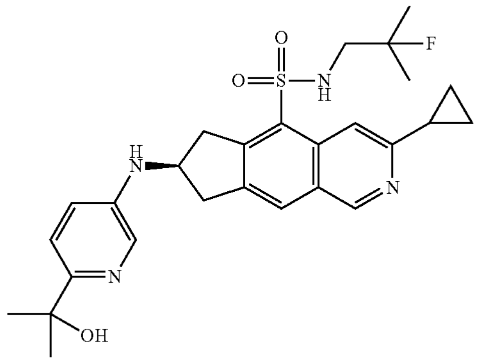 [SMILES: CC(C)(F)CNS(=O)(=O)c1c2c(cc3cnc(C4CC4)cc13)C[C@@H](Nc1ccc(C(C)(C)O)nc1)C2]

(7R)-3-cyclopropyl-N-(2-fluoro-2-methylpropyl)-7-[[6-(2-hydroxypropan-2-yl)pyridin-3-yl]amino]-7,8-dihydro-6H-cyclopenta[g]isoquinoline-5-sulfonamide To a mixture of Intermediate 15 (50 mg, 0.13 mmol), sodium tert-butoxide (38 mg, 0.40 mmol) and tBuXPhos Pd G3 (16 mg, 0.019 mmol) was added a solution of 2-(5-bromo-2-pyridyl) propan-2-ol (43 mg, 0.20 mmol) in 1,4-dioxane (1 mL), The mixture was heated to 100° C. for 1 hour before being cooled and partitioned between dichloromethane (3 mL) and water (1.5 mL). The organics were purified by reverse phase flash chromatography. Lyophilisation furnished the title compound as an off-white solid (48 mg, 71% yield). $\delta_H$ (300 MHz, DMSO-d6) 9.11 (s, 1H), 8.49 (s, 1H), 8.32 (s, 1H), 8.06 (s, 1H), 7.90 (d, J=2.6 Hz, 1H), 7.37 (d, J=8.5 Hz, 1H), 7.00 (dd, J=8.6, 2.8 Hz, 1H), 5.99 (d, J=6.5 Hz, 1H), 4.95 (s, 1H), 4.32-4.16 (m, 1H), 3.81 (dd, J=18.3, 6.7 Hz, 1H), 3.56-3.37 (m, 2H), 2.97 (dd, J=16.5, 4.6 Hz, 1H), 2.85 (d, J=19.5 Hz, 2H), 2.31-2.18 (m, 1H), 1.38 (s, 6H), 1.22-0.92 (m, 10H); LCMS $[M+H]^+$ 513, RT 1.91 min (Method 10).

Example 40

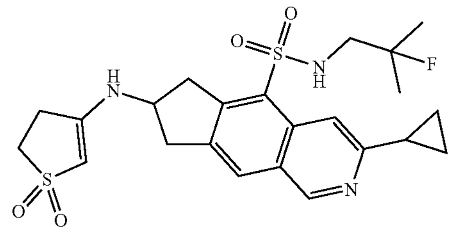 [SMILES: CC(C)(F)CNS(=O)(=O)c1c2c(cc3cnc(C4CC4)cc13)CC(NC1=CS(=O)(=O)CC1)C2]

3-cyclopropyl-7-[(1,1-dioxo-2,3-dihydrothiophen-4-yl)amino]-N-(2-fluoro-2-methylpropyl)-7,8-dihydro-6H-cyclopenta[g]isoquinoline-5-sulfonamide To a suspension of 1,1-dioxothiolan-3-one (21 mg, 0.16 mmol) in tetrahydrofuran (0.5 mL) was added N,N-diisopropylethylamine (14 µL, 0.08 mmol) and Intermediate 12 (30 mg, 0.08 mmol). After 2.5 hours the mixture was concentrated under nitrogen and purified by flash chromatography. Lyophilisation furnished the title compound as a-white solid (2 mg, 5% yield). $\delta_H$ (400 MHz, DMSO-d6) δ 9.15 (s, 1H), 8.44 (d, J=0.9 Hz, 1H), 8.37 (t, J=6.5 Hz, 1H), 8.12 (s, 1H), 7.14 (d, J=6.3 Hz, 1H), 5.47 (s, 1H), 4.13-4.01 (m, 1H), 3.78 (dd, J=18.5, 7.0 Hz, 1H), 3.51-3.38 (m, 2H), 3.23-3.17 (m, 2H), 3.02-2.88 (m, 3H), 2.76-2.66 (m, 2H), 2.31-2.23 (m, 1H), 1.16 (dd, J=21.4, 4.2 Hz, 6H), 1.09-0.95 (m, 4H); LCMS $[M+H]^+$ 494, RT 1.58 min (Method 10).

Example 41

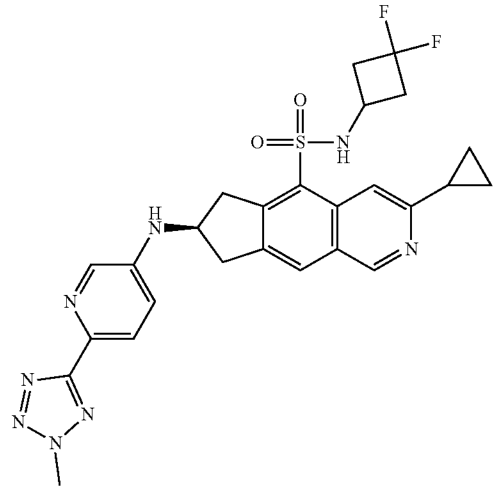 [SMILES: Cn1nnc(-c2ccc(N[C@@H]3Cc4cc5cnc(C6CC6)cc5c(S(=O)(=O)NC5CC(F)(F)C5)c4C3)cn2)n1]

(7R)-3-cyclopropyl-N-(3,3-difluorocyclobutyl)-7-[[6-(2-methyltetrazol-5-yl)pyridin-3-yl]amino]-7,8-dihydro-6H-cyclopenta[g]isoquinoline-5-sulfonamide To a solution of Intermediate 124 (30 mg, 0.076 mmol) in 1,4-dioxane (1.5 mL, 18 mmol), 5-bromo-2-(2-methyl-2H-tetrazol-5-yl)-pyridine (28 mg, 1.10 mmol), tBuXPhos Pd G3 (10 mg, 0.012 mmol) and sodium tert-butoxide (23 mg, 0.24 mmol) were added. After 1 hour at room temperature the mixture was filtered through celite. Concentration under vacuum followed by purification by flash column chromatography (eluting with 0 to 100% EtOAc in hexanes followed by 0 to 5% MeOH in DCM) afforded the title compound (25 mg, 59% Yield). $^1$H NMR (300 MHz, DMSO-$d_6$) δ 9.18 (s, 1H), 8.52 (d, J=7.5 Hz, 1H), 8.36 (s, 1H), 8.22-8.10 (m, 2H), 7.88 (d, J=8.6 Hz, 1H), 7.16 (dd, J=8.7, 2.8 Hz, 1H), 6.76 (d, J=6.4 Hz, 1H), 4.39 (s, 3H), 3.85 (dd, J=18.3, 6.6 Hz, 1H), 3.53 (dt, J=14.8, 7.1 Hz, 3H), 3.11-2.98 (m, 1H), 2.30 (s, 4H), 2.25 (d, J=6.2 Hz, 1H), 1.09-1.00 (m, 4H). LCMS [M+H]$^+$ 553, RT 2.07 min (Method 10).

Example 42

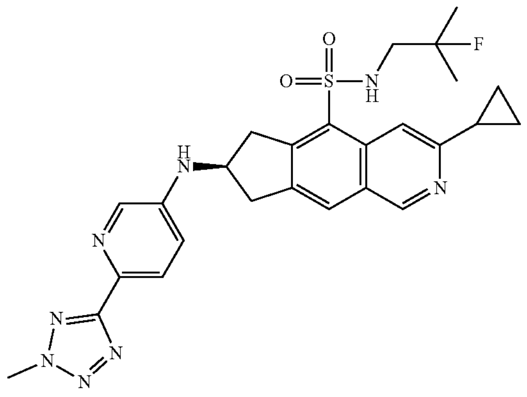

(7R)-3-cyclopropyl-N-(2-fluoro-2-methylpropyl)-7-[[6-(2-methyltetrazol-5-yl)pyridin-3-yl]amino]-7,8-dihydro-6H-cyclopenta[g]isoquinoline-5-sulfonamide To a solution of Intermediate 15 (800 mg, 2.11 mmol) in 1,4-dioxane (30 mL), sodium tert-butoxide (600 mg, 6.23 mmol), tBuXPhos Pd G3 (260 mg, 0.31 mmol) and 5-bromo-2-(2-methyl-2h-tetrazol-5-yl)-pyridine (1 g, 4.16 mmol) were added. The reaction mixture was sparged with nitrogen and the reaction mixture stirred at room temperature for another 1.5 hours. The mixture was diluted with EtOAc and filtered through celite, then concentrated and the resulting residue by column chromatography (eluting with 0 to 100% EtOAc in hexanes followed by 0 to 5% MeOH in DCM) to give the product as a light brown solid (0.9 g). This was suspended in a mixture of MeCN (5 mL) and water (1 mL). Filtration then afforded the title compound as a white solid (675 mg, 59% Yield). 1H NMR (300 MHz, DMSO-$d_6$) δ 9.15 (s, 1H), 8.45 (d, J=1.0 Hz, 1H), 8.34 (s, 1H), 8.13 (d, J=2.2 Hz, 2H), 7.88 (d, J=8.6 Hz, 1H), 7.15 (dd, J=8.7, 2.8 Hz, 1H), 6.74 (d, J=6.4 Hz, 1H), 4.39 (s, 3H), 3.86 (dd, J=18.4, 6.6 Hz, 1H), 3.60-3.45 (m, 2H), 3.03 (dd, J=16.6, 4.5 Hz, 1H), 2.93 (s, 1H), 2.87 (s, 1H), 2.28 (p, J=6.9 Hz, 1H), 1.19-0.97 (m, 10H). LCMS [M+H]$^+$ 537, RT 2.03 min (Method 10).

Example 43

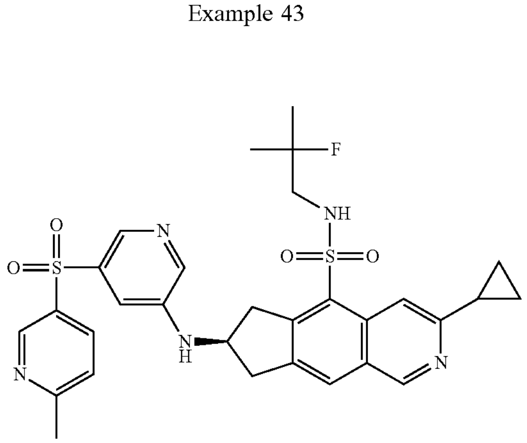

(7R)-3-cyclopropyl-N-(2-fluoro-2-methylpropyl)-7-[[5-(6-methylpyridin-3-yl) sulfonylpyridin-3-yl]amino]-7,8-dihydro-6H-cyclopenta[g]isoquinoline-5-sulfonamide Into a pressure tube were introduced Intermediate 54 (99 mg, 0.315 mmol), sodium tert-butoxide (51 mg, 0.525 mmol), tBuXPhos Pd G3 (21 mg, 0.026 mmol) and tBuXPhos (11 mg, 0.026 mmol). Separately, nitrogen was bubbled through a solution of Intermediate 15 (99 mg, 0.262 mmol) in a mixture of anhydrous 1,4-dioxane (2.0 mL) and tert-butanol (1.0 mL) for 10 minutes. This solution was transferred to the pressure tube, the tube was closed under an atmosphere of nitrogen and warmed to 100° C. for 60 minutes. After cooling to room temperature, the reaction mixture was concentrated in-vacuo and the residue dissolved in dichloromethane and adsorbed onto silica in-vacuo. The dry-loaded material was purified by column chromatography eluting with a 0-4% by volume solution of methanolic ammonia (7 M ammonia in methanol) in dichloromethane to furnish the title compound (175 mg, 90% yield). $\delta_H$ (500 MHz, d-chloroform) 9.05-9.00 (m, 2H), 8.41 (d, J=1.8 Hz, 1H), 8.29 (s, 1H), 8.13 (d, J=2.7 Hz, 1H), 8.08 (dd, J=8.2, 2.4 Hz, 1H), 7.88 (s, 1H), 7.35 (t, J=2.3 Hz, 1H), 7.31 (d, J=8.2 Hz, 1H), 5.36 (t, J=5.9 Hz, 1H), 4.54 (d, J=6.7 Hz, 1H), 4.41-4.36 (m, 1H), 3.87 (dd, J=18.4, 6.6 Hz, 1H), 3.67-3.58 (m, 1H), 3.50 (dd, J=16.3, 6.4 Hz, 1H), 3.11-3.03 (m, 2H), 3.01-2.91 (m, 1H), 2.63 (s, 3H), 2.18 (ddd, J=12.9, 8.2, 4.8 Hz, 1H), 1.26 (d, J=21.9 Hz, 3H), 1.22 (d, J=21.9 Hz, 3H), 1.15-1.12 (m, 2H), 1.07-1.03 (m, 2H); $\delta_F$ (235 MHz, d-chloroform, H-decoupled)-144.0; LCMS [M+H]$^+$ 610, RT 2.97 min (Method 2).

Example 44

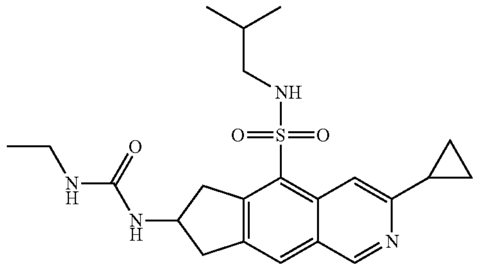 [SMILES: CCNC(=O)NC1Cc2cc3cnc(C4CC4)cc3c(S(=O)(=O)NCC(C)C)c2C1]

1-[3-cyclopropyl-5-(2-methylpropylsulfamoyl)-7,8-dihydro-6H-cyclopenta[g]isoquinolin-7-yl]-3-ethyl-urea To a solution of Intermediate 122 (42 mg at 53% purity LCMS-$UV_{215}$, 0.062 mmol) in anhydrous dichloromethane (2 mL) at 0° C. under an atmosphere of nitrogen, a solution of ethyl isocyanate (8.3 mg, 0.117 mmol) in DCM (0.1 mL) was added. The reaction mixture was warmed to room temperature. After 50 minutes the reaction mixture was concentrated in-vacuo and the residue purified by high pH preparative liquid chromatography to furnish the title compound (13.9 mg, 52% yield). $\delta_H$ (500 MHz, d-chloroform) 9.03 (s, 1H), 8.33 (s, 1H), 7.86 (s, 1H), 4.85 (t, J=6.4 Hz, 1H), 4.61 (h, J=6.8 Hz, 1H), 4.54-4.53 (m, 1H), 4.29 (t, J=5.3 Hz, 1H), 3.82 (dd, J=18.4, 7.1 Hz, 1H), 3.50-3.39 (m, 2H), 3.23-3.13 (m, 2H), 3.00 (dd, J=16.4, 5.4 Hz, 1H), 2.72 (dt, J=13.3, 6.7 Hz, 1H), 2.64 (dt, J=12.7, 6.5 Hz, 1H), 2.21 (ddd, J=13.0, 8.2, 4.8 Hz, 1H), 1.66 (dp, J=13.4, 6.7 Hz, 1H), 1.15-1.12 (m, 2H), 1.11 (t, J=7.2 Hz, 3H), 1.07-1.04 (m, 2H), 0.80 (d, J=6.6 Hz, 3H), 0.79 (d, J=6.6 Hz, 3H); LCMS $[M+H]^+$ 431, RT 2.42 min (Method 2).

Examples 45 & 46

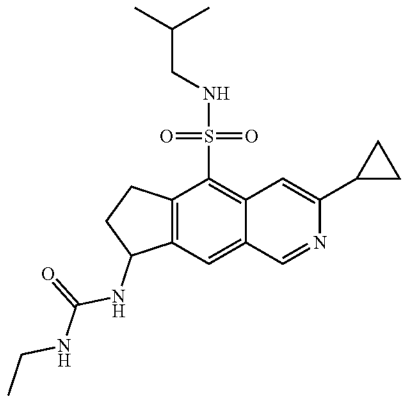

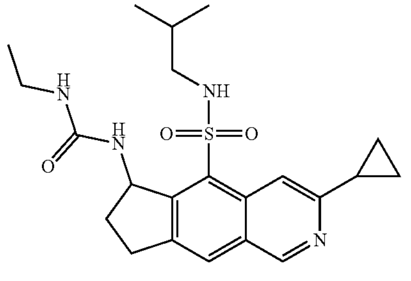

1-[3-cyclopropyl-5-(2-methylpropylsulfamoyl)-7,8-dihydro-6H-cyclopenta[g]isoquinolin-8-yl]-3-ethyl-urea (45)

1-[3-cyclopropyl-5-(2-methylpropylsulfamoyl)-7,8-dihydro-6H-cyclopenta[g]isoquinolin-6-yl]-3-ethyl-urea (46)

To a solution of a 1:1 mixture of Intermediates 89 and 90 (200 mg at 59% purity LCMS-$UV_{215}$, estimated 0.330 mmol) in dichloromethane (6 mL) at room temperature were introduced diisopropylethylamine (36 mg, 0.278 mmol) and ethyl isocyanate (40 mg, 0.556 mmol). After 24 hours the reaction mixture was concentrated in-vacuo. Purification by preparative HPLC (acidic conditions) furnished the title compounds:

Example 45 (9.7 mg, 7% yield) $\delta_H$ (500 MHz, d6-dmso) 9.21 (s, 1H), 8.43 (s, 1H), 8.01 (s, 1H), 7.98 (t, J=5.4 Hz, 1H), 6.41 (d, J=8.4 Hz, 1H), 5.86 (t, J=5.6 Hz, 1H), 5.23 (q, J=7.9 Hz, 1H), 3.61 (ddd, J=18.1, 8.4, 2.7 Hz, 1H), 3.22-3.13 (m, 1H), 3.13-3.05 (m, 2H), 2.58-2.53 (m, 2H), 2.42 (dtd, J=15.4, 8.0, 2.8 Hz, 1H), 2.30-2.21 (m, 1H), 1.79-1.69 (m, 1H), 1.54 (hept, J=6.8 Hz, 1H), 1.07-1.00 (m, 7H), 0.706 (d, J=6.7 Hz, 3H), 0.704 (d, J=6.7 Hz, 3H); LCMS $[M+H]^+$ 431, RT 2.52 min (Method 2).

Example 46 (10.5 mg, 7% yield) $\delta_H$ (500 MHz, d6-dmso) 9.17 (s, 1H), 8.45 (s, 1H), 8.14 (s, 1H), 7.98 (s, 1H), 6.13 (d, J=7.0 Hz, 1H), 5.74 (dt, J=7.1, 3.6 Hz, 1H), 5.59 (t, J=5.5 Hz, 1H), 3.20 (dt, J=17.9, 9.4 Hz, 1H), 3.05-2.91 (m, 3H), 2.61 (d, J=7.0 Hz, 1H), 2.54 (d, J=6.9 Hz, 1H), 2.27 (p, J=6.8 Hz, 1H), 2.09 (dt, J=11.3, 6.2 Hz, 2H), 1.57 (hept., J=6.8 Hz, 1H), 1.06-1.00 (m, 4H), 0.96 (t, J=7.2 Hz, 3H), 0.74 (d, J=6.2 Hz, 3H), 0.72 (d, J=6.3 Hz, 3H); LCMS $[M+H]^+$ 431, RT 2.64 min (Method 2).

Examples 47 & 48

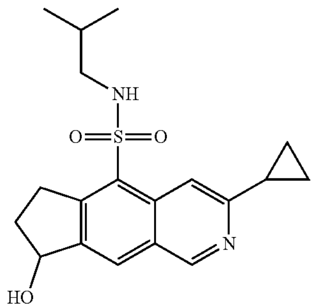

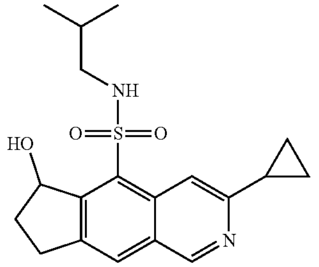

3-cyclopropyl-8-hydroxy-N-(2-methylpropyl)-7,8-dihydro-6H-cyclopenta[g]isoquinoline-5-sulfonamide (47)

3-cyclopropyl-6-hydroxy-N-(2-methylpropyl)-7,8-dihydro-6H-cyclopenta[g]isoquinoline-5-sulfonamide (48)

A 1:1 mixture of Intermediates 80 and 81 (80 mg at 85% purity $^1H$ NMR, 0.160 mmol) was dissolved in a mixture of 1,2-dimethoxyethane (4.0 mL) and water (1.2 mL). Silver (I) carbonate (156 mg, 0.566 mmol) was added to the solution and the reaction mixture warmed to 40° C. for 24 hours. After cooling to room temperature, the reaction mixture was diluted with ethyl acetate (20 mL), the aqueous phase separated, and the organic phase dried over sodium sulfate.

The dried organic extract was filtered through a shallow bed of kieselguhr (vacuum filtration) and the filtrate concentrated in-vacuo. Purification of the residue by preparative HPLC (acidic conditions) furnished the title compounds:

Example 47 (6.1 mg, 10% yield). $\delta_H$ (500 MHz, d-chloroform) 9.12 (s, 1H), 8.36 (s, 1H), 8.10 (s, 1H), 5.36 (q, J=5.9 Hz, 1H), 4.68 (t, J=6.3 Hz, 1H), 3.75 (ddd, J=18.6, 8.6, 4.5 Hz, 1H), 3.38 (dt, J=18.5, 8.1 Hz, 1H), 2.68 (td, J=6.6, 1.6 Hz, 2H), 2.63-2.52 (m, 1H), 2.22 (ddd, J=13.0, 8.2, 4.8 Hz, 1H), 2.09-1.99 (m, 2H), 1.66 (dp, J=13.5, 6.7 Hz, 1H), 1.17-1.14 (m, 2H), 1.09-1.04 (m, 2H), 0.80 (d, J=6.7 Hz, 6H). LCMS $[M+H]^+$ 361, RT 2.41 min (Method 2).

Example 48 (8.2 mg, 14% yield). $\delta_H$ (500 MHz, d-chloroform) 9.09 (s, 1H), 8.39 (s, 1H), 7.96 (s, 1H), 5.91-5.81 (m, 1H), 4.98 (t, J=5.8 Hz, 1H), 3.74-3.66 (m, 1H), 3.41-3.29 (m, 1H), 3.02 (dddd, J=16.2, 8.6, 3.8, 1.0 Hz, 1H), 2.78 (dt, J=13.2, 6.7 Hz, 1H), 2.69 (dt, J=12.4, 6.1 Hz, 1H), 2.44-2.35 (m, 1H), 2.32-2.25 (m, 1H), 2.22 (tt, J=8.2, 4.8 Hz, 1H), 1.72-1.60 (m, 1H), 1.18-1.10 (m, 2H), 1.09-1.02 (m, 2H), 0.81 (d, J=6.6 Hz, 3H), 0.80 (d, J=6.6 Hz, 3H); LCMS $[M+H]^+$ 361, RT 2.90 min (Method 2).

Example 49

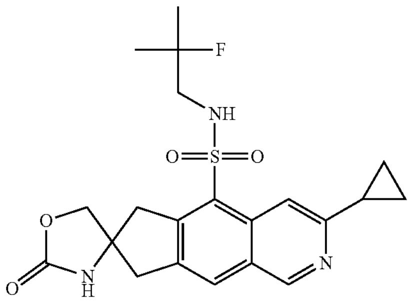 [SMILES: CC(C)(F)CNS(=O)(=O)c1c2c(cc3cnc(C4CC4)cc13)CC1(COC(=O)N1)C2]

3'-cyclopropyl-N-(2-fluoro-2-methylpropyl)-2-oxospiro[1,3-oxazolidine-4,7'-6,8-dihydrocyclopenta[g]isoquinoline]-5'-sulfonamide To a solution of Intermediate 85 (53 mg at 85% purity LCMS-$UV_{215}$, 0.084 mmol) in anhydrous tetrahydrofuran (1.8 mL), triethylamine (25 mg, 0.247 mmol) and diphenylphosphoryl azide (30 mg, 0.109 mmol) were added. The reaction was warmed to 75° C. in a pressure vessel for 90 minutes under an atmosphere of nitrogen. After cooling to 0° C., 1 M aq. hydrochloric acid (3 mL) was added dropwise at 0° C. The reaction was then allowed to warm to room temperature. Additional tetrahydrofuran (1.5 mL) was introduced to the acidic solution. After 45 minutes at room temperature, the solution was concentrated in-vacuo to remove tetrahydrofuran and the pH of the aqueous residue adjusted to pH 7.5 by addition of saturated aqueous sodium bicarbonate. Following extraction of the basic aqueous solution with ethyl acetate (10 mL), the pH of the aqueous solution was adjusted to pH 12 with 1 M aqueous sodium carbonate and extracted again with ethyl acetate (10 mL). The pooled ethyl acetate extracts were dried over magnesium sulfate, filtered and the filtrate concentrated in-vacuo. Purification of the residue by preparative HPLC (basic conditions) furnished the title compound (20.80 mg, 57% yield) as a colourless solid. $\delta_H$ (500 MHz, d6-dmso) 9.13 (s, 1H), 8.47 (s, 1H), 8.38 (s, 1H), 8.21 (s, 1H), 8.06 (s, 1H), 4.30 (s, 2H), 3.75 (d, J=18.3 Hz, 1H), 3.63 (d, J=18.3 Hz, 1H), 3.32 (d, J=16.8 Hz, 1H), 3.23 (d, J=16.8 Hz, 1H), 2.99-2.85 (m, 2H), 2.26 (p, J=6.4 Hz, 1H), 1.17 (d, J=21.4 Hz, 3H), 1.16 (d, J=21.5 Hz, 3H), 1.01 (app. d, J=6.8 Hz, 4H); $\delta_F$ (235 MHz, d6-dmso, H-decoupled)-139.4; LCMS $[M+H]^+$ 434, RT 2.25 min (Method 2).

Example 50

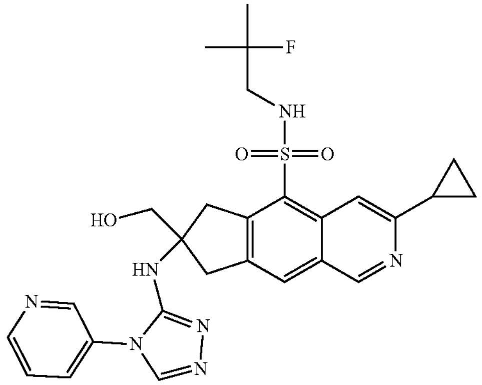 [SMILES: CC(C)(F)CNS(=O)(=O)c1c2c(cc3cnc(C4CC4)cc13)CC(CO)(Nc1nncn1-c1cccnc1)C2]

3-cyclopropyl-N-(2-fluoro-2-methylpropyl)-7-(hydroxymethyl)-7-[(4-pyridin-3-yl-1,2,4-triazol-3-yl)amino]-6,8-dihydrocyclopenta[g]isoquinoline-5-sulfonamide To a solution of Intermediate 88 (50 mg at 86% purity LCMS-$UV_{215}$, 0.066 mmol) in dichloromethane (5 mL) at room temperature was introduced trifluoroacetic acid (2.5 mL) dropwise. After 4 hours, the reaction mixture was concentrated in-vacuo, dissolved in dichloromethane (5 mL) and concentrated in-vacuo. The residue was purified by preparative HPLC (basic conditions) to furnish the title compound (19.5 mg, 54% yield) as a colourless solid. $\delta_H$ (500 MHz, d6-dmso) 9.09 (s, 1H), 8.60 (dd, J=4.8, 1.4 Hz, 1H), 8.57 (d, J=2.4 Hz, 1H), 8.44 (s, 1H), 8.30 (s, 1H), 8.25 (s, 1H), 8.01 (s, 1H), 7.81 (ddd, J=8.2, 2.5, 1.5 Hz, 1H), 7.53-7.48 (m, 1H), 5.91 (s, 1H), 5.14 (s, 1H), 3.96 (d, J=18.8 Hz, 1H), 3.75 (q, J=10.8, 10.3 Hz, 2H), 3.62 (d, J=18.8 Hz, 1H), 3.53 (d, J=17.0 Hz, 1H), 3.25 (d, J=17.5 Hz, 1H), 2.86 (d, J=19.7 Hz, 2H), 2.26 (p, J=7.7, 6.8 Hz, 1H), 1.11 (d, J=21.4 Hz, 3H), 1.08-0.99 (m, 7H); LCMS $[M+H]^+$ 552, RT 1.85 min (Method 2).

Example 51

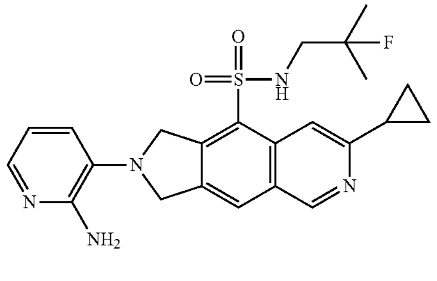 [SMILES: CC(C)(F)CNS(=O)(=O)c1c2c(cc3cnc(C4CC4)cc13)CN(c1cccnc1N)C2]

2-(2-aminopyridin-3-yl)-7-cyclopropyl-N-(2-fluoro-2-methylpropyl)-1,3-dihydropyrrolo[3,4-g]isoquinoline-9-sulfonamide Intermediate 94 (20 mg, 0.04 mmol) was suspended in a 4:1 mixture of ethanol and water (2 mL) in a sealable tube. Ammonium chloride (11 mg, 0.21 mmol) was added followed by iron powder (9.2 mg, 0.16 mmol). The tube was sealed and heated to 90° C. with stirring for 1.5 hours. After cooling to room temperature, the mixture was filtered through Celite, washing with ethanol. The solution was concentrated under reduced pressure, dissolved in EtOAc (20 mL) and then washed with sat. aq. $NaHCO_3$ (20 mL) followed by brine (20 mL). The organic layer was dried over $MgSO_4$ and concentrated under reduced pressure. Purification by column chromatography with a gradient of ethyl acetate in heptane followed by reverse phase HPLC (basic conditions) gave the title compound (3.1 mg, 16% yield). $\delta_H$ (500 MHz, $d_6$-DMSO) 9.23 (s, 1H), 8.48-8.41 (m, 2H), 8.22 (s, 1H), 7.70 (dd, J=4.9, 1.4 Hz, 1H), 7.35 (dd, J=7.7, 1.3 Hz, 1H), 6.59 (dd, J=7.6, 4.9 Hz, 1H), 5.69 (s, 2H), 4.84 (s, 2H), 4.54 (s, 2H), 2.99 (d, J=20.6 Hz, 2H), 2.35-2.29 (m, 1H), 1.18 (d, J=21.4 Hz, 6H), 1.09-1.02 (m, 4H). LCMS $[M+H]^+$ 456.3, RT 1.86 min (Method 2).

Example 52

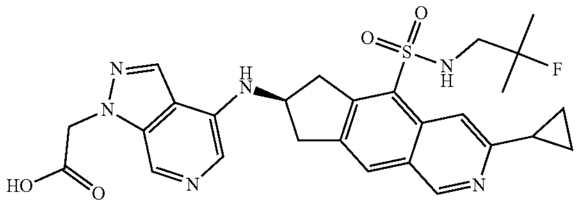 [SMILES: CC(C)(F)CNS(=O)(=O)c1c2c(cc3cnc(C4CC4)cc13)C[C@@H](Nc1cncc3c1cnn3CC(=O)O)C2]

2-[4-[[(7R)-3-cyclopropyl-5-[(2-fluoro-2-methylpropyl) sulfamoyl]-7,8-dihydro-6H-cyclopenta[g]isoquinolin-7-yl]amino]pyrazolo[3,4-c]pyridin-1-yl] acetic acid A mixture of Intermediate 15 (50 mg, 0.13 mmol), Intermediate 57 (50 mg, 0.16 mmol), Sodium tert-butoxide (38 mg, 0.40 mmol) and $^t$BuXPhos Pd G3 (11 mg, 13.3 μmol) was dissolved in a mixture of THF (3 mL) and $^t$BuOH (1.5 mL). The reaction mixture was stirred at room temperature for 6 hours, then filtered through Celite and concentrated under reduced pressure. Purification by column chromatography with a gradient of methanol in dichloromethane followed by reverse phase HPLC (basic conditions) gave the title compound (6.3 mg, 8% yield). $\delta_H$ (500 MHz, $d_6$-DMSO) 13.37 (br s, 1H), 9.17 (s, 1H), 8.85 (s, 1H), 8.65 (s, 1H), 8.45 (s, 1H), 8.39 (t, J=6.5 Hz, 1H), 8.16 (s, 1H), 7.89 (s, 1H), 7.75 (s, 1H), 5.46 (s, 2H), 4.62 (d, J=6.3 Hz, 1H), 3.98 (dd, J=18.5, 7.0 Hz, 1H), 3.70-3.59 (m, 2H), 3.18 (dd, J=16.7, 4.6 Hz, 1H), 3.00-2.85 (m, 2H), 2.32-2.25 (m, 1H), 1.10 (d, J=21.4 Hz, 3H), 1.07 (d, J=21.4 Hz, 3H), 1.05-1.01 (m, 4H). LCMS $[M+H]^+$ 553.2, RT 1.80 min (Method 2).

Example 53

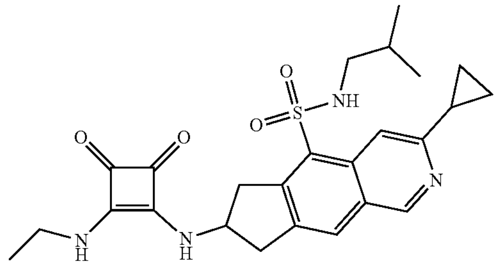 [SMILES: CCNc1c(NC2Cc3cc4cnc(C5CC5)cc4c(S(=O)(=O)NCC(C)C)c3C2)c(=O)c1=O]

3-cyclopropyl-7-[[2-(ethylamino)-3,4-dioxocyclobuten-1-yl]amino]-N-(2-methylpropyl)-7,8-dihydro-6H-cyclopenta[g]isoquinoline-5-sulfonamide To a solution of Intermediate 122 (30 mg, 0.08 mmol) in ethanol (1 mL), DIPEA (20 μL, 0.11 mmol) and 3,4-diethoxycyclobut-3-ene-1,2-dione (17 μL, 0.11 mmol) were added. The solution was stirred at room temperature for 1 hour. 2 M ethylamine in THF (60 μL) was then added and the solution was left to stand at room temperature for 16 hours. After this time, 2 M ethylamine in THF (100 μL) was added. After standing for 2 hours at room temperature, a white precipitate formed. The reaction mixture was concentrated under reduced pressure and the residue purified by reverse phase HPLC (basic conditions) to give the title compound (2.4 mg, 7% yield). $\delta_H$ (500 MHz, $d_6$-DMSO) 9.15 (s, 1H), 8.42 (s, 1H), 8.14 (s, 1H), 7.97 (m, 2H), 7.61 (br s, 1H), 4.85-4.71 (m, 1H), 3.77 (dd, J=17.8, 6.3 Hz, 1H), 3.68-3.52 (m, 4H, obs. by water), 3.13 (dd, J=16.6, 4.6 Hz, 1H), 2.55-2.51 (m, 2H, obs. by DMSO), 2.25 (dt, J=12.9, 6.4 Hz, 1H), 1.61-1.49 (m, 1H), 1.12 (t, J=7.2 Hz, 3H), 1.04-0.99 (m, 4H), 0.69 (d, J=6.6 Hz, 6H). LCMS $[M+H]^+$ 483.2, RT 2.44 min (Method 2).

Example 54

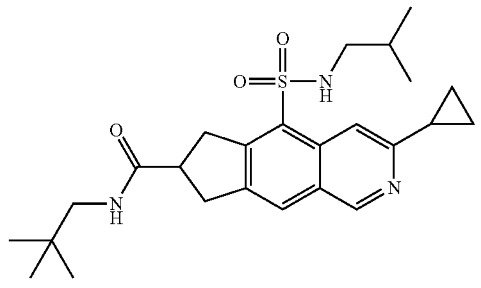 [SMILES: CC(C)CNS(=O)(=O)c1c2c(cc3cnc(C4CC4)cc13)CC(C(=O)NCC(C)(C)C)C2]

3-cyclopropyl-N-(2,2-dimethylpropyl)-5-(2-methylpropylsulfamoyl)-7,8-dihydro-6H-cyclopenta[g] isoquinoline-7-carboxamide Intermediate 95 (170 mg, 0.38 mmol) was dissolved in a mixture of DCM (10 mL) and water (46 μL, 2.55 mmol). Acetic acid (107 μL, 1.87 mmol) and sulfuryl dichloride (152 μL, 1.88 mmol) were then added and the reaction mixture was stirred at room temperature for 1 hour. Water (10 mL) and DCM (20 mL) were added and the mixture was passed through a hydrophobic frit. The solution was then treated with 2-methylpropan-1-amine (136 μL, 1.37 mmol) and left to stand at room temperature for 15 minutes. The solution was concentrated under reduced pressure and purified by column chromatography with a gradient of ethyl acetate in heptane to give the title compound (45 mg, 68% yield). $\delta_H$ (500 MHz, d-chloroform) 9.03 (s, 1H), 8.33 (s, 1H), 7.84 (s, 1H), 5.67 (t, J=6.0 Hz, 1H), 4.78 (t, J=6.4 Hz, 1H), 3.98 (dd, J=18.3, 8.4 Hz, 1H), 3.67 (dd, J=18.3, 8.2 Hz, 1H), 3.45 (ddd, J=16.2, 8.4, 1.4 Hz, 1H), 3.29 (dd, J=16.7, 8.4 Hz, 1H), 3.17 (p, J=8.4 Hz, 1H), 3.13 (dd, J=16.1, 6.5 Hz, 1H), 3.10 (dd, J=16.1, 6.3 Hz, 1H), 2.74-2.67 (m, 1H), 2.64-2.58 (m, 1H), 2.23-2.16 (m, 1H), 1.69-1.60 (m, 1H, overlaps with water), 1.17-1.09 (m, 2H), 1.07-1.01 (m, 2H), 0.92 (s, 9H), 0.81-0.77 (m, 6H). LCMS $[M+H]^+$ 458.2, RT 3.28 min (Method 2).

Example 55

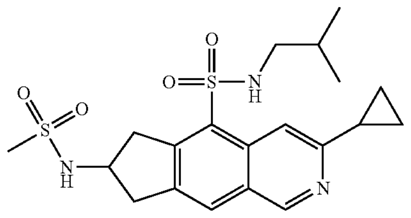 [SMILES: CC(C)CNS(=O)(=O)c1c2c(cc3cnc(C4CC4)cc13)CC(NS(C)(=O)=O)C2]

3-cyclopropyl-7-(methanesulfonamido)-N-(2-methylpropyl)-7,8-dihydro-6H-cyclopenta[g]isoquinoline-5-sulfonamide Intermediate 122 (30 mg, 0.08 mmol) was dissolved in DCM (1 mL) and DIPEA (33 μL, 0.19 mmol) followed by methanesulfonyl chloride (7 μL, 0.09 mmol) were added. The solution was stirred at room temperature for 30 minutes before being concentrated under reduced pressure. The residue was purified by column chromatography with a gradient of ethyl acetate in heptane to give the title compound (13 mg, 38% yield). $\delta_H$ (500 MHz, $d_6$-DMSO) 9.13 (s, 1H), 8.40 (s, 1H), 8.08 (s, 1H), 7.99 (s, 1H), 7.42 (s, 1H), 4.17 (p, J=6.9 Hz, 1H), 3.80 (dd, J=18.3, 7.2 Hz, 1H), 3.46-3.36 (m, 2H), 3.06-3.00 (m, 1H), 3.00 (s, 3H), 2.60-2.53 (m, 2H), 2.28-2.22 (m, 1H), 1.60-1.49 (m, 1H), 1.04-0.99 (m, 4H), 0.71 (d, J=6.7 Hz, 3H), 0.71 (d, J=6.7 Hz, 3H). LCMS $[M+H]^+$ 438.2, RT 2.57 min (Method 2).

Example 56

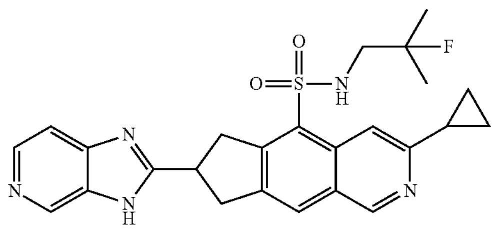 [SMILES: CC(C)(F)CNS(=O)(=O)c1c2c(cc3cnc(C4CC4)cc13)CC(c1nc3ccncc3[nH]1)C2]

3-cyclopropyl-N-(2-fluoro-2-methylpropyl)-7-(3H-imidazo[4,5-c]pyridin-2-yl)-7,8-dihydro-6H-cyclopenta[g]isoquinoline-5-sulfonamide Intermediate 11 (100 mg, 0.22 mmol) was dissolved in DMF (1 mL) and DIPEA (0.09 mL, 0.52 mmol) followed by HATU (95 mg, 0.25 mmol) were added. The reaction mixture was stirred at room temperature for 5 minutes before adding pyridine-3,4-diamine (25 mg, 0.23 mmol). After stirring at room temperature for 1 hour the solution was diluted with EtOAc (20 mL) and washed with water (2×10 mL). The organic layer was dried over $MgSO_4$, filtered and concentrated under reduced pressure. The residue was dissolved in acetic acid (1 mL) and heated to 60° C. for 1 hour. Once at room temperature the solution was diluted with EtOAc (20 mL) and sat. aq. $NaHCO_3$ was added, forming an emulsion which was filtered. The white solid collected was washed with EtOAc and water and dried under vacuum to give the title compound (30 mg, 27% yield). $\delta_H$ (500 MHz, $d_6$-DMSO) 9.13 (s, 1H), 8.76 (s, 1H), 8.46 (s, 1H), 8.20 (d, J=5.5 Hz, 1H), 8.12 (s, 1H), 7.45 (d, J=5.4 Hz, 1H), 4.08-3.96 (m, 2H), 3.95-3.85 (m, 1H), 3.61-3.49 (m, 2H, obs. by water), 3.01 (dd, J=19.7, 14.3 Hz, 1H), 2.91 (dd, J=19.6, 14.3 Hz, 1H), 2.31-2.23 (m, 1H), 1.18-1.06 (m, 6H), 1.02 (dd, J=6.2, 4.1 Hz, 4H). Two exchangeable protons not observed. LCMS $[M+H]^+$ 480.3, RT 2.78 min (Method 2).

Example 57

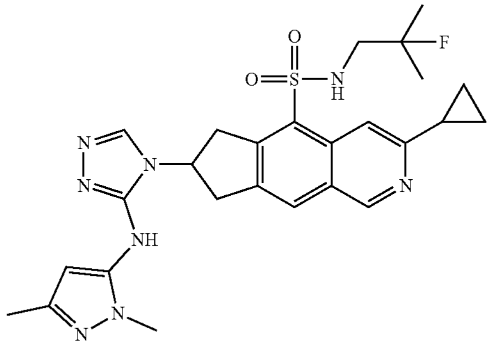 [SMILES: Cc1cc(Nc2nncn2C2Cc3cc4cnc(C5CC5)cc4c(S(=O)(=O)NCC(C)(C)F)c3C2)n(C)n1]

3-cyclopropyl-7-[3-[(2,5-dimethylpyrazol-3-yl)amino]-1,2,4-triazol-4-yl]-N-(2-fluoro-2-methylpropyl)-7,8-dihydro-6H-cyclopenta[g]isoquinoline-5-sulfonamide The title compound was obtained using General Procedure 3 with Intermediate 96 (215 mg, 0.34 mmol, 85% pure). Purification by column chromatography followed by an SCX cartridge and reverse phase HPLC (acidic conditions) gave the title compound (2 mg, 1 yield). $\delta_H$ (500 MHz, DMSO-d6) 11.73 (s, 1H, Isomer A), 9.18 (s, 1H), 8.56 (s, 1H, Isomer B), 8.46 (s, 1H), 8.45-8.34 (m, 1H), 8.23-8.12 (m, 2H, isoquinoline ArH+Isomer B), 8.02 (s, 1H, Isomer A), 5.91 (s, 1H, Isomer B), 5.71 (s, 1H, Isomer A), 5.11-4.94 (m, 1H), 4.12-3.97 (m, 1H), 3.87-3.37 (m, 5H), 2.93 (d, J=20.1 Hz, 2H), 2.34-2.24 (m, 1H), 2.10 (s, 3H, Isomer B), 2.04 (s, 3H, Isomer A), 1.19-1.06 (m, 6H), 1.06-0.97 (m, 4H). 9:1 ratio of suspected rotamers A and B. LCMS $[M+2H]^{2+}$ 270.2 (major), $[M+H]^+$ 539.2 (minor), RT 1.99 min (Method 2).

Example 58

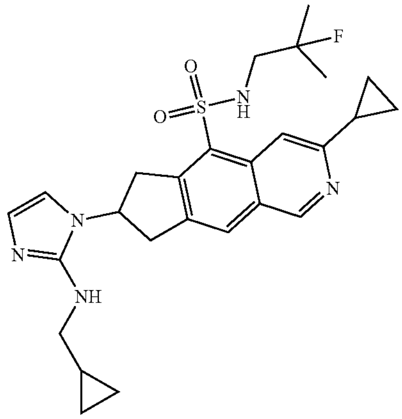 [SMILES: CC(C)(F)CNS(=O)(=O)c1c2c(cc3cnc(C4CC4)cc13)CC(n1ccnc1NCC1CC1)C2]

3-cyclopropyl-7-[2-(cyclopropylmethylamino) imidazol-1-yl]-N-(2-fluoro-2-methylpropyl)-7,8-dihydro-6H-cyclopenta[g]isoquinoline-5-sulfonamide Intermediate 97 (247 mg, 0.39 mmol) was stirred in DMF (5 mL) and 2,2-diethoxyethanamine (170 μL, 1.17 mmol) was added followed by mercury dichloride (315 mg, 1.16 mmol). The reaction mixture was stirred at room temperature for 5 minutes before triethylamine (160 μL, 1.15 mmol) was added and the mixture was heated at 90° C. with stirring for 30 minutes. p-Toluenesulfonic acid monohydrate (440 mg, 2.31 mmol) was added and stirring was continued at 90° C. for 2.5 hours before cooling to room temperature. The reaction mixture was diluted with DCM and Celite was added. The mixture was filtered through a plug of Celite washing through with DCM. The filtrate was concentrated under reduced pressure and the residue dissolved in ethyl acetate (50 mL), washed with water (2×20 mL) and brine, dried over $MgSO_4$ and concentrated under reduced pressure. Purification by column chromatography with a gradient of methanol in dichloromethane followed by reverse phase HPLC (acidic conditions) gave the title compound (2.8 mg, 1% yield). $\delta_H$ (500 MHz, d-chloroform) 9.11 (s, 1H), 8.33 (s, 1H), 7.99 (s, 1H), 6.57 (d, J=1.6 Hz, 1H), 6.23 (d, J=1.7 Hz, 1H), 5.11-5.01 (m, 1H), 4.92-4.83 (m, 1H), 4.00 (dd, J=18.7, 7.3 Hz, 1H), 3.79 (dd, J=18.7, 4.0 Hz, 1H), 3.67-3.59 (m, 1H), 3.59-3.52 (m, 1H), 3.36 (dd, J=16.8, 4.1 Hz, 1H), 3.23-3.15 (m, 2H), 3.05-2.92 (m, 1H), 2.92-2.80 (m, 1H), 2.28-2.16 (m, 1H), 1.31 (d, J=21.5 Hz, 3H), 1.21 (d, J=21.4 Hz, 3H), 1.19-1.13 (m, 3H), 1.13-1.05 (m, 2H), 0.57-0.50 (m, 2H), 0.28-0.19 (m, 2H). LCMS $[M+H]^+$ 498.2, RT 2.09 min (Method 2).

Example 59

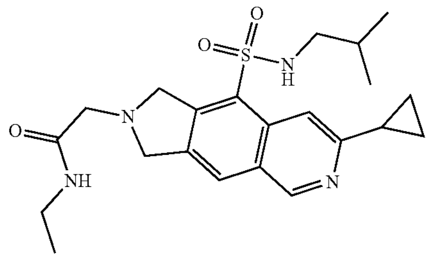 [SMILES: CCNC(=O)CN1Cc2cc3cnc(C4CC4)cc3c(S(=O)(=O)NCC(C)C)c2C1]

2-[7-cyclopropyl-9-(2-methylpropylsulfamoyl)-1,3-dihydropyrrolo[3,4-g]isoquinolin-2-yl]-N-ethylacetamide To a solution of example 60 (20 mg, 0.06 mmol) in MeCN (2 mL), $K_2CO_3$ (20 mg, 0.14 mmol) and 2-bromo-N-ethylacetamide (11.5 mg, 0.07 mmol) were added. The solution was stirred at room temperature for 16 hours. The solvent was removed under reduced pressure and the residue diluted with DCM (20 mL) and water. The organic layer was dried over $MgSO_4$, concentrated under reduced pressure and purified by column chromatography eluting with 50-100% EtOAc/heptane to give title compound (8 mg, 32% yield). $\delta_H$ (500 MHz, Methanol-d4) 9.09 (s, 1H), 8.44 (s, 1H), 8.07 (s, 1H), 4.55 (s, 2H), 4.18 (s, 2H), 3.47 (s, 2H), 3.30-3.25 (m, 2H), 2.65 (d, J=6.9 Hz, 2H), 2.32-2.27 (m, 1H), 1.63-1.56 (m, 1H), 1.16 (t, J=7.2 Hz, 3H), 1.11-1.06 (m, 4H), 0.76 (d, J=6.7 Hz, 6H). LCMS $[M+H]^+$ 431, RT 2.01 min (Method 2).

Example 60

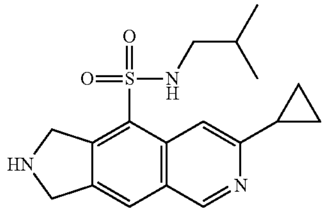 [SMILES: CC(C)CNS(=O)(=O)c1c2c(cc3cnc(C4CC4)cc13)CNC2]

7-cyclopropyl-N-(2-methylpropyl)-2,3-dihydro-1H-pyrrolo[3,4-g]isoquinoline-9-sulfonamide Intermediate 29 (13 mg, 0.29 mmol) was dissolved in MeOH (0.5 mL) and 1 M aq. $K_2CO_3$ (0.14 mL) was added. The solution was stirred at room temperature for 16 h. The solvent was removed under reduced pressure and the residue diluted with DCM (10 mL) and water. The organic layer was dried over $MgSO_4$, concentrated under reduced pressure and purified by column chromatography eluting with 0-20% MeOH in DCM to give title compound (2.5 mg, 25% yield). $\delta_H$ (500 MHz, Methanol-d4) 9.10 (s, 1H), 8.45 (s, 1H), 8.11 (s, 1H), 4.67 (s, 2H), 4.32 (s, 2H), 2.64 (d, J=6.9 Hz, 2H), 2.33-2.26 (m, 1H), 1.64-1.54 (m, 1H), 1.12-1.04 (m, 4H), 0.75 (d, J=6.7 Hz, 6H). LCMS $[M+H]^+$ 346, RT 1.74 min (Method 2).

Example 61

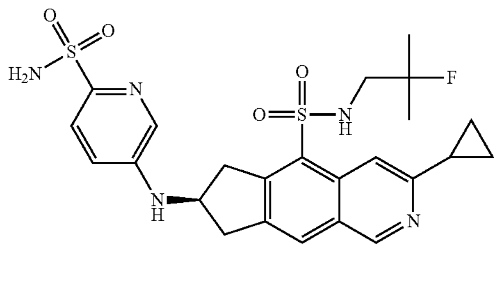 [SMILES: CC(C)(F)CNS(=O)(=O)c1c2c(cc3cnc(C4CC4)cc13)C[C@@H](Nc1ccc(S(N)(=O)=O)nc1)C2]

(7R)-3-cyclopropyl-N-(2-fluoro-2-methylpropyl)-7-[(6-sulfamoylpyridin-3-yl)amino]-7,8-dihydro-6H-cyclopenta[g]isoquinoline-5-sulfonamide Intermediate 98 (85 mg, 0.10 mmol) was dissolved in DCM (3 mL) and cooled to 0° C. TFA (0.41 mL, 5.3 mmol) was added and the reaction mixture warmed to room temperature and stirred for 16 hours. The solvent was removed, and the residue dissolved in a mixture of AcOH (6 mL) and water (3 mL) and heated at 70° C. for 2 hours. The solvent was removed, and the brown residue was purified by acidic reverse phase HPLC to afford the title compound (22 mg, 38% yield). $\delta_H$ (500 MHz, DMSO-d6) 9.14 (s, 1H), 8.44 (s, 1H), 8.34 (t, J=6.5 Hz, 1H), 8.12 (s, 1H), 8.03 (d, J=2.7 Hz, 1H), 7.66 (d, J=8.6 Hz, 1H), 7.10 (dd, J=8.7, 2.8 Hz, 1H), 7.05 (s, 2H), 6.94 (d, J=6.5 Hz, 1H), 4.41-4.33 (m, 1H), 3.86 (dd, J=18.3, 6.8 Hz, 1H), 3.56-3.45 (m, 2H), 3.00 (dd, J=16.6, 4.3 Hz, 1H), 2.90 (dd, J=20.6, 6.6 Hz, 2H), 2.31-2.23 (m, 1H), 1.13 (d, J=21.4 Hz, 3H), 1.11 (d, J=21.4 Hz, 3H), 1.05-1.00 (m, 4H). LCMS $[M+H]^+$ 534, RT 2.35 min (Method 2).

Example 62

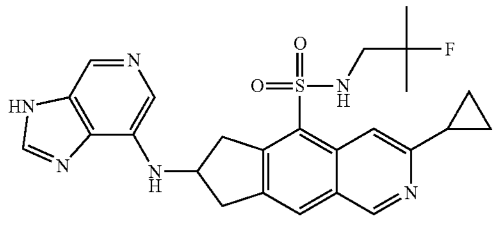 [SMILES: CC(C)(F)CNS(=O)(=O)c1c2c(cc3cnc(C4CC4)cc13)CC(Nc1cncc3[nH]cnc13)C2]

3-cyclopropyl-N-(2-fluoro-2-methylpropyl)-7-(3H-imidazo[4,5-c]pyridin-7-ylamino)-7,8-dihydro-6H-cyclopenta[g]isoquinoline-5-sulfonamide A mixture of intermediates 78 and 79 (74 mg, 0.11 mmol) was dissolved in DCM (3 mL) and cooled to 0° C. TFA (0.45 mL, 5.9 mmol) was added and the reaction mixture stirred at room temperature for 16 hours. The mixture was then diluted with DCM (15 mL) and the solution washed with sat. aq. $NaHCO_3$ (10 mL). The aqueous layer was extracted with DCM (3x10 mL), organics combined, dried over sodium sulphate and concentrated under vacuum. Purification by basic reverse phase HPLC afforded the title compound (10.5 mg, 18% yield). $\delta_H$ (500 MHz, DMSO-d6) 12.48 (b s., 1H), 9.15 (s, 1H), 8.45 (s, 1H), 8.40-8.21 (b s., 1H), 8.28 (s, 1H), 8.19 (s, 1H), 8.13 (s, 1H), 7.77 (s, 1H), 5.84 (s, 1H), 4.70 (s, 1H), 3.90 (dd, J=18.4, 6.8 Hz, 1H), 3.64-3.47 (m, 2H), 3.20-3.10 (m, 1H), 2.88 (d, J=20.2 Hz, 2H), 2.32-2.24 (m, 1H), 1.16-0.95 (m, 10H). LCMS $[M+H]^+$ 495, RT 1.60 min (Method 2).

Example 63

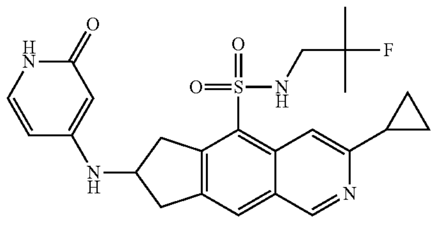 [SMILES: CC(C)(F)CNS(=O)(=O)c1c2c(cc3cnc(C4CC4)cc13)CC(Nc1cc[nH]c(=O)c1)C2]

3-cyclopropyl-N-(2-fluoro-2-methylpropyl)-7-[(2-oxo-1H-pyridin-4-yl)amino]-7,8-dihydro-6H-cyclopenta[g]isoquinoline-5-sulfonamide A mixture of Intermediate 75 (30 mg, 0.062 mmol) and Lithium iodide (166 mg, 1.23 mmol) was dissolved in N-methyl-2-pyrrolidone (1.5 mL) and stirred under microwave radiation at 200° C. for 30 min. Water (10 mL) was added and reaction mixture extracted with DCM (3x10 mL). Organics dried over sodium sulphate and concentrated under vacuum. The resulting residue was purified by acidic reverse phase HPLC to afford title compound (1.4 mg, 5% yield). $\delta_H$ (500 MHz, Methanol-d4) 9.06 (s, 1H), 8.48 (s, 1H), 8.08 (s, 1H), 7.11 (d, J=7.3 Hz, 1H), 5.89 (d, J=6.9 Hz, 1H), 5.57 (d, J=2.0 Hz, 1H), 4.39-4.30 (m, 1H), 3.86 (dd, J=18.4, 6.6 Hz, 1H), 3.67 (dd, J=18.4, 3.9 Hz, 1H), 3.53 (dd, J=17.0, 6.2 Hz, 1H), 3.11 (dd, J=16.4, 3.9 Hz, 1H), 3.00 (d, J=19.8 Hz, 2H), 2.34-2.25 (m, 1H), 1.18-1.05 (m, 10H). LCMS $[M+H]^+$ 471, RT 2.04 min (Method 2).

Example 64

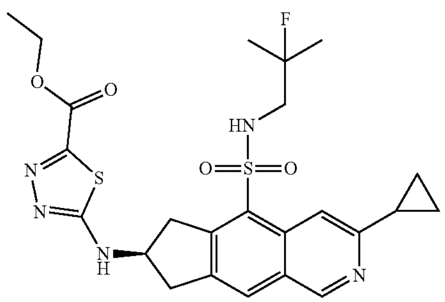 [SMILES: CCOC(=O)c1nnc(N[C@@H]2Cc3cc4cnc(C5CC5)cc4c(S(=O)(=O)NCC(C)(C)F)c3C2)s1]

ethyl 5-[[(7R)-3-cyclopropyl-5-[(2-fluoro-2-methylpropyl) sulfamoyl]-7,8-dihydro-6H-cyclopenta[g]isoquinolin-7-yl]amino]-1,3,4-thiadiazole-2-carboxylate To a solution of Intermediate 15 (50 mg, 0.13 mmol) in DMF (4 mL) were added ethyl 5-chloro-1,3,4-thiadiazole-2-carboxylate (30.6 mg, 0.16 mmol) and DIPEA (0.09 mL, 0.53 mmol). The solution was heated at 90° C. for 6 hours.

Water (10 mL) and EtOAc (15 mL) were added to the mixture. The organic layer was separated and washed with brine (5 ml) and then passed through a phase separator frit. The solvent was removed to give a brown oil. The oil was purified by flash column chromatography eluting with 0 to 100% of EtOAc in heptane gradient to afford the title compound as a brown oil (62 mg, 88% yield). $\delta_H$ (400 MHz, chloroform-d) 9.02 (s, 1H), 8.27 (s, 1H), 7.89 (s, 1H), 6.72 (s, 1H), 5.45 (t, J=6.2 Hz, 1H), 4.56-4.50 (m, 1H), 4.46 (q, J=7.1 Hz, 2H), 3.92 (dd, J=18.5, 6.7 Hz, 1H), 3.78 (dd, J=18.6, 3.8 Hz, 1H), 3.53 (dd, J=17.1, 5.9 Hz, 1H), 3.26 (dd, J=16.5, 3.9 Hz, 1H), 3.03 (dddd, J=43.4, 19.9, 13.6, 6.6 Hz, 2H), 2.14 (ddd, J=13.0, 8.2, 4.9 Hz, 1H), 1.43 (t, J=7.1 Hz, 3H), 1.26 (t, J=22.1 Hz, 6H), 1.18-1.01 (m, 4H). LCMS $[M+H]^+$ 534, RT 2.89 minutes (Method 2).

Example 65

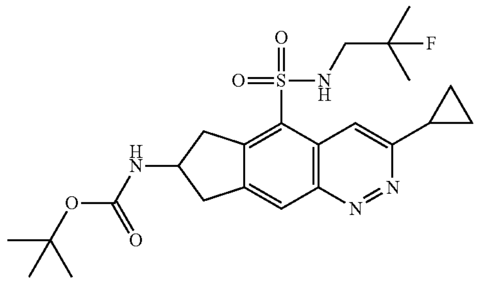 [SMILES: CC(C)(F)CNS(=O)(=O)c1c2c(cc3nnc(C4CC4)cc13)CC(NC(=O)OC(C)(C)C)C2]

tert-butyl N-[3-cyclopropyl-5-[(2-fluoro-2-methyl-propyl) sulfamoyl]-7,8-dihydro-6H-cyclopenta[g] cinnolin-7-yl]carbamate To a suspension of intermediate 69 (160 mg, 0.29 mmol) in tert-butyl alcohol (10 mL) were added DIPEA (130 μL, 0.75 mmol) and diphenylphosphoryl azide (70 μL, 0.32 mmol). The resultant mixture was heated at 85° C. in a sealed vessel for 4 h 40 min. The reaction mixture was diluted with DCM (30 mL) and sat. $NaHCO_3$ (30 mL) and the phases separated. The aqueous layer was extracted with DCM (2×20 mL) and the combined organics dried and conc. in vacuo. Purification by column chromatography eluting with 0-50% EtOAc in iso-hexane gave the title compound (43 mg, 26% Yield). $\delta_H$ (300 MHz, d6-DMSO) 8.60 (d, J=1.0 Hz, 1H), 8.37 (s, 1H), 7.33-7.01 (m, 1H), 4.29 (d, J=6.4 Hz, 1H), 3.75 (dd, J=18.7, 7.3 Hz, 1H), 3.45-3.35 (m, 2H), 3.17-2.85 (m, 3H), 2.46-2.40 (m, 1H), 1.40 (s, 9H), 1.32-1.05 (m, 10H). One NH was not observed. LCMS $[M+H]^+$ 479, RT 1.11 min (Method 6).

Example 66

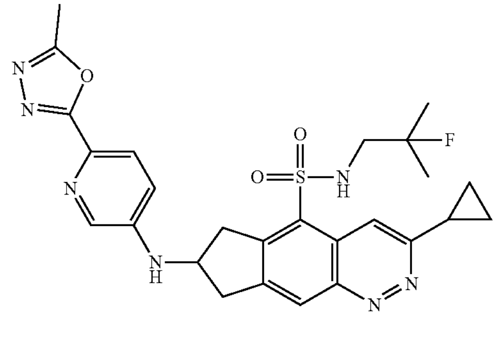 [SMILES: Cc1nnc(-c2ccc(NC3Cc4cc5nnc(C6CC6)cc5c(S(=O)(=O)NCC(C)(C)F)c4C3)cn2)o1]

3-cyclopropyl-N-(2-fluoro-2-methylpropyl)-7-[[6-(5-methyl-1,3,4-oxadiazol-2-yl)pyridin-3-yl]amino]-7,8-dihydro-6H-cyclopenta[g]cinnoline-5-sulfonamide The title compound was obtained following General Procedure 1 using intermediate 91 (72 mg, 0.16 mmol), 2-(5-bromo-2-pyridyl)-5-methyl-1,3,4-oxadiazole (78 mg, 0.32 mmol), dioxane (2 mL), tBuXPhos (20 mg, 0.02 mmol) and sodium tert-butoxide (47 mg, 0.49 mmol). Purification by column chromatography eluting with 0-30% MeOH in EtOAc gave the title compound (63 mg, 68% yield). $\delta_H$ (400 MHz, d-Chloroform) 8.54 (s, 1H), 8.47 (s, 1H), 8.11 (d, J=2.8 Hz, 1H), 8.03 (d, J=8.6 Hz, 1H), 7.04 (dd, J=8.7, 2.8 Hz, 1H), 5.41 (s, 1H), 4.49 (d, J=3.3 Hz, 1H), 3.90 (dd, J=18.7, 6.3 Hz, 1H), 3.76 (d, J=19.3 Hz, 1H), 3.59 (dd, J=16.8, 6.2 Hz, 1H), 3.30-3.20 (m, 1H), 3.09 (dddd, J=28.0, 21.0, 13.9, 6.8 Hz, 2H), 2.62 (s, 3H), 2.37 (tt, J=8.5, 4.8 Hz, 1H), 1.43-1.36 (m, 2H), 1.28-1.18 (m, $\delta_H$). One NH was not observed. LCMS $[M+H]^+$ 538, RT 1.76 min (Method 10).

Example 67

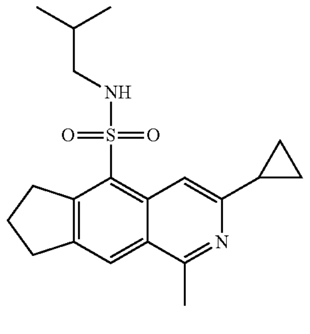 [SMILES: Cc1nc(C2CC2)cc2c(S(=O)(=O)NCC(C)C)c3c(cc12)CCC3]

3-cyclopropyl-1-methyl-N-(2-methylpropyl)-7,8-dihydro-6H-cyclopenta[g]isoquinoline-5-sulfonamide A mixture of Example 69 (7 mg, 0.020 mmol) and $[Ir[dF(CF_3)ppy]_2(dtbpy)]PF_6$ (1.3 mg, 0.0012 mmol) was dissolved in a mixture of MeCN (100 μL) and TFA (100 μL). The reaction mixture was sparged with argon and treated with tert-butyl peroxyacetate (19 μL, 0.059 mmol). Under an atmosphere of Argon the reaction was irradiated using an array of LED lights (120 mWatt, 470 nm wavelength) for 18 hours. The mixture was purified by reverse phase HPLC to give the title compound (926 μg, 13% yield). $^1$H NMR (400 MHz, DMSO-$d_6$) δ 8.28 (s, 1H), 8.21 (d, J=1.3 Hz, 1H), 7.92 (brs, 1H), 3.42 (t, J=7.5 Hz, 2H), 3.06 (td, J=7.6, 1.4 Hz, 2H), 2.81 (s, 3H), 2.19 (tt, J=8.0, 5.0 Hz, 1H), 2.05 (p, J=7.5 Hz, 2H), 1.53 (hept, J=6.7 Hz, 1H), 1.03-0.92 (m, 4H), 0.70 (d, J=6.7 Hz, 6H). LCMS [M+H]$^+$ 359, RT 7.14 min (Method 13).

Example 68

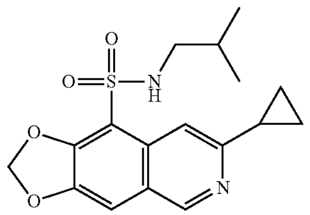 [SMILES: CC(C)CNS(=O)(=O)c1c2c(cc3cnc(C4CC4)cc13)OCO2]

7-cyclopropyl-N-(2-methylpropyl)-[1,3]dioxolo[4,5-g]isoquinoline-9-sulfonamide

Intermediate 33 (34 mg, 0.16 mmol) was dissolved in DCM (2 mL) and chlorosulfonic acid (37 mg, 0.32 mmol) was added. The solution was stirred at room temperature for 15 minutes and then heated at 40° C. for 20 minutes. The mixture was added dropwise to a stirred bi-phasic solution of DCM (10 mL) and ice-water (10 mL). After 2 minutes of stirring the organic layer was separated. The aqueous phase was further extracted with DCM (2×5 mL). The combined organic layers were passed through a phase separator and an excess isobutylamine (93 mg, 1.28 mmol) was added. The solution was stirred for 18 hours, then concentrated under reduced pressure. The resulting residue was purified by flash column chromatography eluting with 0 to 60% of EtOAc in heptane gradient to afford the title compound as a brown solid (6.3 mg, 13% yield). $\delta_H$ (400 MHz, chloroform-d) 8.89 (d, J=0.8 Hz, 1H), 8.40 (s, 1H), 7.31 (d, J=0.8 Hz, 1H), 6.25 (s, 2H), 4.97 (t, J=6.5 Hz, 1H), 2.86 (t, J=6.6 Hz, 2H), 2.21 (tt, J=8.1 and 4.9 Hz, 1H), 1.81 (dt, J=13.4 and 6.7 Hz, 1H), 1.00-1.16 (m, 4H), 0.93 (d, J=6.7 Hz, 6H). LCMS [M+H]$^+$ 349, RT 1.94 minutes (Method 4).

Example 69

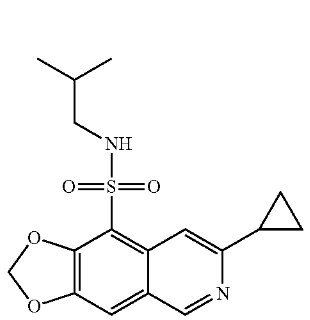 [SMILES: CC(C)CNS(=O)(=O)c1c2c(cc3cnc(C4CC4)cc13)OCO2]

3-cyclopropyl-N-isobutyl-7,8-dihydro-6H-cyclopenta[g]isoquinoline-5-sulfonamide

Nitrogen was bubbled through a mixture of 1,4-dioxane (6.0 mL) and 2 M aqueous potassium carbonate (0.44 mL, 0.88 mmol) for 10 minutes then Intermediate 51 (100 mg, 0.295 mmol), cyclopropaneboronic acid (51 mg, 0.590 mmol) and Bedford's catalyst (32 mg, 0.030 mmol) were introduced. After a further 5 minutes of nitrogen bubbling the reaction vessel was closed and warmed to 120° C. for 2 hours. The reaction mixture was treated with additional cyclopropaneboronic acid (51 mg, 0.590 mmol) and Bedford's catalyst (32 mg, 0.030 mmol) then warmed to 120° C. for a further 2 hours. After cooling, the reaction mixture was diluted with ethyl acetate (30 mL) and washed with water (2×5 mL) and brine (1×5 mL). The organic phase was dried over sodium sulfate, filtered and the filtrate concentrated in-vacuo. Purification of the residue by preparative HPLC (acidic conditions) furnished the title compound (62 mg, 61% yield) as a colourless solid. $\delta_H$ (500 MHz, d-chloroform) 9.04 (s, 1H), 8.34 (s, 1H), 7.88 (s, 1H), 4.65 (t, J=6.4 Hz, 1H), 3.55 (t, J=7.5 Hz, 2H), 3.09 (td, J=7.7, 1.2 Hz, 2H), 2.67 (t, J=6.6 Hz, 2H), 2.24-2.19 (m, 1H), 2.16 (p, J=7.5 Hz, 2H), 1.65 (hept, J=6.8 Hz, 1H), 1.13 (dt, J=6.0, 3.0 Hz, 2H), 1.07-1.02 (m, 2H), 0.80 (d, J=6.7 Hz, 6H); LCMS [M+H]$^+$ 345, RT 3.25 min (Method 2).

Example 70

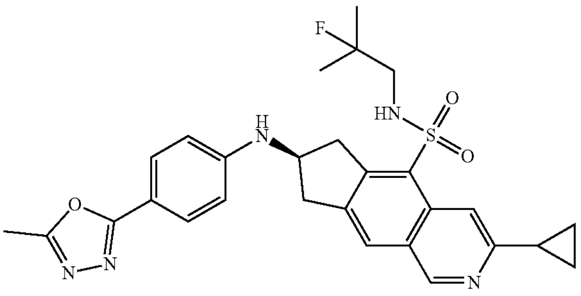 [SMILES: Cc1nnc(-c2ccc(N[C@@H]3Cc4cc5cnc(C6CC6)cc5c(S(=O)(=O)NCC(C)(C)F)c4C3)cc2)o1]

(7R)-3-cyclopropyl-N-(2-fluoro-2-methylpropyl)-7-[4-(5-methyl-1,3,4-oxadiazol-2-yl) anilino]-7,8-dihydro-6H-cyclopenta[g]isoquinoline-5-sulfonamide To a solution of Intermediate 15 (25 mg, 0.066 mmol) in 1,4-dioxane (2 mL) were added 2-(4-bromophenyl)-5-methyl-1,3,4-oxadiazole (24 mg, 0.10 mmol) and sodium tert-butoxide (19 mg, 0.20 mmol). The mixture was degassed (vacuum/nitrogen cycle (×3)) and tBuXPhos Palladium G3 (8 mg, 0.01 mmol) added. The mixture was degassed again (vacuum/nitrogen cycle (×3)) and then stirred at 75° C. for 2 hours then at room temperature overnight. The solution was filtered through celite and washed with dioxane (×3). The filtrate was then evaporated to leave a yellow gum which was purified by column chromatography eluting with 10-100% EtOAc in isohexane to give the title compound (24 mg, 67% yield), $\delta_H$ (300 MHz, d-DMSO) 9.14 (s, 1H), 8.44 (s, 1H), 8.37-8.29 (m, 1H), 8.12 (s, 1H), 7.73-7.67 (m, 2H), 6.80-6.72 (m, 3H), 4.41-4.28 (m, 1H), 3.85 (dd, J=18.4, 6.7 Hz, 1H), 3.58-3.45 (m, 2H), 3.17 (d, J=5.3 Hz, 3H), 3.02 (dd, J=16.6, 4.5 Hz, 1H), 2.95-2.90 (m, 1H), 2.89-2.82 (m, 1H), 2.34-2.22 (m, 1H), 1.20-0.97 (m, 10H). LCMS $[M+H]^+$ 536, RT 2.22 min (Method 10).

Example 71

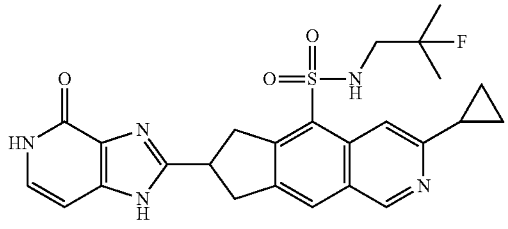 [SMILES: CC(C)(F)CNS(=O)(=O)c1c2c(cc3cnc(C4CC4)cc13)CC(c1nc3c(=O)[nH]ccc3[nH]1)C2]

3-cyclopropyl-N-(2-fluoro-2-methylpropyl)-7-(4-oxo-1,5-dihydroimidazo[4,5-c]pyridin-2-yl)-7,8-dihydro-6H-cyclopenta[g]isoquinoline-5-sulfonamide A mixture of Intermediate 11 (100 mg, 0.25 mmol), 2-methoxypyridine-3,4-diamine (35 mg, 0.25 mmol), DBU (147 µL, 0.98 mmol) and T3P (50% in DMF) (435 µL, 0.74 mmol) in DMF (1 mL) was heated at 180° C. in a microwave for 10 minutes. The reaction was diluted with ethyl acetate (10 mL), washed with saturated $NaHCO_3$ (10 mL), the layers separated and the aqueous extracted with more ethyl acetate (10 mL). The combined organics were washed with brine (10 mL), dried over magnesium sulfate, filtered and concentrated. The residue was purified by acidic, preparative HPLC to afford the title compound (5 mg, 4% yield) as a beige solid.

$^1$H NMR (500 MHz, Methanol-d4) $\delta_H$ 9.08 (s, 1H), 8.50 (s, 1H), 8.11 (s, 1H), 7.19 (d, J=7.0 Hz, 1H), 6.66 (d, J=7.0 Hz, 1H), 4.20 (dd, J=18.0, 8.1 Hz, 1H), 4.02-3.93 (m, 1H), 3.85 (dd, J=18.0, 8.3 Hz, 1H), 3.67-3.51 (m, 2H), 3.10-2.93 (m, 2H), 2.33-2.26 (m, 1H), 1.19-1.04 (m, 10H). LCMS $[M+H]^+$ 496, RT 1.91 min (Method 2)

Example 72

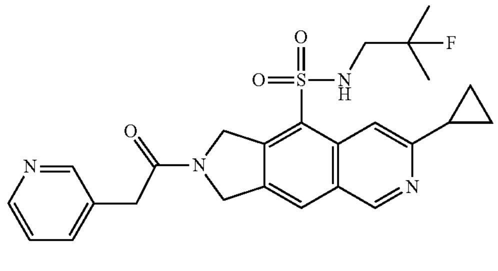 [SMILES: CC(C)(F)CNS(=O)(=O)c1c2c(cc3cnc(C4CC4)cc13)CN(C(=O)Cc1cccnc1)C2]

7-cyclopropyl-N-(2-fluoro-2-methylpropyl)-2-(2-pyridin-3-ylacetyl)-1,3-dihydropyrrolo[3,4-g]isoquinoline-9-sulfonamide To Intermediate 27 (30 mg, 0.083 mmol) in anhydrous DCM (2 mL) was added pyridin-3-ylacetic acid hydrochloride (1:1) (17 mg, 0.099 mmol), DIPEA (43 µL, 0.248 mmol) and HATU (38 mg, 0.099 mmol) and the resulting mixture was stirred at room temperature under nitrogen for 1 hour. Reaction diluted with DCM (15 mL), washed with sat. aq. $NH_4Cl$ (10 mL), water (10 mL), sat. aq. $NaHCO_3$ (10 mL), brine (10 mL), then dried over magnesium sulfate, filtered and concentrated. The crude material was purified by acidic, preparative HPLC to afford the title compound (4.7 mg, 12% yield) as an off-white solid. $^1$H NMR (500 MHz, Chloroform-d) $\delta_H$ 9.15 (s, 1H, rotamer 1), 9.13 (s, 1H, rotamer 2), 8.64 (br. s, 2H), 8.30 (s, 1H, rot. 2), 8.23 (s, 1H, rot. 1), 8.02 (s, 1H, rot. 1), 7.96 (s, 1H, rot. 2), 7.79 br. (s, 1H), 7.37 (br. s, 1H), 5.39 (s, 2H, rot. 1), 5.33 (s, 2H, rot. 2), 5.19-5.09 (m, 1H), 5.03 (s, 2H, rot. 2), 4.99 (s, 2H, rot. 1), 3.86 (s, 2H, rot. 1), 3.82 (s, 2H, rot. 2), 3.00 (dt, J=19.8, 6.5 Hz, 2H), 2.27-2.18 (m, 1H), 1.30 (m, 6H), 1.20-1.16 (m, 2H), 1.13-1.05 (m, 2H). LCMS $[M+H]^+$ 483, RT 1.83 min (Method 2)

Example 73

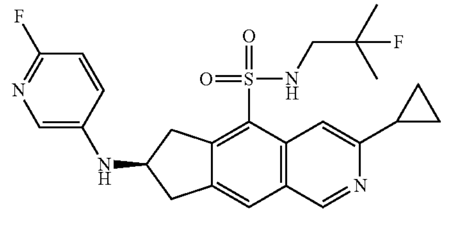 [SMILES: CC(C)(F)CNS(=O)(=O)c1c2c(cc3cnc(C4CC4)cc13)C[C@@H](Nc1ccc(F)nc1)C2]

(7R)-3-cyclopropyl-N-(2-fluoro-2-methylpropyl)-7-[(6-fluoropyridin-3-yl)amino]-7,8-dihydro-6H-cyclopenta[g]isoquinoline-5-sulfonamide A mixture of Intermediate 15 (30 mg, 0.079 mmol), 5-bromo-2-fluoro-pyridine (21 mg, 0.12 mmol), tBuXPhos Pd G3 (9.5 mg, 0.012 mmol) and sodium tert-butoxide (23 mg, 0.24 mmol) in anhydrous dioxane/tBuOH (2:1, 1.5 mL) was stirred at room temperature for 2 hours. Solvent removed and residue purified by acidic, preparative HPLC to afford the title compound (5.9 mg, 16% yield) as a beige solid. $^1$H NMR (500 MHz, DMSO-d6) $\delta_H$ 9.13 (s, 1H), 8.44 (s, 1H), 8.33 (br. s, 1H), 8.10 (s, 1H), 7.56-7.51 (m, 1H), 7.24-7.17 (m, 1H), 6.92 (dd, J=8.8, 3.2 Hz, 1H), 6.11 (d, J=6.5 Hz, 1H), 4.30-4.21 (m, 1H), 3.80 (dd, J=18.3, 6.7 Hz, 1H), 3.51-3.41 (m, 2H), 2.96 (dd, J=16.6, 4.3 Hz, 1H), 2.88 (d, J=20.1 Hz, 2H), 2.31-2.23 (m, 1H), 1.12 (d, J=21.4 Hz, 3H), 1.10 (d, J=21.4 Hz, 3H), 1.05-0.99 (m, 4H). LCMS $[M+H]^+$ 473, RT 2.99 min (Method 2)

Example 74

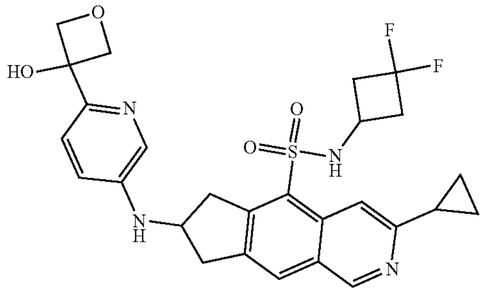 [SMILES: O=S(=O)(NC1CC(F)(F)C1)c1c2c(cc3cnc(C4CC4)cc13)CC(Nc1ccc(C3(O)COC3)nc1)C2]

3-cyclopropyl-N-(3,3-difluorocyclobutyl)-7-[[6-(3-hydroxyoxetan-3-yl)pyridin-3-yl]amino]-7,8-dihydro-6H-cyclopenta[g]isoquinoline-5-sulfonamide To Intermediate 119 (205 mg, 0.52 mmol) were added 3-(5-bromopyridin-2-yl) oxetan-3-ol (180 mg, 0.78 mmol), tBuXPhos Pd G3 (63 mg, 0.08 mmol) and sodium tert-butoxide (152 mg, 1.58 mmol) followed by a mixture 2:1 of anhydrous dioxane/tBuOH (15 mL). The reaction mixture was sonicated under a flow of nitrogen for 5 minutes, then stirred at 100° C. for 2.5 hours. Reaction diluted with ethyl acetate (20 mL), washed with water (15 mL), the layers separated and the aqueous extracted with ethyl acetate (15 mL). The combined organics were washed with sat. aq. $NH_4Cl$ (10 mL), brine (10 mL), dried over magnesium sulfate, concentrated and the residues purified by silica column chromatography eluting with 0 to 100% ethyl acetate in heptane, followed by 0 to 20% methanol in ethyl acetate to afford the title compound (160 mg, 57% yield) as a pale yellow solid.

$^1H$ NMR (500 MHz, DMSO-d6) $\delta_H$ 9.16 (s, 1H), 8.50 (s, 1H), 8.36 (s, 1H), 8.15 (s, 1H), 8.04 (d, J=2.7 Hz, 1H), 7.34 (d, J=8.5 Hz, 1H), 7.05 (dd, J=8.6, 2.8 Hz, 1H), 6.25-6.16 (m, 2H), 4.86 (dd, J=5.9, 1.8 Hz, 2H), 4.60 (d, J=5.9 Hz, 2H), 4.37-4.29 (m, 1H), 3.81 (dd, J=18.4, 6.7 Hz, 1H), 3.55-3.43 (m, 3H), 3.00 (dd, J=16.5, 4.4 Hz, 1H), 2.62-2.53 (m, 2H), 2.33-2.19 (m, 3H), 1.08-0.93 (m, 4H). LCMS $[M+H]^+$ 543, RT 1.95 min (Method 2)

Example 75

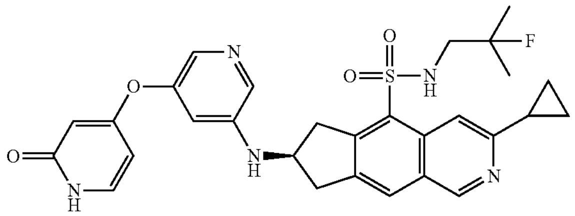 [SMILES: CC(C)(F)CNS(=O)(=O)c1c2c(cc3cnc(C4CC4)cc13)C[C@@H](Nc1cncc(Oc3cc[nH]c(=O)c3)c1)C2]

(7R)-3-cyclopropyl-N-(2-fluoro-2-methylpropyl)-7-[[5-[(2-oxo-1H-pyridin-4-yl)oxy]pyridin-3-yl]amino]-7,8-dihydro-6H-cyclopenta[g]isoquinoline-5-sulfonamide To a suspension of Example 16 (30 mg, 0.052 mmol) and sodium iodide (39 mg, 0.26 mmol) in anhydrous acetonitrile (3 mL) was added TMSCl (13 μL, 0.11 mmol) and the mixture stirred at 60° C. More TMSCl (13 μL, 0.11 mmol) was added and stirring was continued at 60° C. for 3 hours. Reaction filtered through celite, washing with ethyl acetate, the celite washed through with methanol which was collected, and the solvent removed. The residue was purified by acidic, preparative HPLC to afford the title compound (3 mg, 10%) as an off white solid.

$^1H$ NMR (500 MHz, Methanol-d4) $\delta_H$ 9.05 (s, 1H), 8.48 (s, 1H), 8.08 (s, 1H), 7.91 (s, 1H), 7.64 (s, 1H), 7.45 (d, J=7.3 Hz, 1H), 6.90 (t, J=2.3 Hz, 1H), 6.26 (dd, J=7.3, 2.5 Hz, 1H), 5.77 (d, J=2.4 Hz, 1H), 4.40-4.31 (m, 1H), 3.88 (dd, J=18.4, 6.5 Hz, 1H), 3.64 (dd, J=18.3, 3.9 Hz, 1H), 3.53 (dd, J=17.6, 6.7 Hz, 1H), 3.10 (dd, J=16.4, 4.1 Hz, 1H), 2.99 (d, J=19.8 Hz, 2H), 2.33-2.24 (m, 1H), 1.16-1.05 (m, 10H). LCMS $[M+H]^+$ 564, RT 2.09 min (Method 2)

Example 76

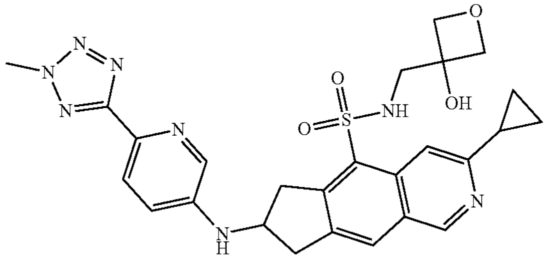 [SMILES: Cn1nnc(-c2ccc(NC3Cc4cc5cnc(C6CC6)cc5c(S(=O)(=O)NCC5(O)COC5)c4C3)cn2)n1]

3-cyclopropyl-N-[(3-hydroxyoxetan-3-yl)methyl]-7-[[6-(2-methyltetrazol-5-yl)pyridin-3-yl]amino]-7,8-dihydro-6H-cyclopenta[g]isoquinoline-5-sulfonamide A mixture of Intermediate 46 (145 mg, 0.37 mmol), 5-bromo-2-(2-methyltetrazol-5-yl)pyridine (134 mg, 0.36 mmol), tBuXPhos Pd G3 (44 mg, 0.056 mmol) and sodium tert-butoxide (107 mg, 1.12 mmol) in anhydrous dioxane/tBuOH (2:1, 4.5 mL) was stirred at room temperature for 1.5 hours. The reaction mixture was diluted with ethyl acetate/methanol (4:1, 20 mL) and treated with sat. aq. $NH_4Cl$ (5 mL) and water (5 mL). The layers were separated and the aqueous was extracted with more ethyl acetate (10 mL). The combined organics were washed with brine (10 mL), dried over magnesium sulfate and solvent removed. Residues purified by silica column chromatography eluting with 0 to 100% ethyl acetate in heptane, followed by 0 to 20% methanol in ethyl acetate to afford the title compound (85 mg, 42% yield) as a white solid.

$^1H$ NMR (500 MHz, DMSO-d6) $\delta_H$ 9.15 (s, 1H), 8.47 (s, 1H), 8.18 (br. s, 1H), 8.14 (s, 1H), 8.13 (d, J=2.7 Hz, 1H), 7.88 (d, J=8.6 Hz, 1H), 7.15 (dd, J=8.7, 2.8 Hz, 1H), 6.75 (d, J=6.5 Hz, 1H), 5.79 (br. s, 1H), 4.42-4.35 (m, 4H), 4.30-4.23 (m, 4H), 3.90 (dd, J=18.3, 6.8 Hz, 1H), 3.57-3.49 (m, 2H), 3.04 (dd, J=16.9, 4.7 Hz, 1H), 3.00-2.90 (m, 2H), 2.32-2.25 (m, 1H), 1.05-0.99 (m, 4H). LCMS $[M+H]^+$ 549, RT 2.05 min (Method 2)

Example 77

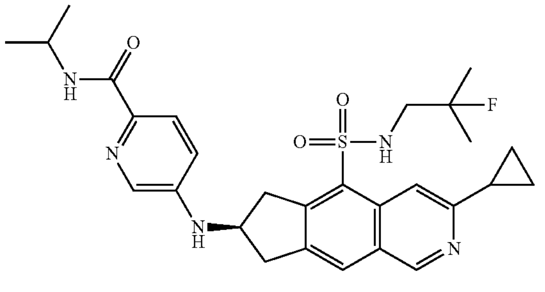 [SMILES: CC(C)NC(=O)c1ccc(N[C@@H]2Cc3cc4cnc(C5CC5)cc4c(S(=O)(=O)NCC(C)(C)F)c3C2)cn1]

5-[[(7R)-3-cyclopropyl-5-[(2-fluoro-2-methylpropyl)sulfamoyl]-7,8-dihydro-6H-cyclopenta[g]isoquinolin-7-yl]amino]-N-propan-2-ylpyridine-2-carboxamide To a stirring solution of Example 15 (20 mg, 0.04 mmol) in anhydrous DMF (0.5 mL) was added HATU (18 mg, 0.048 mmol), DIPEA (21 μL, 0.12 mmol) and isopropylamine (5.2 μL, 0.06 mmol) and the resulting mixture stirred for 1 hour at room temperature. Reaction concentrated and the residue purified by acidic preparative HPLC to afford the title compound (9.8 mg, 45% yield) as a pale yellow solid.

$^1$H NMR (500 MHz, DMSO-d6) $\delta_H$ 9.14 (s, 1H), 8.43 (s, 1H), 8.33 (t, J=6.5 Hz, 1H), 8.12 (s, 1H), 8.00-7.93 (m, 2H), 7.79 (d, J=8.6 Hz, 1H), 7.09 (dd, J=8.6, 2.7 Hz, 1H), 6.81 (d, J=6.1 Hz, 1H), 4.40-4.32 (m, 1H), 4.11-4.01 (m, 1H), 3.84 (dd, J=18.3, 6.7 Hz, 1H), 3.56-3.46 (m, 2H), 3.00 (dd, J=16.5, 4.2 Hz, 1H), 2.89 (dd, J=20.3, 6.5 Hz, 2H), 2.28 (p, J=6.2 Hz, 1H), 1.16 (d, J=6.6 Hz, 6H), 1.11 (d, J=21.4 Hz, 3H), 1.09 (d, J=21.4 Hz, 3H), 1.05-1.00 (m, 4H). LCMS [M+H]$^+$ 540, RT 3.04 min (Method 2)

Example 78

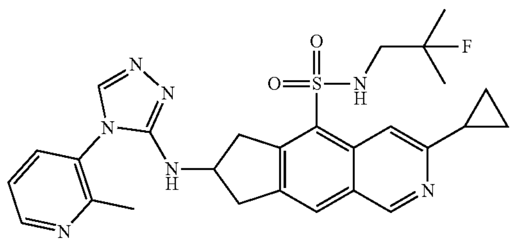 [SMILES: Cc1ncccc1-n1cnnc1NC1Cc2cc3cnc(C4CC4)cc3c(S(=O)(=O)NCC(C)(C)F)c2C1]

3-cyclopropyl-N-(2-fluoro-2-methylpropyl)-7-[[4-(2-methylpyridin-3-yl)-1,2,4-triazol-3-yl]amino]-7,8-dihydro-6H-cyclopenta[g]isoquinoline-5-sulfonamide To a stirring solution of Intermediate 157 (326 mg, 0.62 mmol) in dry DMF (5 mL) was added formic hydrazide (111 mg, 1.85 mmol) followed by mercury dichloride (503 mg, 1.85 mmol). The reaction was stirred at room temperature for 5 minutes then triethylamine (258 μL, 1.85 mmol) was added and the reaction heated to 90° C. for 1 hour. The reaction was diluted with ethyl acetate (20 mL), washed with sat. aq. $NH_4Cl$ (15 mL), water (15 mL), $NH_4Cl$ (15 mL), water (15 mL), brine (10 mL), dried over magnesium sulfate, filtered and concentrated under reduced pressure. The residue was purified by silica column chromatography, eluting with 0-100% ethyl acetate in heptane followed by 0 to 50% methanol in ethyl acetate to afford a crude mixture which was further purified by preparative HPLC to afford the title compound (98 mg, 30% yield).

$^1$H NMR (250 MHz, DMSO-$d_6$) $\delta_H$ 9.09 (s, 1H), 8.55 (dd, J=4.8, 1.5 Hz, 1H), 8.44 (s, 1H), 8.30 (br. s, 1H), 8.17 (s, 1H), 8.03 (s, 1H), 7.72 (dd, J=7.9, 1.5 Hz, 1H), 7.38 (dd, J=7.9, 4.8 Hz, 1H), 6.19 (d, J=5.7 Hz, 1H), 4.57-4.32 (m, 1H), 3.84 (dd, J=18.5, 7.1 Hz, 1H), 3.58-3.36 (m, 2H), 3.07 (dd, J=16.6, 6.1 Hz, 1H), 2.88 (d, J=19.5 Hz, 2H), 2.32-2.20 (m, 1H), 2.19 (s, 3H), 1.19-0.96 (m, 10H). LCMS [M+H]$^+$ 536, RT 1.97 min (Method 2)

Example 79

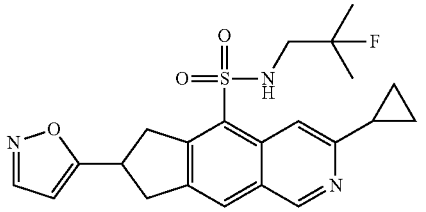 [SMILES: CC(C)(F)CNS(=O)(=O)c1c2c(cc3cnc(C4CC4)cc13)CC(c1ccno1)C2]

3-cyclopropyl-N-(2-fluoro-2-methylpropyl)-7-(1,2-oxazol-5-yl)-7,8-dihydro-6H-cyclopenta[g]isoquinoline-5-sulfonamide A tube was charged with Intermediate 138 (100 mg, 0.25 mmol), potassium metabisulfite (111 mg, 0.5 mmol), tetrabutylammonium bromide (88 mg, 0.27 mmol), sodium formate (37 mg, 0.55 mmol), palladium acetate (3 mg, 0.012 mmol), triphenylphosphine (10 mg, 0.037 mmol), 1,10-phenanthroline (7 mg, 0.037 mmol) and anhydrous DMSO (1 mL). The mixture was degassed by sonicating under a flow of nitrogen for 10 minutes, then the tube was sealed and the mixture stirred at 70° C. After 2 hours, a suspension of fluoroisobutylamine hydrochloride (64 mg, 0.5 mmol) and triethylamine (69 μL, 0.5 mmol) in anhydrous THF (1 mL) and DMSO (0.5 mL) was added and the reaction mixture cooled to 0° C. in an ice-bath. A solution of NBS (89 mg, 0.5 mmol) in anhydrous THF (1 mL) was added dropwise after which the ice-bath was removed and the mixture was allowed to reach room temperature. The reaction mixture was diluted with ethyl acetate (10 mL) and washed with brine (5 mL) and water (5 mL). The aqueous layer was extracted with more ethyl acetate (15 mL) and the combined organics dried over magnesium sulfate, filtered and concentrated. The residue was purified by silica column chromatography eluting with 0 to 50% ethyl acetate in heptane, followed by further purification by preparative HPLC to afford the title compound (9.4 mg, 9% yield) as a white solid. $^1$H NMR (500 MHz, Methanol-d4) $\delta_H$ 9.06 (s, 1H), 8.49 (s, 1H), 8.27 (d, J=1.8 Hz, 1H), 8.09 (s, 1H), 6.25 (d, J=1.3 Hz, 1H), 4.06 (dd, J=17.8, 8.0 Hz, 1H), 3.97 (p, J=7.3 Hz, 1H), 3.75 (dd, J=17.8, 6.5 Hz, 1H), 3.60 (dd, J=16.9, 8.0 Hz, 1H), 3.38-3.32 (m, 1H), 3.08-2.92 (m, 2H), 2.34-2.26 (m, 1H), 1.20-1.02 (m, 10H). LCMS [M+H]$^+$ 430, RT 2.92 min (Method 2).

Example 80

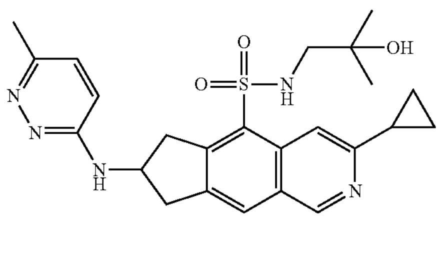 [SMILES: Cc1ccc(NC2Cc3cc4cnc(C5CC5)cc4c(S(=O)(=O)NCC(C)(C)O)c3C2)nn1]

3-cyclopropyl-N-(2-hydroxy-2-methylpropyl)-7-[(6-methylpyridazin-3-yl)amino]-7,8-dihydro-6H-cyclopenta[g]isoquinoline-5-sulfonamide To a stirring solution of Intermediate 156 (32 mg, 0.045 mmol) in THF (2 mL) was added tetrabutylammonium fluoride (1M in THF), (68 μL, 0.1068 mmol) and the mixture stirred overnight at room temperature. The mixture was concentrated to dryness and the residue was purified by acidic, preparative HPLC afford the title compound (8.4 mg, 39% yield) as a red-orange solid. $^1$H NMR (500 MHz, DMSO-d6) $\delta_H$ 9.13 (s, 1H), 8.46 (s, 1H), 8.11 (s, 1H), 7.81 (t, J=6.4 Hz, 1H), 7.13 (d, J=9.1 Hz, 1H), 6.91 (d, J=6.1 Hz, 1H), 6.72 (d, J=9.1 Hz, 1H), 4.68 (h, J=5.9 Hz, 1H), 4.33 (s, 1H), 3.84 (dd, J=18.4, 6.9 Hz, 1H), 3.56-3.45 (m, 2H), 3.03 (dd, J=16.7, 5.3 Hz, 1H), 2.63-2.56 (m, 2H), 2.39 (s, 3H), 2.32-2.24 (m, 1H), 1.08-0.97 (m, 4H), 0.93 (s, 3H), 0.89 (s, 3H). LCMS [M+H]$^+$ 468, RT 1.40 min (Method 2).

Example 81

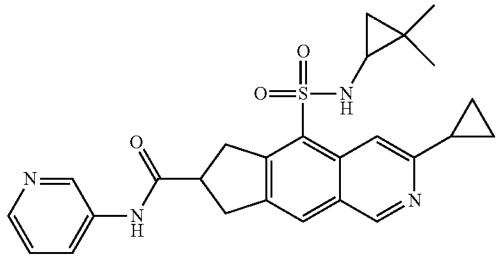 [SMILES: CC1(C)CC1NS(=O)(=O)c1c2c(cc3cnc(C4CC4)cc13)CC(C(=O)Nc1cccnc1)C2]

3-cyclopropyl-5-[(2,2-dimethylcyclopropyl) sulfamoyl]-N-pyridin-3-yl-7,8-dihydro-6H-cyclopenta[g]isoquinoline-7-carboxamide To a stirring solution of Intermediate 153 (55 mg, 0.14 mmol) in anhydrous DMF (1 mL) was added DIPEA (72 μL, 0.41 mmol), HATU (63 mg, 0.17 mmol) and pyridin-3-amine (20 mg, 0.21 mmol) and the mixture was stirred for 3 hours at room temperature under an atmosphere of nitrogen. The mixture was diluted with ethyl acetate (15 mL), water (5 ml) and sat. aq. $NH_4Cl$ (5 mL). The layers were separated and the aqueous was extracted with more ethyl acetate (15 mL). The combined organics were washed with water (10 mL), sat. aq. $NH_4Cl$ (10 mL), brine (10 mL), then dried over magnesium sulfate, filtered and concentrated. The residue was purified by acidic, preparative HPLC to afford the title compound (29 mg, 44% yield) as an off white solid.

$^1$H NMR (500 MHz, DMSO-d6) $\delta_H$ 10.36 (d, J=6.8 Hz, 1H), 9.14 (s, 1H), 8.76 (s, 1H), 8.44 (d, J=9.4 Hz, 1H), 8.27-8.21 (m, 2H), 8.13 (s, 1H), 8.04 (d, J=8.4 Hz, 1H), 7.34 (dd, J=8.2, 4.7 Hz, 1H), 3.93-3.82 (m, 1H), 3.74-3.63 (m, 1H), 3.52-3.45 (m, 1H), 3.43-3.36 (m, 2H), 2.22 (p, J=6.2 Hz, 1H), 1.93-1.78 (m, 1H), 1.06-0.89 (m, 4H), 0.74 (d, J=18.6 Hz, 3H), 0.70 (d, J=19.3 Hz, 3H), 0.48-0.41 (m, 1H), 0.33-0.22 (m, 1H). LCMS [M+H]$^+$ 477, RT 2.13 min (Method 2).

Example 82

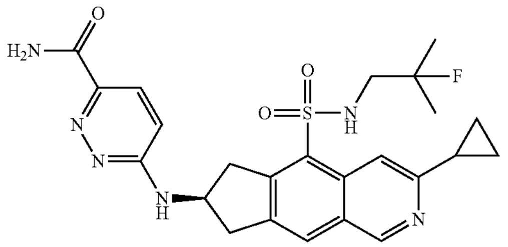 [SMILES: CC(C)(F)CNS(=O)(=O)c1c2c(cc3cnc(C4CC4)cc13)C[C@@H](Nc1ccc(C(N)=O)nn1)C2]

6-[[(7R)-3-cyclopropyl-5-[(2-fluoro-2-methylpropyl) sulfamoyl]-7,8-dihydro-6H-cyclopenta[g]isoquinolin-7-yl]amino]pyridazine-3-carboxamide Intermediate 163 (30 mg, 0.06 mmol) was heated in 7 M $NH_3$ in MeOH (1.5 mL) in a microwave at 100° C. for 1 hour. Reaction was concentrated and purified by preparative reverse phase acidic HPLC to afford the title compound (11 mg, 38%) as a white solid.

$^1$H NMR (500 MHz, DMSO-d6) $\delta_H$ 9.14 (s, 1H), 8.44 (s, 1H), 8.33 (br s, 1H), 8.13 (s, 1H), 8.12-8.08 (m, 1H), 7.75 (d, J=9.2 Hz, 1H), 7.70 (d, J=5.9 Hz, 1H), 7.49-7.43 (m, 1H), 6.88 (d, J=9.3 Hz, 1H), 4.84-4.74 (m, 1H), 3.89 (dd, J=18.4, 7.0 Hz, 1H), 3.62-3.48 (m, 2H), 3.10 (dd, J=16.7, 5.0 Hz, 1H), 2.89 (d, J=19.9 Hz, 2H), 2.32-2.24 (m, 1H), 1.12 (d, J=21.4 Hz, 3H), 1.09 (d, J=21.4 Hz, 3H), 1.06-0.97 (m, 4H). LCMS [M+H]$^+$ 499.2, RT 2.09 min (Method 2).

Example 83

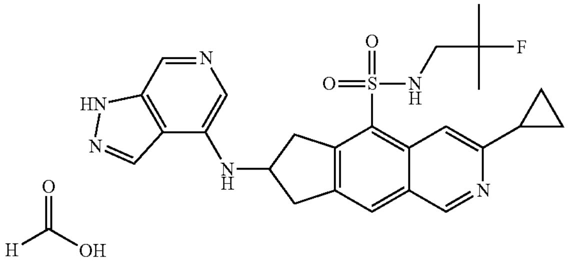 [SMILES: O=CO ; CC(C)(F)CNS(=O)(=O)c1c2c(cc3cnc(C4CC4)cc13)CC(Nc1cncc3[nH]ncc13)C2]

3-cyclopropyl-N-(2-fluoro-2-methyl-propyl)-7-(1H-pyrazolo[3,4-c]pyridin-4-ylamino)-7,8-dihydro-6H-cyclopenta[g]isoquinoline-5-sulfonamide, formate salt To both Batch 1 (47 mg (93% purity), 0.070 mmol) and Batch 2 (27 mg (78% purity), 0.034 mmol) of Intermediates 160 and 161 was added DCM (1.75 mL) and TFA (0.25 mL) and reactions stirred at room temperature for 16 hours. The reactions were combined, quenched with saturated $NaHCO_3$ (15 mL) and extracted with DCM (3×10 mL). Organics were dried over sodium sulfate and concentrated under vacuum. The residue was purified by silica column chromatography eluting with 0-10% MeOH in DCM to afford the title compound which was further purified by acidic, reverse phase preparative HPLC to afford the title compound (5.5 mg, 10% yield) as a white solid $^1$H NMR (500 MHz, DMSO-d6) $\delta_H$ 13.23 (s, 1H), 9.15 (s, 1H), 8.44 (s, 1H), 8.33 (t, J=6.5 Hz, 1H), 8.27 (s, 1H), 8.23 (s, 1H), 8.19 (s, 1H), 8.13 (s, 1H), 7.64-7.51 (m, 1H), 6.68-6.57 (m, 1H), 4.59-4.49 (m, 1H), 3.97-3.88 (m, 1H), 3.67-3.55 (m, 2H), 3.14 (dd, J=16.8, 4.5 Hz, 1H), 2.89 (dd, J=20.2, 6.4 Hz, 2H), 2.32-2.24 (m, 1H), 1.13-0.98 (m, 10H). LCMS [M+H]$^+$ 495.2, RT 1.71 min (Method 2)

Example 84

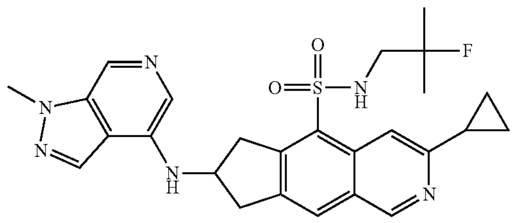 [SMILES: Cn1ncc2c(NC3Cc4cc5cnc(C6CC6)cc5c(S(=O)(=O)NCC(C)(C)F)c4C3)cncc21]

3-cyclopropyl-N-(2-fluoro-2-methylpropyl)-7-[(1-methylpyrazolo[3,4-c]pyridin-4-yl)amino]-7,8-dihydro-6H-cyclopenta[g]isoquinoline-5-sulfonamide Intermediate 12 (40 mg, 0.106 mmol), 4-bromo-1-methyl-1H-pyrazolo[3,4-c]pyridine (34 mg, 0.159 mmol), sodium tert-butoxide (31 mg, 0.318 mmol) and tBuXPhos Pd G3 (8.4 mg, 0.011 mmol) in dioxane (3 mL) and tBuOH (1.5 mL) in a 20 mL pressure tube was flushed with nitrogen, sealed and heated to 110° C. for 2 hours, followed by stirring at room temperature for 16 hours. Water (10 mL) was added, extracted with DCM (3×10 mL), the organics dried over sodium sulfate and concentrated under vacuum. The residue was purified by silica column chromatography eluting with 0-10% MeOH in DCM followed by preparative acidic reverse phase HPLC to afford the title compound (24 mg) as a yellow solid.

$^1$H NMR (500 MHz, DMSO-d6) $\delta_H$ 9.15 (s, 1H), 8.44 (s, 1H), 8.36 (s, 1H), 8.33 (t, J=6.5 Hz, 1H), 8.17 (s, 1H), 8.13 (s, 1H), 7.59 (s, 1H), 6.64 (d, J=6.4 Hz, 1H), 4.54 (h, J=6.7 Hz, 1H), 4.05 (s, 3H), 3.92 (dd, J=18.4, 6.9 Hz, 1H), 3.65-3.55 (m, 2H), 3.13 (dd, J=16.6, 4.5 Hz, 1H), 2.88 (dd, J=20.2, 6.4 Hz, 2H), 2.31-2.24 (m, 1H), 1.14-0.98 (m, 10H). LCMS [M+H]$^+$ 509.2, RT 1.82 min (Method 2).

Example 85

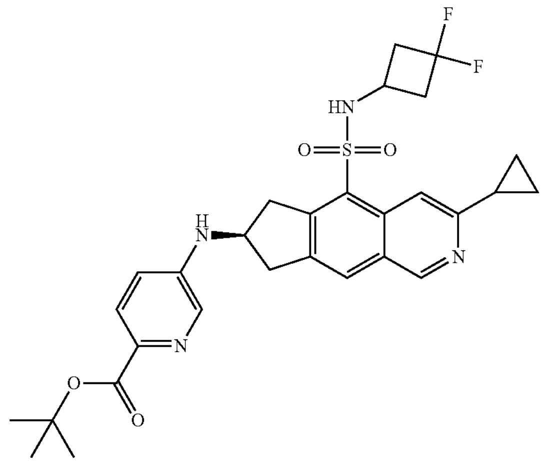 [SMILES: CC(C)(C)OC(=O)c1ccc(N[C@@H]2Cc3cc4cnc(C5CC5)cc4c(S(=O)(=O)NC4CC(F)(F)C4)c3C2)cn1]

tert-butyl 5-[[(7R)-3-cyclopropyl-5-[(3,3-difluorocyclobutyl) sulfamoyl]-7,8-dihydro-6H-cyclopenta[g] isoquinolin-7-yl]amino]pyridine-2-carboxylate Intermediate 124 (80 mg, 0.2 mmol), tert-butyl 5-bromopyridine-2-carboxylate (79 mg, 0.3 mmol), sodium tert-butoxide (39 mg, 0.41 mmol) and tBuXPhos Pd G3 (16 mg, 0.02 mmol) were stirred in dry dioxane (3 mL) and tBuOH (1.5 ml) under nitrogen for 17 hour. Water (10 mL) was added and extracted with DCM (3×10 mL), organics dried over sodium sulfate and concentrated under vacuum. Residue was purified by silica column chromatography eluting with 0-10% MeOH In DCM followed by further purification by silica column chromatography eluting with 100% ethyl acetate in heptane to afford the title compound (90 mg, 74%) as a yellow solid $^1$H NMR (500 MHz, DMSO-d6) $\delta_H$ 9.17 (s, 1H), 8.51 (s, 1H), 8.35 (s, 1H), 8.17 (s, 1H), 8.05 (d, J=2.8 Hz, 1H), 7.78 (d, J=8.6 Hz, 1H), 7.03 (dd, J=8.7, 2.8 Hz, 1H), 7.00 (d, J=6.5 Hz, 1H), 4.39 (h, J=6.6 Hz, 1H), 3.84 (dd, J=18.4, 6.7 Hz, 1H), 3.58-3.44 (m, 3H), 3.02 (dd, J=16.7, 4.3 Hz, 1H), 2.62-2.53 (m, 2H), 2.35-2.22 (m, 3H), 1.52 (s, 9H), 1.09-0.99 (m, 4H). LCMS [M+H]$^+$ 571.1, RT 3.33 min (Method 2)

Example 86

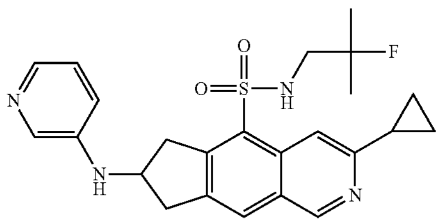 [SMILES: CC(C)(F)CNS(=O)(=O)c1c2c(cc3cnc(C4CC4)cc13)CC(Nc1cccnc1)C2]

3-cyclopropyl-N-(2-fluoro-2-methylpropyl)-7-(pyridin-3-ylamino)-7,8-dihydro-6H-cyclopenta[g]isoquinoline-5-sulfonamide Intermediate 12 (40 mg, 0.11 mmol), sodium tert-butoxide (31 mg, 0.32 mmol), tBuXPhos (9 mg, 0.02 mmol), $Pd_2(dba)_3$ (10 mg, 0.01 mmol) and 3-bromopyridine (25 mg, 0.16 mmol) were heated in dry toluene (3 mL) in a 20 mL pressure tube at 110° C. with stirring for 1.5 hours. Reaction was diluted with water (10 mL), extracted with DCM (3×10 mL), the organics dried over sodium sulfate and concentrated under vacuum. The residue was purified by silica column chromatography eluting with 0-20% MeOH in DCM, then further purified by preparative reverse phase basic HPLC to afford the title compound (24 mg) as a white solid.

$^1$H NMR (500 MHz, DMSO-d6) $\delta_H$ 9.13 (s, 1H), 8.44 (s, 1H), 8.31 (s, 1H), 8.10 (s, 1H), 8.00 (d, J=2.6 Hz, 1H), 7.79 (d, J=3.8 Hz, 1H), 7.11 (dd, J=8.2, 4.6 Hz, 1H), 7.03-6.96 (m, 1H), 6.15 (d, J=6.4 Hz, 1H), 4.28 (h, J=7.1 Hz, 1H), 3.82 (dd, J=18.3, 6.7 Hz, 1H), 3.52-3.43 (m, 2H), 2.98 (dd, J=16.5, 4.4 Hz, 1H), 2.88 (d, J=20.2 Hz, 2H), 2.32-2.22 (m, 1H), 1.12 (d, J=21.4 Hz, 3H), 1.09 (d, J=21.4 Hz, 3H), 1.06-0.97 (m, 4H). LCMS $[M+H]^+$ 455.2, RT 1.69 min (Method 2).

Example 87

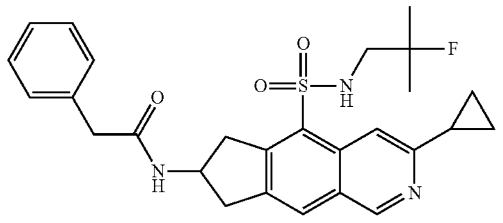 [SMILES: CC(C)(F)CNS(=O)(=O)c1c2c(cc3cnc(C4CC4)cc13)CC(NC(=O)Cc1ccccc1)C2]

N-[3-cyclopropyl-5-[(2-fluoro-2-methylpropyl) sulfamoyl]-7,8-dihydro-6H-cyclopenta[g]isoquinolin-7-yl]-2-phenylacetamide Intermediate 12 (30 mg, 0.08 mmol) was dissolved in DCM (3 mL) and DIPEA (42 μl, 0.24 mmol) added followed by phenylacetyl chloride (12.62 μl, 0.1 mmol). Reaction stirred at room temperature for 30 minutes, washed with aq. saturated $NaHCO_3$ (2×1 mL), brine, dried over sodium sulfate and concentrated under vacuum. The residue was purified by silica column chromatography using 0-100% ethyl acetate in heptane followed by preparative basic HPLC to afford the title compound (16 mg, 41% yield) as a white solid.

$^1$H NMR (500 MHz, Chloroform-d) $\delta_H$ 9.04 (s, 1H), 8.28 (s, 1H), 7.85 (s, 1H), 7.36-7.31 (m, 2H), 7.30-7.27 (m, 1H), 7.25-7.21 (m, 2H), 5.59 (d, J=7.2 Hz, 1H), 5.01 (t, J=6.4 Hz, 1H), 4.74 (h, J=7.3 Hz, 1H), 3.86 (dd, J=18.4, 7.6 Hz, 1H), 3.56 (s, 2H), 3.46 (dd, J=17.3, 7.4 Hz, 1H), 3.32 (dd, J=18.5, 6.4 Hz, 1H), 3.03 (ddd, J=20.6, 13.4, 6.9 Hz, 1H), 2.98-2.86 (m, 2H), 2.24-2.17 (m, 1H), 1.31 (d, J=21.5 Hz, 3H), 1.25 (d, J=21.5 Hz, 3H), 1.17-1.12 (m, 2H), 1.09-1.03 (m, 2H). LCMS $[M+H]^+$ 496.2, RT 2.94 min (Method 2).

Example 88

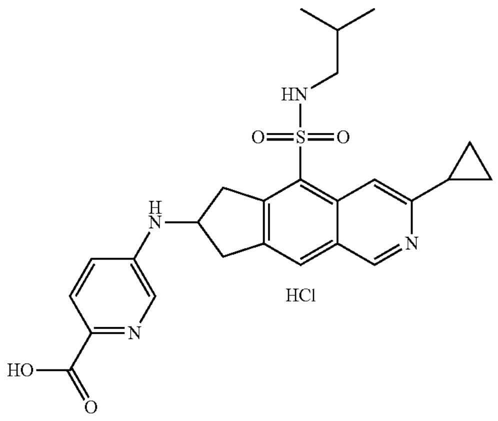 [SMILES: CC(C)CNS(=O)(=O)c1c2c(cc3cnc(C4CC4)cc13)CC(Nc1ccc(C(=O)O)nc1)C2 ; Cl]

5-[[3-cyclopropyl-5-(isobutylsulfamoyl)-7,8-dihydro-6H-cyclopenta[g]isoquinolin-7-yl]amino]pyridine-2-carboxylic acid; hydrochloride Intermediate 162 (28 mg, 0.06 mmol) was stirred in THF (1 mL) and 2M aq. LiOH (85 μL) added. Reaction stirred at 50° C. for 2 hours. The THF was removed by evaporation and to the remaining aqueous was added 3M aq. HCl (1 mL). The resulting precipitate was collected by vacuum filtration, washed with water followed by diethyl ether to afford the title compound (22 mg, 75% yield) as a yellow solid.

$^1$H NMR (500 MHz, Methanol-d4) $\delta_H$ 9.24 (s, 1H), 8.60 (s, 1H), 8.22 (s, 1H), 8.10 (d, J=8.8 Hz, 1H), 8.03 (d, J=2.7 Hz, 1H), 7.43 (dd, J=8.9, 2.8 Hz, 1H), 4.57-4.48 (m, 1H), 3.96 (dd, J=18.6, 6.5 Hz, 1H), 3.75 (dd, J=18.5, 3.7 Hz, 1H), 3.69-3.60 (m, 1H), 3.20 (dd, J=16.7, 4.0 Hz, 1H), 2.66-2.56 (m, 2H), 2.39-2.31 (m, 1H), 1.60-1.49 (m, 1H), 1.22-1.10 (m, 4H), 0.70 (d, J=6.7 Hz, 3H), 0.69 (d, J=6.7 Hz, 3H). LCMS $[M+H]^+$ 481.2, RT 3.29 min (Method 2).

Example 89

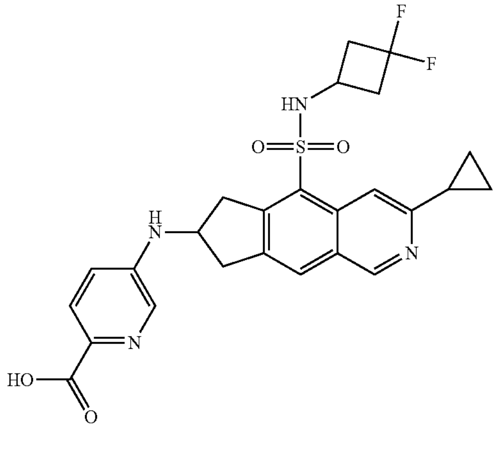 [SMILES: O=C(O)c1ccc(NC2Cc3cc4cnc(C5CC5)cc4c(S(=O)(=O)NC4CC(F)(F)C4)c3C2)cn1]

5-[[3-cyclopropyl-5-[(3,3-difluorocyclobutyl) sulfamoyl]-7,8-dihydro-6H-cyclopenta[g]isoquinolin-7-yl]amino]pyridine-2-carboxylic acid Intermediate 119 (50 mg, 0.13 mmol), methyl 5-bromopyridine-2-carboxylate (41 mg, 0.19 mmol), sodium tert-butoxide (24 mg, 0.25 mmol) and tBuXPhos Pd G3 (10 mg, 0.01 mmol) were heated in dioxane (3 mL) and tBuOH (1.5 mL) in a sealed tube with stirring at 110° C. for 2.5 hours. Reaction was concentrated under vacuum, THF (2 mL) and 2M aq. LiOH (0.19 mL) were added. Reaction was heated to 50° C. with stirring for 45 minutes. Reaction was concentrated under vacuum and the residue purified by preparative reverse phase acidic HPLC to afford the title compound (12 mg, 17%) as a dark yellow solid.

$^1H$ NMR (500 MHz, Methanol-d4) $\delta_H$ 9.08 (s, 1H), 8.44 (s, 1H), 8.12 (s, 1H), 8.06-7.92 (m, 2H), 7.20 (dd, J=8.6, 2.5 Hz, 1H), 4.47 (br s, 1H), 3.91 (dd, J=18.4, 6.5 Hz, 1H), 3.67 (dd, J=18.2, 3.3 Hz, 1H), 3.63-3.51 (m, 2H), 3.20-3.06 (m, 1H), 2.62-2.48 (m, 2H), 2.37-2.19 (m, 3H), 1.14-1.01 (m, 4H). LCMS $[M+H]^+$ 515.05, RT 3.33 min (Method 2).

Example 90

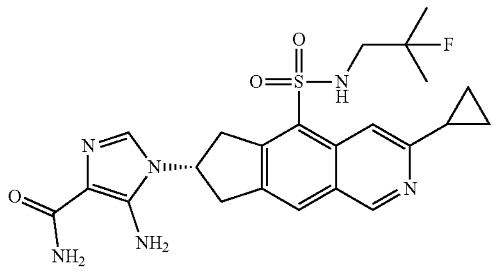 [SMILES: CC(C)(F)CNS(=O)(=O)c1c2c(cc3cnc(C4CC4)cc13)C[C@H](n1cnc(C(N)=O)c1N)C2]

5-amino-1-[(7S)-3-cyclopropyl-5-[(2-fluoro-2-methylpropyl) sulfamoyl]-7,8-dihydro-6H-cyclopenta[g]isoquinolin-7-yl]imidazole-4-carboxamide 2-amino-2-cyanoacetamide (92%, 28 mg, 0.26 mmol) was stirred in dry MeCN (3 mL) in a 20 mL pressure tube. Triethylorthoformate (44 μL, 0.26 mmol) was added, reaction sealed and heated at 90° C. for 1 hour. Reaction allowed to cool to room temperature and Intermediate 118 (100 mg, 0.26 mmol) was added. Reaction was heated to 90° C. with stirring for 1 hour, then concentrated under vacuum and purified by silica column chromatography eluting with 0-15% MeOH in DCM to afford the title compound (42 mg, 32% yield) as a white solid.

$^1H$ NMR (500 MHz, DMSO-d6) $\delta_H$ 9.17 (s, 1H), 8.46 (s, 1H), 8.41 (br s, 1H), 8.18 (s, 1H), 7.01 (s, 1H), 6.72 (br s, 1H), 6.60 (br s, 1H), 5.93 (s, 2H), 4.99-4.89 (m, 1H), 3.99 (dd, J=18.2, 7.3 Hz, 1H), 3.72 (dd, J=18.2, 5.7 Hz, 1H), 3.59 (dd, J=17.0, 7.2 Hz, 1H), 3.41 (dd, J=16.7, 5.8 Hz, 1H), 2.98-2.82 (m, 2H), 2.32-2.25 (m, 1H), 1.15 (d, J=21.4 Hz, 3H), 1.10 (d, J=21.4 Hz, 3H), 1.07-1.00 (m, 4H). LCMS $[M+H]^+$ 487.3, RT 1.94 min (Method 2).

Example 91

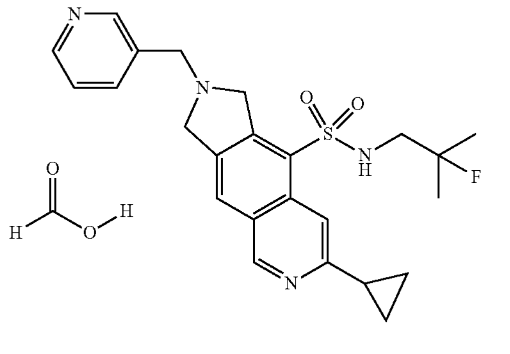 [SMILES: O=CO ; CC(C)(F)CNS(=O)(=O)c1c2c(cc3cnc(C4CC4)cc13)CN(Cc1cccnc1)C2]

7-cyclopropyl-N-(2-fluoro-2-methyl-propyl)-2-(3-pyridylmethyl)-1,3-dihydropyrrolo[3,4-g]isoquinoline-9-sulfonamide; formic acid Intermediate 27 hydrochloride (20 mg, 0.052 mmol) was dissolved in MeCN (2 mL). $K_2CO_3$ (29 mg, 0.20 mmol) and 3-(bromomethyl)pyridine hydrobromide (1:1) (14.6 mg, 0.058 mmol) were added. The solution was stirred at room temperature for 16 hours. The solvent was removed under reduced pressure, diluted with DCM (20 mL) washed with water, the organic layer dried over $MgSO_4$ and filtered and concentrated under reduced pressure. Residue purified by silica column chromatography eluting with 50-100% EtOAc/heptane then 0-10% MeOH in DCM followed by acidic preparative HPLC to afford the title compound (6.8 mg, 27% yield).

$^1H$ NMR (500 MHz, Methanol-d4) $\delta_H$ 9.08 (s, 1H), 8.65 (s, 1H), 8.53 (s, 1H), 8.45 (s, 1H), 8.11 (s, 1H), 8.04 (s, 1H), 7.96 (d, J=7.8 Hz, 1H), 7.53-7.44 (m, 1H), 4.52 (s, 2H), 4.09 (s, 2H), 4.06 (s, 2H), 3.01 (d, J=19.8 Hz, 2H), 2.34-2.27 (m, 1H), 1.16 (d, J=21.1 Hz, 6H), 1.11-1.05 (m, 4H). LCMS $[M+H]^+$ 455.2, RT 1.68 min (Method 2)

Example 92

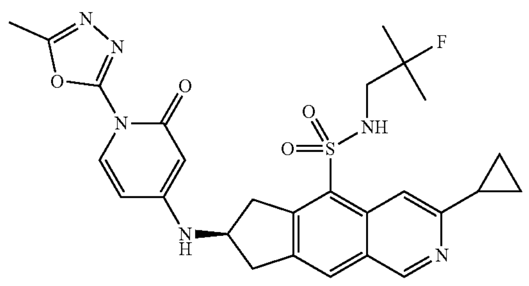 [SMILES: Cc1nnc(-n2ccc(N[C@@H]3Cc4cc5cnc(C6CC6)cc5c(S(=O)(=O)NCC(C)(C)F)c4C3)cc2=O)o1]

(7R)-3-cyclopropyl-N-(2-fluoro-2-methylpropyl)-7-[[1-(5-methyl-1,3,4-oxadiazol-2-yl)-2-oxopyridin-4-yl]amino]-7,8-dihydro-6H-cyclopenta[g]isoquinoline-5-sulfonamide Intermediate 15 (22 mg, 0.058 mmol), Intermediate 189 (16.4 mg, 0.064 mmol), sodium tert-butoxide (11.2 mg, 0.11 mmol) and tBuXPhos Pd G3 (6.9 mg, 0.009 mmol) were stirred at room temperature in dry dioxane (3 mL) for 4 hours. The reaction mixture was partitioned between water and DCM, the organic layer dried ($MgSO_4$), evaporated and the residue purified by acidic preparative HPLC to afford the title compound (3.2 mg, 10% yield) as a white solid.

$^1$H NMR (500 MHz, Methanol-d4) $\delta_H$ 9.07 (s, 1H), 8.49 (s, 1H), 8.10 (s, 1H), 7.39 (d, J=7.1 Hz, 1H), 6.12-5.93 (br, 1H), 5.56 (d, J=2.2 Hz, 1H), 4.45-4.36 (m, 1H), 3.90 (dd, J=18.5, 6.7 Hz, 1H), 3.72 (dd, J=18.4, 3.7 Hz, 1H), 3.56 (dd, J=17.6, 6.7 Hz, 1H), 3.16 (dd, J=16.5, 3.7 Hz, 1H), 3.02 (d, J=19.8 Hz, 2H), 2.59 (s, 3H), 2.36-2.24 (m, 1H), 1.16 (d, J=21.1 Hz, 3H), 1.15 (d, J=21.1 Hz, 3H), 1.11-1.05 (m, 4H). LCMS [M+H]$^+$ 553.2, RT 2.34 min (Method 2).

Example 93

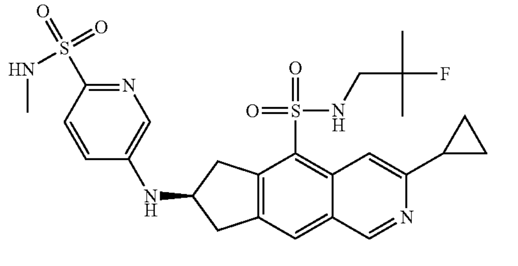 [SMILES: CNS(=O)(=O)c1ccc(N[C@@H]2Cc3cc4cnc(C5CC5)cc4c(S(=O)(=O)NCC(C)(C)F)c3C2)cn1]

(7R)-3-cyclopropyl-N-(2-fluoro-2-methylpropyl)-7-[[6-(methylsulfamoyl)pyridin-3-yl]amino]-7,8-dihydro-6H-cyclopenta[g]isoquinoline-5-sulfonamide Intermediate 15 (30 mg, 0.079 mmol), Intermediate 190 (27.9 mg, 0.079 mmol), sodium tert-butoxide (22.9 mg, 0.23 mmol) and tBuXPhos Pd G3 (9.4 mg, 0.012 mmol) were heated in dry dioxane/tBuOH (3 mL and 1 mL) in a 20 mL pressure tube at 65° C. with stirring for 2 hours. Solvent was removed, water (10 mL) added and reaction extracted with DCM (3×10 mL). Organics were dried over sodium sulfate and concentrated under vacuum. The residue was purified by silica column chromatography eluting with 50%-100% EtOAc in heptane, then 0%-10% MeOH in DCM followed by acidic preparative HPLC to afford the title compound (9 mg, 20% yield) as a white solid.

$^1$H NMR (500 MHz, DMSO-d6) $\delta_H$ 9.15 (s, 1H), 8.44 (s, 1H), 8.35 (t, J=6.0 Hz, 1H), 8.13 (s, 1H), 8.06 (d, J=2.7 Hz, 1H), 7.66 (d, J=8.6 Hz, 1H), 7.25 (q, J=5.0 Hz, 1H), 7.12 (dd, J=8.7, 2.8 Hz, 1H), 7.04 (d, J=6.4 Hz, 1H), 4.41-4.33 (m, 1H), 3.85 (dd, J=18.4, 6.7 Hz, 1H), 3.56-3.45 (m, 2H), 3.01 (dd, J=16.6, 4.1 Hz, 1H), 2.89 (dd, J=20.1, 4.3 Hz, 2H), 2.44 (d, J=5.0 Hz, 3H), 2.32-2.24 (m, 1H), 1.12 (d, J=21.4 Hz, 3H), 1.09 (d, J=21.4 Hz, 3H), 1.05-1.00 (m, 4H). LCMS [M+H]$^+$ 548.2, RT 2.62 min (Method 2).

Example 94

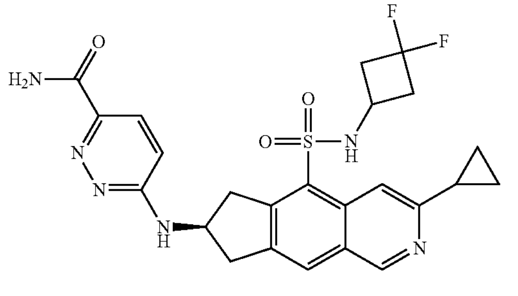 [SMILES: NC(=O)c1ccc(N[C@@H]2Cc3cc4cnc(C5CC5)cc4c(S(=O)(=O)NC4CC(F)(F)C4)c3C2)nn1]

6-[[(7R)-3-cyclopropyl-5-[(3,3-difluorocyclobutyl)sulfamoyl]-7,8-dihydro-6H-cyclopenta[g]isoquinolin-7-yl]amino]pyridazine-3-carboxamide Intermediate 169 (64 mg, 0.099 mmol, 82% purity) was heated in 7M $NH_3$ in MeOH (2.0 mL) in a microwave at 100° C. for 1 hour. Reaction concentrated and resulting residue purified by acidic preparative HPLC to afford the title compound (25 mg, 49% yield) as a grey solid.

$^1$H NMR (500 MHz, DMSO-d6) $\delta_H$ 9.17 (s, 1H), 8.50 (d, J=7.6 Hz, 1H), 8.35 (s, 1H), 8.19 (s, 1H), 8.10 (s, 1H), 7.75 (d, J=9.2 Hz, 1H), 7.71 (d, J=5.9 Hz, 1H), 7.46 (s, 1H), 6.88 (d, J=9.3 Hz, 1H), 4.88-4.77 (m, 1H), 3.87 (dd, J=18.5, 6.9 Hz, 1H), 3.64-3.43 (m, 3H), 3.11 (dd, J=16.9, 4.8 Hz, 1H), 2.61-2.54 (m, 2H), 2.33-2.21 (m, 3H), 1.05-1.02 (m, 4H). LCMS [M+H]$^+$ 515.1, RT 2.29 min (Method 2).

Example 95

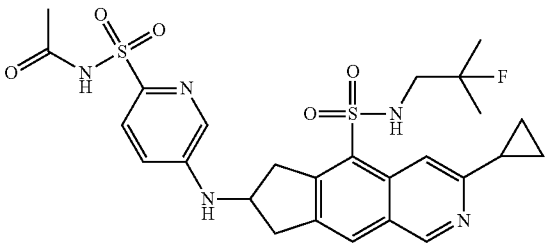 [SMILES: CC(=O)NS(=O)(=O)c1ccc(NC2Cc3cc4cnc(C5CC5)cc4c(S(=O)(=O)NCC(C)(C)F)c3C2)cn1]

N-[5-[[(7R)-3-cyclopropyl-5-[(2-fluoro-2-methylpropyl) sulfamoyl]-7,8-dihydro-6H-cyclopenta[g]isoquinolin-7-yl]amino]pyridin-2-yl]sulfonylacetamide Intermediate 15 (50 mg, 0.13 mmol), Intermediate 181 (70.4 mg, 0.17 mmol), sodium tert-butoxide (38 mg, 0.39 mmol) and tBuXPhos Pd G3 (15.7 mg, 0.02 mmol) were heated in dry dioxane/tert-butanol (4 mL and 1 mL) in a 20 mL pressure tube at 60° C. with stirring for 2 hours. Solvent was removed and residue re-dissolved in DCM (5 mL) and TFA (0.2 mL) was added and stirred at room temperature for 16 hours. Solvent was removed. Water (10 mL) added and reaction extracted with DCM (3×10 mL), then IPA/chloroform (1:1) (2×10 mL). Organics dried over sodium sulfate and concentrated under vacuum. The residue was purified by silica column chromatography eluting with 20% to 100% EtOAc in heptane then 0-10% MeOH in DCM followed by acidic preparative HPLC to afford the title compound (1.5 mg, 2% yield) as an off white solid $^1$H NMR (500 MHz, Methanol-d4) $\delta_H$ 9.05 (s, 1H), 8.48 (s, 1H), 8.07 (s, 1H), 7.99 (d, J=2.7 Hz, 1H), 7.90 (d, J=8.7 Hz, 1H), 7.14 (dd, J=8.8, 2.7 Hz, 1H), 4.48-4.39 (m, 1H), 3.90 (dd, J=18.4, 6.5 Hz, 1H), 3.66 (dd, J=18.3, 3.8 Hz, 1H), 3.55 (dd, J=16.6, 6.5 Hz, 1H), 3.11 (dd, J=16.5, 3.9 Hz, 1H), 2.98 (d, J=19.9 Hz, 2H), 2.33-2.25 (m, 1H), 1.98 (s, 3H), 1.15-1.05 (m, 10H). LCMS [M+H]$^+$ 576.2, RT 1.81 min (Method 9).

Example 96

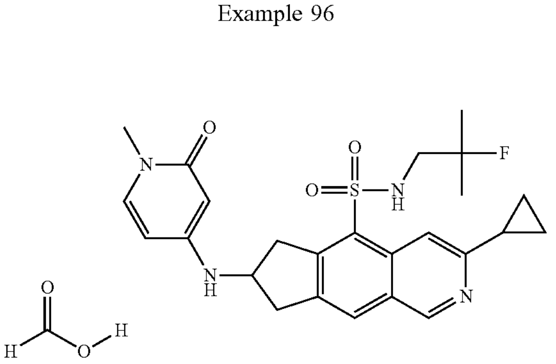

3-cyclopropyl-N-(2-fluoro-2-methyl-propyl)-7-[(1-methyl-2-oxo-4-pyridyl)amino]-7,8-dihydro-6H-cyclopenta[g]isoquinoline-5-sulfonamide; formate salt Intermediate 12 (40 mg, 0.10 mmol), 4-bromo-1-methyl-1,2-dihydropyridin-2-one (29.8 mg, 0.15 mmol), sodium tert-butoxide (30.5 mg, 0.31 mmol), $Pd_2(dba)_3$ (9.7 mg, 0.011 mmol) and tBuXPhos (9.0 mg, 0.021 mmol) were heated in dry dioxane/tert-butanol (3 and 1.5 mL) in a 20 mL pressure tube at 110° C. with stirring for 4 hours. Water (15 mL) was added and reaction extracted with DCM (3×10 mL), organics dried over sodium sulfate and concentrated under vacuum. The residue was purified by silica column chromatography eluting with 0-20% MeOH in DCM followed by acidic preparative HPLC to afford the title compound (25 mg, 44% yield) as an off white solid.

$^1$H NMR (500 MHz, DMSO-d6) $\delta_H$ 9.14 (s, 1H), 8.43 (s, 1H), 8.33 (t, J=6.5 Hz, 1H), 8.11 (s, 1H), 7.26 (d, J=7.4 Hz, 1H), 6.72 (d, J=6.2 Hz, 1H), 5.65 (dd, J=7.4, 2.3 Hz, 1H), 5.31 (d, J=2.4 Hz, 1H), 4.23-4.15 (m, 1H), 3.76 (dd, J=18.4, 6.8 Hz, 1H), 3.50 (dd, J=18.4, 4.1 Hz, 1H), 3.44 (dd, J=17.3, 6.8 Hz, 1H), 3.23 (s, 3H), 2.99 (dd, J=16.7, 4.1 Hz, 1H), 2.90 (dd, J=20.2, 6.5 Hz, 2H), 2.31-2.24 (m, 1H), 1.15-1.09 (m, 6H), 1.05-0.99 (m, 4H). LCMS [M+H]$^+$ 485.2, RT 2.22 min (Method 2).

Example 97

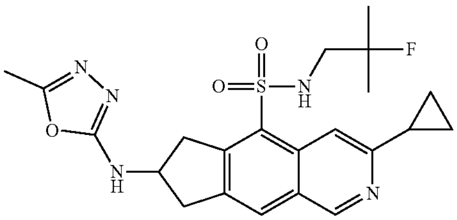 [SMILES: Cc1nnc(NC2Cc3cc4cnc(C5CC5)cc4c(S(=O)(=O)NCC(C)(C)F)c3C2)o1]

3-cyclopropyl-N-(2-fluoro-2-methylpropyl)-7-[(5-methyl-1,3,4-oxadiazol-2-yl)amino]-7,8-dihydro-6H-cyclopenta[g]isoquinoline-5-sulfonamide Intermediate 12 (50 mg, 0.13 mmol), 2-bromo-5-methyl-1,3,4-oxadiazole (30 mg, 0.18 mmol) and DIPEA (46.1 mL, 0.26 mmol) were heated in dry DMF (5 mL) in a 20 mL pressure tube at 90° C. with stirring for 16 hours. Solvent was removed, water (10 mL) added and reaction extracted with DCM (3×10 mL). Organics dried over sodium sulfate, concentrated under vacuum and the residue purified by silica column chromatography eluting with 50% to 100% EtOAc in heptane then 0-15% MeOH in DCM, followed by acidic preparative HPLC to afford the title compound (22 mg, 36% yield).

$^1$H NMR (500 MHz, DMSO-d6) $\delta_H$ 9.13 (s, 1H), 8.43 (s, 1H), 8.32 (t, J=6.5 Hz, 1H), 8.10 (s, 1H), 7.70 (d, J=5.8 Hz, 1H), 4.38-4.28 (m, 1H), 3.77 (dd, J=18.4, 6.9 Hz, 1H), 3.58 (dd, J=18.4, 4.7 Hz, 1H), 3.44-3.39 (m, 1H), 3.10 (dd, J=16.4, 4.7 Hz, 1H), 2.91 (dd, J=19.9, 6.4 Hz, 2H), 2.31-2.23 (m, 4H), 1.18-1.09 (m, 6H), 1.05-0.99 (m, 4H). LCMS [M+H]$^+$ 460.3, RT 2.21 min (Method 2).

Example 98

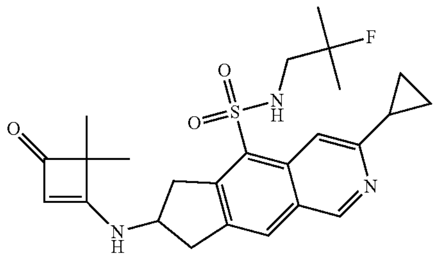 [SMILES: CC(C)(F)CNS(=O)(=O)c1c2c(cc3cnc(C4CC4)cc13)CC(NC1=CC(=O)C1(C)C)C2]

3-cyclopropyl-7-[(4,4-dimethyl-3-oxocyclobuten-1-yl)amino]-N-(2-fluoro-2-methylpropyl)-7,8-dihydro-6H-cyclopenta[g]isoquinoline-5-sulfonamide To Intermediate 12 (50 mg, 0.13 mmol) in THF (2 mL) was added DIPEA (34.6 µl, 0.199 mmol), followed by 2,2-dimethylcyclobutane-1,3-dione (22.2 mg, 0.199 mmol). The mixture was stirred at 70° C. for 18 hours. The solvent was removed and residue purified by acidic preparative HPLC to afford the title compound (32 mg, 50% yield) as a white solid.

$^1$H NMR (500 MHz, DMSO-d6) $\delta_H$ 9.16 (s, 1H), 8.50 (d, J=6.7 Hz, 1H), 8.44 (s, 1H), 8.39 (t, J=6.5 Hz, 1H), 8.14 (s, 1H), 4.54 (s, 1H), 4.26-4.16 (m, 1H), 3.82 (dd, J=18.4, 7.2 Hz, 1H), 3.55 (dd, J=18.4, 4.8 Hz, 1H), 3.47 (dd, J=17.3, 7.1 Hz, 1H), 3.09 (dd, J=16.8, 4.8 Hz, 1H), 2.93 (dd, J=19.9, 6.5 Hz, 2H), 2.32-2.25 (m, 1H), 1.19-1.12 (m, 6H), 1.08 (s, 3H), 1.07 (s, 3H), 1.05-1.01 (m, 4H). LCMS [M+H]$^+$ 472.3, RT 2.51 min (Method 2).

Example 99

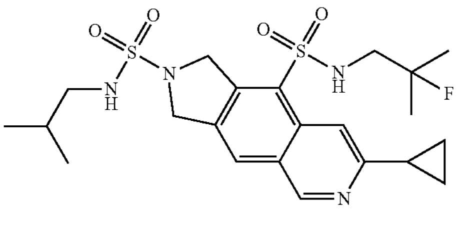 [SMILES: CC(C)CNS(=O)(=O)N1Cc2cc3cnc(C4CC4)cc3c(S(=O)(=O)NCC(C)(C)F)c2C1]

7-cyclopropyl-9-N-(2-fluoro-2-methylpropyl)-2-N-(2-methylpropyl)-1,3-dihydropyrrolo[3,4-g]isoquinoline-2,9-disulfonamide A mixture of Intermediate 173 (20 mg, 0.041 mmol), cyclopropylboronic acid (8.7 mg, 0.10 mmol), $Pd(OAc)_2$ (0.45 mg, 2.0 μmol), $P(Cy)_3 \cdot HBF_4$ (2.2 mg, 6.0 μmol) and $K_3PO_4$ (21.5 mg, 0.10 mmol) in toluene (1 mL)/water (0.05 mL) was stirred and heated to 120° C. for 3 hours under reflux. Reaction diluted with DCM (5 mL), dried over $MgSO_4$, filtered through Celite and concentrated under reduced pressure to give crude product that was purified by silica column chromatography, eluting with 20-60% EtOAc/heptane to afford the title compound (6 mg, 30% yield) as a white solid.

$^1$H NMR (500 MHz, Chloroform-d) $\delta_H$ 9.13 (s, 1H), 8.26 (s, 1H), 7.95 (s, 1H), 5.17-5.10 (m, 3H), 4.82 (s, 2H), 4.36 (t, J=6.3 Hz, 1H), 3.01 (dd, J=19.9, 6.5 Hz, 2H), 2.96 (t, J=6.6 Hz, 2H), 2.26-2.20 (m, 1H), 1.87-1.79 (m, 1H), 1.30 (d, J=21.5 Hz, 6H), 1.20-1.15 (m, 2H), 1.12-1.06 (m, 2H), 0.96 (d, J=6.7 Hz, 6H). LCMS $[M+H]^+$ 499.1, RT 3.44 min (Method 2).

Example 100

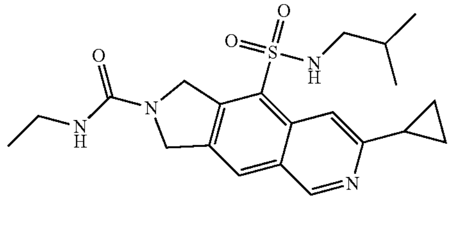 [SMILES: CCNC(=O)N1Cc2cc3cnc(C4CC4)cc3c(S(=O)(=O)NCC(C)C)c2C1]

7-cyclopropyl-N-ethyl-9-(2-methylpropylsulfamoyl)-1,3-dihydropyrrolo[3,4-g]isoquinoline-2-carboxamide Intermediate 180 (20 mg, 0.049 mmol) and cyclopropyl boronic acid (8.4 mg, 0.097 mmol) were dissolved in de gassed dioxane (2 mL) and 2M $K_2CO_3$ (73.0 μL, 0.14 mmol). Under a nitrogen atmosphere, (2-{[bis(2,4-di-tert-butylphenoxy)phosphanyl]oxy}-3,5-di-tert-butylphenyl)(chloro) palladium-tricyclohexylphosphane (1:1) (Bedford catalyst) (5.19 mg, 0.005 mmol) was added. The mixture was stirred for 3 hours at 120° C. in a microwave, after which the dioxane was removed, the reaction diluted with DCM (10 mL), washed with water, the combined organic layers dried over $MgSO_4$ and concentrated under reduced pressure to give a crude product which was purified by silica column chromatography eluting with 50% to 100% EtOAc in heptane followed by preparative HPLC to afford the title compound (2 mg, 10% yield) as a white solid.

$^1$H NMR (500 MHz, Chloroform-d) $\delta_H$ 9.17 (s, 1H), 8.30 (s, 1H), 8.02 (s, 1H), 5.16 (s, 2H), 4.95 (s, 2H), 4.83 (t, J=6.3 Hz, 1H), 4.53 (t, J=5.3 Hz, 1H), 3.44-3.38 (m, 2H), 2.71 (t, J=6.6 Hz, 2H), 2.29-2.21 (m, 1H), 1.73-1.64 (m, 1H), 1.25 (t, J=7.2 Hz, 3H), 1.22-1.17 (m, 2H), 1.13-1.08 (m, 2H), 0.84 (d, J=6.7 Hz, 6H). LCMS $[M+H]^+$ 417.2, RT 2.81 min (Method 2).

Example 101

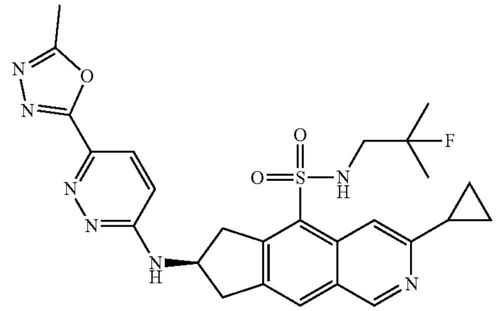 [SMILES: Cc1nnc(-c2ccc(N[C@@H]3Cc4cc5cnc(C6CC6)cc5c(S(=O)(=O)NCC(C)(C)F)c4C3)nn2)o1]

(7R)-3-cyclopropyl-N-(2-fluoro-2-methylpropyl)-7-[[6-(5-methyl-1,3,4-oxadiazol-2-yl)pyridazin-3-yl]amino]-7,8-dihydro-6H-cyclopenta[g]isoquinoline-5-sulfonamide A suspension of Intermediate 151 (20 mg, 0.04 mmol) in $POCl_3$ (1 mL) was heated at 70° C. for 4 hours. The solvent was removed and ice added to the flask followed by EtOAc (10 mL). The aqueous layer was basified to pH10 with saturated $NaHCO_3$ solution and then extracted with EtOAc (2×10 mL). The organic layer was dried ($Na_2SO_4$), the solvent removed and the residue purified by silica column chromatography, eluting with 0-100% 7M $NH_3$ in MeOH/DCM) followed by preparative, basic, reverse phase HPLC to afford the title compound (5 mg, 26% yield) as a white solid.

$^1$H NMR (500 MHz, Methanol-d4) $\delta_H$ 9.07 (s, 1H), 8.50 (s, 1H), 8.10 (s, 1H), 7.94 (d, J=9.4 Hz, 1H), 6.99 (d, J=9.4 Hz, 1H), 4.98-4.91 (m, 1H), 4.01 (dd, J=18.5, 6.8 Hz, 1H), 3.72 (dd, J=18.6, 4.9 Hz, 1H), 3.62 (dd, J=17.6, 6.9 Hz, 1H), 3.19 (dd, J=16.3, 4.7 Hz, 1H), 3.02 (dd, J=19.6, 2.8 Hz, 2H), 2.66 (s, 3H), 2.35-2.25 (m, 1H), 1.17 (s, 3H), 1.12 (s, 3H), 1.11-1.06 (m, 4H). LCMS $[M+H]^+$ 538, RT 2.39 min (Method 2).

Example 102

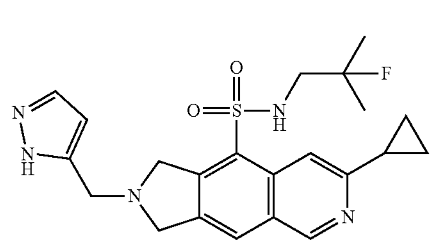 [SMILES: CC(C)(F)CNS(=O)(=O)c1c2c(cc3cnc(C4CC4)cc13)CN(Cc1ccn[nH]1)C2]

7-cyclopropyl-N-(2-fluoro-2-methylpropyl)-2-(1H-pyrazol-5-ylmethyl)-1,3-dihydropyrrolo[3,4-g]iso-quinoline-9-sulfonamide To Intermediate 27 in THF (1 mL) were added 1H-pyrazole-5-carbaldehyde (14 mg, 0.15 mmol) and Ti(IV) isopropoxide (67 μL, 0.23 mmol). The reaction was stirred at room temperature for 3 hours followed by addition of sodium triacetoxy borohydride (53 mg, 0.25 mmol) and a further 16 hours at room temperature. Reaction diluted with EtOAc (10 mL) quenched with $NaHCO_3$ (10 mL), the layers separated and the aqueous extracted with EtOAc (10 mL). The combined organic extracts were washed with brine (10 mL), dried over $MgSO_4$, concentrated under reduced pressure and purified by acidic preparative HPLC to afford the title compound (5 mg, 9% yield) as a red solid.

$^1$H NMR (500 MHz, DMSO-d6) $\delta_H$ 9.15 (s, 1H), 8.41 (s, 2H), 8.08 (s, 1H), 7.59 (s, 1H), 6.22 (d, J=1.9 Hz, 1H), 4.35 (s, 2H), 3.97 (s, 2H), 3.89 (s, 2H), 2.93 (d, J=20.0 Hz, 2H), 2.29 (p, J=6.5, 5.9 Hz, 1H), 1.16 (d, J=21.4 Hz, 6H), 1.06-0.98 (m, 4H). LCMS $[M+H]^+$ 444.3, RT 1.61 min (Method 2)

Example 103

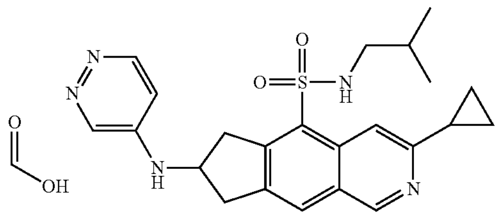 [SMILES: O=CO ; CC(C)CNS(=O)(=O)c1c2c(cc3cnc(C4CC4)cc13)CC(Nc1ccnnc1)C2]

3-cyclopropyl-N-isobutyl-7-(pyridazin-4-ylamino)-7,8-dihydro-6H-cyclopenta[g]isoquinoline-5-sulfonamide; formic acid Intermediate 122 (50 mg, 0.14 mmol), sodium tert-butoxide (40 mg, 417 μmol), XantPhos (16 mg, 28 μmol) and 4-bromopyridazine hydrobromide (1:1) (50 mg, 0.21 mmol) were combined in 2:1 dioxane/tBuOH (4.5 mL) in a sealable tube and degassed with nitrogen. $Pd_2(dba)_3$ (12.7 mg, 13.9 μmol) was added and the sealed tube heated at 110° C. with stirring for 1.5 hours. Reaction diluted with EtOAc (5 mL), filtered through Celite, concentrated and the residues purified by silica column chromatography, eluting with 0-20% MeOH/DCM, followed by acidic preparative HPLC to afford the title compound (8.4 mg, 12% yield) as a white solid.

$^1$H NMR (500 MHz, DMSO-d6) $\delta_H$ 9.16 (s, 1H), 8.58-8.53 (m, 2H), 8.41 (s, 1H), 8.16 (s, 1H), 8.14 (s, 1H), 8.02 (t, J=6.0 Hz, 1H), 7.24 (d, J=6.4 Hz, 1H), 6.72 (dd, J=6.1, 3.1 Hz, 1H), 4.40-4.32 (m, 1H), 3.79 (dd, J=18.3, 6.7 Hz, 1H), 3.56-3.46 (m, 2H), 3.01 (dd, J=16.6, 4.1 Hz, 1H), 2.48-2.45 (m, 2H), 2.29-2.21 (m, 1H), 1.54-1.44 (m, 1H), 1.04-1.00 (m, 4H), 0.63 (d, J=6.7 Hz, 3H), 0.63 (d, J=6.7 Hz, 3H). LCMS $[M+H]^+$ 438.2, RT 1.77 min (Method 2).

Example 104

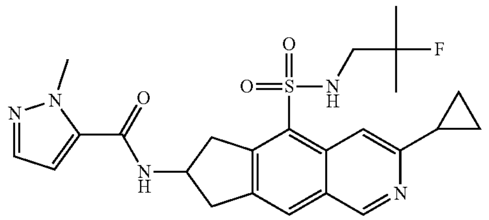 [SMILES: Cn1nccc1C(=O)NC1Cc2cc3cnc(C4CC4)cc3c(S(=O)(=O)NCC(C)(C)F)c2C1]

N-[3-cyclopropyl-5-[(2-fluoro-2-methylpropyl) sulfamoyl]-7,8-dihydro-6H-cyclopenta[g]isoquinolin-7-yl]-2-methylpyrazole-3-carboxamide 1-methyl-1H-pyrazole-5-carboxylic acid (8.02 mg, 0.06 mmol) and DIPEA (19.3 μL, 0.12 mmol) were dissolved in DMF (0.5 mL) and HATU (22.2 mg, 0.06 mmol) was added. After stirring for 10 mins, Intermediate 12 (20 mg, 0.05 mmol) was added and the solution stirred at room temperature for 15 minutes. The solution was diluted with 1:1 MeCN/water (1 mL) and purified by acidic preparative HPLC to afford the title compound (21 mg, 78% yield) as a white solid.

$^1$H NMR (500 MHz, DMSO-d6) $\delta_H$ 9.15 (s, 1H), 8.67 (d, J=6.9 Hz, 1H), 8.44 (s, 1H), 8.35 (t, J=6.5 Hz, 1H), 8.11 (s, 1H), 7.43 (d, J=2.0 Hz, 1H), 6.84 (d, J=2.0 Hz, 1H), 4.69 (h, J=7.0 Hz, 1H), 4.06 (s, 3H), 3.87 (dd, J=18.5, 7.7 Hz, 1H), 3.53-3.41 (m, 2H), 3.10 (dd, J=16.8, 6.3 Hz, 1H), 2.94 (dd, J=20.1, 6.5 Hz, 2H), 2.32-2.25 (m, 1H), 1.13 (d, J=21.4 Hz, 3H), 1.13 (d, J=21.4 Hz, 3H), 1.06-0.99 (m, 4H). LCMS $[M+H]^+$ 486.3, RT 3.09 min (Method 9).

Example 105

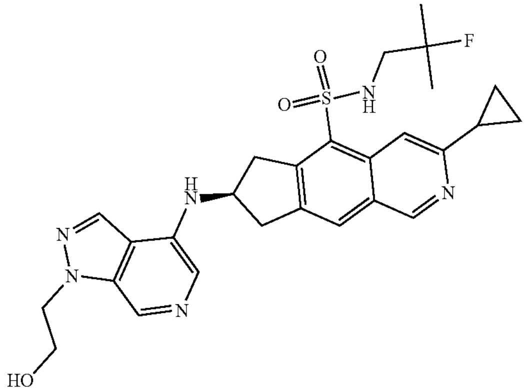 [SMILES: CC(C)(F)CNS(=O)(=O)c1c2c(cc3cnc(C4CC4)cc13)C[C@@H](Nc1cncc3c1cnn3CCO)C2]

(7R)-3-cyclopropyl-N-(2-fluoro-2-methylpropyl)-7-[[1-(2-hydroxyethyl) pyrazolo[3,4-c]pyridin-4-yl]amino]-7,8-dihydro-6H-cyclopenta[g]isoquinoline-5-sulfonamide Intermediate 167 (20 mg, 0.03 mmol) was dissolved in THF (1 mL) and 1M TBAF in THF (61 μL) was added. The solution was left to stand at room temperature for 2 hours, the reaction concentrated and purified by silica column chromatography eluting with 5-20% MeOH/DCM then using a SCX-2 cartridge eluting with methanol followed by 3.5 N ammonia in methanol to afford the title compound (9.9 mg, 59% yield) as a pale yellow solid.

$^1$H NMR (500 MHz, DMSO-d6) $\delta_H$ 9.15 (s, 1H), 8.44 (s, 1H), 8.40 (s, 1H), 8.33 (t, J=6.5 Hz, 1H), 8.22 (s, 1H), 8.13 (s, 1H), 7.58 (s, 1H), 6.69 (d, J=6.0 Hz, 1H), 4.85 (t, J=5.5 Hz, 1H), 4.60-4.50 (m, 1H), 4.44 (t, J=5.5 Hz, 2H), 3.93 (dd, J=18.4, 6.9 Hz, 1H), 3.78 (q, J=5.5 Hz, 2H), 3.66-3.54 (m, 2H), 3.13 (dd, J=16.7, 4.6 Hz, 1H), 2.90 (dd, J=20.3, 6.5 Hz, 2H), 2.32-2.24 (m, 1H), 1.09 (d, J=21.4 Hz, 3H), 1.06 (d, J=21.4 Hz, 3H), 1.03-1.00 (m, 4H). LCMS $[M+H]^+$ 539.2, RT 1.70 min (Method 2).

Example 106

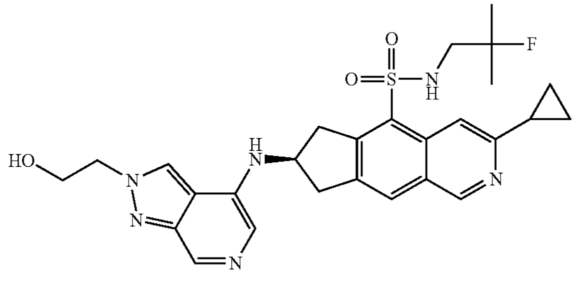 [SMILES: CC(C)(F)CNS(=O)(=O)c1c2c(cc3cnc(C4CC4)cc13)C[C@@H](Nc1cncc3nn(CCO)cc13)C2]

(7R)-3-cyclopropyl-N-(2-fluoro-2-methylpropyl)-7-[[2-(2-hydroxyethyl) pyrazolo[3,4-c]pyridin-4-yl] amino]-7,8-dihydro-6H-cyclopenta[g]isoquinoline-5-sulfonamide Intermediate 168 (30 mg, 0.05 mmol) was dissolved in THF (1 mL) and 1M TBAF in THF (92 μL) was added. The solution was left to stand at room temperature for 2 hours. Water (5 mL) was added, extracted with EtOAc (2×10 mL), dried over $MgSO_4$ and concentrated under reduced pressure. Residue purified by silica column chromatography eluting with 0-20% MeOH/DCM to afford the title compound (6.9 mg, 28% yield) as a yellow solid.

$^1$H NMR (500 MHz, DMSO-d6) $\delta_H$ 9.14 (s, 1H), 8.45-8.43 (m, 2H), 8.39 (s, 1H), 8.34 (t, J=6.2 Hz, 1H), 8.13 (s, 1H), 7.36 (s, 1H), 6.47 (d, J=6.2 Hz, 1H), 5.01 (t, J=5.3 Hz, 1H), 4.51-4.44 (m, 1H), 4.42 (t, J=5.3 Hz, 2H), 3.89 (dd, J=18.5, 6.8 Hz, 1H), 3.82 (q, J=5.3 Hz, 2H), 3.64 (dd, J=18.5, 4.5 Hz, 1H), 3.57 (dd, J=17.2, 6.9 Hz, 1H), 3.13 (dd, J=16.8, 4.2 Hz, 1H), 2.89 (dd, J=20.2, 5.8 Hz, 2H), 2.31-2.24 (m, 1H), 1.13-1.00 (m, 10H). LCMS $[M+H]^+$ 539.1, RT 1.65 min (Method 2).

Example 107

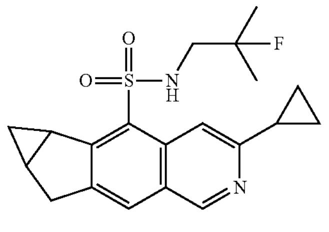 [SMILES: CC(C)(F)CNS(=O)(=O)c1c2c(cc3cnc(C4CC4)cc13)CC1CC21]

13-cyclopropyl-N-(2-fluoro-2-methylpropyl)-12-azatetracyclo[8.4.0.03,8.04,6]tetradeca-1 (10),2,8, 11,13-pentaene-2-sulfonamide Intermediate 144 (60 mg, 0.12 mmol) was dissolved in DCM (5 mL) and TFA (0.5 mL) was added. Reaction stirred at room temperature for 4.5 hours, solvent removed and residue purified by silica column chromatography, eluting with 30-100% EtOAc/heptane, followed by passing through a 2 g SCX-2 cartridge eluting with 3.5 N ammonia in MeOH to afford the title compound (29 mg, 62% yield) as a white solid.

$^1$H NMR (500 MHz, Chloroform-d) $\delta_H$ 8.98 (s, 1H), 8.45 (s, 1H), 7.80 (s, 1H), 5.13 (t, J=6.6 Hz, 1H), 3.43-3.34 (m, 2H), 3.13 (d, J=17.2 Hz, 1H), 3.03-2.87 (m, 2H), 2.25-2.18 (m, 1H), 2.14-2.07 (m, 1H), 1.45 (td, J=8.2, 4.7 Hz, 1H), 1.33 (d, J=21.5 Hz, 3H), 1.31 (d, J=21.5 Hz, 3H), 1.15-1.10 (m, 2H), 1.07-1.01 (m, 2H), 0.24-0.20 (m, 1H). LCMS $[M+H]^+$ 375.3, RT 2.82 min (Method 1).

Example 108

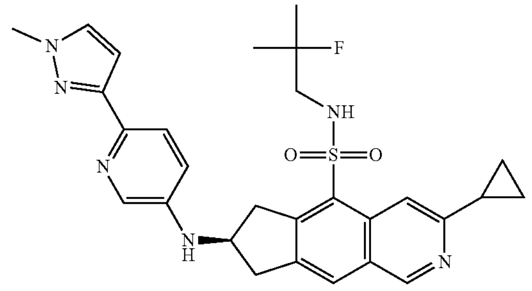 [SMILES: Cn1ccc(-c2ccc(N[C@@H]3Cc4cc5cnc(C6CC6)cc5c(S(=O)(=O)NCC(C)(C)F)c4C3)cn2)n1]

(7R)-3-cyclopropyl-N-(2-fluoro-2-methylpropyl)-7-[[6-(1-methylpyrazol-3-yl)pyridin-3-yl]amino]-7,8-dihydro-6H-cyclopenta[g]isoquinoline-5-sulfonamide Into a pressure tube were introduced Intermediate 15 (100 mg, 0.265 mmol), 5-bromo-2-(1-methylpyrazol-3-yl)pyridine (82 mg, 0.344 mmol), sodium tert-butoxide (51 mg, 0.525 mmol), tBuXPhos Pd G3 (21 mg, 0.026 mmol) and tBuXPhos (11 mg, 0.026 mmol). Separately, nitrogen was bubbled through a mixture of anhydrous 1,4-dioxane (2.0 mL) and tert-butanol (1.0 mL) for 10 minutes then transferred to the pressure tube. After nitrogen bubbling the reaction mixture for a further 2 minutes, the tube was closed under an atmosphere of nitrogen and warmed to 110° C. for 90 minutes. After cooling to room temperature, the reaction mixture was concentrated in-vacuo, the residue dissolved in ethyl acetate (30 mL) then washed with water (10 mL), saturated aqueous sodium bicarbonate (10 mL) and brine (10 mL). The organic phase was dried over sodium sulfate, filtered and the filtrate adsorbed onto silica in-vacuo. Purification by column chromatography, eluting with a gradient of ethyl acetate in heptane then ethanol in ethyl acetate, followed by basic, RP preparative HPLC gave the title compound (78.5 mg, 54% yield) as a solid.

$^1$H NMR (500 MHz, d-chloroform) $\delta_H$ 9.06 (s, 1H), 8.32 (s, 1H), 8.03 (d, J=2.6 Hz, 1H), 7.91 (s, 1H), 7.73 (d, J=8.5 Hz, 1H), 7.36 (d, J=2.2 Hz, 1H), 6.96 (dd, J=8.6, 2.9 Hz, 1H), 6.70 (d, J=2.3 Hz, 1H), 5.12 (s, 1H), 4.44-4.38 (m, 1H), 3.97 (d, J=6.7 Hz, 1H), 3.95 (s, 3H), 3.89 (dd, J=18.4, 6.5 Hz, 1H), 3.65 (dd, J=18.4, 3.6 Hz, 1H), 3.50 (ddd, J=16.3, 6.4, 1.2 Hz, 1H), 3.10 (dd, J=16.4, 3.7 Hz, 1H), 3.06-2.91 (m, 2H), 2.21 (ddd, J=13.0, 8.2, 4.8 Hz, 1H), 1.24 (d, J=21.5 Hz, 3H), 1.23 (d, J=21.5 Hz, 3H), 1.14 (dt, J=5.9, 2.9 Hz, 2H), 1.06 (dt, J=8.2, 3.0 Hz, 2H). LCMS $[M+H]^+$ 535, RT 2.07 min (Method 2).

Example 109

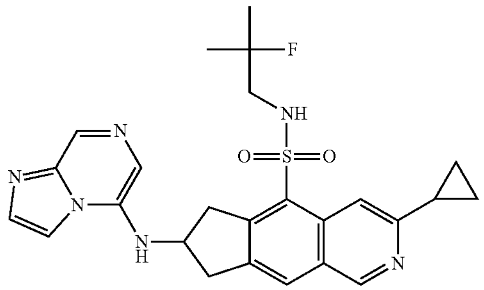 [SMILES: CC(C)(F)CNS(=O)(=O)c1c2c(cc3cnc(C4CC4)cc13)CC(Nc1cncc3nccn13)C2]

3-cyclopropyl-N-(2-fluoro-2-methylpropyl)-7-(imidazo[1,2-a]pyrazin-5-ylamino)-7,8-dihydro-6H-cyclopenta[g]isoquinoline-5-sulfonamide Into a pressure tube were introduced Intermediate 12 (50 mg, 0.132 mmol), 5-bromoimidazo[1,2-a]pyrazine (39 mg, 0.199 mmol), sodium tert-butoxide (25 mg, 0.265 mmol), $Pd_2(dba)_3$ (17 mg, 0.019 mmol) and tBuXPhos (16 mg, 0.037 mmol). Separately, nitrogen was bubbled through a mixture of anhydrous 1,4-dioxane (2.0 mL) and tert-butanol (1.0 mL) for 10 minutes then transferred to the pressure tube. After nitrogen bubbling the reaction mixture for a further 2 minutes, the tube was closed under an atmosphere of nitrogen and warmed to 110° C. for 2.5 hours. After cooling to room temperature the reaction mixture was adsorbed onto silica and purified by column chromatography eluting with a gradient of methanol in dichloromethane. Further purification by acidic preparative HPLC gave the title compound (2.4 mg, 4% yield) as a colourless solid.

$^1$H NMR (500 MHz, d6-dmso) $\delta_H$ 9.16 (s, 1H), 8.46 (s, 1H), 8.45 (s, 1H), 8.36 (s, 1H), 8.14 (s, 1H), 8.11 (s, 1H), 7.72 (s, 1H), 7.39 (s, 1H), 6.96 (d, J=6.0 Hz, 1H), 4.63-4.57 (m, 1H), 4.01 (dd, J=18.5, 7.1 Hz, 1H), 3.75-3.61 (m, 2H), 3.23 (dd, J=16.4, 5.5 Hz, 1H), 2.91 (d, J=20.1 Hz, 2H), 2.28 (p, J=6.4 Hz, 1H), 1.12-0.99 (m, 10H). LCMS [M+H]$^+$ 495, RT 1.91 min (Method 2).

Example 110

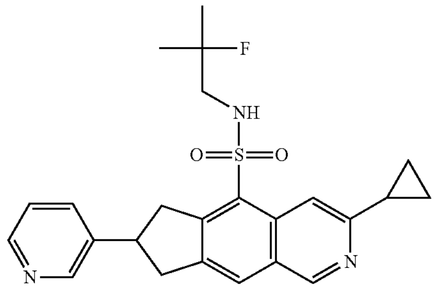 [SMILES: CC(C)(F)CNS(=O)(=O)c1c2c(cc3cnc(C4CC4)cc13)CC(c1cccnc1)C2]

3-cyclopropyl-N-(2-fluoro-2-methylpropyl)-7-pyridin-3-yl-7,8-dihydro-6H-cyclopenta[g]isoquinoline-5-sulfonamide To the solution of Intermediate 164 (27% purity LCMS-$UV_{215}$) in dichloromethane (2 mL) was introduced trifluoroacetic acid (1 mL, dropwise). After 30 minutes the reaction mixture was concentrated in-vacuo and the residue purified by basic preparative HPLC to give the title compound (2.6 mg, 13% yield over two steps).

$^1$H NMR (500 MHz, d-chloroform) $\delta_H$ 9.09 (s, 1H), 8.59 (d, J=1.9 Hz, 1H), 8.53-8.48 (m, 1H), 8.33 (s, 1H), 7.95 (s, 1H), 7.62-7.57 (m, 1H), 7.26-7.22 (m, 1H), 5.05 (t, J=6.5 Hz, 1H), 4.13 (dd, J=18.0, 8.0 Hz, 1H), 3.75 (p, J=8.2 Hz, 1H), 3.57 (dd, J=17.8, 8.5 Hz, 2H), 3.30-3.20 (m, 1H), 3.06-2.87 (m, 2H), 2.23 (tt, J=8.2, 4.8 Hz, 1H), 1.30 (d, J=21.2 Hz, 3H), 1.26 (d, J=21.2 Hz, 3H), 1.15 (dt, J=5.9, 3.0 Hz, 2H), 1.10-1.05 (m, 2H). LCMS [M+H]$^+$ 440, RT 1.93 min (Method 2).

Example 111

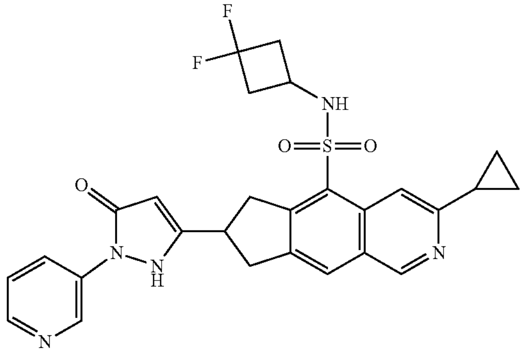 [SMILES: O=c1cc(C2Cc3cc4cnc(C5CC5)cc4c(S(=O)(=O)NC4CC(F)(F)C4)c3C2)[nH]n1-c1cccnc1]

3-cyclopropyl-N-(3,3-difluorocyclobutyl)-7-(3-oxo-2-pyridin-3-yl-1H-pyrazol-5-yl)-7,8-dihydro-6H-cyclopenta[g]isoquinoline-5-sulfonamide To a solution of Intermediate 166 (50 mg at 83% purity, 0.084 mmol) in ethanol (1 mL) was introduced acetic acid (12 mg, 0.203 mmol) and 3-pyridylhydrazine hydrochloride (22 mg, 0.152 mmol). The reaction mixture was warmed to 50° C. for 60 minutes. Potassium carbonate (100 mg) was introduced and warming continued at 50° C. for a further 30 minutes. After cooling to room temperature, the reaction mixture was filtered and the filter-cake washed with ethanol (1 mL). The combined filtrate was concentrated in-vacuo and the residue suspended in pH 6.5 aqueous (phosphate) buffer solution which was extracted with ethyl acetate (2×8 mL). Sodium chloride was then introduced to saturate the buffer solution and this solution extracted with tetrahydrofuran (5 mL). The pooled ethyl acetate and tetrahydrofuran extracts were combined, concentrated in-vacuo and the residue purified by acidic, preparative HPLC, followed by further purification by silica column chromatography using a gradient of methanol in dichloromethane afforded the title compound (7.0 mg, 16% yield) as an oil.

$^1$H NMR (500 MHz, d-chloroform) $\delta_H$ 9.09 (d, J=2.2 Hz, 1H), 9.07 (s, 1H), 8.42 (dd, J=4.7, 1.3 Hz, 1H), 8.31 (s, 1H), 8.23 (d, J=8.3 Hz, 1H), 7.96 (s, 1H), 7.33 (dd, J=8.4, 4.7 Hz, 1H), 5.85 (s, 1H), 3.99 (dd, J=18.2, 8.1 Hz, 1H), 3.77-3.64 (m, 2H), 3.60 (p, J=8.0 Hz, 1H), 3.53 (s, 2H), 3.44 (qd, J=16.3, 8.1 Hz, 2H), 2.69 (th, J=12.8, 6.2 Hz, 2H), 2.42-2.25 (m, 2H), 2.14 (tt, J=8.3, 4.8 Hz, 1H), 1.13 (dt, J=8.1, 4.2 Hz, 2H), 1.03 (dq, J=6.8, 3.9 Hz, 2H). LCMS [M+H]$^+$ 538, RT 2.54 min (Method 2).

Example 112

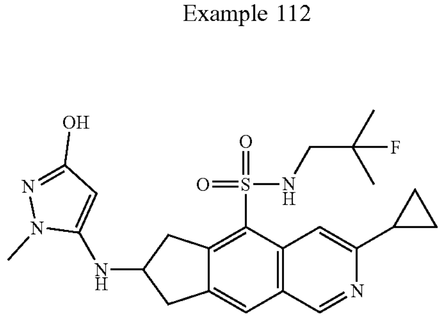

3-cyclopropyl-N-(2-fluoro-2-methylpropyl)-7-[(5-hydroxy-2-methylpyrazol-3-yl)amino]-7,8-dihydro-6H-cyclopenta[g]isoquinoline-5-sulfonamide To a stirred solution of Intermediate 145 (55 mg, 0.0976 mmol) in absolute ethanol (2 mL) was added palladium on carbon (5 mg). The reaction was stirred overnight at room temperature under a hydrogen atmosphere. Reaction filtered through Celite, solvent removed and residue purified by C18 reverse phase column chromatography eluting with 0-100% MeCN in $H_2O$ (pH3, formic acid) to afford the title compound (7.0 mg, 13% yield).

$^1$H NMR (400 MHz, DMSO-d6) $\delta_H$ 9.19 (s, 1H), 9.12 (s, 1H), 8.43 (d, J=1.0 Hz, 1H), 8.32 (d, J=6.4 Hz, 1H), 8.08 (s, 1H), 5.82 (s, 1H), 4.68 (s, 1H), 4.02 (q, J=5.8 Hz, 1H), 3.76 (dd, J=18.5, 6.8 Hz, 1H), 3.50 (dd, J=18.5, 4.8 Hz, 1H), 3.40 (dd, J=16.6, 6.9 Hz, 1H), 3.13 (s, 3H), 3.02 (dd, J=16.7, 4.8 Hz, 1H), 2.91 (dd, J=20.2, 5.6 Hz, 2H), 2.27 (q, J=6.8 Hz, 1H), 1.13 (dd, J=21.4, 11.5 Hz, 6H), 1.06-0.98 (m, 4H). LCMS $[M+H]^+$ 474.0, RT 1.52 min (Method 10)

Example 113

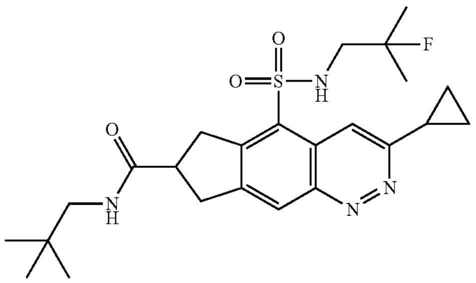 [SMILES: CC(C)(C)CNC(=O)C1Cc2cc3nnc(C4CC4)cc3c(S(=O)(=O)NCC(C)(C)F)c2C1]

3-cyclopropyl-N-(2,2-dimethylpropyl)-5-[(2-fluoro-2-methylpropyl) sulfamoyl]-7,8-dihydro-6H-cyclopenta[g]cinnoline-7-carboxamide To a solution of Intermediate 69 (10 mg, 0.0245 mmol) in anhydrous DMF (1 mL) at room temperature was added N,N-diisopropylethylamine (20 µL, 0.115 mmol). To the resultant solution was added HATU (14 mg, 0.0357 mmol) followed by a few drops of neopentylamine after a few minutes. Reaction stirred overnight, diluted with 30 mL DCM and 50 mL $H_2O$, the phases separated and the aqueous re-extracted with 2×20 mL DCM. The combined organic phases were dried (phase separator), concentrated and purified by silica column chromatography, eluting with 0-100% ethyl acetate in iso-hexane to afford the title compound (6.1 mg, 52% yield) as an off-white solid.

$^1$H NMR (400 MHz, Chloroform-d) $\delta_H$ 8.55 (s, 1H), 8.45 (s, 1H), 5.63 (t, J=6.4 Hz, 1H), 5.04 (t, J=6.6 Hz, 1H), 3.90 (dd, J=18.6, 8.2 Hz, 1H), 3.76 (dd, J=18.7, 7.3 Hz, 1H), 3.57-3.38 (m, 2H), 3.22 (p, J=7.9 Hz, 1H), 3.17-2.92 (m, 4H), 2.39 (tt, J=8.6, 4.9 Hz, 1H), 1.43-1.38 (m, 2H), 1.34 (d, J=21.5 Hz, 3H), 1.25 (dd, J=8.2, 2.9 Hz, 2H), 1.20 (d, J=21.5 Hz, 3H), 0.93 (s, 9H). LCMS $[M+H]^+$ 477.0, RT 2.08 min (Method 10).

Example 114

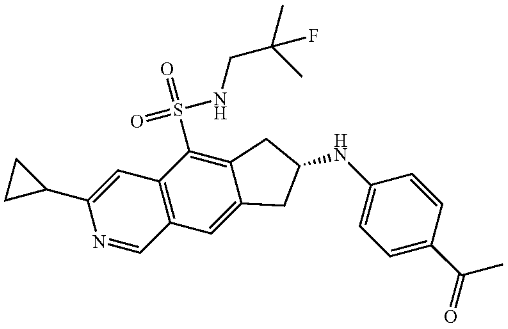 [SMILES: CC(=O)c1ccc(N[C@@H]2Cc3cc4cnc(C5CC5)cc4c(S(=O)(=O)NCC(C)(C)F)c3C2)cc1]

(7R)-7-(4-acetylanilino)-3-cyclopropyl-N-(2-fluoro-2-methylpropyl)-7,8-dihydro-6H-cyclopenta[g]isoquinoline-5-sulfonamide To 4'-iodoacetophenone (24.9 mg) were added Intermediate 15 (25 mg, 0.0662 mmol) in 1,4-dioxane (2 mL) and sodium tert-butoxide (19.1 mg, 0.199 mmol). The reaction was degassed under vacuum and filled with an atmosphere of nitrogen (×3). tBuXPhos Pd G3 (8 mg, 0.0099 mmol) was added and reaction stirred at 75° C. for 2 hours then at room temperature overnight. Reaction filtered through celite, washed with dioxane (×3) and filtrate evaporated. Residue purified by silica column chromatography eluting with 10-100% EtOAc in hexane to yield the title compound (18 mg, 55% yield). LCMS $[M+H]^+$ 496.2, RT 2.26 min (Method 10).

Examples 115 and 116

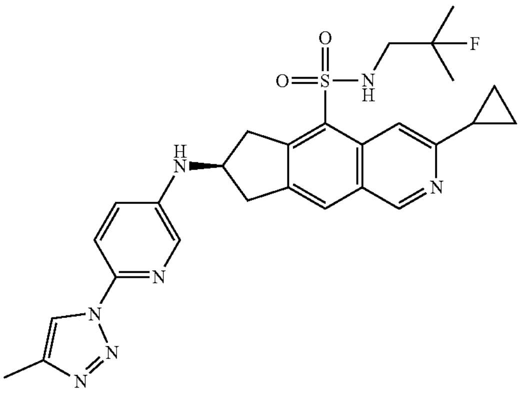

and

-continued

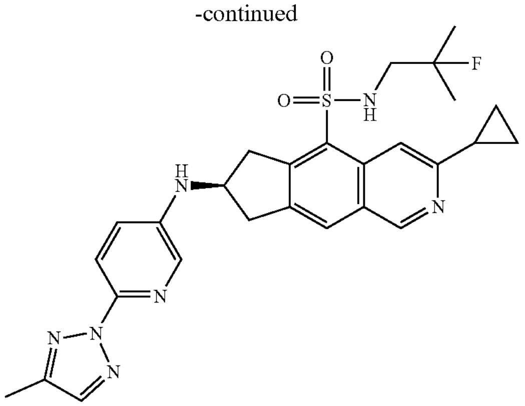

(7R)-3-cyclopropyl-N-(2-fluoro-2-methylpropyl)-7-[[6-(4-methyltriazol-1-yl)pyridin-3-yl]amino]-7,8-dihydro-6H-cyclopenta[g]isoquinoline-5-sulfonamide and (7R)-3-cyclopropyl-N-(2-fluoro-2-methylpropyl)-7-[[6-(4-methyltriazol-2-yl)pyridin-3-yl]amino]-7,8-dihydro-6H-cyclopenta[g]isoquinoline-5-sulfonamide Intermediate 15 (50 mg, 0.133 mmol) and a 57:39 mixture of Intermediates 182 & 183 (63 mg, 0.264 mmol) were placed in a ChemGlass vial (8 mL), the vessel purged with vacuum/nitrogen flush (×3) and then dissolved in anhydrous 1,4-dioxane (2 mL). Sodium tert-butoxide (38 mg, 0.395 mmol) and tBuXPhos Pd G3 (16 mg, 0.0195 mmol) were added and the reaction stirred at room temperature for 72 hours. Reaction diluted with water (2.5 mL) and DCM (2.5 mL), DCM layer filtered through phase separator and aqueous re-extracted with DCM (×2). Combined organics concentrated in vacuo and purified by silica column chromatography eluting with 0-30% MeOH/DCM to afford a mixture of the title compounds which was further purified by SFC to afford Example 115 (17 mg, 24% yield) and Example 116 (16 mg, 23% yield).

Example 115: $^1$H NMR (400 MHz, DMSO-d6) $\delta_H$ 9.13 (s, 1H), 8.49 (s, 1H), 8.36 (d, J=1.0 Hz, 1H), 8.33 (s, 1H), 8.09 (s, 1H), 7.92 (d, J=2.8 Hz, 1H), 7.80 (d, J=8.8 Hz, 1H), 7.28 (dd, J=8.9, 2.9 Hz, 1H), 6.60 (d, J=6.4 Hz, 1H), 4.39-4.30 (m, 1H), 3.86 (dd, J=18.3, 6.7 Hz, 1H), 3.56-3.47 (m, 2H), 3.01 (dd, J=16.4, 4.4 Hz, 1H), 2.87 (d, J=19.4 Hz, 2H), 2.31 (d, J=0.9 Hz, 3H), 2.30-2.22 (m, 1H), 1.13 (d, J=10.3 Hz, 3H), 1.07 (d, J=10.3 Hz, 3H), 1.04-0.99 (m, 4H). LCMS $[M-H]^-$ 534.2, RT 2.17 min (Method 10).

Example 116: 1H NMR (400 MHz, DMSO-d6) $\delta_H$ 9.12 (s, 1H), 8.50 (s, 1H), 8.33 (s, 1H), 8.08 (s, 1H), 7.90 (d, J=2.7 Hz, 1H), 7.78 (d, J=0.6 Hz, 1H), 7.67 (d, J=8.8 Hz, 1H), 7.22 (dd, J=8.9, 2.9 Hz, 1H), 6.52 (d, J=6.5 Hz, 1H), 4.34 (q, J=6.0 Hz, 1H), 3.86 (dd, J=18.3, 6.7 Hz, 1H), 3.56-3.46 (m, 2H), 3.00 (dd, J=16.5, 4.6 Hz, 1H), 2.87 (d, J=19.3 Hz, 2H), 2.34 (s, 3H), 2.30-2.22 (m, 1H), 1.13 (d, J=10.3 Hz, 3H), 1.07 (d, J=10.3 Hz, 3H), 1.04-0.97 (m, 4H). LCMS $[M+H]^+$ 536.2, RT 2.21 min (Method 10).

Example 117

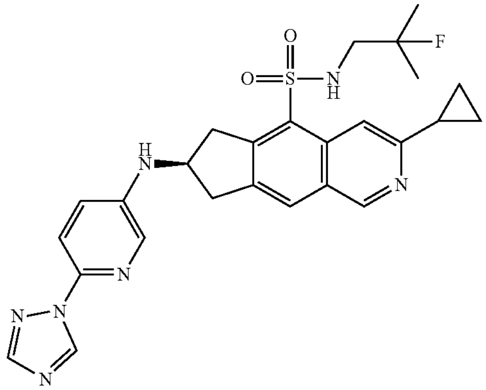 [SMILES: CC(C)(F)CNS(=O)(=O)c1c2c(cc3cnc(C4CC4)cc13)C[C@@H](Nc1ccc(-n3cncn3)nc1)C2]

(7R)-3-cyclopropyl-N-(2-fluoro-2-methylpropyl)-7-[[6-(1,2,4-triazol-1-yl)pyridin-3-yl]amino]-7,8-dihydro-6H-cyclopenta[g]isoquinoline-5-sulfonamide Procedure, scale and workup as for Examples 115/116 replacing 57:39 mixture of Intermediates 182 & 183 with 5-bromo-2-(1,2,4-triazol-1-yl)pyridine (60 mg, 0.2666 mmol) and stirring at room temperature for 3 hours. Purified by silica column chromatography eluting with 0-30% EtOAc/DCM; then 0-15% MeOH/DCM, followed by reverse phase C18 chromatography to yield the title compound (51 mg, 74% yield) as an off-white solid.

$^1$H NMR (400 MHz, DMSO-d6) $\delta_H$ 9.15 (s, 1H), 9.12 (s, 1H), 8.44 (s, 1H), 8.34 (t, J=6.5 Hz, 1H), 8.18 (s, 1H), 8.13 (s, 1H), 7.91 (d, J=2.5 Hz, 1H), 7.63 (d, J=8.7 Hz, 1H), 7.27 (dd, J=8.9, 2.9 Hz, 1H), 6.56 (d, J=6.4 Hz, 1H), 4.41-4.31 (m, 1H), 3.85 (dd, J=18.3, 6.7 Hz, 1H), 3.57-3.44 (m, 2H), 3.01 (dd, J=16.6, 4.5 Hz, 1H), 2.90 (dd, J=20.1, 6.4 Hz, 2H), 2.32-2.24 (m, 1H), 1.14 (d, J=9.1 Hz, 3H), 1.09 (d, J=9.1 Hz, 3H), 1.05-0.96 (m, 4H). LCMS $[M+H]^+$ 522.0, RT 2.06 min (Method 10).

Example 118

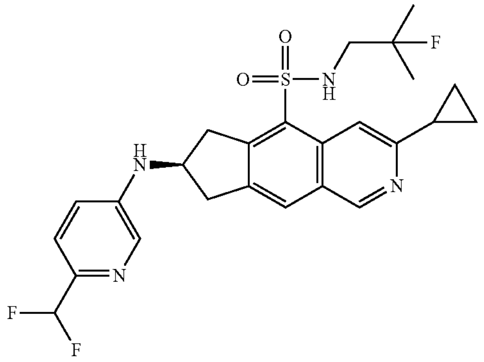 [SMILES: CC(C)(F)CNS(=O)(=O)c1c2c(cc3cnc(C4CC4)cc13)C[C@@H](Nc1ccc(C(F)F)nc1)C2]

(7R)-3-cyclopropyl-7-[[6-(difluoromethyl)pyridin-3-yl]amino]-N-(2-fluoro-2-methylpropyl)-7,8-dihydro-6H-cyclopenta[g]isoquinoline-5-sulfonamide Intermediate 15 (50 mg, 0.133 mmol) and 5-bromo-2-(difluoromethyl)pyridine (39 mg, 0.188 mmol) were dissolved in 1,4-dioxane (1 mL). The vessel was purged with vacuum/nitrogen flush (×3), sodium tert-butoxide (38 mg, 0.395 mmol) and tBuXPhos Pd G3 (11 mg, 0.0134 mmol) added and the reaction stirred at room temperature overnight. Reaction diluted with water (2 mL) and DCM (2 mL), the DCM layer removed, the aqueous layer re-extracted with DCM (2 mL×2) and the combined organics filtered through a phase separator and solvent removed. The residue was purified by silica column chromatography eluting with 0-30% EtOAc/DCM, then 0-20% MeOH/DCM to afford the title compound (61 mg, 91% yield) as a pale brown gum.

$^1$H NMR (400 MHz, DMSO-d6) $\delta_H$ 9.14 (d, J=0.8 Hz, 1H), 8.44 (s, 1H), 8.37-8.30 (m, 1H), 8.03 (d, J=2.5 Hz, 1H), 7.42 (d, J=8.5 Hz, 1H), 7.10 (dd, J=8.6, 2.7 Hz, 1H), 6.75 (t, J=55.7 Hz, 1H), 6.69 (d, J=6.4 Hz, 1H), 4.39-4.30 (m, 1H), 3.83 (dd, J=18.3, 6.7 Hz, 1H), 3.55-3.44 (m, 2H), 3.00 (dd, J=16.5, 4.4 Hz, 1H), 2.88 (dd, J=20.2, 5.2 Hz, 2H), 2.31-2.24 (m, 1H), 1.13 (d, J=11.9 Hz, 3H), 1.08 (d, J=12.0 Hz, 3H), 1.05-0.99 (m, 4H). LCMS [M+H]$^+$ 505.2, RT 2.25 min (Method 10).

Example 119

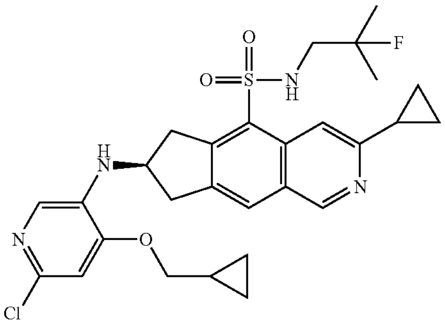 [SMILES: CC(C)(F)CNS(=O)(=O)c1c2c(cc3cnc(C4CC4)cc13)C[C@@H](Nc1cnc(Cl)cc1OCC1CC1)C2]

(7R)-7-[[6-chloro-4-(cyclopropylmethoxy)pyridin-3-yl]amino]-3-cyclopropyl-N-(2-fluoro-2-methylpropyl)-7,8-dihydro-6H-cyclopenta[g]isoquinoline-5-sulfonamide Procedure as for Examples 115/116 replacing 57:39 mixture of Intermediates 182 & 183 with Intermediate 184 (68 mg, 0.2153 mmol) and using sodium tert-butoxide (57 mg, 0.5925 mmol) and tBuXPhos Pd G3 (24 mg, 0.0293 mmol). Purified by silica column chromatography eluting with 0-30% MeOH/DCM, followed by reverse phase basic gradient chromatography to afford the title compound (54 mg, 69% yield) as an off-white foam $^1$H NMR (400 MHz, DMSO-d6) $\delta_H$ 9.13 (s, 1H), 8.44 (s, 1H), 8.38-8.31 (m, 1H), 8.09 (s, 1H), 7.72 (s, 1H), 6.90 (s, 1H), 5.03 (d, J=7.0 Hz, 1H), 4.42-4.32 (m, 1H), 3.92 (d, J=7.0 Hz, 2H), 3.87 (d, J=6.9 Hz, 1H), 3.55-3.45 (m, 2H), 3.09 (dd, J=16.4, 5.5 Hz, 1H), 2.99-2.88 (m, 2H), 2.31-2.23 (m, 1H), 1.26-1.18 (m, 1H), 1.15 (d, J=5.0 Hz, 3H), 1.10 (d, J=4.9 Hz, 3H), 1.04-0.99 (m, 4H), 0.57-0.48 (m, 2H), 0.33-0.26 (m, 2H). LCMS [M+H]$^+$ 559.2, RT 2.60 min (Method 10)

Example 120

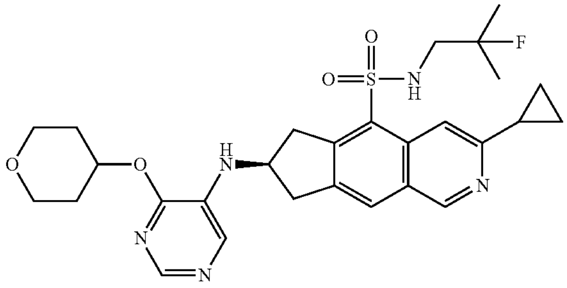 [SMILES: CC(C)(F)CNS(=O)(=O)c1c2c(cc3cnc(C4CC4)cc13)C[C@@H](Nc1cncnc1OC1CCOCC1)C2]

(7R)-3-cyclopropyl-N-(2-fluoro-2-methylpropyl)-7-[[4-(oxan-4-yloxy)pyrimidin-5-yl]amino]-7,8-dihydro-6H-cyclopenta[g]isoquinoline-5-sulfonamide Intermediate 15 (43 mg, 0.114 mmol) and tBuXPhos Pd G3 (13.6 mg, 0.0168 mmol) were added to the crude solution of Intermediate 146 under an atmosphere of nitrogen and stirred at room temperature for 2.5 hours then 80° C. for 1 hour. Reaction quenched with water (20 mL), extracted with DCM (3×20 mL), dried and solvent removed. Residue purified by silica column chromatography eluting with 0-100% EtOAc/hexanes then 0-20% MeOH/EtOAc to afford the title compound (37 mg, 58% yield) as an off white solid.

$^1$H NMR (400 MHz, Chloroform-d) $\delta_H$ 9.11 (s, 1H), 8.34 (s, 1H), 8.23 (s, 1H), 7.97 (s, 1H), 7.93 (s, 1H), 5.40-5.31 (m, 1H), 5.16 (t, J=6.6 Hz, 1H), 4.43-4.33 (m, 1H), 4.16 (d, J=6.4 Hz, 1H), 4.08-3.93 (m, 3H), 3.69-3.53 (m, 4H), 3.14 (dd, J=16.6, 4.9 Hz, 1H), 3.11-2.94 (m, 2H), 2.30-2.20 (m, 1H), 2.14-2.04 (m, 2H), 1.85-1.73 (m, 2H), 1.30 (dd, J=21.4, 4.3 Hz, 6H), 1.21-1.05 (m, 4H). LCMS [M+H]$^+$ 556.0, RT 2.02 min (Method 10)

Example 121

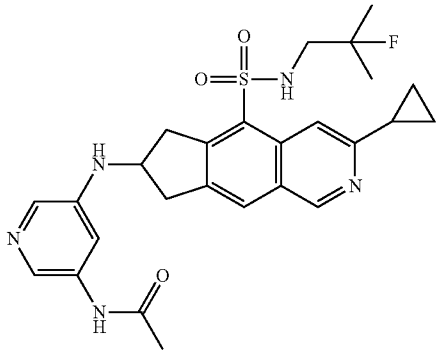 [SMILES: CC(=O)Nc1cncc(NC2Cc3cc4cnc(C5CC5)cc4c(S(=O)(=O)NCC(C)(C)F)c3C2)c1]

N-[5-[[3-cyclopropyl-5-[(2-fluoro-2-methylpropyl)sulfamoyl]-7,8-dihydro-6H-cyclopenta[g]isoquinolin-7-yl]amino]pyridin-3-yl]acetamide Intermediate 12 (59.4 mg, 0.157 mmol), N-(5-bromo-3-pyridyl) acetamide (52.1 mg, 0.242 mmol), sodium tert-butoxide (48.0 mg, 0.499 mmol) and tBuXPhos Pd G3 (20.4 mg, 0.0249 mmol) in 1,4-dioxane (1.8 mL) under nitrogen were heated at 100° C. for 4.5 hours. Reaction diluted with DCM (20 mL) and saturated aqueous $NaHCO_3$ (20 mL), extracted with DCM (2×15 mL), dried and the solvent removed. Residue purified by reverse phase, C18 preparative HPLC to afford the title compound (9 mg, 11.2% yield) as a white solid.

$^1$H NMR (400 MHz, DMSO-d6) $\delta_H$ 9.91 (s, 1H), 9.12 (s, 1H), 8.48 (s, 1H), 8.32 (s, 1H), 8.08 (s, 1H), 7.95 (d, J=2.0 Hz, 1H), 7.70 (d, J=2.5 Hz, 1H), 7.41 (t, J=2.3 Hz, 1H), 6.24 (d, J=6.2 Hz, 1H), 4.27-4.16 (m, 1H), 3.82 (dd, J=18.3, 6.7 Hz, 1H), 3.53-3.39 (m, 2H), 2.99 (dd, J=16.5, 4.7 Hz, 1H), 2.88 (d, J=19.7 Hz, 2H), 2.55 (s, 1H), 2.31-2.22 (m, 1H), 2.04 (s, 3H), 1.14 (d, J=11.2 Hz, 3H), 1.09 (d, J=11.2 Hz, 3H), 1.06-0.92 (m, 4H). LCMS [M+H]$^+$ 512.2, RT 1.70 min (Method 10).

Example 122

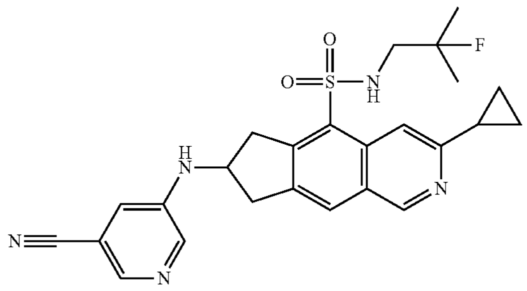 [SMILES: CC(C)(F)CNS(=O)(=O)c1c2c(cc3cnc(C4CC4)cc13)CC(Nc1cncc(C#N)c1)C2]

7-[(5-cyanopyridin-3-yl)amino]-3-cyclopropyl-N-(2-fluoro-2-methylpropyl)-7,8-dihydro-6H-cyclopenta[g]isoquinoline-5-sulfonamide To a solution of Intermediate 12 (50 mg, 0.133 mmol) in anhydrous 1,4-dioxane (2 mL) were added 5-bromonicotinonitrile (48 mg, 0.262 mmol), sodium tert-butoxide (38 mg, 0.395 mmol) and tBuXPhos Pd G3 (16 mg, 0.0195 mmol). The resultant solution was purged with nitrogen and heated to 100° C. for 1 hour. Solvent removed and the crude residue purified by silica column chromatography eluting with 0 to 100% EtOAc in hexane followed by 0 to 5% MeOH to afford the title compound (26 mg, 37% yield) as a yellow solid. LCMS [M+H]$^+$ 480.0, RT 1.94 min (Method 10).

Example 123

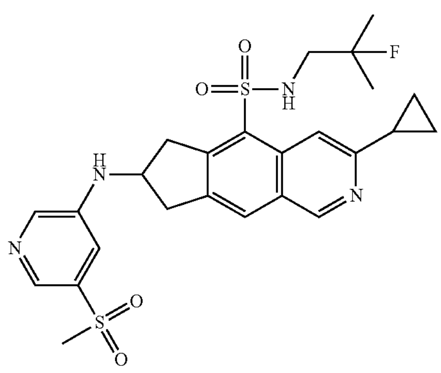 [SMILES: CC(C)(F)CNS(=O)(=O)c1c2c(cc3cnc(C4CC4)cc13)CC(Nc1cncc(S(C)(=O)=O)c1)C2]

3-cyclopropyl-N-(2-fluoro-2-methylpropyl)-7-[(5-methylsulfonylpyridin-3-yl)amino]-7,8-dihydro-6H-cyclopenta[g]isoquinoline-5-sulfonamide Method, purification and scale as for Example 122 replacing 5-bromonicotinonitrile with 3-bromo-5-(methylsulphonyl)pyridine (63 mg, 0.262 mmol) and stirring at room temperature for 18 hours Afforded the title compound (51 mg) as a white solid. LCMS [M−H]$^-$ 531.2, RT 1.79 min (Method 10).

Example 124

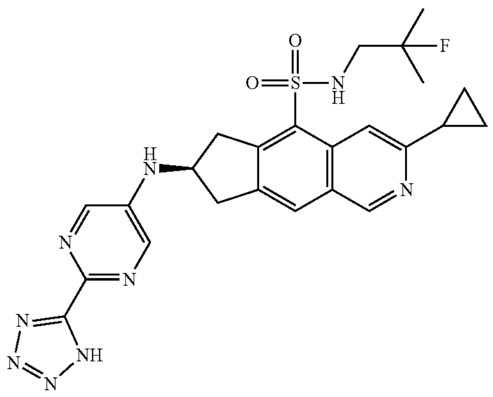 [SMILES: CC(C)(F)CNS(=O)(=O)c1c2c(cc3cnc(C4CC4)cc13)C[C@@H](Nc1cnc(-c3nnn[nH]3)nc1)C2]

(7R)-3-cyclopropyl-N-(2-fluoro-2-methylpropyl)-7-[[2-(1H-tetrazol-5-yl)pyrimidin-5-yl]amino]-7,8-dihydro-6H-cyclopenta[g]isoquinoline-5-sulfonamide A slurry of Intermediate 147 (26 mg, 0.054 mmol), ammonium chloride (15 mg, 0.280 mmol) and sodium azide (17 mg) in anhydrous DMF (1 mL) was sealed in a microwave vial and heated to 100° C. with stirring. After 1 hour the same amount of sodium azide and ammonium chloride were added again, and the reaction heated at 110° C. for 18 hours. Reaction diluted with EtOAc, washed with brine and the organics dried and evaporated. The residue was purified by reverse phase chromatography to afford the title compound (7 mg, 25% yield). LCMS [M+H]$^+$ 524.0, RT 1.65 min (Method 10).

Example 125

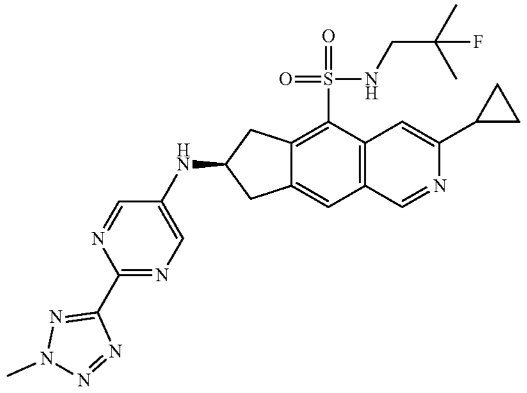

(7R)-3-cyclopropyl-N-(2-fluoro-2-methylpropyl)-7-[4-(2-methyltetrazol-5-yl) anilino]-7,8-dihydro-6H-cyclopenta[g]isoquinoline-5-sulfonamide Intermediate 15 (40 mg, 0.1060 mmol) was dissolved in 1,4-dioxane (2 mL) and tBuXPhos Pd G3 (13 mg, 0.0159 mmol), sodium tert-butoxide (30 mg, 0.312 mmol) and 5-(4-bromophenyl)-2-methyl-tetrazole (33 mg, 0.1380 mmol) were added and stirred at room temperature for 1 hour. Reaction filtered through celite and purified by silica column chromatography, eluting with 0 to 100% EtOAc in hexane to afford the title compound (25 mg, 44% yield). LCMS $[M-H]^-$ 534.2, RT 2.37 min (Method 10).

Example 126

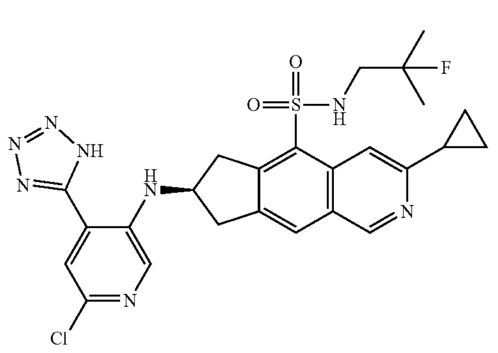 [SMILES: CC(C)(F)CNS(=O)(=O)c1c2c(cc3cnc(C4CC4)cc13)C[C@@H](Nc1cnc(Cl)cc1-c1nnn[nH]1)C2]

(7R)-7-[[6-chloro-4-(1H-tetrazol-5-yl)pyridin-3-yl]amino]-3-cyclopropyl-N-(2-fluoro-2-methylpropyl)-7,8-dihydro-6H-cyclopenta[g]isoquinoline-5-sulfonamide A slurry of Intermediate 148 (30 mg, 0.0584 mmol), ammonium chloride (15 mg, 0.280 mmol) and sodium azide (20 mg, 0.305 mmol) in anhydrous DMF (1 mL) was sealed in a microwave vial and heated to 96° C. with stirring for 3.5 hours. Reaction diluted with EtOAc, washed with brine, the organics dried and evaporated. The residue was purified by basic reverse phase chromatography to afford the title compound (2.4 mg, 7% yield) as a white solid. LCMS $[M+H]^+$ 557.0, RT 1.70 min (Method 10).

Example 127

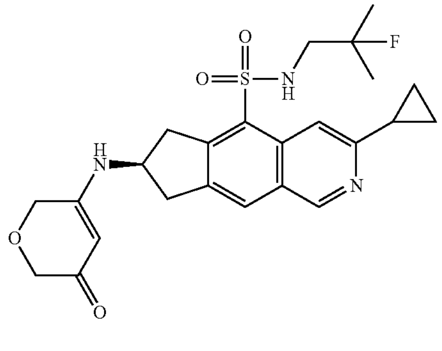 [SMILES: CC(C)(F)CNS(=O)(=O)c1c2c(cc3cnc(C4CC4)cc13)C[C@@H](NC1=CC(=O)COC1)C2]

(7R)-3-cyclopropyl-N-(2-fluoro-2-methylpropyl)-7-[(5-oxo-2H-pyran-3-yl)amino]-7,8-dihydro-6H-cyclopenta[g]isoquinoline-5-sulfonamide To a solution of Intermediate 15 (35 mg, 0.093 mmol) and 2H-pyran-3,5 (4H,6H)-dione (22 mg, 0.185 mmol) in THF (400 mg) was added DIPEA (12 mg, 0.093 mmol). The reaction was sealed and heated to 75° C. with stirring for 2.5 hours. The reaction was concentrated and purified by reverse phase C18 column chromatography, eluting with a 0-100% gradient of MeCN in water (+0.1% of 25% aqueous ammonia) to afford the title compound (25 mg, 57% yield) as a cream solid.

$^1H$ NMR (400 MHz, DMSO-d6) $\delta_H$ 9.15 (s, 1H), 8.43 (s, 1H), 8.41-8.34 (m, 1H), 8.12 (s, 1H), 7.57 (d, J=6.2 Hz, 1H), 5.12 (s, 1H), 4.31-4.20 (m, 1H), 4.17 (s, 2H), 3.87 (s, 2H), 3.78 (dd, J=18.5, 7.0 Hz, 1H), 3.60-3.39 (m, 2H), 3.03 (dd, J=16.9, 4.2 Hz, 1H), 2.98-2.85 (m, 2H), 2.32-2.21 (m, 1H), 1.15 (dd, J=21.4, 3.6 Hz, 6H), 1.08-0.98 (m, 4H). LCMS $[M-H]^-$ 472.2, RT 1.65 min (Method 10).

Example 128

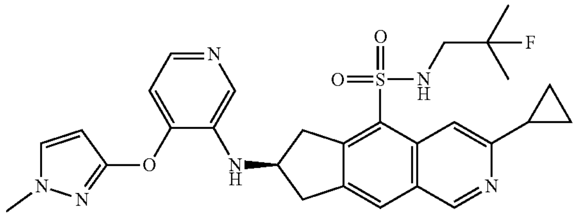 [SMILES: Cn1ccc(Oc2ccncc2N[C@@H]2Cc3cc4cnc(C5CC5)cc4c(S(=O)(=O)NCC(C)(C)F)c3C2)n1]

(7R)-3-cyclopropyl-N-(2-fluoro-2-methylpropyl)-7-[[4-(1-methylpyrazol-3-yl)oxypyridin-3-yl]amino]-7,8-dihydro-6H-cyclopenta[g]isoquinoline-5-sulfonamide Intermediate 15 (50 mg, 0.133 mmol), Intermediate 185 (85 mg, 0.331 mmol), sodium tert-butoxide (38 mg, 0.397 mmol) and tBuXPhos Pd G3 (16 mg, 0.0199 mmol) were degassed with stirring using 3 cycles of nitrogen/vacuum. Anhydrous 1,4-dioxane (2.5 mL) was added and the resultant solution stirred at room temperature for 45 minutes. Additional sodium tert-butoxide (38 mg, 0.397 mmol) and tBuXPhos Pd G3 (16 mg, 0.0199 mmol) were added under nitrogen and reaction stirred at room temperature for a further 45 minutes. The reaction was diluted with EtOAc (5 mL) and washed with water (5 mL). The organic layer was dried over $Na_2SO_4$, concentrated in vacuo, and the residue purified by silica column chromatography eluting with a 0-100% gradient of EtOAc in isohexane followed by 0-40% MeOH in EtOAc then by basic reverse phase preparative HPLC to afford the title compound (19 mg, 27% yield) as a beige powder.

$^1H$ NMR (400 MHz, DMSO-d6) $\delta_H$ 9.13 (s, 1H), 8.46-8.40 (m, 1H), 8.33 (s, 1H), 8.14 (s, 1H), 8.09 (s, 1H), 7.79 (d, J=5.3 Hz, 1H), 7.66 (d, J=2.3 Hz, 1H), 6.73 (d, J=5.3 Hz, 1H), 5.91 (d, J=2.3 Hz, 1H), 5.49 (d, J=7.0 Hz, 1H), 4.52-4.42 (m, 1H), 3.91 (dd, J=18.3, 6.9 Hz, 1H), 3.73 (s, 3H), 3.64-3.41 (m, 2H), 3.15 (dd, J=16.5, 5.4 Hz, 1H), 3.00-2.86 (m, 2H), 2.31-2.21 (m, 1H), 1.11 (dd, J=21.4, 7.6 Hz, 6H), 1.05-0.96 (m, 4H). LCMS $[M+H]^+$ 551.2, RT 2.03 min (Method 10)

Example 129

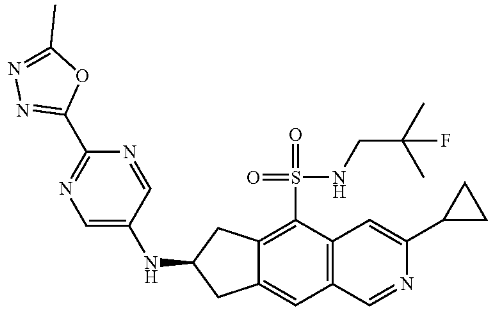 [SMILES: Cc1nnc(-c2ncc(N[C@@H]3Cc4cc5cnc(C6CC6)cc5c(S(=O)(=O)NCC(C)(C)F)c4C3)cn2)o1]

(7R)-3-cyclopropyl-N-(2-fluoro-2-methylpropyl)-7-[[2-(5-methyl-1,3,4-oxadiazol-2-yl)pyrimidin-5-yl]amino]-7,8-dihydro-6H-cyclopenta[g]isoquinoline-5-sulfonamide Method as for Intermediate 147, replacing 5-bromopyrimidine-2-carbonitrile with Intermediate 187 (64 mg, 0.2649 mmol). The crude product was purified by silica column chromatography eluting with a 0-100% gradient of EtOAc in isohexane followed by 0-30% MeOH in EtOAc, followed by C18 reverse phase chromatography eluting with a gradient of 0-100% MeCN in water (+0.1% of 25% ammonia in water) to afford the title compound (4 mg, 7% yield) as a colourless solid.

$^1$H NMR (400 MHz, DMSO-d6) $\delta_H$ δ 9.16 (s, 1H), 8.48-8.42 (m, 1H), 8.39-8.28 (m, 3H), 8.14 (s, 1H), 7.19 (d, J=6.6 Hz, 1H), 4.58-4.38 (m, 1H), 3.89 (dd, J=18.3, 6.8 Hz, 1H), 3.61-3.45 (m, 2H), 3.04 (dd, J=16.7, 4.6 Hz, 1H), 2.91 (dd, J=20.3, 5.6 Hz, 2H), 2.57 (s, 3H), 2.31-2.22 (m, 1H), 1.12 (dd, J=21.4, 5.9 Hz, 6H), 1.07-0.98 (m, 4H). LCMS $[M+H]^+$ 538.2, RT 1.83 min (Method 10).

Example 130

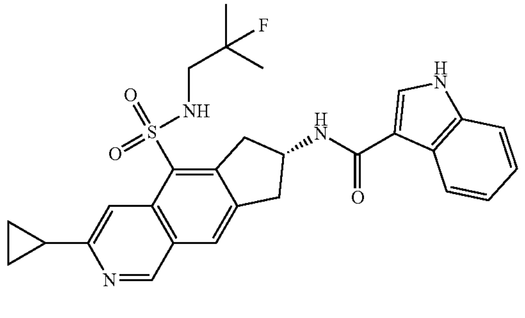 [SMILES: CC(C)(F)CNS(=O)(=O)c1c2c(cc3cnc(C4CC4)cc13)C[C@@H](NC(=O)c1c[nH]c3ccccc13)C2]

N-[(7R)-3-cyclopropyl-5-[(2-fluoro-2-methylpropyl)sulfamoyl]-7,8-dihydro-6H-cyclopenta[g]isoquinolin-7-yl]-1H-indole-3-carboxamide Procedure as for Example 132 except 1-methylindole-3-carboxylic acid replaced with indole-3-carboxylic acid (10.4 mg). Purified by basic, reverse phase HPLC to afford the title compound (16 mg). LCMS $[M-H]^-$ 519.2, RT 2.04 min (Method 10).

Example 131

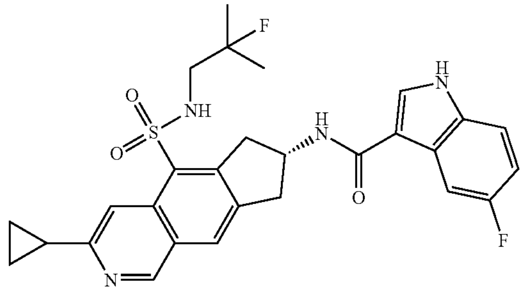 [SMILES: CC(C)(F)CNS(=O)(=O)c1c2c(cc3cnc(C4CC4)cc13)C[C@@H](NC(=O)c1c[nH]c3ccc(F)cc13)C2]

N-[(7R)-3-cyclopropyl-5-[(2-fluoro-2-methylpropyl)sulfamoyl]-7,8-dihydro-6H-cyclopenta[g]isoquinolin-7-yl]-5-fluoro-1H-indole-3-carboxamide Procedure as for Example 132 except 1-methylindole-3-carboxylic acid replaced with 5-fluoro-1H-indole-3-carboxylic acid (11.4 mg). Purified by basic, reverse phase HPLC to afford the title compound (5.3 mg).

$^1$H NMR (300 MHz, DMSO-d6) $\delta_H$ 11.75-11.54 (m, 1H), 9.14 (s, 1H), 8.45 (s, 1H), 8.38-8.26 (m, 1H), 8.18-8.05 (m, 3H), 7.83 (dd, J=10.3, 2.6 Hz, 1H), 7.42 (dd, J=8.9, 4.6 Hz, 1H), 6.99 (td, J=9.2, 2.7 Hz, 1H), 4.81-4.64 (m, 1H), 3.88 (dd, J=18.5, 7.5 Hz, 1H), 3.58-3.38 (m, 2H), 3.10 (dd, J=16.5, 6.4 Hz, 1H), 2.94 (d, J=19.4 Hz, 2H), 2.30-2.23 (m, 1H), 1.12 (dd, J=21.4, 5.7 Hz, 6H), 1.06-0.97 (m, 4H). LCMS $[M-H]^-$ 537.0, RT 2.12 min (Method 10).

Example 132

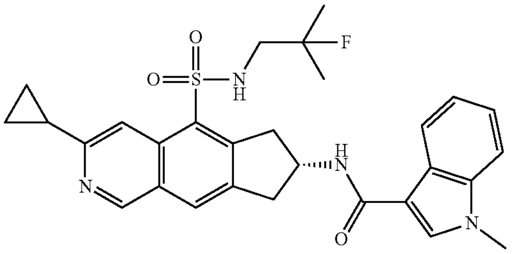 [SMILES: Cn1cc(C(=O)N[C@@H]2Cc3cc4cnc(C5CC5)cc4c(S(=O)(=O)NCC(C)(C)F)c3C2)c2ccccc21]

N-[(7R)-3-cyclopropyl-5-[(2-fluoro-2-methylpropyl)sulfamoyl]-7,8-dihydro-6H-cyclopenta[g]isoquinolin-7-yl]-1-methylindole-3-carboxamide 1-methylindole-3-carboxylic acid (12 mg, 0.0636 mmol) was dissolved in DMF (0.5 mL) containing DIPEA (17 mg, 0.133 mmol) and HBTU (31 mg, 0.0795 mmol). The reaction was stirred for 10 min prior to addition of a solution of Intermediate 15 (20 mg, 0.0523 mmol) in DMF (0.5 mL). Reaction stirred at room temperature overnight. Reaction diluted with DCM, washed with water (1 mL) and purified by silica column chromatography, eluting with a 0-100% gradient of EtOAc in isohexane followed by 0-30% MeOH in EtOAc to afford the title compound (10.3 mg, 36% yield).

$^1$H NMR (300 MHz, DMSO-d6) $\delta_H$ 9.15 (s, 1H), 8.45 (s, 1H), 8.38-8.26 (m, 1H), 8.18-8.07 (m, 3H), 7.99 (s, 1H), 7.56-7.40 (m, 1H), 7.32-7.09 (m, 2H), 4.73 (q, J=6.7 Hz, 1H), 3.87 (dd, J=18.6, 7.5 Hz, 1H), 3.80 (s, 3H), 3.59-3.39 (m, 2H), 3.10 (dd, J=16.5, 6.4 Hz, 1H), 2.94 (dd, J=20.3, 5.9 Hz, 2H), 2.33-2.23 (m, 1H), 1.12 (dd, J=21.4, 5.0 Hz, 6H), 1.06-0.96 (m, 4H). LCMS [M+H]+ 535, RT 2.21 min (Method 10).

Example 133

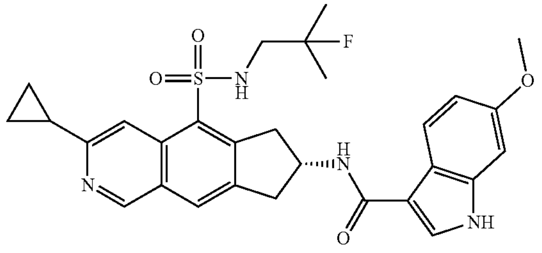 [SMILES: COc1ccc2c(C(=O)N[C@@H]3Cc4cc5cnc(C6CC6)cc5c(S(=O)(=O)NCC(C)(C)F)c4C3)c[nH]c2c1]

N-[(7R)-3-cyclopropyl-5-[(2-fluoro-2-methylpropyl) sulfamoyl]-7,8-dihydro-6H-cyclopenta[g]isoquinolin-7-yl]-6-methoxy-1H-indole-3-carboxamide Procedure as for Example 132 except 1-methylindole-3-carboxylic acid replaced with 6-methoxy-1H-indole-3-carboxylic acid (12 mg) to afford the title compound (16.9 mg, 58% yield).

$^1$H NMR (300 MHz, Methanol-d4) $\delta_H$ 9.06 (d, J=0.8 Hz, 1H), 8.53-8.45 (m, 1H), 8.07 (s, 1H), 7.98 (s, 1H), 7.93 (d, J=8.8 Hz, 1H), 6.92 (d, J=2.2 Hz, 1H), 6.80 (dd, J=8.8, 2.3 Hz, 1H), 4.91-4.87 (m, 1H), 3.99 (dd, J=18.5, 7.3 Hz, 1H), 3.81 (s, 4H), 3.72-3.46 (m, 2H), 3.26-3.13 (m, 1H), 3.09-3.00 (m, 2H), 2.30 (tt, J=7.5, 5.5 Hz, 1H), 1.20-0.99 (m, 10H). LCMS [M+H]+ 551, RT 2.04 min (Method 10).

Example 134

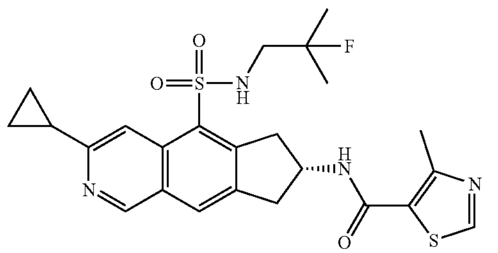 [SMILES: Cc1ncsc1C(=O)N[C@@H]1Cc2cc3cnc(C4CC4)cc3c(S(=O)(=O)NCC(C)(C)F)c2C1]

N-[(7R)-3-cyclopropyl-5-[(2-fluoro-2-methylpropyl) sulfamoyl]-7,8-dihydro-6H-cyclopenta[g]isoquinolin-7-yl]-4-methyl-1,3-thiazole-5-carboxamide Procedure as for Example 132 except 1-methylindole-3-carboxylic acid replaced with 4-methylthiazole-5-carboxylic acid (9.4 mg) to afford the title compound (2.1 mg, 8% yield).

$^1$H NMR (400 MHz, Methanol-d4) $\delta_H$ 9.07 (s, 1H), 8.93 (s, 1H), 8.50-8.48 (m, 1H), 8.10-8.05 (m, 1H), 4.84-4.75 (m, 1H), 3.99 (dd, J=18.6, 7.4 Hz, 1H), 3.61 (dd, J=18.5, 6.2 Hz, 1H), 3.53 (ddd, J=16.4, 7.5, 1.4 Hz, 1H), 3.23-3.16 (m, 1H), 3.04 (d, J=19.8 Hz, 2H), 2.61 (s, 3H), 2.36-2.24 (m, 1H), 1.15 (d, J=21.1 Hz, 6H), 1.11-1.05 (m, 4H). LCMS [M+H]+ 503.0, RT 1.85 min (Method 10).

Example 135

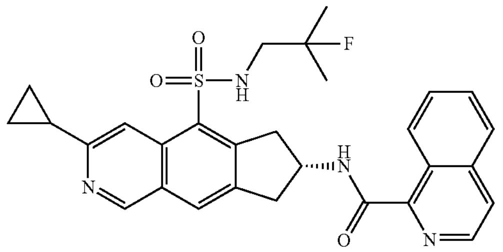 [SMILES: CC(C)(F)CNS(=O)(=O)c1c2c(cc3cnc(C4CC4)cc13)C[C@@H](NC(=O)c1nccc3ccccc13)C2]

N-[(7R)-3-cyclopropyl-5-[(2-fluoro-2-methylpropyl) sulfamoyl]-7,8-dihydro-6H-cyclopenta[g]isoquinolin-7-yl]isoquinoline-1-carboxamide Procedure as for Example 132 except 1-methylindole-3-carboxylic acid replaced with isoquinoline-1-carboxylic acid (11.1 mg) to afford the title compound (4.4 mg, 16% yield).

$^1$H NMR (400 MHz, Methanol-d4) $\delta_H$ 9.07 (s, 1H), 8.96-8.89 (m, 1H), 8.52-8.48 (m, 1H), 8.44 (d, J=5.6 Hz, 1H), 8.11 (s, 1H), 8.01-7.96 (m, 1H), 7.92 (d, J=5.6 Hz, 1H), 7.80 (ddd, J=8.2, 6.9, 1.3 Hz, 1H), 7.73 (ddd, J=8.4, 6.9, 1.4 Hz, 1H), 5.03-4.92 (m, 1H), 4.05 (dd, J=18.6, 7.2 Hz, 1H), 3.74-3.71 (m, 1H), 3.66-3.55 (m, 1H), 3.06 (d, J=20.0 Hz, 2H), 2.35-2.26 (m, 1H), 1.18-1.04 (m, 10H). LCMS [M+H]+ 533.2, RT 2.36 min (Method 10)

Example 136

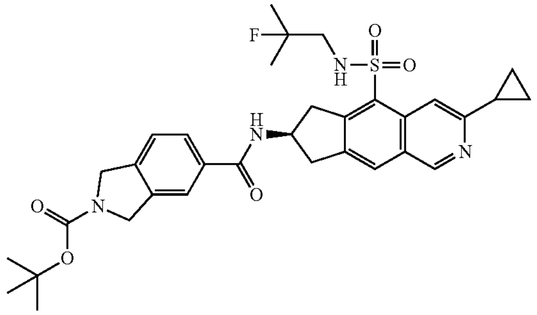 [SMILES: CC(C)(F)CNS(=O)(=O)c1c2c(cc3cnc(C4CC4)cc13)C[C@@H](NC(=O)c1ccc3c(c1)CN(C(=O)OC(C)(C)C)C3)C2]

tert-butyl 5-[[(7R)-3-cyclopropyl-5-[(2-fluoro-2-methylpropyl) sulfamoyl]-7,8-dihydro-6H-cyclopenta[g]isoquinolin-7-yl]carbamoyl]-1,3-dihydroisoindole-2-carboxylate Procedure as for Example 132 except 1-methylindole-3-carboxylic acid replaced with 2-(tert-butoxycarbonyl) isoindoline-5-carboxylic acid (18 mg) to afford the title compound (8.5 mg, 26% yield).

$^1$H NMR (400 MHz, Chloroform-d) $\delta_H$ 9.07 (s, 1H), 8.31 (s, 1H), 7.93 (s, 1H), 7.68-7.56 (m, 2H), 7.29-7.22 (m, 2H), 6.38 (dd, J=15.8, 7.1 Hz, 1H), 5.16-5.07 (m, 1H), 5.03-4.91 (m, 1H), 4.72-4.59 (m, 4H), 3.93 (dd, J=18.6, 7.2 Hz, 1H), 3.73-3.62 (m, 1H), 3.61-3.51 (m, 1H), 3.23-3.07 (m, 2H), 3.04-2.90 (m, 1H), 2.22 (tt, J=8.2, 4.9 Hz, 1H), 1.51 (s, 9H), 1.34-1.17 (m, 6H), 1.17-1.03 (m, 4H). LCMS [M+H]$^+$ 623.2, RT 2.50 min (Method 10).

Example 137

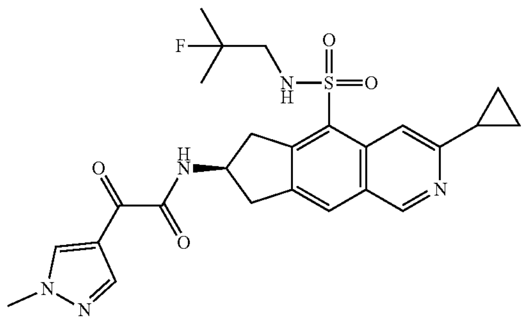 [SMILES: Cn1cc(C(=O)C(=O)N[C@@H]2Cc3cc4cnc(C5CC5)cc4c(S(=O)(=O)NCC(C)(C)F)c3C2)cn1]

N-[(7R)-3-cyclopropyl-5-[(2-fluoro-2-methylpropyl) sulfamoyl]-7,8-dihydro-6H-cyclopenta[g]isoquinolin-7-yl]-2-(1-methylpyrazol-4-yl)-2-oxoacetamide Procedure as for Example 132 except 1-methylindole-3-carboxylic acid replaced with 2-(1-methyl-1H-pyrazol-4-yl)-2-oxoacetic acid (10 mg) to afford the title compound (11.3 mg, 42% yield).

$^1$H NMR (400 MHz, DMSO-d6) $\delta_H$ 9.14 (s, 1H), 9.08 (d, J=7.4 Hz, 1H), 8.68 (s, 1H), 8.47-8.41 (m, 1H), 8.33 (t, J=6.5 Hz, 1H), 8.11 (d, J=0.6 Hz, 1H), 8.08 (s, 1H), 4.70-4.58 (m, 1H), 3.92 (s, 3H), 3.84 (dd, J=18.4, 7.6 Hz, 1H), 3.49 (dd, J=18.4, 6.6 Hz, 1H), 3.38 (ddd, J=16.3, 7.7, 1.3 Hz, 1H), 3.15 (ddd, J=16.3, 6.8, 1.5 Hz, 1H), 2.94 (dd, J=20.1, 6.4 Hz, 2H), 2.28 (tt, J=7.4, 5.6 Hz, 1H), 1.14 (dd, J=21.4, 4.1 Hz, 6H), 1.06-0.96 (m, 4H). LCMS [M+H]$^+$ 514.0, RT 1.88 min (Method 10).

Example 138

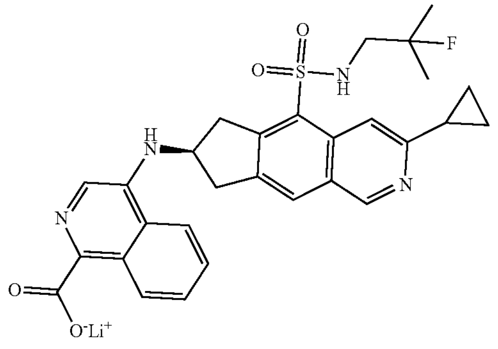

lithium; 4-[[(7R)-3-cyclopropyl-5-[(2-fluoro-2-methyl-propyl) sulfamoyl]-7,8-dihydro-6H-cyclopenta[g]isoquinolin-7-yl]amino]isoquinoline-1-carboxylate To a solution Intermediate 152 (59 mg, 0.105 mmol) in THF (1 mL) and water (0.5 mL) was added lithium hydroxide monohydrate (8.8 mg, 0.210) and the reaction stirred vigorously at room temperature for 7 hours. The solvent was removed and the residue purified by reverse phase C18 chromatography eluting with a 0-50% gradient of MeCN in water (with 0.1% of 25% aqueous ammonia) to afford the title compound (25 mg, 43% yield) as an off-white powder.

$^1$H NMR (400 MHz, DMSO-d6) $\delta_H$ 9.27 (s, 1H), 9.13 (s, 1H), 8.45 (s, 1H), 8.33 (s, 1H), 8.14-8.08 (m, 2H), 7.70 (s, 1H), 7.62-7.45 (m, 2H), 6.31 (s, 1H), 4.61-4.48 (m, 1H), 3.96 (dd, J=18.5, 6.9 Hz, 1H), 3.69 (dd, J=18.5, 4.7 Hz, 1H), 3.57 (dd, J=16.6, 7.0 Hz, 1H), 3.23 (dd, J=16.8, 4.8 Hz, 1H), 2.89 (d, J=20.2 Hz, 2H), 2.31-2.22 (m, 1H), 1.13-0.95 (m, 10H). LCMS [M+H]$^+$ 549.0, RT 1.52 min (Method 10)

Example 139

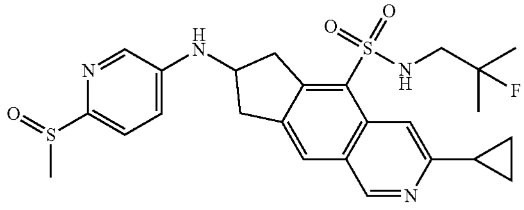 [SMILES: CS(=O)c1ccc(NC2Cc3cc4cnc(C5CC5)cc4c(S(=O)(=O)NCC(C)(C)F)c3C2)cn1]

3-cyclopropyl-N-(2-fluoro-2-methylpropyl)-7-[(6-methylsulfinylpyridin-3-yl)amino]-7,8-dihydro-6H-cyclopenta[g]isoquinoline-5-sulfonamide Intermediate 12 (50 mg, 0.133 mmol), 5-bromo-2-methylsulfinyl-pyridine (838 mg, 3.808 mmol), sodium tert-butoxide (38 mg, 0.397 mmol) and tBuXPhos Pd G3 (16 mg, 0.0199 mmol) were degassed with 3 cycles of vacuum/Nitrogen prior to addition of dry 1,4-dioxane (1 mL). A further cycle of vac/Nitrogen then the vial was sealed and heated to 100° C. with stirring for 1 hour. The reaction was diluted with EtOAc (2 mL), washed with water (1 mL), the organic layer dried over $Na_2SO_4$ and concentrated in vacuo. The crude product was purified by silica column chromatography, eluting with a 0-100% gradient of EtOAc in isohexane to afford the title compound (44 mg, 64% yield) as an off-white powder.

$^1$H NMR (400 MHz, DMSO-d6) $\delta_H$ 9.19-9.09 (m, 1H), 8.48-8.41 (m, 1H), 8.34 (t, J=6.5 Hz, 1H), 8.12 (s, 1H), 8.08-8.00 (m, 1H), 7.62 (dd, J=8.6, 1.3 Hz, 1H), 7.22 (ddd, J=8.6, 2.8, 1.5 Hz, 1H), 6.78 (d, J=6.4 Hz, 1H), 4.44-4.26 (m, 1H), 3.84 (dd, J=18.3, 6.6 Hz, 1H), 3.58-3.44 (m, 2H), 3.01 (dd, J=16.6, 4.5 Hz, 1H), 2.94-2.84 (m, 2H), 2.68 (d, J=1.2 Hz, 3H), 2.32-2.23 (m, 1H), 1.18-1.06 (m, 6H), 1.05-0.98 (m, 4H). LCMS [M+H]$^+$ 517.0, RT 1.68 min (Method 10)

Example 140

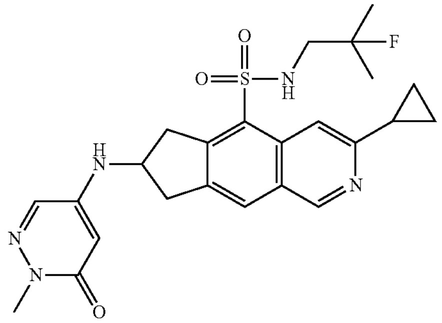 [SMILES: Cn1ncc(NC2Cc3cc4cnc(C5CC5)cc4c(S(=O)(=O)NCC(C)(C)F)c3C2)cc1=O]

3-cyclopropyl-N-(2-fluoro-2-methylpropyl)-7-[(1-methyl-6-oxopyridazin-4-yl)amino]-7,8-dihydro-6H-cyclopenta[g]isoquinoline-5-sulfonamide Intermediate 12 (50 mg, 0.133 mmol), 5-iodo-2-methyl-pyridazin-3-one (78 mg, 0.331 mmol), sodium tert-butoxide (38 mg, 0.397 mmol) and tBuXPhos Pd G3 (16 mg, 0.0199 mmol) were degassed with 3 cycles of vacuum/Nitrogen prior to addition of dry 1,4-dioxane (0.5 mL) A further cycle of vac/Nitrogen then the vial was sealed and heated to 100° C. with stirring for 1.25 hour. The reaction was diluted with EtOAc (5 mL), washed with water (5 mL), the organic layer dried over $Na_2SO_4$ and concentrated in vacuo. The crude product was purified by silica column chromatography, eluting with a 0-100% gradient of EtOAc in isohexane to afford the title compound (17.5 mg, 27% yield) as a colourless powder.

$^1H$ NMR (400 MHz, DMSO-d6) $\delta_H$ 9.15 (d, J=0.8 Hz, 1H), 8.44 (d, J=0.9 Hz, 1H), 8.39-8.29 (m, 1H), 8.13 (s, 1H), 7.38 (d, J=2.6 Hz, 1H), 7.20 (d, J=6.2 Hz, 1H), 5.67 (d, J=2.6 Hz, 1H), 4.33-4.14 (m, 1H), 3.78 (dd, J=18.5, 6.8 Hz, 1H), 3.57-3.43 (m, 5H), 3.00 (dd, J=16.7, 4.1 Hz, 1H), 2.96-2.84 (m, 2H), 2.32-2.23 (m, 1H), 1.12 (dd, J=21.4, 6.8 Hz, 6H), 1.06-0.97 (m, 4H). LCMS $[M+H]^+$ 486.2, RT 1.65 min (Method 10)

Example 141

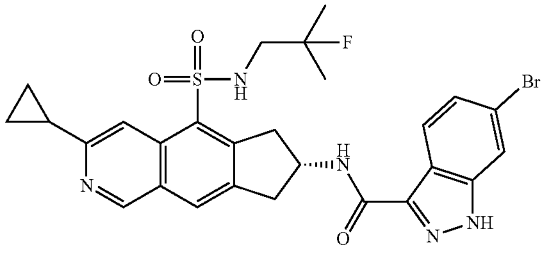 [SMILES: CC(C)(F)CNS(=O)(=O)c1c2c(cc3cnc(C4CC4)cc13)C[C@@H](NC(=O)c1n[nH]c3cc(Br)ccc13)C2]

6-bromo-N-[(7R)-3-cyclopropyl-5-[(2-fluoro-2-methylpropyl) sulfamoyl]-7,8-dihydro-6H-cyclopenta[g]isoquinolin-7-yl]-1H-indazole-3-carboxamide Procedure as for Example 132 except 1-methylindole-3-carboxylic acid replaced with 6-bromo-1H-indazole-3-carboxylic acid (16 mg) to afford the title compound (7.1 mg, 22% yield).

$^1H$ NMR (300 MHz, Methanol-d4) $\delta_H$ 9.05 (s, 1H), 8.52-8.46 (m, 1H), 8.13 (dd, J=8.6, 0.7 Hz, 1H), 8.09-8.04 (m, 1H), 7.76 (dd, J=1.6, 0.7 Hz, 1H), 7.37 (dd, J=8.7, 1.6 Hz, 1H), 4.97-4.88 (m, 1H), 3.99 (dd, J=18.5, 7.3 Hz, 1H), 3.69 (dd, J=18.5, 5.9 Hz, 1H), 3.54 (ddd, J=16.5, 7.3, 1.4 Hz, 1H), 3.29-3.20 (m, 1H), 3.11-3.00 (m, 2H), 2.29 (tt, J=7.6, 5.4 Hz, 1H), 1.17-1.03 (m, 10H). LCMS $[M+H]^+$ 600.0/602.0, RT 2.41 min (Method 10).

Example 142

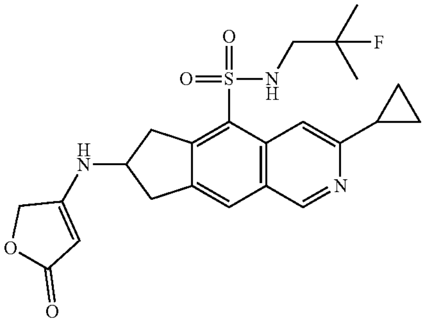 [SMILES: CC(C)(F)CNS(=O)(=O)c1c2c(cc3cnc(C4CC4)cc13)CC(NC1=CC(=O)OC1)C2]

3-cyclopropyl-N-(2-fluoro-2-methylpropyl)-7-[(5-oxo-2H-furan-3-yl)amino]-7,8-dihydro-6H-cyclopenta[g]isoquinoline-5-sulfonamide To a mixture of Intermediate 12 (20 mg, 0.053 mmol) and tetronic acid (6 mg, 0.058 mmol) was added ethanol (0.5 mL). The mixture was heated to 80° C. for 18 hours. The mixture was purified by flash chromatography to afford the title compound as an off-white solid (3 mg, 12% yield).

$^1H$ NMR (300 MHz, DMSO-d6) $\delta_H$ 9.07 (s, 1H), 8.61 (s, 1H), 7.98 (s, 1H), 7.79 (s, 1H), 4.71 (s, 1H), 4.56 (s, 2H), 4.12 (s, 1H), 3.76 (dd, J=18.4, 6.9 Hz, 1H), 3.58-3.37 (m, 2H), 3.08-2.91 (m, 1H), 2.82 (d, J=17.2 Hz, 2H), 2.26-2.13 (m, 1H), 1.11 (d, J=21.6 Hz, 6H), 0.99 (d, J=6.5 Hz, 4H). LCMS $[M+H]^+$ 460, RT 1.63 (Method 10).

In Vitro Biochemical Assay:

Protocol for Preparation of IgE-Tb Reagent 86 nmoles of IgE-Fc (N265Q, N371Q) (Young et al., 1995) at 172 μM in 100 mM $NaHCO_3$, pH 9.5 was added to 1 mg of LanthaScreen™ Amine Reactive Tb Chelate (ThermoFisher catalogue number PV3583) and incubated for 16 hours at 20° C. The material was then buffer exchanged into Phosphate Buffered Saline (being, 137 mM NaCl, 2.7 mM KCl, 10 mM $Na_2HPO_4$, 1.8 mM $K_2HPO_4$, pH 7.4) and the material quantified and the degree of Tb conjugation determined by measuring the absorption at 280 nm and 343 nm.

The integrity of the conjugated material was determined by analytical size exclusion chromatography on a S200 HR 10×300 column (GE Healthcare). Typical conjugation ratios were 4:1 Tb: IgE-Fc.

Young R J., Owens, R J., Mackay G A., Chan C M W., Shi J., Hide M., Francis D M., Henry A J., Sutton B J., and Gould H J (1995) Protein Engineering 8:193-199

Protocol for preparation of sFcεR1α-Y131A-AF488 reagent 400 nmoles FcεR1α (Y131A mutant) (Cook et al., 1997) at 400 μM in 100 mM NaOAc pH 5.5 was reacted with 1 mM final concentration sodium periodate (in 100 mM NaOAc, pH 5.5) for 60 minutes at 22° C. Oxidation was quenched with the addition of 40 μl of ethanediol and incubation for 60 minutes at 22° C. The protein was buffer exchanged in to conjugation buffer (50 mM $NaHCO_3$, 150 mM NaCl, pH 9.5) and concentrated to 750 μM.

175 nmoles of protein was added to 1 mg of Alexa Fluor™ 488 hydrazide (Invitrogen) and incubated for 16 hours at 22° C. Sodium cyanoborohydride (at 100 mM in conjugation buffer) was added to a final concentration of 1 mM and incubated for 60 minutes on ice. The protein was buffer exchanged into Phosphate Buffered Saline (being, 137 mM NaCl, 2.7 mM KCl, 10 mM $Na_2HPO_4$, 1.8 mM $K_2HPO_4$, pH 7.4) and the material quantified and the degree of Alexa Fluor™ 488 conjugation determined by measuring the absorption at 280 nm and 495 nm.

The integrity of the conjugated material was determined by analytical size exclusion chromatography on a S200 HR 10×300 column (GE Healthcare). Typical conjugation ratios were 2:1 Alexa Fluor™488: sFcεR1α

Cook J P D., Henry A J., McDonnell J M., Owens R J., Sutton B J., and Gould H J (1997) Biochemistry 36:15579-15588

The aim was to measure binding of IgE-Tb to receptor, and the inhibition thereof by compounds, using an in vitro Fluorescence Resonance Energy Transfer (FRET) Assay.

Reagents

FRET reagents used were IgE labelled with Terbium (FRET donor), and soluble IgE receptor FcεRIα with a Y131A mutation, labelled with Alexa Fluor™ 488 (FRET acceptor). Unlabelled FcεRIα was also used to generate a background control. The assay buffer consisted of 20 mM Tris pH7.2, 150 mM NaCl, and 0.002% Tween, 1% DMSO.

Assay Reaction

The assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by IgE-Tb diluting 10-fold in assay buffer. For the assay, 5 μl of diluted compound was added to 10 μl of, followed by addition of 10 μl FcεRIα-Y131A-AF488. FRET reagents FACs were 5 nM IgE-Tb, 25 nM FcεRIα-Y131A-AF488. Usually the top FAC of compound in the assay was 10 μM. The final DMSO concentration was 2%. The minimum signal (MIN) was measured by adding 5 μl unlabelled FcεRIα at 1 μM (FAC=200 nM) to the FRET reagents. The maximum FRET signal (MAX) was measured in wells containing FRET reagents but no compound.

The assay was incubated for 2 hours at room temperature, protected from light and evaporation, and with gentle agitation.

FRET Measurement

Measurement of FRET for each well was carried out by exciting at 330 nm and measuring emission at 495/520 nm using an Envision plate reader (Perkin Elmer). FRET ratio was calculated as follows:

Emission at 520/Emission at 495×1000.

The FRET ratio was used for the data analysis.

Data Analysis

Z' was calculated as follows (σ=standard deviation and μ=mean):

$$1-(3\times\sigma_{MAX})+(3\times\sigma_{MIN})/(\alpha_{MAX}-\mu_{MIN})$$

Z' above 0.5 was considered a good assay.

Background signal (MIN) was subtracted from all wells. Using the background subtracted values, the percent inhibition by compound in each test-well was calculated as follows:

100−Test-well FRET ratio/MAX FRET ratio×100.

Percent inhibition was plotted against compound concentration. IC50 values for each compound were determined using four parameter logistic fit model using the XLFIT5 software package.

The results are as follows:

Some of the compounds show an IC50 value ranging from 2 nM to 10830 nM

The table below shows the range of IC50 values for each example:

| Example Number | FRET $IC_{50}$ range |
|---|---|
| 1, 10, 18, 31, 36, 37 | 1-10 nanomolar |
| 2, 3, 4, 5, 11, 12, 13, 14, 15, 19, 20, 23, 24, 28, 29, 30, 32, 33, 34, 35, 38, 39, 43, 44, 53, 54, 61, 62, 63, 64, 66, 70, 73, 74, 75, 77, 83, 84, 85, 86, 92, 93 94, 96, 103, 106, 108, 109, 118, 121, 123, 124, 129, 130, 131, 132, 133, 136, 139, 140 | 10-50 nanomolar |
| 6, 7, 16, 21, 55, 56, 69, 71, 87, 88, 95, 104, 114, 119, 120, 125, 128, 138 | 50-100 nanomolar |
| 8, 9, 17, 22, 225, 26, 27, 40, 45, 46, 47, 48, 49, 50, 51, 57, 58, 59, 60, 65, 67, 68, 72, 78, 79, 80, 81, 89, 90, 91, 97, 98, 99, 100, 102, 107, 110, 111, 112, 113, 122, 126, 127, 134, 135, 137, 141, 142 | 0.1-2 micromolar |

The invention claimed is:

1. A compound of formula (I) or a pharmaceutically acceptable salt thereof:

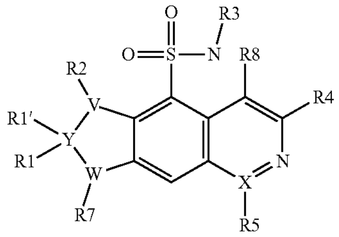

Wherein:

X, Y independently represent C or N;

V, W independently represent C or O;

If either V or W represent O then Y represents C;

If Y represents N then R1' is absent;

If V represents O then R2 is absent;

If W represents O then R7 is absent;

R1 represents:

Hydrogen; or

C(O)NH—C1-6-alkyl; or

C(O)NH-heteroaryl; or heteroaryl optionally substituted with one or more (i) oxo, (ii) hydroxy, (iii) amino, (iv) $C(O)NH_2$, (v) C(O)O—C1-6-alkyl, (vi) heteroaryl, (vii) NH—C1-6-alkyl, (viii) NH—C1-6-alkyl-C3-6-cycloalkyl or (ix) NH-heteroaryl optionally substituted with one or more $R1_a$; or C1-6-alkyl-C(O)—C1-6-alkylamino; or C1-6-alkyl-heteroaryl; or C(O)—C1-6-alkyl-heteroaryl; or NHC(O)-heteroaryl optionally substituted with one or more $R1_a$; or NH—C3-8-cycloalkyl optionally substituted with one or more $R1_a$; or NH—C3-8-heterocycloalkyl optionally substituted with one or more $R1_a$; or NHC(O)—C1-6-alkyl optionally substituted with one or more-aryl; aryl or heteroaryl; or NHC(O)—NH—C1-6-alkyl; or NHC(O)O—C1-6-alkyl; or NH-aryl optionally substituted with one or more (i) C1-6-alkyl, (ii) C(O)—C1-6-alkyl, or (iii) heteroaryl optionally substituted with one or more C1-6-alkyl; or $SO_2$-C1-6-alkyl; or $SO_2$—NH—C1-6-alkyl; or NH—$SO_2$-C1-6-alkyl; or NHC(O)—C(O)-heteroaryl optionally substituted with one or more halogen or C1-6-alkyl; or —NH-Heteroaryl substituted with one or more:

(i) Hydrogen, (ii) $R1_b$, (iii) hydroxy, (iv) halogen, (v) oxo, (vi) C1-6-alkyl, (vii) C1-6-alkoxy, (viii) C1-6-hydroxyalkyl, (ix) C1-6-haloalkyl, (x) C1-6-alkyl-C(O)OH, (xi) $C(O)NH_2$, (xii) $SO_2NH_2$, (xiii) S(O)—C1-6-alkyl, (xiv) $SO_2$-C1-6-alkyl, (xv) $SO_2$NHC(O)—C1-6-alkyl, (xvi) $SO_2$-C1-6-alkylamino, (xvi) S(O)(NH)—C1-6-alkyl, (xviii) C1-6-alkyl-C3-8-cycloalkyl, (xix) C3-8-cycloalkyl-C1-6-alkyl, (xx) C1-6-alkoxy-C3-8-cycloalkyl, (xxi) C3-8-cycloalkyl-C1-6-alkoxy, (xxii) C1-6-alkylamino-C3-8-cycloalkyl, (xxiii) C3-8-cycloalkyl-C1-6-alkylamino, (xxiv) C(O)OH, (xxv) C(O)O—C1-6-alkyl, (xxvi) C(O)NH—C1-6-alkyl, (xxvii) NHC(O)—C1-6-alkyl, (xxviii) cyano, (xxix) C3-8-heterocycloalkyl optionally substituted with one or more hydroxy, oxo, C1-6-alkyl or cyano, (xxx) heterocycloalkyloxy optionally substituted with one or more hydroxy, oxo, C1-6-alkyl, C1-6-alkoxy, C3-8-cycloalkyl-C1-6-alkoxy, C(O)NH—C1-6-alkyl or NHSO2-C1-6-alkyl, (xxxi) heteroaryloxy optionally substituted with one or more hydroxy, oxo, C1-6-alkyl or C1-6-alkoxy, (xxxii) heteroarylamino optionally substituted with one or more hydroxy, oxo, C1-6-alkyl or C1-6-alkoxy, or (xxxiii) $SO_2$-heteroaryl optionally substituted with one or more C1-3-alkyl or oxo;

$R1_a$ represents a group selected from the group consisting of:

(i) Hydrogen, (ii) Halogen, (iii) hydroxy, (iv) oxo, (v) amino, (vi) C1-6-alkyl, (vii) C1-6-alkoxy, (viii) C(O)O—C1-6-alkyl, (ix) C1-6-alkylamino, (x) cyano, (xi) C1-6-haloalkyl, (xii) C1-6-haloalkoxy, (xiii) C(O)OH, and (xiv) C3-8-cycloalkyl;

$R1_b$ represents a group selected from the group consisting of:

Heteroaryl optionally substituted with one or more (i) halogen, (ii) hydroxy, (iii) oxo, (iv) C1-6-alkyl, (v) C1-6-alkanediyl-C(O)OH, (vi) $C(O)NH_2$, (vii) carbamoyl, (viii) C(O)O—C1-6-alkyl, (ix) S(O)NH—C1-6-alkyl, (x) C3-8-cycloalkyl, (xi) heteroarylamino, (xii) C1-6-alkoxy, (xiii) cyano, (xiv) C1-6-haloalkyl, (xv) C1-6-haloalkoxy or (xvi) C(O)OH;

R1' represents: hydrogen; C1-3-alkyl; or C1-3-hydroxyalkyl;

R2 represents a group selected from the group consisting of:

Hydrogen; C1-3-hydroxyalkyl; NHC(O)NH—C1-6-alkyl; and hydroxy;

R1' and R2 can form together a cyclopropyl ring incorporating V and Y;

R1 and R1' can form together a heterocycloalkyl ring optionally substituted with one or more oxo, halogen or C1-6-alkyl;

R3 represents a group selected from the group consisting of:

C1-6-alkyl optionally substituted with one or more $R3^a$ groups;

C1-3-alkanediyl-C3-6-cycloalkyl optionally substituted with one or more $R3^a$ groups;

C1-3-alkanediyl-C3-6-heterocycloalkyl optionally substituted with one or more $R3^a$ groups;

C3-6-heterocycloalkyl optionally substituted with one or more $R3^a$ groups; and C3-6-cycloalkyl optionally substituted with one or more $R3^a$ groups;

$R3^a$ represents a group selected from the group consisting of hydrogen; Halogen; C1-2-alkyl; hydroxy; and C1-2-alkoxy;

R4 represents:

C3-6-cycloalkyl optionally substituted with one or more $R4^a$ group; or C1-6-alkanediyl-C3-6-cycloalkyl optionally substituted with one or more $R4^a$ group; or C1-6-alkanediyl-C3-6-heterocycloalkyl optionally substituted with one or more $R4^a$ group; $R4^a$ represents a group selected from the group consisting of hydroxy; Halogen; and C1-2-alkyl;

R5 represents a group selected from the group consisting of:

Hydrogen; hydroxy; Halogen; C1-3-alkyl optionally substituted with one or more halogen; and C1-3-alkoxy;

R6 represents a group selected from the group consisting of:

Hydrogen; halogen; amino; NHC(O) C1-6-alkyl; C1-3-alkyl optionally substituted with one or more halogen; and C1-3-alkoxy;

R7 represents a group selected from the group consisting of:

Hydrogen; NHC(O)NH—C1-6-alkyl; Halogen; and hydroxy;

R1' and R7 can form together a cyclopropyl ring incorporating W and Y; and

R8 represents hydrogen; halogen; hydroxy; C1-3 alkyl; or cyclopropyl.

2. A compound of formula (I) according to claim 1 wherein R1 represents:

Hydrogen; or

C(O)NH—C1-6-alkyl; or

C(O)NH-heteroaryl; or heteroaryl optionally substituted with one or more (i) oxo, (ii) hydroxy, (iii) amino, (iv) $C(O)NH_2$, (v) C(O)O—C1-6-alkyl, (vi) heteroaryl, (vii) NH—C1-6-alkyl, (viii) NH—C1-6-alkyl-C3-6-cycloalkyl or (ix) NH-heteroaryl optionally substituted with one or more $R1_a$; or C1-6-alkyl-C(O)—C1-6-alkylamino; or C1-6-alkyl-heteroaryl; or C(O)—C1-6-alkyl-heteroaryl; or NHC(O)-heteroaryl optionally substituted with one or more $R1_a$; or NH—C3-8-cycloalkyl optionally substituted with one or more $R1_a$; or NH—C3-8-heterocycloalkyl optionally substituted with one or more $R1_a$; or NHC(O)—C1-6-alkyl optionally substituted with one or more aryl or heteroaryl; or NHC(O)—NH—C1-6-alkyl; or NHC(O)O—C1-6-alkyl; or NH-aryl optionally substituted with one or more (i) C1-6-alkyl, (ii) C(O)—C1-6-alkyl or (iii) heteroaryl optionally substituted with one or more C1-6-alkyl; or $SO_2$-C1-6-alkyl; or $SO_2$—NH—C1-6-alkyl; or NH—$SO_2$-C1-6-alkyl; or NHC(O)—C(O)-heteroaryl optionally substituted with one or more halogen or C1-6-alkyl;

$R1_a$ represents a group selected from the group consisting of:

Hydrogen; Halogen; hydroxy; oxo; amino; C1-6-alkyl; C1-6-alkoxy; C(O)O—C1-6-alkyl; C1-6-alkylamino; cyano; C1-6-haloalkyl; C1-6-haloalkoxy; C(O)OH; and C3-8-cycloalkyl.

3. A compound of formula (I) according to claim 2 wherein R4 represents cyclopropyl optionally substituted with one or more groups chosen independently from the group consisting of hydroxy, Chloro, Fluoro, Bromo, and Methyl.

4. A compound of formula (I) according to claim 2, wherein R4 is cyclopropyl.

5. A compound of formula (I) according to claim 1 wherein R1 represents —NH-Heteroaryl substituted with one or more:

(i) Hydrogen; (ii) $R1_b$; (iii) hydroxy; (iv) halogen; (v) oxo; (vi) C1-6-alkyl; (vii) C1-6-alkoxy; (viii) C1-6-hydroxyalkyl; (ix) C1-6-haloalkyl; (x) C1-6-alkyl-C(O)OH; (xi) $C(O)NH_2$; (xii) $SO_2NH_2$; (xiii) S(O)—C1-6-alkyl; (xiv) $SO_2$-C1-6-alkyl; (xv) $SO_2$NHC(O)—C1-6-alkyl; (xvi) $SO_2$-C1-6-alkylamino; (xvii) S(O)(NH)—C1-6-alkyl; (xviii) C1-6-alkyl-C3-8-cycloalkyl; (xix) C3-8-cycloalkyl-C1-6-alkyl; (xx) C1-6-alkoxy-C3-8-cycloalkyl; (xxi) C3-8-cycloalkyl-C1-6-alkoxy; (xxii) C1-6-alkylamino-C3-8-cycloalkyl; (xxiii) C3-8-cycloalkyl-C1-6-alkylamino; (xxiv) C(O)OH; (xxv) C(O)O—C1-6-alkyl; (xxvi) C(O)NH—C1-6-alkyl; (xxvii) NHC(O)—C1-6-alkyl; (xxviii) cyano; (xxix) C3-8-heterocycloalkyl optionally substituted with one or more hydroxy, oxo, C1-6-alkyl or cyano; (xxx) heterocycloalkyloxy optionally substituted with one or more hydroxy, oxo, C1-6-alkyl, C1-6-alkoxy, C3-8-cycloalkyl-C1-6-alkoxy, C(O)NH-C1-6-alkyl or NHSO2-C1-6-alkyl; (xxxi) heteroaryloxy optionally substituted with one or more hydroxy, oxo, C1-6-alkyl or C1-6-alkoxy; (xxii) heteroarylamino optionally substituted with one or more hydroxy, oxo, C1-6-alkyl or C1-6-alkoxy; or (xxxiii) $SO_2$-heteroaryl optionally substituted with one or more C1-3-alkyl or oxo; and $R1_b$ represents a group selected from the group consisting of:

Heteroaryl optionally substituted with one or more (i) halogen, (ii) hydroxy, (iii) oxo, (iv) C1-6-alkyl, (v) C1-6-alkanediyl-C(O)OH, (vi) $C(O)NH_2$, (vii) carbamoyl, (viii) C(O)O—C1-6-alkyl, (ix) S(O) NH—C1-6-alkyl, (x) C3-8-cycloalkyl, (xi) heteroarylamino, (xii) C1-6-alkoxy, (xiii) cyano, (xiv) C1-6-haloalkyl, (xv) C1-6-haloalkoxy or (xvi) C(O)OH.

6. A compound of formula (I) according to claim 5 wherein R4 represents cyclopropyl optionally substituted with one or more groups chosen independently from the group consisting of hydroxy, Chloro, Fluoro, Bromo, and Methyl.

7. A compound of formula (I) according to claim 5, wherein R4 is cyclopropyl.

8. A compound of formula (I) according to claim 1 wherein R4 represents cyclopropyl optionally substituted with one or more groups chosen independently from the group consisting of hydroxy, Chloro, Fluoro, Bromo, and Methyl.

9. A compound of formula (I) according to claim 8, wherein R4 is cyclopropyl.

10. A compound of formula (I) according to claim 1, wherein R4 is cyclopropyl.

11. A compound of formula (I) according to claim 1, which is:

(7R)-3-cyclopropyl-N-(3-fluorocyclobutyl)-7-[[6-(2-methyltetrazol-5-yl)pyridin-3-yl]amino]-7,8-dihydro-6H-cyclopenta[g]isoquinoline-5-sulfonamide;

13-cyclopropyl-~{N}-(2-methylpropyl)-6-(5-pyridin-3-yl-1~{H}-imidazol-2-yl)-12-azatetracyclo[8.4.0.0^{3,8}.0^{4,6}]tetradeca-1,3 (8),9,11,13-pentaene-2-sulfonamide;

(7R*)-3-cyclopropyl-N-(2-methylpropyl)-7-[(4-pyridin-3-yl-1,2,4-triazol-3-yl)amino]-7,8-dihydro-6H-cyclopenta[g]isoquinoline-5-sulfonamide [* or S];

3-cyclopropyl-N-(2-methylpropyl)-7-[(3-oxocyclopenten-1-yl)amino]-7,8-dihydro-6H-cyclopenta[g]isoquinoline-5-sulfonamide;

3-cyclopropyl-7-[[4-(cyclopropylmethyl)-1,2,4-triazol-3-yl]amino]-N-(2-methylpropyl)-7,8-dihydro-6H-cyclopenta[g]isoquinoline-5-sulfonamide;

N-[3-cyclopropyl-5-[(2-fluoro-2-methylpropyl) sulfamoyl]-7,8-dihydro-6H-cyclopenta[g]isoquinolin-7-yl] pyridine-3-carboxamide;

3-cyclopropyl-N-(2-fluoro-2-methylpropyl)-7-[(3-oxocyclohexen-1-yl)amino]-7,8-dihydro-6H-cyclopenta[g] isoquinoline-5-sulfonamide;

ethyl 5-amino-1-[(7S)-3-cyclopropyl-5-[(2-fluoro-2-methylpropyl) sulfamoyl]-7,8-dihydro-6H-cyclopenta [g]isoquinolin-7-yl]imidazole-4-carboxylate;

3-cyclopropyl-5-[(3-methyloxetan-3-yl)methylsulfamoyl]-N-pyridin-3-yl-7,8-dihydro-6H-cyclopenta[g] isoquinoline-7-carboxamide;

(7R)-3-cyclopropyl-N-(2-fluoro-2-methylpropyl)-7-[[5-(6-methylpyridin-3-yl)oxypyridin-3-yl]amino]-7,8-dihydro-6H-cyclopenta[g]isoquinoline-5-sulfonamide;

5-[[(7R)-3-cyclopropyl-5-[(2-fluoro-2-methylpropyl) sulfamoyl]-7,8-dihydro-6H-cyclopenta[g]isoquinolin-7-yl]amino]pyridine-2-carboxamide;

(7R)-3-cyclopropyl-N-(2-fluoro-2-methylpropyl)-7-[[6-(hydroxymethyl)pyridin-3-yl]amino]-7,8-dihydro-6H-cyclopenta[g]isoquinoline-5-sulfonamide;

3-cyclopropyl-N-[(3-fluorooxetan-3-yl)methyl]-7-[[6-(2-methyltetrazol-5-yl)pyridin-3-yl]amino]-7,8-dihydro-6H-cyclopenta[g]isoquinoline-5-sulfonamide;

3-cyclopropyl-N-[(3-hydroxyoxetan-3-yl)methyl]-7-[(2-methylpyrazolo[3,4-c]pyridin-4-yl)amino]-7,8-dihydro-6H-cyclopenta[g]isoquinoline-5-sulfonamide;

5-[[(7R)-3-cyclopropyl-5-[(2-fluoro-2-methylpropyl) sulfamoyl]-7,8-dihydro-6H-cyclopenta[g]isoquinolin-7-yl]amino]pyridine-2-carboxylic acid;

(7R)-3-cyclopropyl-N-(2-fluoro-2-methylpropyl)-7-[[5-(2-methoxypyridin-4-yl)oxypyridin-3-yl]amino]-7,8-dihydro-6H-cyclopenta[g]isoquinoline-5-sulfonamide;

3-cyclopropyl-N-(2-hydroxypropyl)-7,8-dihydro-6H-cyclopenta[g]isoquinoline-5-sulfonamide;

3-cyclopropyl-N-(2-fluoro-2-methylpropyl)-7-[[4-(pyridin-3-ylamino)pyrimidin-5-yl]amino]-7,8-dihydro-6H-cyclopenta[g]isoquinoline-5-sulfonamide;

3-cyclopropyl-7-[[4-(cyclopropylmethylamino)pyrimidin-5-yl]amino]-N-(2-fluoro-2-methylpropyl)-7,8-dihydro-6H-cyclopenta[g]isoquinoline-5-sulfonamide;

7-(1H-benzimidazol-2-ylamino)-3-cyclopropyl-N-(2-fluoro-2-methylpropyl)-7,8-dihydro-6H-cyclopenta[g]isoquinoline-5-sulfonamide;

9-amino-3-cyclopropyl-N-(2-methylpropyl)-7,8-dihydro-6H-cyclopenta[g]isoquinoline-5-sulfonamide;

N-[3-cyclopropyl-5-(2-methylpropylsulfamoyl)-7,8-dihydro-6H-cyclopenta[g]isoquinolin-9-yl]acetamide;

5-[[3-cyclopropyl-1-fluoro-5-[(2-fluoro-2-methyl-propyl)sulfamoyl]-7,8-dihydro-6H-cyclopenta[g]isoquinolin-7-yl]amino]pyridine-2-carboxamide;

methyl 5-[[3-cyclopropyl-1-fluoro-5-[(2-fluoro-2-methyl-propyl) sulfamoyl]-7,8-dihydro-6H-cyclopenta[g]isoquinolin-7-yl]amino]pyridine-2-carboxylate;

3-cyclopropyl-1-fluoro-N-(2-fluoro-2-methylpropyl)-7-[[6-(3-hydroxyoxetan-3-yl)pyridin-3-yl]amino]-7,8-dihydro-6H-cyclopenta[g]isoquinoline-5-sulfonamide;

3-cyclopropyl-N-(2-fluoro-2-methylpropyl)-7-[[6-(3-hydroxyoxetan-3-yl)pyridin-3-yl]amino]-1-methoxy-7,8-dihydro-6H-cyclopenta[g]isoquinoline-5-sulfonamide;

3-cyclopropyl-N-(2-fluoro-2-methylpropyl)-7-[[6-(3-hydroxy-3-methylazetidin-1-yl)pyridin-3-yl]amino]-7,8-dihydro-6H-cyclopenta[g]isoquinoline-5-sulfonamide;

3-cyclopropyl-N-(2-fluoro-2-methylpropyl)-7-[(6-methoxypyridazin-3-yl)amino]-7,8-dihydro-6H-cyclopenta[g]isoquinoline-5-sulfonamide;

3-cyclopropyl-1-fluoro-N-(2-fluoro-2-methyl-propyl)-7-[(1-methyl-6-oxo-pyridazin-4-yl)amino]-7,8-dihydro-6H-cyclopenta[g]isoquinoline-5-sulfonamide;

(7R)-3-cyclopropyl-N-(2-fluoro-2-methylpropyl)-7-[[2-(3-hydroxyoxetan-3-yl)pyrimidin-5-yl]amino]-7,8-dihydro-6H-cyclopenta[g]isoquinoline-5-sulfonamide;

(7R)-3-cyclopropyl-N-(2-fluoro-2-methylpropyl)-7-[[6-(5-methyl-1,2,4-oxadiazol-3-yl)pyridin-3-yl]amino]-7,8-dihydro-6H-cyclopenta[g]isoquinoline-5-sulfonamide;

(7R)-7-[(6-chloropyridin-3-yl)amino]-3-cyclopropyl-N-(2-fluoro-2-methylpropyl)-7,8-dihydro-6H-cyclopenta[g]isoquinoline-5-sulfonamide;

N-[(7R)-3-cyclopropyl-5-[(2-fluoro-2-methylpropyl) sulfamoyl]-7,8-dihydro-6H-cyclopenta[g]isoquinolin-7-yl]-6-methyl-1H-indole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-1H-benzotriazole-5-carboxamide;

3-cyclopropyl-N-(2-fluoro-2-methylpropyl)-7-[[6-(methylsulfonimidoyl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(3-methyl-1,2,4-oxadiazol-5-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(5-methyl-1,3,4-oxadiazol-2-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(3-hydroxyoxetan-3-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(2-hydroxypropan-2-yl)pyridin-3-yl]amino]-7,8-dihydro-6H-cyclopenta[g]isoquinoline-5-sulfonamide;

3-cyclopropyl-7-[(1,1-dioxo-2,3-dihydrothiophen-4-yl)amino]-N-(2-fluoro-2-methylpropyl)-7,8-dihydro-6H-cyclopenta[g]isoquinoline-5-sulfonamide;

(7R)-3-cyclopropyl-N-(3,3-difluorocyclobutyl)-7-[[6-(2-methyltetrazol-5-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(2-methyltetrazol-5-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[5-(6-methylpyridin-3-yl)sulfonylpyridin-3-yl]amino]-7,8-dihydro-6H-cyclopenta[g]isoquinoline-5-sulfonamide;

1-[3-cyclopropyl-5-(2-methylpropylsulfamoyl)-7,8-dihydro-6H-cyclopenta[g]isoquinolin-7-yl]-3-ethylurea;

1-[3-cyclopropyl-5-(2-methylpropylsulfamoyl)-7,8-dihydro-6H-cyclopenta[g]isoquinolin-8-yl]-3-ethylurea;

1-[3-cyclopropyl-5-(2-methylpropylsulfamoyl)-7,8-dihydro-6H-cyclopenta[g]isoquinolin-6-yl]-3-ethylurea;

3-cyclopropyl-8-hydroxy-N-(2-methylpropyl)-7,8-dihydro-6H-cyclopenta[g]isoquinoline-5-sulfonamide;

3-cyclopropyl-6-hydroxy-N-(2-methylpropyl)-7,8-dihydro-6H-cyclopenta[g]isoquinoline-5-sulfonamide;

3'-cyclopropyl-N-(2-fluoro-2-methylpropyl)-2-oxospiro[1,3-oxazolidine-4,7'-6,8-dihydrocyclopenta[g]isoquinoline]-5'-sulfonamide;

3-cyclopropyl-N-(2-fluoro-2-methylpropyl)-7-(hydroxymethyl)-7-[(4-pyridin-3-yl-1,2,4-triazol-3-yl)amino]-6,8-dihydrocyclopenta[g]isoquinoline-5-sulfonamide;

2-(2-aminopyridin-3-yl)-7-cyclopropyl-N-(2-fluoro-2-methylpropyl)-1,3-dihydropyrrolo[3,4-g]isoquinoline-9-sulfonamide;

2-[4-[[(7R)-3-cyclopropyl-5-[(2-fluoro-2-methylpropyl)sulfamoyl]-7,8-dihydro-6H-cyclopenta[g]isoquinolin-7-yl]amino]pyrazolo[3,4-c]pyridin-1-yl]acetic acid;

3-cyclopropyl-7-[[2-(ethylamino)-3,4-dioxocyclobuten-1-yl]amino]-N-(2-methylpropyl)-7,8-dihydro-6H-cyclopenta[g]isoquinoline-5-sulfonamide;

3-cyclopropyl-N-(2,2-dimethylpropyl)-5-(2-methylpropylsulfamoyl)-7,8-dihydro-6H-cyclopenta[g]isoquinoline-7-carboxamide;

3-cyclopropyl-7-(methanesulfonamido)-N-(2-methylpropyl)-7,8-dihydro-6H-cyclopenta[g]isoquinoline-5-sulfonamide;

3-cyclopropyl-N-(2-fluoro-2-methylpropyl)-7-(3H-imidazo[4,5-c]pyridin-2-yl)-7,8-dihydro-6H-cyclopenta[g]isoquinoline-5-sulfonamide;

3-cyclopropyl-7-[3-[(2,5-dimethylpyrazol-3-yl)amino]-1,2,4-triazol-4-yl]-N-(2-fluoro-2-methylpropyl)-7,8-dihydro-6H-cyclopenta[g]isoquinoline-5-sulfonamide;

3-cyclopropyl-7-[2-(cyclopropylmethylamino) imidazol-1-yl]-N-(2-fluoro-2-methylpropyl)-7,8-dihydro-6H-cyclopenta[g]isoquinoline-5-sulfonamide;

2-[7-cyclopropyl-9-(2-methylpropylsulfamoyl)-1,3-dihydropyrrolo[3,4-g]isoquinolin-2-yl]-N-ethylacetamide;

7-cyclopropyl-N-(2-methylpropyl)-2,3-dihydro-1H-pyrrolo[3,4-g]isoquinoline-9-sulfonamide;

(7R)-3-cyclopropyl-N-(2-fluoro-2-methylpropyl)-7-[(6-sulfamoylpyridin-3-yl)amino]-7,8-dihydro-6H-cyclopenta[g]isoquinoline-5-sulfonamide;

3-cyclopropyl-N-(2-fluoro-2-methylpropyl)-7-(3H-imidazo[4,5-c]pyridin-7-ylamino)-7,8-dihydro-6H-cyclopenta[g]isoquinoline-5-sulfonamide;

3-cyclopropyl-N-(2-fluoro-2-methylpropyl)-7-[(2-oxo-1H-pyridin-4-yl)amino]-7,8-dihydro-6H-cyclopenta[g]isoquinoline-5-sulfonamide;
ethyl 5-[[(7R)-3-cyclopropyl-5-[(2-fluoro-2-methylpropyl) sulfamoyl]-7,8-dihydro-6H-cyclopenta[g]isoquinolin-7-yl]amino]-1,3,4-thiadiazole-2-carboxylate;
tert-butyl N-[3-cyclopropyl-5-[(2-fluoro-2-methylpropyl) sulfamoyl]-7,8-dihydro-6H-cyclopenta[g]cinnolin-7-yl]carbamate;
3-cyclopropyl-N-(2-fluoro-2-methylpropyl)-7-[[6-(5-methyl-1,3,4-oxadiazol-2-yl)pyridin-3-yl]amino]-7,8-dihydro-6H-cyclopenta[g]cinnoline-5-sulfonamide;
3-cyclopropyl-1-methyl-N-(2-methylpropyl)-7,8-dihydro-6H-cyclopenta[g]isoquinoline-5-sulfonamide;
7-cyclopropyl-N-(2-methylpropyl)-[1,3]dioxolo[4,5-g]isoquinoline-9-sulfonamide;
3-cyclopropyl-N-isobutyl-7,8-dihydro-6H-cyclopenta[g]isoquinoline-5-sulfonamide;
(7R)-3-cyclopropyl-N-(2-fluoro-2-methylpropyl)-7-[4-(5-methyl-1,3,4-oxadiazol-2-yl) anilino]-7,8-dihydro-6H-cyclopenta[g]isoquinoline-5-sulfonamide;
3-cyclopropyl-N-(2-fluoro-2-methylpropyl)-7-(4-oxo-1,5-dihydroimidazo[4,5-c]pyridin-2-yl)-7,8-dihydro-6H-cyclopenta[g]isoquinoline-5-sulfonamide;
7-cyclopropyl-N-(2-fluoro-2-methylpropyl)-2-(2-pyridin-3-ylacetyl)-1,3-dihydropyrrolo[3,4-g]isoquinoline-9-sulfonamide;
(7R)-3-cyclopropyl-N-(2-fluoro-2-methylpropyl)-7-[(6-fluoropyridin-3-yl)amino]-7,8-dihydro-6H-cyclopenta[g]isoquinoline-5-sulfonamide;
3-cyclopropyl-N-(3,3-difluorocyclobutyl)-7-[[6-(3-hydroxyoxetan-3-yl)pyridin-3-yl]amino]-7,8-dihydro-6H-cyclopenta[g]isoquinoline-5-sulfonamide;
(7R)-3-cyclopropyl-N-(2-fluoro-2-methylpropyl)-7-[[5-[(2-oxo-1H-pyridin-4-yl)oxy]pyridin-3-yl]amino]-7,8-dihydro-6H-cyclopenta[g]isoquinoline-5-sulfonamide;
3-cyclopropyl-N-[(3-hydroxyoxetan-3-yl)methyl]-7-[[6-(2-methyltetrazol-5-yl)pyridin-3-yl]amino]-7,8-dihydro-6H-cyclopenta[g]isoquinoline-5-sulfonamide;
5-[[(7R)-3-cyclopropyl-5-[(2-fluoro-2-methylpropyl) sulfamoyl]-7,8-dihydro-6H-cyclopenta[g]isoquinolin-7-yl]amino]-N-propan-2-ylpyridine-2-carboxamide;
3-cyclopropyl-N-(2-fluoro-2-methylpropyl)-7-[[4-(2-methylpyridin-3-yl)-1,2,4-triazol-3-yl]amino]-7,8-dihydro-6H-cyclopenta[g]isoquinoline-5-sulfonamide;
3-cyclopropyl-N-(2-fluoro-2-methylpropyl)-7-(1,2-oxazol-5-yl)-7,8-dihydro-6H-cyclopenta[g]isoquinoline-5-sulfonamide;
3-cyclopropyl-N-(2-hydroxy-2-methylpropyl)-7-[(6-methylpyridazin-3-yl)amino]-7,8-dihydro-6H-cyclopenta[g]isoquinoline-5-sulfonamide;
3-cyclopropyl-5-[(2,2-dimethylcyclopropyl) sulfamoyl]-N-pyridin-3-yl-7,8-dihydro-6H-cyclopenta[g]isoquinoline-7-carboxamide;
6-[[(7R)-3-cyclopropyl-5-[(2-fluoro-2-methylpropyl) sulfamoyl]-7,8-dihydro-6H-cyclopenta[g]isoquinolin-7-yl]amino]pyridazine-3-carboxamide;
3-cyclopropyl-N-(2-fluoro-2-methyl-propyl)-7-(1H-pyrazolo[3,4-c]pyridin-4-ylamino)-7,8-dihydro-6H-cyclopenta[g]isoquinoline-5-sulfonamide, formate salt;
3-cyclopropyl-N-(2-fluoro-2-methylpropyl)-7-[(1-methylpyrazolo[3,4-c]pyridin-4-yl)amino]-7,8-dihydro-6H-cyclopenta[g]isoquinoline-5-sulfonamide;
tert-butyl 5-[[(7R)-3-cyclopropyl-5-[(3,3-difluorocyclobutyl) sulfamoyl]-7,8-dihydro-6H-cyclopenta[g]isoquinolin-7-yl]amino]pyridine-2-carboxylate;
3-cyclopropyl-N-(2-fluoro-2-methylpropyl)-7-(pyridin-3-ylamino)-7,8-dihydro-6H-cyclopenta[g]isoquinoline-5-sulfonamide;
N-[3-cyclopropyl-5-[(2-fluoro-2-methylpropyl) sulfamoyl]-7,8-dihydro-6H-cyclopenta[g]isoquinolin-7-yl]-2-phenylacetamide;
5-[[3-cyclopropyl-5-(isobutylsulfamoyl)-7,8-dihydro-6H-cyclopenta[g]isoquinolin-7-yl]amino]pyridine-2-carboxylic acid, hydrochloride;
5-[[3-cyclopropyl-5-[(3,3-difluorocyclobutyl) sulfamoyl]-7,8-dihydro-6H-cyclopenta[g]isoquinolin-7-yl]amino]pyridine-2-carboxylic acid;
5-amino-1-[(7S)-3-cyclopropyl-5-[(2-fluoro-2-methylpropyl) sulfamoyl]-7,8-dihydro-6H-cyclopenta[g]isoquinolin-7-yl]imidazole-4-carboxamide;
7-cyclopropyl-N-(2-fluoro-2-methyl-propyl)-2-(3-pyridylmethyl)-1,3-dihydropyrrolo[3,4-g]isoquinoline-9-sulfonamide; formic acid;
(7R)-3-cyclopropyl-N-(2-fluoro-2-methylpropyl)-7-[[1-(5-methyl-1,3,4-oxadiazol-2-yl)-2-oxopyridin-4-yl]amino]-7,8-dihydro-6H-cyclopenta[g]isoquinoline-5-sulfonamide;
(7R)-3-cyclopropyl-N-(2-fluoro-2-methylpropyl)-7-[[6-(methylsulfamoyl)pyridin-3-yl]amino]-7,8-dihydro-6H-cyclopenta[g]isoquinoline-5-sulfonamide;
6-[[(7R)-3-cyclopropyl-5-[(3,3-difluorocyclobutyl) sulfamoyl]-7,8-dihydro-6H-cyclopenta[g]isoquinolin-7-yl]amino]pyridazine-3-carboxamide;
N-[5-[[(7R)-3-cyclopropyl-5-[(2-fluoro-2-methylpropyl) sulfamoyl]-7,8-dihydro-6H-cyclopenta[g]isoquinolin-7-yl]amino]pyridin-2-yl]sulfonylacetamide;
3-cyclopropyl-N-(2-fluoro-2-methyl-propyl)-7-[(1-methyl-2-oxo-4-pyridyl)amino]-7,8-dihydro-6H-cyclopenta[g]isoquinoline-5-sulfonamide, formate salt;
3-cyclopropyl-N-(2-fluoro-2-methylpropyl)-7-[(5-methyl-1,3,4-oxadiazol-2-yl)amino]-7,8-dihydro-6H-cyclopenta[g]isoquinoline-5-sulfonamide;
3-cyclopropyl-7-[(4,4-dimethyl-3-oxocyclobuten-1-yl) amino]-N-(2-fluoro-2-methylpropyl)-7,8-dihydro-6H-cyclopenta[g]isoquinoline-5-sulfonamide;
7-cyclopropyl-9-N-(2-fluoro-2-methylpropyl)-2-N-(2-methylpropyl)-1,3-dihydropyrrolo[3,4-g]isoquinoline-2,9-disulfonamide;
7-cyclopropyl-N-ethyl-9-(2-methylpropylsulfamoyl)-1,3-dihydropyrrolo[3,4-g]isoquinoline-2-carboxamide;
(7R)-3-cyclopropyl-N-(2-fluoro-2-methylpropyl)-7-[[6-(5-methyl-1,3,4-oxadiazol-2-yl)pyridazin-3-yl]amino]-7,8-dihydro-6H-cyclopenta[g]isoquinoline-5-sulfonamide;
7-cyclopropyl-N-(2-fluoro-2-methylpropyl)-2-(1H-pyrazol-5-ylmethyl)-1,3-dihydropyrrolo[3,4-g]isoquinoline-9-sulfonamide;
3-cyclopropyl-N-isobutyl-7-(pyridazin-4-ylamino)-7,8-dihydro-6H-cyclopenta[g]isoquinoline-5-sulfonamide; formic acid;
N-[3-cyclopropyl-5-[(2-fluoro-2-methylpropyl) sulfamoyl]-7,8-dihydro-6H-cyclopenta[g]isoquinolin-7-yl]-2-methylpyrazole-3-carboxamide;
(7R)-3-cyclopropyl-N-(2-fluoro-2-methylpropyl)-7-[[1-(2-hydroxyethyl) pyrazolo[3,4-c]pyridin-4-yl]amino]-7,8-dihydro-6H-cyclopenta[g]isoquinoline-5-sulfonamide;
(7R)-3-cyclopropyl-N-(2-fluoro-2-methylpropyl)-7-[[2-(2-hydroxyethyl) pyrazolo[3,4-c]pyridin-4-yl]amino]-7,8-dihydro-6H-cyclopenta[g]isoquinoline-5-sulfonamide;

13-cyclopropyl-N-(2-fluoro-2-methylpropyl)-12-azatetracyclo[8.4.0.03,8.04,6]tetradeca-1 (10),2,8,11,13-pentaene-2-sulfonamide;

(7R)-3-cyclopropyl-N-(2-fluoro-2-methylpropyl)-7-[[6-(1-methylpyrazol-3-yl)pyridin-3-yl]amino]-7,8-dihydro-6H-cyclopenta[g]isoquinoline-5-sulfonamide;

3-cyclopropyl-N-(2-fluoro-2-methylpropyl)-7-(imidazo[1,2-a]pyrazin-5-ylamino)-7,8-dihydro-6H-cyclopenta[g]isoquinoline-5-sulfonamide;

3-cyclopropyl-N-(2-fluoro-2-methylpropyl)-7-pyridin-3-yl-7,8-dihydro-6H-cyclopenta[g]isoquinoline-5-sulfonamide;

3-cyclopropyl-N-(3,3-difluorocyclobutyl)-7-(3-oxo-2-pyridin-3-yl-1H-pyrazol-5-yl)-7,8-dihydro-6H-cyclopenta[g]isoquinoline-5-sulfonamide;

3-cyclopropyl-N-(2-fluoro-2-methylpropyl)-7-[(5-hydroxy-2-methylpyrazol-3-yl)amino]-7,8-dihydro-6H-cyclopenta[g]isoquinoline-5-sulfonamide;

3-cyclopropyl-N-(2,2-dimethylpropyl)-5-[(2-fluoro-2-methylpropyl) sulfamoyl]-7,8-dihydro-6H-cyclopenta[g]cinnoline-7-carboxamide;

(7R)-7-(4-acetylanilino)-3-cyclopropyl-N-(2-fluoro-2-methylpropyl)-7,8-dihydro-6H-cyclopenta[g]isoquinoline-5-sulfonamide;

(7R)-3-cyclopropyl-N-(2-fluoro-2-methylpropyl)-7-[[6-(4-methyltriazol-1-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(4-methyltriazol-2-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(1,2,4-triazol-1-yl)pyridin-3-yl]amino]-7,8-dihydro-6H-cyclopenta[g]isoquinoline-5-sulfonamide;

(7R)-3-cyclopropyl-7-[[6-(difluoromethyl)pyridin-3-yl]amino]-N-(2-fluoro-2-methylpropyl)-7,8-dihydro-6H-cyclopenta[g]isoquinoline-5-sulfonamide;

(7R)-7-[[6-chloro-4-(cyclopropylmethoxy)pyridin-3-yl]amino]-3-cyclopropyl-N-(2-fluoro-2-methylpropyl)-7,8-dihydro-6H-cyclopenta[g]isoquinoline-5-sulfonamide;

(7R)-3-cyclopropyl-N-(2-fluoro-2-methylpropyl)-7-[[4-(oxan-4-yloxy)pyrimidin-5-yl]amino]-7,8-dihydro-6H-cyclopenta[g]isoquinoline-5-sulfonamide;

N-[5-[[3-cyclopropyl-5-[(2-fluoro-2-methylpropyl) sulfamoyl]-7,8-dihydro-6H-cyclopenta[g]isoquinolin-7-yl]amino]pyridin-3-yl]acetamide;

7-[(5-cyanopyridin-3-yl)amino]-3-cyclopropyl-N-(2-fluoro-2-methylpropyl)-7,8-dihydro-6H-cyclopenta[g]isoquinoline-5-sulfonamide;

3-cyclopropyl-N-(2-fluoro-2-methylpropyl)-7-[(5-methylsulfonylpyridin-3-yl)amino]-7,8-dihydro-6H-cyclopenta[g]isoquinoline-5-sulfonamide;

(7R)-3-cyclopropyl-N-(2-fluoro-2-methylpropyl)-7-[[2-(1H-tetrazol-5-yl)pyrimidin-5-yl]amino]-7,8-dihydro-6H-cyclopenta[g]isoquinoline-5-sulfonamide;

(7R)-3-cyclopropyl-N-(2-fluoro-2-methylpropyl)-7-[4-(2-methyltetrazol-5-yl) anilino]-7,8-dihydro-6H-cyclopenta[g]isoquinoline-5-sulfonamide;

(7R)-7-[[6-chloro-4-(1H-tetrazol-5-yl)pyridin-3-yl]amino]-3-cyclopropyl-N-(2-fluoro-2-methylpropyl)-7,8-dihydro-6H-cyclopenta[g]isoquinoline-5-sulfonamide;

(7R)-3-cyclopropyl-N-(2-fluoro-2-methylpropyl)-7-[(5-oxo-2H-pyran-3-yl)amino]-7,8-dihydro-6H-cyclopenta[g]isoquinoline-5-sulfonamide;

(7R)-3-cyclopropyl-N-(2-fluoro-2-methylpropyl)-7-[[4-(1-methylpyrazol-3-yl)oxypyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[2-(5-methyl-1,3,4-oxadiazol-2-yl)pyrimidin-5-yl]amino]-7,8-dihydro-6H-cyclopenta[g]isoquinoline-5-sulfonamide;

N-[(7R)-3-cyclopropyl-5-[(2-fluoro-2-methylpropyl) sulfamoyl]-7,8-dihydro-6H-cyclopenta[g]isoquinolin-7-yl]-1H-indole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-5-fluoro-1H-indole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-1-methylindole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-6-methoxy-1H-indole-3-carboxamide;

N-[(7R)-3-cyclopropyl-5-[(2-fluoro-2-methylpropyl) sulfamoyl]-7,8-dihydro-6H-cyclopenta[g]isoquinolin-7-yl]-4-methyl-1,3-thiazole-5-carboxamide;

N-[(7R)-3-cyclopropyl-5-[(2-fluoro-2-methylpropyl) sulfamoyl]-7,8-dihydro-6H-cyclopenta[g]isoquinolin-7-yl]isoquinoline-1-carboxamide;

tert-butyl 5-[[(7R)-3-cyclopropyl-5-[(2-fluoro-2-methylpropyl) sulfamoyl]-7,8-dihydro-6H-cyclopenta[g]isoquinolin-7-yl]carbamoyl]-1,3-dihydroisoindole-2-carboxylate;

N-[(7R)-3-cyclopropyl-5-[(2-fluoro-2-methylpropyl) sulfamoyl]-7,8-dihydro-6H-cyclopenta[g]isoquinolin-7-yl]-2-(1-methylpyrazol-4-yl)-2-oxoacetamide;

4-[[(7R)-3-cyclopropyl-5-[(2-fluoro-2-methyl-propyl) sulfamoyl]-7,8-dihydro-6H-cyclopenta[g]isoquinolin-7-yl]amino]isoquinoline-1-carboxylate lithium;

3-cyclopropyl-N-(2-fluoro-2-methylpropyl)-7-[(6-methylsulfinylpyridin-3-yl)amino]-7,8-dihydro-6H-cyclopenta[g]isoquinoline-5-sulfonamide;

3-cyclopropyl-N-(2-fluoro-2-methylpropyl)-7-[(1-methyl-6-oxopyridazin-4-yl)amino]-7,8-dihydro-6H-cyclopenta[g]isoquinoline-5-sulfonamide;

6-bromo-N-[(7R)-3-cyclopropyl-5-[(2-fluoro-2-methylpropyl) sulfamoyl]-7,8-dihydro-6H-cyclopenta[g]isoquinolin-7-yl]-1H-indazole-3-carboxamide; or 3-cyclopropyl-N-(2-fluoro-2-methylpropyl)-7-[(5-oxo-2H-furan-3-yl)amino]-7,8-dihydro-6H-cyclopenta[g]isoquinoline-5-sulfonamide.

12. A method for the treatment or prevention of disorders caused by IgE comprising administration to a patient in need thereof a compound according to claim 1 or a pharmaceutically acceptable salt thereof.

13. A method for the treatment or prevention of allergy, non-allergic mast cell responses, type 1 hypersensitivity-, urticaria, or familiar sinus inflammation comprising administration to a patient in need thereof a compound according to claim 1 or a pharmaceutically acceptable salt thereof.

14. A method for the treatment or prevention of airway constriction in asthma, local inflammation in eczema, increased mucus secretion in allergic rhinitis, urticaria, or increased vascular permeability comprising administration to a patient in need thereof a compound according to claim 1 or a pharmaceutically acceptable salt thereof.

15. A method for the treatment or prevention of eosinophilic granulomatosis with polyangiitis, aspirin exacerbated respiratory disease, or cutaneous T-cell lymphoma comprising administration to a patient in need thereof a compound according to claim 1 or a pharmaceutically acceptable salt thereof.

16. A pharmaceutical composition comprising a compound of formula (I) according to claim 1 or a pharmaceutically acceptable salt thereof in association with a pharmaceutically acceptable carrier.

17. A method for the treatment or prevention of allergy, non-allergic mast cell responses, type 1 hypersensitivity, urticaria, familiar sinus inflammation, eosinophilic granulomatosis with polyangiitis, aspirin exacerbated respiratory disease, or cutaneous T-cell lymphoma, which comprises the administration of a compound according to claim 1 or a pharmaceutically acceptable salt thereof in a therapeutically effective amount to a patient.

18. A compound of formula (I) according to claim 1, which is:

(7R)-3-cyclopropyl-N-(3-fluorocyclobutyl)-7-[[6-(2-methyltetrazol-5-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[5-(6-methylpyridin-3-yl)oxypyridin-3-yl]amino]-7,8-dihydro-6H-cyclopenta[g]isoquinoline-5-sulfonamide;

3-cyclopropyl-N-(2-fluoro-2-methylpropyl)-7-[[4-(pyridin-3-ylamino)pyrimidin-5-yl]amino]-7,8-dihydro-6H-cyclopenta[g]isoquinoline-5-sulfonamide;

(7R)-3-cyclopropyl-N-(2-fluoro-2-methylpropyl)-7-[[6-(5-methyl-1,2,4-oxadiazol-3-yl)pyridin-3-yl]amino]-O 7,8-dihydro-6H-cyclopenta[g]isoquinoline-5-sulfonamide;

(7R)-3-cyclopropyl-N-(2-fluoro-2-methylpropyl)-7-[[6-(3-methyl-1,2,4-oxadiazol-5-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(5-methyl-1,3,4-oxadiazol-2-yl)pyridin-3-yl]amino]-7,8-dihydro-6H-cyclopenta[g]isoquinoline-5-sulfonamide;

(7R)-3-cyclopropyl-N-(3,3-difluorocyclobutyl)-7-[[6-(2-methyltetrazol-5-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(2-methyltetrazol-5-yl)pyridin-3-yl]amino]-7,8-dihydro-6H-cyclopenta[g]isoquinoline-5-sulfonamide;

2-[4-[[(7R)-3-cyclopropyl-5-[(2-fluoro-2-methylpropyl)sulfamoyl]-7,8-dihydro-6H-cyclopenta[g]isoquinolin-7-yl]amino]pyrazolo[3,4-c]pyridin-1-yl]acetic acid;

3-cyclopropyl-N-[(3-hydroxyoxetan-3-yl)methyl]-7-[[6-(2-methyltetrazol-5-yl)pyridin-3-yl]amino]-7,8-dihydro-6H-cyclopenta[g]isoquinoline-5-sulfonamide;

6-[[(7R)-3-cyclopropyl-5-[(2-fluoro-2-methylpropyl) sulfamoyl]-7,8-dihydro-6H-cyclopenta[g]isoquinolin-7-yl]amino]pyridazine-3-carboxamide;

(7R)-3-cyclopropyl-N-(2-fluoro-2-methylpropyl)-7-[[6-(5-methyl-1,3,4-oxadiazol-2-yl)pyridazin-3-yl]amino]-7,8-dihydro-6H-cyclopenta[g]isoquinoline-5-sulfonamide;

(7R)-3-cyclopropyl-N-(2-fluoro-2-methylpropyl)-7-[[1-(2-hydroxyethyl) pyrazolo[3,4-c]pyridin-4-yl]amino]-7,8-dihydro-6H-cyclopenta[g]isoquinoline-5-sulfonamide;

(7R)-3-cyclopropyl-N-(2-fluoro-2-methylpropyl)-7-[[6-(4-methyltriazol-1-yl)pyridin-3-yl]amino]-7,8-dihydro-6H-cyclopenta[g]isoquinoline-5-sulfonamide;

(7R)-3-cyclopropyl-N-(2-fluoro-2-methylpropyl)-7-[[6-(4-methyltriazol-2-yl)pyridin-3-yl]amino]-7,8-dihydro-6H-cyclopenta[g]isoquinoline-5-sulfonamide; or (7R)-3-cyclopropyl-N-(2-fluoro-2-methylpropyl)-7-[[6-(1,2,4-triazol-1-yl)pyridin-3-yl]amino]-7,8-dihydro-6H-cyclopenta[g]isoquinoline-5-sulfonamide.

* * * * *